United States Patent
Xu et al.

(10) Patent No.: US 10,047,093 B2
(45) Date of Patent: Aug. 14, 2018

(54) SUBSTITUTED IMIDAZO[1,2-B]PYRIDAZINES AS PROTEIN KINASE INHIBITORS

(71) Applicant: Tolero Pharmaceuticals, Inc., Lehi, UT (US)

(72) Inventors: Yong Xu, Midvale, UT (US); Benjamin Gary Brenning, Zapopan (MX); Steven G. Kultgen, Salt Lake City, UT (US); Xiaohui Liu, Holladay, UT (US); Michael David Saunders, Sandy, UT (US); Koc-Kan Ho, Holladay, UT (US)

(73) Assignee: TOLERO PHARMACEUTICALS, INC., Lehi, UT (US)

( * ) Notice: Subject to any disclaimer, the term of this patent is extended or adjusted under 35 U.S.C. 154(b) by 0 days.

(21) Appl. No.: 15/207,224

(22) Filed: Jul. 11, 2016

(65) Prior Publication Data

US 2017/0002014 A1    Jan. 5, 2017

Related U.S. Application Data

(62) Division of application No. 14/234,109, filed as application No. PCT/US2012/047685 on Jul. 20, 2012, now Pat. No. 9,416,132.

(60) Provisional application No. 61/608,028, filed on Mar. 7, 2012, provisional application No. 61/632,826, filed on Mar. 1, 2012, provisional application No. 61/510,207, filed on Jul. 21, 2011, provisional application No. 61/632,834, filed on Jul. 21, 2011.

(51) Int. Cl.
*C07D 487/04*    (2006.01)
*C07D 471/04*    (2006.01)

(52) U.S. Cl.
CPC ......... *C07D 487/04* (2013.01); *C07D 471/04* (2013.01)

(58) Field of Classification Search
CPC .................................................. C07D 487/04
USPC ......................................................... 544/236
See application file for complete search history.

(56) References Cited

U.S. PATENT DOCUMENTS

| | | | |
|---|---|---|---|
| 6,169,088 | B1 | 1/2001 | Matsuno et al. |
| 7,750,000 | B2 | 7/2010 | Prien et al. |
| 7,750,007 | B2 | 7/2010 | Bearss et al. |
| 7,998,966 | B2 | 8/2011 | Bearss et al. |
| 8,710,057 | B2 | 4/2014 | Bearss et al. |
| 2005/0227992 | A1 | 10/2005 | Hurley et al. |
| 2007/0093490 | A1 | 4/2007 | Prien et al. |
| 2009/0093475 | A1 | 4/2009 | Prien et al. |
| 2011/0046127 | A1 | 2/2011 | Pevarello et al. |
| 2011/0166122 | A1 | 7/2011 | Andrews et al. |
| 2011/0269772 | A1 | 11/2011 | Bearss et al. |
| 2012/0058997 | A1 | 3/2012 | Xu et al. |
| 2012/0059162 | A1 | 3/2012 | Kusakabe et al. |

FOREIGN PATENT DOCUMENTS

| | | |
|---|---|---|
| DE | 10 2005 042 742 A1 | 3/2007 |
| DE | 10 2006 029 447 A1 | 12/2007 |
| EP | 1 900 739 A1 | 3/2008 |
| JP | 2009-541242 A | 11/2009 |
| JP | 2010-504933 A | 2/2010 |
| WO | 96/31509 A1 | 10/1996 |
| WO | 02/16351 A1 | 2/2002 |
| WO | 2004/024895 A2 | 3/2004 |
| WO | 2004/058769 A2 | 7/2004 |
| WO | 2004/058772 A1 | 7/2004 |

(Continued)

OTHER PUBLICATIONS

Jordan, V. C. Nature Reviews: Drug Discovery, 2, 2003, 205.*

(Continued)

*Primary Examiner* — Douglas M Willis
(74) *Attorney, Agent, or Firm* — Seed Intellectual Property Law Group LLP

(57) ABSTRACT

The present invention provides protein kinase having one of the following structures (I), (II) or (III):

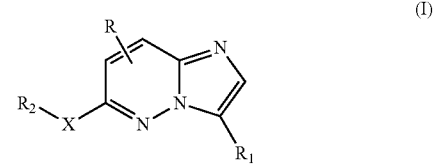

(I)

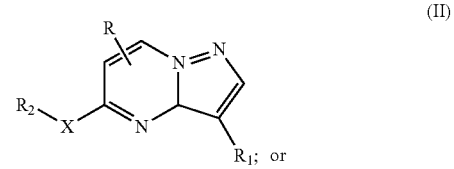

(II)

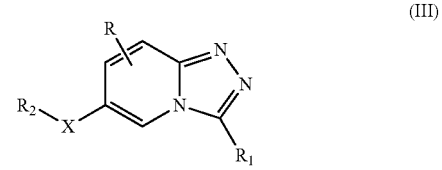

(III)

or a stereoisomer, prodrug, tautomer or pharmaceutically acceptable salt thereof, wherein R, $R_1$, $R_2$ and X are as defined herein. Compositions and methods for using the same in the treatment of cancer, autoimmune, inflammatory and other Pim kinase-associated conditions are also disclosed.

42 Claims, 8 Drawing Sheets

(56) References Cited

FOREIGN PATENT DOCUMENTS

| | | | |
|---|---|---|---|
| WO | 2004/072072 | A1 | 8/2004 |
| WO | 2005/037825 | A2 | 4/2005 |
| WO | 2006/018718 | A2 | 2/2006 |
| WO | 2006/054652 | A1 | 5/2006 |
| WO | 2006/116733 | A2 | 11/2006 |
| WO | 2007/013673 | A1 | 2/2007 |
| WO | 2007/020888 | A1 | 2/2007 |
| WO | 2007/025090 | A2 | 3/2007 |
| WO | 2007/025540 | A2 | 3/2007 |
| WO | 2007/041712 | A1 | 4/2007 |
| WO | 2007/091152 | A1 | 8/2007 |
| WO | 2007/146838 | A2 | 12/2007 |
| WO | 2007/147646 | A1 | 12/2007 |
| WO | 2007/147647 | A1 | 12/2007 |
| WO | 2008/025822 | A1 | 3/2008 |
| WO | 2008/030579 | A2 | 3/2008 |
| WO | 2008/037477 | A1 | 4/2008 |
| WO | 2008/052734 | A1 | 5/2008 |
| WO | 2008/055233 | A1 | 5/2008 |
| WO | 2008/058126 | A2 | 5/2008 |
| WO | 2009/060197 | A1 | 5/2009 |
| WO | 2012/032031 | A1 | 3/2012 |

OTHER PUBLICATIONS

Hackam, et al. JAMA, 296(14), 2006, 1731-1732.*
Adam et al., "Targeting PIM Kinases Impairs Survival of Hematopoietic Cells Transformed by Kinase Inhibitor-Sensitive and Kinase Inhibitor-Resistant Forms of Fms-Like Tyrosine Kinase 3 and BCR/ABL," *Cancer Res* 66(7):3828-3835, Apr. 1, 2006.
Alvarado et al., "The PIM kinases in hematological cancers," *Expert Rev. Hematol.* 5(1):81-96, 2012.
Beharry et al., "The Pim protein kinases regulate energy metabolism and cell growth," *PNAS* 108(2):528-533, Jan. 11, 2011.
Blanco-Aparicio et al., "Pim 1 kinase inhibitor ETP-45299 suppresses cellular proliferation and synergizes with PI3K inhibition," *Cancer Letters* 300:145-153, 2011.
Brault et al., "PIM serine/threonine kinases in the pathogenesis and therapy of hematologic malignancies and solid cancers," *Haematologica* 95(6):1004-1015, 2010.
Bullock et al., "Structural Basis of Inhibitor Specificity of the Human Protooncogene Proviral Insertion Site in Moloney Murine Leukemia Virus (PIM-1) Kinase," *J. Med. Chem.* 48:7604-7614, 2005.
Chang et al., "PIM Kinase Inhibitors Downregulate STAT3$^{Tyr705}$ Phosphorylation," *Mol Cancer Ther* 9(9):2478-2487, Sep. 2010.
Chen et al., "Mechanisms of cytotoxicity to Pim kinase inhibitor, SGI-1776, in acute myeloid leukemia," *Blood* 118(3):693-702, Jul. 21, 2011.
Chezal et al., "Efficient synthesis of novel dipyridoimidazoles and pyrido[1',2';1,2]imidazo[4,5-d]pyridazine derivatives," *Tetrahedron* 59:5869-5878, 2003.
European Office Action, dated Jul. 5, 2012, for EP Application No. 07863964.8, 5 pages.
Fathi et al., "A potential therapeutic target for FLT3-ITD AML: PIM1 Kinase," *Leuk Res.* 36(2):224-231, Feb. 2012.
Guo et al., "Overexpression of Pim-1 in bladder cancer," *Journal of Experimental & Clinical Cancer Research* 29:161, 2010, 7 pages.
International Search Report and Written Opinion, dated Sep. 21, 2012, for International Application No. PCT/US12/47685, 8 pages.
Jackson et al., "The role of PIM kinases in human and mouse CD4+ T cell activation and inflammatory bowel disease," *Cellular Immunology* 272:200-213, 2012.
Jacobs et al., "Pim-1 Ligand-bound Structures Reveal the Mechanism of Serine/Threonine Kinase Inhibition by LY294002," *Journal of Biological Chemistry* 280(14):13728-13734, 2005.
Kottaridis et al., "The presence of a FLT3 internal tandem duplication in patients with acute myeloid leukemia (AML) adds important prognostic information to cytogenetic risk group and response to the first cycle of chemotherapy: analysis of 854 patients from the United Kingdom Medical Research Council AML 10 and 12 trials," *Blood* 98(6):1752-1759, Sep. 15, 2001.
Kumar et al., "Crystal Structures of Proto-oncogene Kinase Pim1: A Target of Aberrant Somatic Hypermutations in Diffuse Large Cell Lymphoma," *J. Mol. Biol.* 348:183-193, 2005.
Lima et al., "Bioisosterism: A Useful Strategy for Molecular Modification and Drug Design," *Current Medicinal Chemistry* 12:23-49, 2005.
Lin et al., "A small molecule inhibitor of Pim protein kinases blocks the growth of precursor T-cell lymphoblastic leukemia/lymphoma," *Blood* 115(4):824-833, Jan. 28, 2010.
Magnuson et al., "Why target PIM1 for cancer diagnosis and treatment?" *Future Oncol.* 6(9):1467-1478, 2010, 27 pages.
Matsuno et al., "Potent and Selective Inhibitors of Platelet-Derived Growth Factor Receptor Phosphorylation. 1. Synthesis, Structure-Activity Relationship, and Biological Effects of a New Class of Quinazoline Derivatives," *J. Med. Chem.* 45:3057-3066, 2002.
Millan et al., "Design and Synthesis of Inhaled p38 Inhibitors for the Treatment of Chronic Obstructive Pulmonary Disease," *Journal of Medicinal Chemistry* 54:7797-7814, 2011.
Nawijn et al., "For better or for worse: the role of Pim oncogenes in tumorigenisis," *Nature Reviews Cancer* 11:23-34, Jan. 2011.
Pierre et al., "Novel potent dual inhibitors of CK2 and Pim kinases with antiproliferative activity against cancer cells," *Bioorganic & Medicinal Chemistry Letters* 22:3327-3331, 2012.
Qian et al., "Hit to Lead Account of the Discovery of a New Class of Inhibitors of Pim Kinases and Crystallographic Studies Revealing an Unusual Kinase Binding Mode," *Journal of Medicinal Chemistry* 52(7):1814-1827, 2009.
Qian et al., "Structural Basis of Constitutive Activity and a Unique Nucleotide Binding Mode of Human Pim-1 Kinase," *Journal of Biological Chemistry* 280(7):6130-6137, Feb. 18, 2005.
Raboisson et al., "Efficient preparation of imidazo[1,2-b]pyridazines under Swern oxidative conditions," *Tetrahedron Letters* 44:2919-2921, 2003.
Robertson et al., "A Comparison of the Requirements for Antitumour Activity and Antibacteriophage Lambda Activity for a Series of Non-intercalative DNA-binding Agents," *Eur J Cancer Clin Oncol* 18(3):271-279, 1982.
Singh et al., "Chemotherapy of Filariasis—On the Search of New Agents Effective on the Reproductive System of Female Adult Worms," *Z. Naturforsch.* 45c:1210-1214, 1990.
Tamburini et al., "Protein synthesis is resistant to rapamycin and constitutes a promising therapeutic target in acute myeloid leukemia," *Blood* 114(8):1618-1627, Aug. 20, 2009.
Warner et al., "Identification of a lead small-molecule inhibitor of the Aurora kinases using a structure-assisted, fragment-based approach," *Mol Cancer Ther* 5(7):1764-1773, Jul. 2006.
Williamson et al., "Structure-guided design of pyrazolo[1,5-α] pyrimidines as inhibitors of human cyclin-dependent kinase 2," *Bioorganic & Medicinal Chemistry Letters* 15:863-867, 2005.
Xia et al., "Synthesis and Evaluation of Novel Inhibitors of Pim-1 and Pim-2 Protein Kinases," *J. Med. Chem.* 52:74-86, 2009.

* cited by examiner

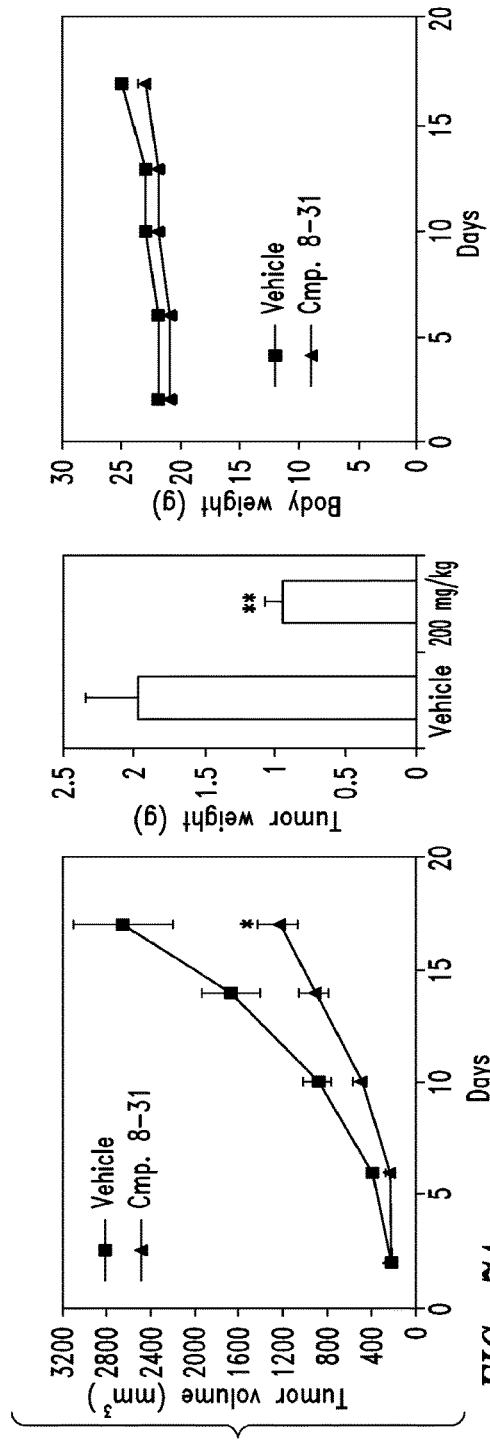
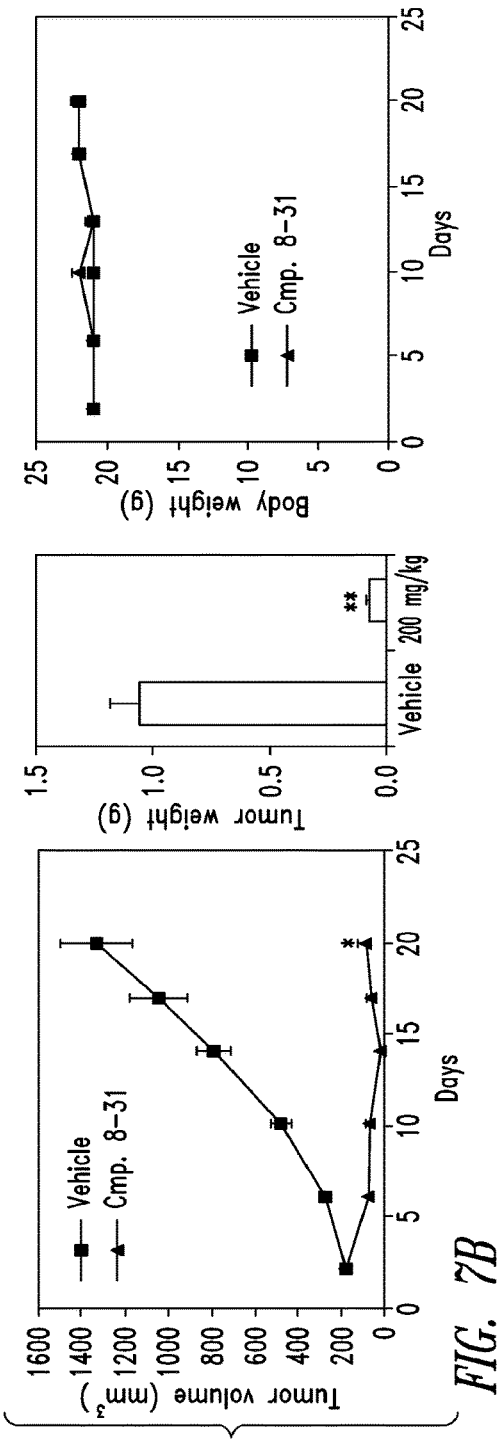
FIG. 7A
FIG. 7B

SUBSTITUTED IMIDAZO[1,2-B]PYRIDAZINES AS PROTEIN KINASE INHIBITORS

BACKGROUND OF THE INVENTION

Technical Field

The present invention relates, in general, to compounds that inhibit protein kinase activity, and to compositions and methods related thereto.

Description of the Related Art

Cancer (and other hyperproliferative diseases) is characterized by uncontrolled cell proliferation. This loss of the normal control of cell proliferation often appears to occur as the result of genetic damage to cell pathways that control progress through the cell cycle. The cell cycle consists of DNA synthesis (S phase), cell division or mitosis (M phase), and non-synthetic periods referred to as gap 1 (G1) and gap 2 (G2). The M-phase is composed of mitosis and cytokinesis (separation into two cells). All steps in the cell cycle are controlled by an orderly cascade of protein phosphorylation and several families of protein kinases are involved in carrying out these phosphorylation steps. In addition, the activity of many protein kinases increases in human tumors compared to normal tissue and this increased activity can be due to many factors, including increased levels of a kinase or changes in expression of co-activators or inhibitory proteins.

Cells have proteins that govern the transition from one phase of the cell cycle to another. For example, the cyclins are a family of proteins whose concentrations increase and decrease throughout the cell cycle. The cyclins turn on, at the appropriate time, different cyclin-dependent protein kinases (CDKs) that phosphorylate substrates essential for progression through the cell cycle. Activity of specific CDKs at specific times is essential for both initiation and coordinated progress through the cell cycle. For example, CDK1 is the most prominent cell cycle regulator that orchestrates M-phase activities. However, a number of other mitotic protein kinases that participate in M-phase have been identified, which include members of the polo, aurora, and NIMA (Never-In-Mitosis-A) families and kinases implicated in mitotic checkpoints, mitotic exit, and cytokinesis.

Pim kinases (e.g., Pim-1 kinase, Pim-2 kinase, Pim-3 kinase) are a family of oncogenic serine/threonine kinases. Pim-1 kinase is known to be involved in a number of cytokine signaling pathways as a downstream effector. Once activated, Pim-1 kinase causes progression of the cell cycle, inhibition of apoptosis and modulation of other signal transduction pathways, including its own. Pim-1 kinase is also known to effect activation of transcription factors such as NFAT, p100, c-Myb and Pap-1, and inhibition of others such as HP1. Normal expression of Pim-1 kinase is seen in cells of hematopoietic origin, such as fetal liver, thymus, spleen and bone marrow. Additionally, expression is seen in prostate and oral epithelial cells Pim-1 kinase is believed to be involved in the initiation or progression of malignant transformation leading to malignancies including Burkitt's lymphoma, prostate cancer, oral cancer and diffuse large cell lymphomas, among others.

Pim kinases also play a role in immune regulation. For example, enhanced Pim expression has been observed in a variety of inflammatory states. Pim-2 is also implicated in cytokine induced T-cell growth and survival. A recent publication (Jackson et al., Cell Immunology, 2012, 272, 200-213) demonstrated in vivo efficacy for a dual PIM-1 and PIM-3 inhibitor in a mouse inflammatory bowel disease model. Therefore, PIM kinases are attractive targets for various autoimmune and/or inflammatory diseases.

Based on their involvement in a number of human malignancies, there is a need for the rational design of specific and selective inhibitors for the treatment of cancer and other conditions that are mediated and/or associated with Pim kinase proteins. The present invention fulfills these needs and offers other related advantages.

BRIEF SUMMARY

The present invention is generally directed to compounds, and pharmaceutical compositions comprising said compounds, where the compounds have the following general structures (I), (II) and (III):

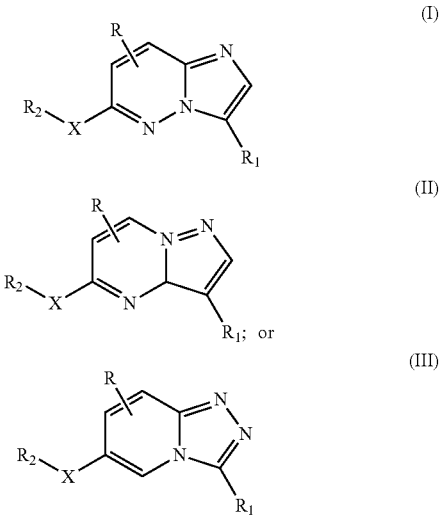

including stereoisomers, prodrugs, tautomers and pharmaceutically acceptable salts thereof, wherein R, $R_1$, $R_2$ and X are as defined herein.

These compounds of the present invention have utility over a broad range of therapeutic applications, and may be used to treat diseases, such as cancer and various inflammatory conditions, that are mediated at least in part by protein kinase activity. Accordingly, in one aspect of the invention, the compounds described herein are formulated as pharmaceutically acceptable compositions for administration to a subject in need thereof.

In another aspect, the invention provides methods for treating or preventing a protein kinase-mediated disease, such as cancer, which method comprises administering to a patient in need of such a treatment a therapeutically effective amount of a compound described herein or a pharmaceutically acceptable composition comprising said compound. In certain embodiments, the protein kinase-mediated disease is a Pim kinase-mediated disease, such as a Pim-1 kinase-expressing cancer.

Another aspect of the invention relates to inhibiting protein kinase activity in a biological sample, which method comprises contacting the biological sample with a compound described herein, or a pharmaceutically acceptable composition comprising said compound. In certain embodiments, the protein kinase is Pim kinase.

Another aspect of this invention relates to a method of inhibiting protein kinase activity in a patient, which method comprises administering to the patient a compound described herein or a pharmaceutically acceptable composition comprising said compound. In certain embodiments, the protein kinase is a Pim kinase.

In another embodiment, the present invention is directed to methods for treatment of various autoimmune and/or inflammatory conditions mediated by Pim kinase. The methods comprise administration of any of the disclosed compounds to a mammal, for example a mammal in need of treatment for an autoimmune and/or inflammatory condition mediated by Pim kinase. Inflammatory conditions which may be treated according to the disclosed methods include, but are not limited to: osteoarthritis, rheumatoid arthritis, pain, inflammatory bowel diseases, respiratory disorders, skin disorders or combinations thereof.

These and other aspects of the invention will be apparent upon reference to the following detailed description and attached figures. To that end, certain patent and other documents are cited herein to more specifically set forth various aspects of this invention. Each of these documents is hereby incorporated by reference in its entirety.

BRIEF DESCRIPTION OF THE DRAWINGS

FIGS. 7A and 7B show tumor regression and body weight data.

DETAILED DESCRIPTION OF THE INVENTION

Figure 1:
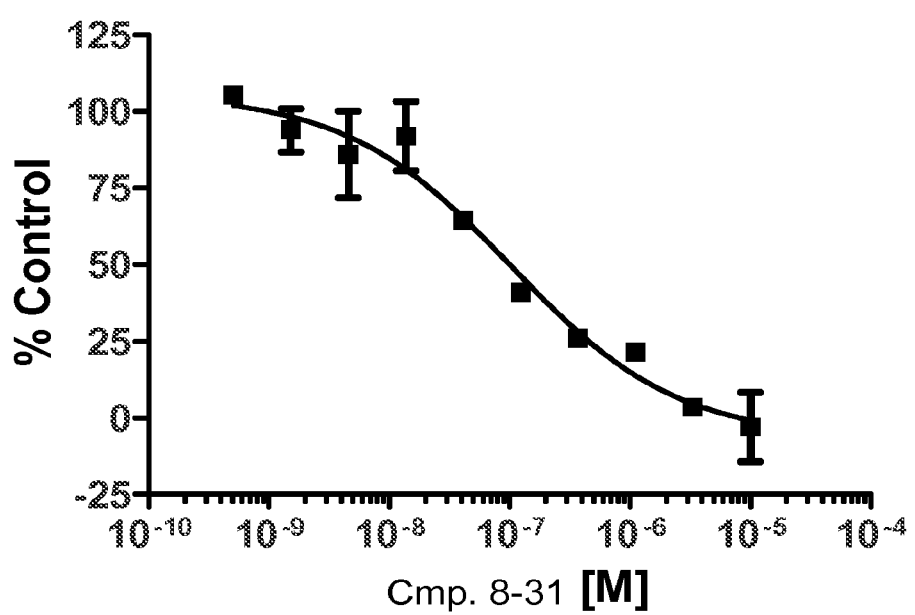
FIG. 1 shows results of a cell-based assay of a representative compound

According to a general aspect of the present invention, there are provided compounds useful as protein kinase inhibitors and compositions and methods relating thereto. Compounds of the invention have structures set forth in (I), (II) or (III) below:

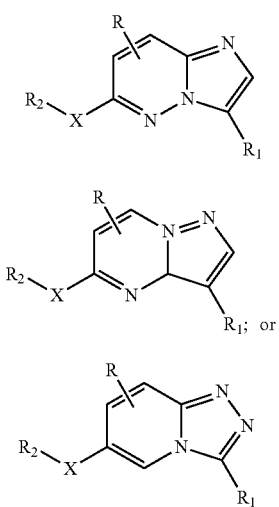

including stereoisomers, prodrugs, tautomers and pharmaceutically acceptable salts thereof, wherein:

X is a direct bond, NH, N(alkyl), S, O, SO or $SO_2$;

R is H, —OH, halo, alkyl, haloalkyl, alkoxy, haloalkoxy, —$NH_2$, —NH(alkyl), —N(alkyl)$_2$, or —CN;

$R_1$ is optionally substituted carbocycle, optionally substituted heterocycle or $R_1$ has the following structure:

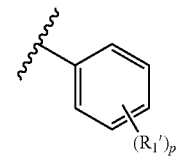

where $R_1'$ is at, each occurrence, independently selected from hydrogen cyano, alkyl, alkoxy, halo, haloalkyl, haloalkoxy, —$OCF_3$, —$OCHF_2$, —$CF_3$, —$OCH_3$, —$NH_2$, —$NO_2$, —OH, —$COCH_3$, —$NHSO_2CH_3$ and —$N(CH_3)_2$ and p is 1, 2 or 3.

$R_2$ is

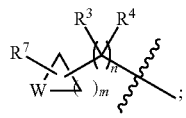

—$(CH_2)_n$-cyclobutyl, —$(CH_2)_n$-cyclohexyl, —$SO_2$—$CH_3$, —$(CH_2)_n$-piperonyl, —$(CH_2)_n$-piperidin-2-onyl, —$(CH_2)_n$-piperazinyl, —$(CH_2)_n$-thiophenyl, —$(CH_2)_n$-pyridyl, —$(CH_2)_n$-pyrimidyl, —$(CH_2)_n$-thiomorpholinylsulfone, —$(CH_2)_n$-phenyl, (e.g., unsubstituted phenyl) —$(CH_2)_n$-tetrahydropyranyl, —$(CH_2)_n$-tetrahydrothiopyranyl, —$(CH_2)_n$-tetrahydrothiopyranylsulfone, —$(CH_2)_n$-morpholinyl, —$(CH_2)_nOCH_3$, —$(CH_2)_nOH$, —$(CH_2)_nC(CH_3)_2OH$ or —$(CH_2)_nN(CH_3)_2$, where W is —O—, —S(O)$_z$— or >C(R$^9$)[(CR$^{10}$R$^{11}$)$_y$R$^{12}$]; R$^3$, R$^4$, R$^7$, R$^9$, R$^{10}$ and R$^{11}$ are, at each occurrence, independently H or alkyl; R$^{12}$ is —OH, —CN or alkoxy; m is 1, 2, 3, 4, 5 or 6; n is 0, 1, 2, 3 or 4; y and z are each independently 0, 1 or 2, and each of the above moieties are optionally substituted with one or more substituents; or $R_2$ has one of the following structures:

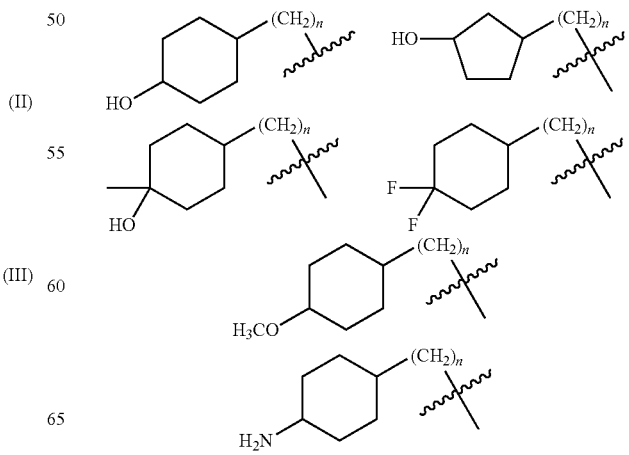

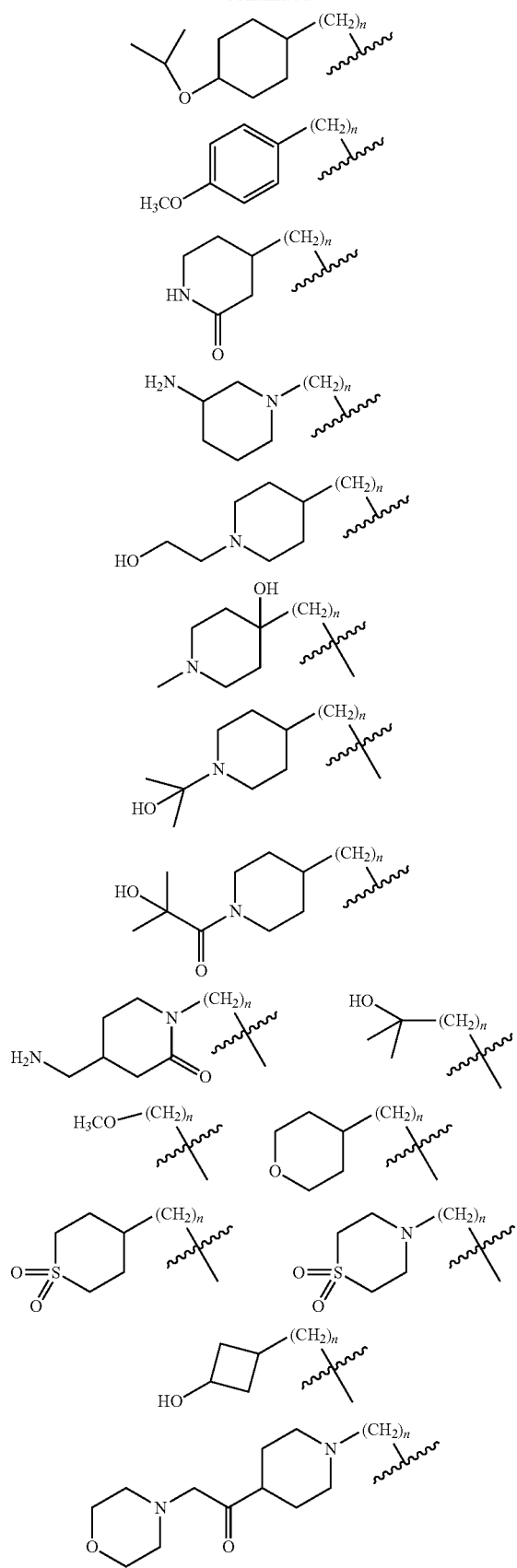
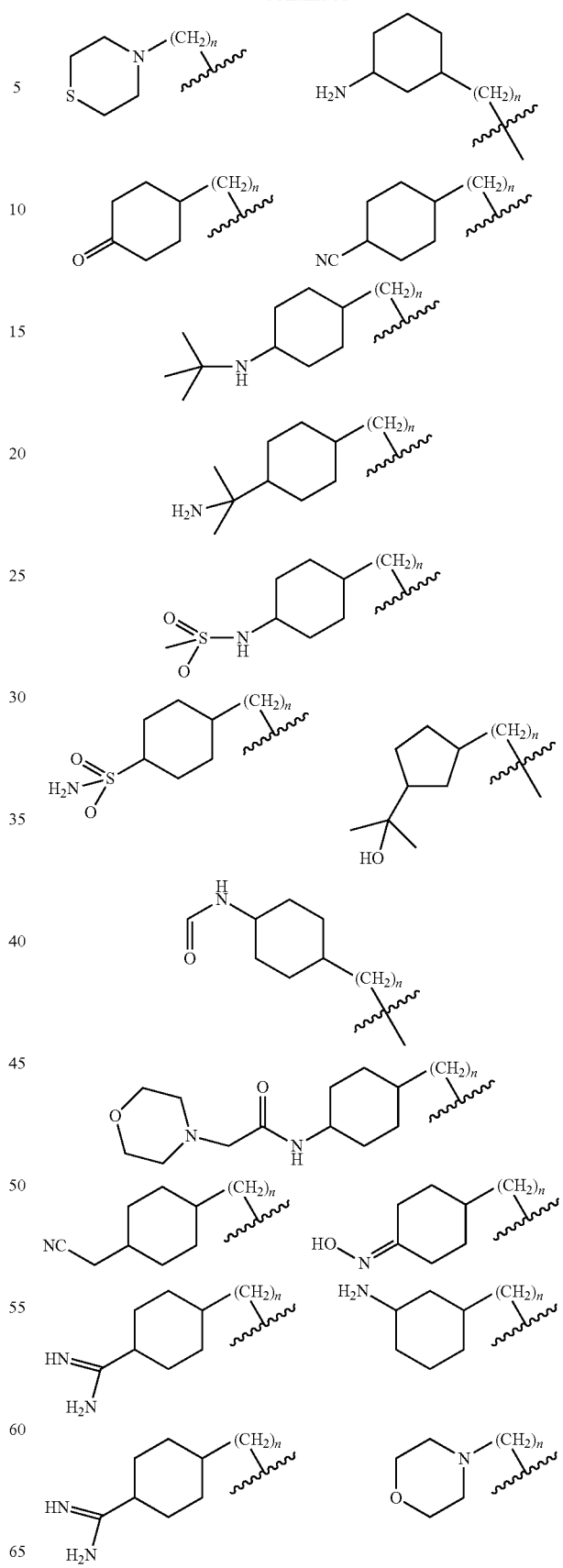

-continued

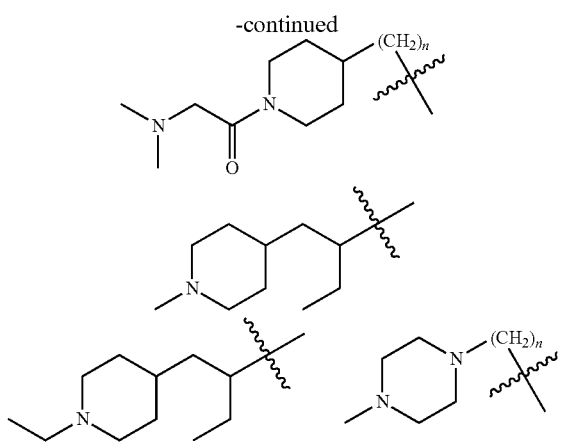

where n is 0, 1, 2, 3 or 4 and each of the above moieties are optionally substituted with one or more substituents.

Unless otherwise stated the following terms used in the specification and claims have the meanings discussed below:

"Alkyl" refers to a saturated straight or branched hydrocarbon radical of one to six carbon atoms (i.e., $C_1$-$C_6$), preferably one to four carbon atoms, e.g., methyl, ethyl, propyl, 2-propyl, n-butyl, iso-butyl, tert-butyl, pentyl, hexyl, and the like, preferably methyl, ethyl, propyl, or 2-propyl. Representative saturated straight chain alkyls include methyl, ethyl, n-propyl, n-butyl, n-pentyl, n-hexyl, and the like; while saturated branched alkyls include isopropyl, sec-butyl, isobutyl, tert-butyl, isopentyl, and the like. Representative saturated cyclic alkyls include cyclopropyl, cyclobutyl, cyclopentyl, cyclohexyl, —$CH_2$-cyclohexyl, and the like; while unsaturated cyclic alkyls include cyclopentenyl, cyclohexenyl, —$CH_2$-cyclohexenyl, and the like. Cyclic alkyls are also referred to herein as a "cycloalkyl." Unsaturated alkyls contain at least one double or triple bond between adjacent carbon atoms (referred to as an "alkenyl" or "alkynyl", respectively.) Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1-butynyl, and the like.

"Alkylene" means a linear saturated divalent hydrocarbon radical of one to six carbon atoms or a branched saturated divalent hydrocarbon radical of three to six carbon atoms, e.g., methylene, ethylene, 2,2-dimethylethylene, propylene, 2-methylpropylene, butylene, pentylene, and the like, preferably methylene, ethylene, or propylene.

"Cycloalkyl" refers to a saturated cyclic hydrocarbon radical of three to eight carbon atoms, e.g., cyclopropyl, cyclobutyl, cyclopentyl or cyclohexyl.

"Alkoxy" means a radical —$OR_a$ where $R_a$ is an alkyl as defined above, e.g., methoxy, ethoxy, propoxy, butoxy and the like.

"Halo" means fluoro, chloro, bromo, or iodo, preferably fluoro and chloro.

"Haloalkyl" means alkyl substituted with one or more, preferably one, two or three, same or different halo atoms, e.g., —$CH_2Cl$, —$CF_3$, —$CH_2CF_3$, —$CH_2CCl_3$, and the like.

"Haloalkoxy" means a radical —$OR_b$ where $R_b$ is an haloalkyl as defined above, e.g., trifluoromethoxy, trichloroethoxy, 2,2-dichloropropoxy, and the like.

"Acyl" means a radical —$C(O)R_c$ where $R_c$ is hydrogen, alkyl, or haloalkyl as defined herein, e.g., formyl, acetyl, trifluoroacetyl, butanoyl, and the like.

"Aryl" refers to an all-carbon monocyclic or fused-ring polycyclic (i.e., rings which share adjacent pairs of carbon atoms) groups of 6 to 12 carbon atoms having a completely conjugated pi-electron system. Examples, without limitation, of aryl groups are phenyl, naphthyl and anthracenyl. The aryl group may be substituted or unsubstituted. When substituted, the aryl group is substituted with one or more substituents as this term is defined below, more preferably one, two or three, even more preferably one or two substituents independently selected from the group consisting of alkyl (wherein the alkyl may be optionally substituted with one or two substituents), haloalkyl, halo, hydroxy, alkoxy, mercapto, alkylthio, cyano, acyl, nitro, phenoxy, heteroaryl, heteroaryloxy, haloalkyl, haloalkoxy, carboxy, alkoxycarbonyl, amino, alkylamino dialkylamino, aryl, heteroaryl, carbocycle or heterocycle (wherein the aryl, heteroaryl, carbocycle or heterocycle may be optionally substituted).

"Heteroaryl" refers to a monocyclic or fused ring (i.e., rings which share an adjacent pair of atoms) group of 5 to 12 ring atoms containing one, two, three or four ring heteroatoms selected from N, O, or S, the remaining ring atoms being C, and, in addition, having a completely conjugated pi-electron system. Examples, without limitation, of unsubstituted heteroaryl groups are pyrrole, furan, thiophene, imidazole, oxazole, thiazole, pyrazole, pyridine, pyrimidine, quinoline, isoquinoline, purine, triazole, tetrazole, triazine, and carbazole. The heteroaryl group may be substituted or unsubstituted. When substituted, the heteroaryl group is substituted with one or more substituents as this term is defined below, more preferably one, two or three, even more preferably one or two substituents independently selected from the group consisting of alkyl (wherein the alkyl may be optionally substituted with one or two substituents), haloalkyl, halo, hydroxy, alkoxy, mercapto, alkylthio, cyano, acyl, nitro, haloalkyl, haloalkoxy, carboxy, alkoxycarbonyl, amino, alkylamino dialkylamino, aryl, heteroaryl, carbocycle or heterocycle (wherein the aryl, heteroaryl, carbocycle or heterocycle may be optionally substituted).

"Carbocycle" refers to a saturated, unsaturated or aromatic ring system having 3 to 14 ring carbon atoms. The term "carbocycle", whether saturated or partially unsaturated, also refers to rings that are optionally substituted. The term "carbocycle" includes aryl. The term "carbocycle" also includes aliphatic rings that are fused to one or more aromatic or nonaromatic rings, such as in a decahydronaphthyl or tetrahydronaphthyl, where the radical or point of attachment is on the aliphatic ring. The carbocycle group may be substituted or unsubstituted. When substituted, the carbocycle group is substituted with one or more substituents as this term is defined below, more preferably one, two or three, even more preferably one or two substituents independently selected from the group consisting of alkyl (wherein the alkyl may be optionally substituted with one or two substituents), haloalkyl, halo, hydroxy, alkoxy, mercapto, alkylthio, cyano, acyl, nitro, haloalkyl, haloalkoxy, carboxy, alkoxycarbonyl, amino, alkylamino dialkylamino, aryl, heteroaryl, carbocycle or heterocycle (wherein the aryl, heteroaryl, carbocycle or heterocycle may be optionally substituted).

"Heterocycle" refers to a saturated, unsaturated or aromatic cyclic ring system having 3 to 14 ring atoms in which one, two or three ring atoms are heteroatoms selected from N, O, or $S(O)_m$ (where m is an integer from 0 to 2), the remaining ring atoms being C, where one or two C atoms may optionally be replaced by a carbonyl group. The term "heterocycle" includes heteroaryl. The heterocyclyl ring may be optionally substituted independently with one or more substituents as this term is defined below, preferably one, two, or three substituents selected from alkyl (wherein the alkyl may be optionally substituted with one or two substituents), haloalkyl, cycloalkylamino, cycloalkylalkyl, cycloalkylaminoalkyl, cycloalkylalkylaminoalkyl, cyanoalkyl, halo, nitro, cyano, hydroxy, alkoxy, amino, alkylamino, dialkylamino, hydroxyalkyl, carboxyalkyl, aminoalkyl, alkylaminoalkyl, dialkylaminoalkyl, aralkyl, heteroaralkyl, aryl, heteroaryl, carbocycle, heterocycle (wherein the aryl, heteroaryl, carbocycle or heterocycle may be optionally substituted), aralkyl, heteroaralkyl, saturated or unsaturated heterocycloamino, saturated or unsaturated heterocycloaminoalkyl, and —COR$_d$ (where R$_d$ is alkyl). More specifically the term heterocyclyl includes, but is not limited to, tetrahydropyranyl, 2,2-dimethyl-1,3-dioxolane, piperidino, N-methylpiperidin-3-yl, piperazino, N-methylpyrrolidin-3-yl, pyrrolidino, morpholino, 4-cyclopropylmethylpiperazino, thiomorpholino, thiomorpholino-1-oxide, thiomorpholino-1,1-dioxide, 4-ethyloxycarbonylpiperazino, 3-oxopiperazino, 2-imidazolidone, 2-pyrrolidinone, 2-oxohomopiperazino, tetrahydropyrimidin-2-one, and the derivatives thereof. In certain embodiments, the heterocycle group is optionally substituted with one or two substituents independently selected from halo, alkyl, alkyl substituted with carboxy, ester, hydroxy, alkylamino, saturated or unsaturated heterocycloamino, saturated or unsaturated heterocycloaminoalkyl, or dialkylamino.

"Piperidin-2-onyl" refers to a moiety having the following structure:

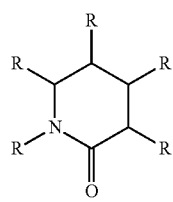

wherein each R is independently hydrogen, a point of attachment or an optional substituent as defined herein, "Thiomorpholinylsulfone" refers to a moiety having the following structure:

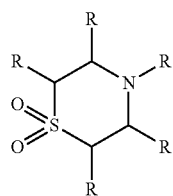

wherein each R is independently hydrogen, a point of attachment or an optional substituent as defined herein, "Tetrahydrothiopyranylsulfone" refers to a moiety having the following structure:

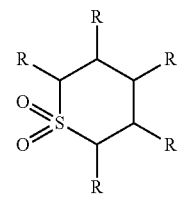

wherein each R is independently hydrogen, a point of attachment or an optional substituent as defined herein, "Tetrahydrothiopyranyl" refers to a moiety having the following structure:

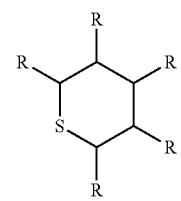

wherein each R is independently hydrogen, a point of attachment or an optional substituent as defined herein.

"Piperidyl" refers to a moiety having the following structure:

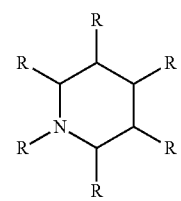

wherein each R is independently hydrogen, a point of attachment or an optional substituent as defined herein.

"Tetrahydropyranyl" refers to a moiety having the following structure:

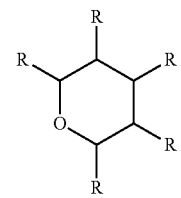

wherein each R is independently hydrogen, a point of attachment or an optional substituent as defined herein.

"Tautomer" refers to a compound that results from the formal migration of a hydrogen atom accompanied by a switch of a single bond and adjacent double bond. For example, the enol and keto form of a compound are tautomers of each other.

"Optional" or "optionally" means that the subsequently described event or circumstance may but need not occur, and that the description includes instances where the event or circumstance occurs and instances in which it does not. For example, "heterocyclic group optionally substituted with an alkyl group" means that the alkyl may but need not be present, and the description includes situations where the heterocycle group is substituted with an alkyl group and situations where the heterocycle group is not substituted with the alkyl group.

Lastly, the term "substituted" as used herein means any of the above groups (e.g., alkyl, aryl, heteroaryl, carbocycle, heterocycle, etc.) wherein at least one hydrogen atom is replaced with a substituent. In the case of an oxo substituent ("=O") two hydrogen atoms are replaced. "Substituents" within the context of this invention include halogen, hydroxy, oxo, cyano, nitro, amino, alkylamino, dialkylamino, alkyl, alkoxy, thioalkyl, haloalkyl, hydroxyalkyl, aryl, substituted aryl, arylalkyl, substituted arylalkyl, heteroaryl, substituted heteroaryl, heteroarylalkyl, substituted heteroarylalkyl, heterocycle, substituted heterocycle, heterocyclealkyl, substituted heterocyclealkyl, amidynyl (—C(=NH)NH$_2$), guanidinyl, (—NHC(=NH)NH$_2$), oximyl (=NOH), —NR$_e$R$_f$, —NR$_e$C(=O)R$_f$, —NR$_e$C(=O)NR$_e$R$_f$, —NR$_e$C(=O)OR$_f$, —NR$_e$SO$_2$R$_f$, —OR$_e$, —C(=O)R$_e$, —C(=O)OR$_e$, —C(=O)NR$_e$R$_f$, —OC(=O)NR$_e$R$_f$, —SH, —SR$_e$, —SOR$_e$, —S(=O)NH$_2$, —S(=O)$_2$R$_e$, —OS(=O)$_2$R$_e$, —S(=O)$_2$OR$_e$, wherein R$_e$ and R$_f$ are the same or different and independently hydrogen, alkyl, haloalkyl, substituted alkyl, aryl, substituted aryl, arylalkyl, substituted arylalkyl, heteroaryl, substituted heteroaryl, heteroarylalkyl, substituted heteroarylalkyl, heterocycle, substituted heterocycle, heterocyclealkyl or substituted heterocyclealkyl.

Certain illustrative compounds according to structures (I), (II) and (III), for use as described herein, are set forth below.

In some embodiments, the compounds of the present invention have structure (I). In other embodiments, the compounds have structure (II). In still other embodiments, the compounds have structure (III).

In certain embodiments of structures (I), (II) and (III), X is a direct bond. In other embodiments, X is —NH—. In still other embodiments, X is —O—.

In other embodiments of structures (I), (II) and (III), R is H, while in different embodiments R is methyl.

In some embodiments of structures (I), (II) and (III), when R$_2$ is —(CH$_2$)$_n$-tetrahydropyranyl, then R$_1$ is not phenyl substituted with carboxy (—CO$_2$H).

In some more specific embodiments of structures (I), (II) and (III), R$_1$ is

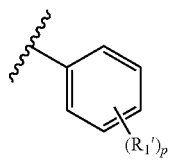

where R$_1$' is at, each occurrence, independently selected from hydrogen cyano, alkyl, alkoxy, halo, haloalkyl, haloalkoxy, —OCF$_3$, —OCHF$_2$, —CF$_3$, —OCH$_3$, —NH$_2$, —NO$_2$, —OH, —COCH$_3$, —NHSO$_2$CH$_3$ and —N(CH$_3$)$_2$ and p is 1, 2 or 3.

In other embodiments of structures (I), (II) and (III), p is 1. In some embodiments p is 2. In other embodiments, p is 3.

In a more specific aspect of structures (I) and (III) above, R$_1$ is p, o and/or m substituted phenyl with one or more occurrences of cyano, halo, —F, —Cl, —CF$_3$, —OCF$_3$, —OCHF$_2$, —OCH$_3$, —CH$_3$, NO$_2$, —N(CH$_3$)$_2$, —NH$_2$, —NHSO$_2$CH$_3$, —COCH$_3$, and —OH. In certain other embodiments, R$_1$ is p, o and/or m substituted phenyl with one or more occurrences of cyano, halo, —OCF$_3$, —OCHF$_2$, —CF$_3$, —OCH$_3$ and —OH.

In a more specific aspect of structures (I), (II) and (III) above, p is 1 and R$_1$' is independently selected from hydrogen cyano, halo. —OCF$_3$, —CF$_3$, —OCH$_3$, —OCHF$_2$, NH$_2$, NO$_2$, OH, —COCH$_3$, —NHSO$_2$CH$_3$, and —N(CH$_3$)$_2$. In certain other embodiments of the foregoing, R1' is cyano, halo, —OCF$_3$, —OCHF$_2$, —CF$_3$, —OCH$_3$ or —OH, for example in some embodiments R1' is cyano, chloro, —OCF$_3$, or —CF$_3$. In some other embodiments R1' is cyano. In some other embodiments R1' is chloro. In some other embodiments R1' is —OCF$_3$. In some other embodiments R1' is —CF$_3$. In certain more specific embodiments of the foregoing, R1' is in the meta position.

In a more specific aspect of structures (I), (II) and (III), R$_1$ has a structure selected from one of the following structures:

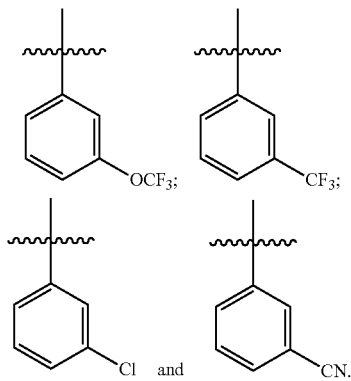

In a more specific aspect of structures (I), (II) and (III), R$_2$ is

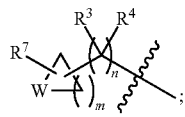

—(CH$_2$)$_n$-cyclobutyl, —(CH$_2$)$_n$-piperidin-2-onyl, —(CH$_2$)$_n$-thiomorpholinylsulfone, —(CH$_2$)$_n$-phenyl (e.g., unsubstituted phenyl), —(CH$_2$)$_n$-tetrahydropyranyl, —(CH$_2$)$_n$-tetrahydrothiopyranyl, —(CH$_2$)$_n$-tetrahydrothiopyranylsulfone, or —(CH$_2$)$_n$C(CH$_3$)$_2$OH, where W is —O—, —S(O)$_z$— or >C(R$^9$)[(CR$^{10}$R$^{11}$)$_y$R$^{12}$]; R$^3$, R$^4$, R$^7$, R$^9$, R$^{10}$ and R$^{11}$ are, at each occurrence, independently H or alkyl; R$^{12}$ is —OH, —CN or alkoxy; m is 1, 2, 3, 4, 5 or 6; n is 0, 1, 2, 3 or 4; y and z are each independently 0, 1 or 2 and unless otherwise specified, each of the above moieties are optionally substituted with one or more substituents; or R$_2$ is a structure selected from one of the following structures:

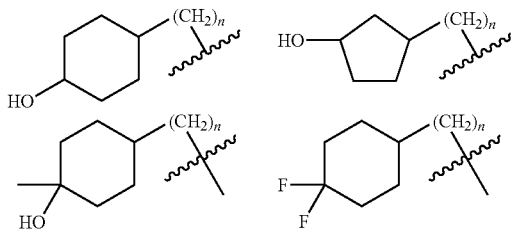

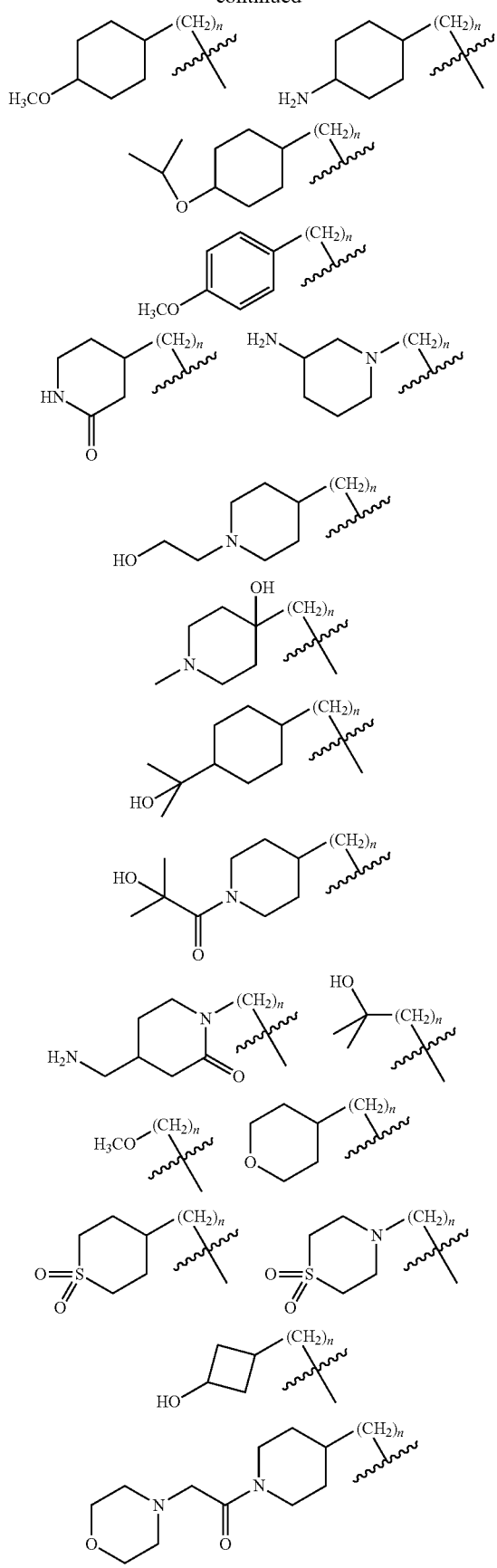
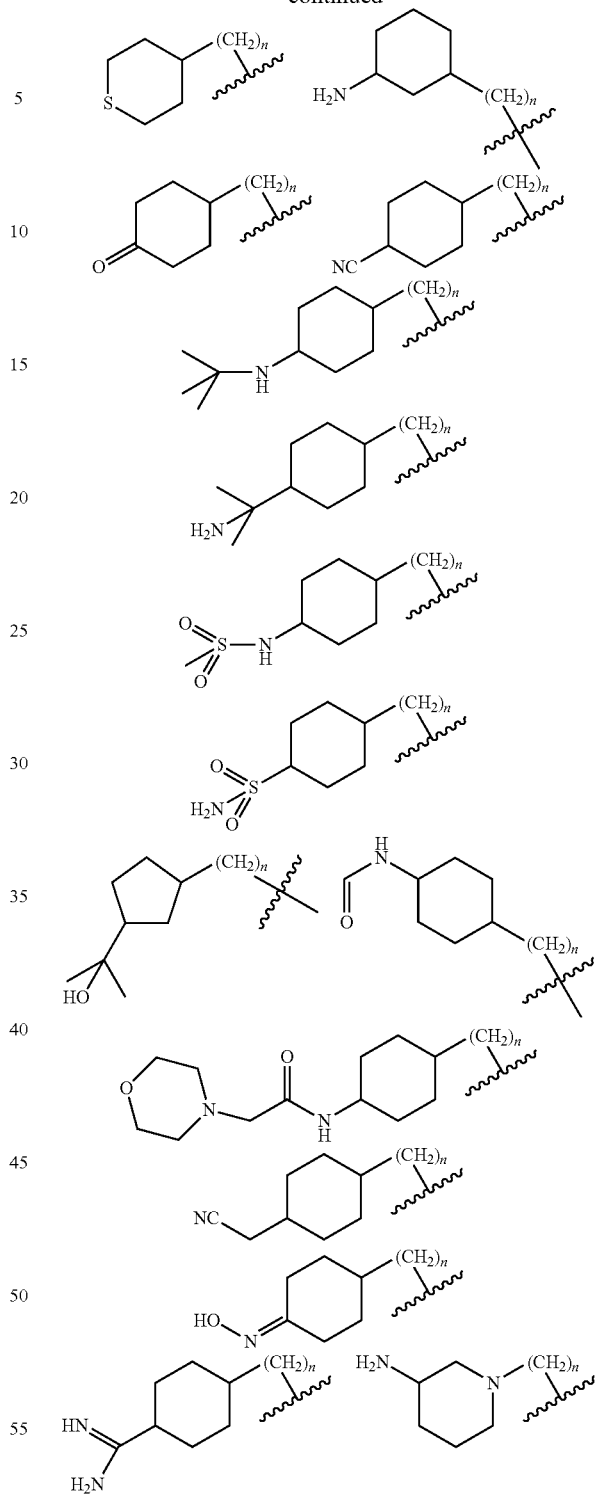
where n is 0, 1, 2, 3 or 4 and each of the above moieties are optionally substituted with one or more substituents.
In some embodiments, $R_2$ is —$(CH_2)_n$-unsubstituted phenyl, and in other embodiments $R_2$ is —$(CH_2)$-piperidin-2- only.
In some other embodiments, $R_2$ is —$(CH_2)_n$-morpholinyl. In even other embodiments, R2 has one of the following structures:

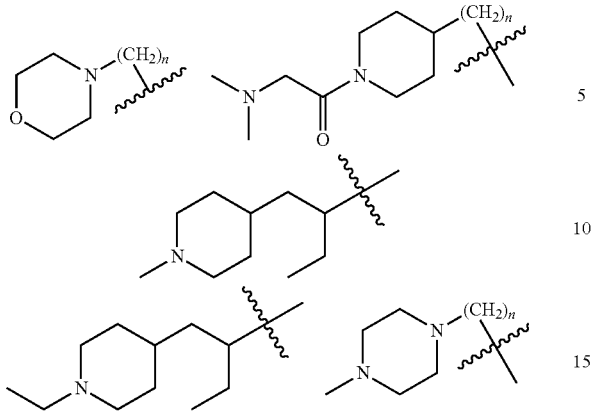

In certain embodiments, of structure (I) or (II), R1' is cyano, halo, —OCF$_3$, —OCHF$_2$, —CF$_3$, —OCH$_3$ or —OH and R$_2$ is

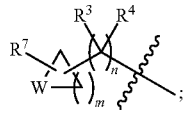

—(CH$_2$)$_n$-cyclobutyl, —(CH$_2$)$_n$-piperidin-2-onyl, —(CH$_2$)$_n$-thiomorpholinylsulfone, —(CH$_2$)$_n$-phenyl, —(CH$_2$)$_n$-tetrahydropyranyl, —(CH$_2$)$_n$-tetrahydrothiopyranyl, —(CH$_2$)$_n$-tetrahydrothiopyranylsulfone, —(CH$_2$)$_n$C(CH$_3$)$_2$OH, or a structure selected from one of the following structures:

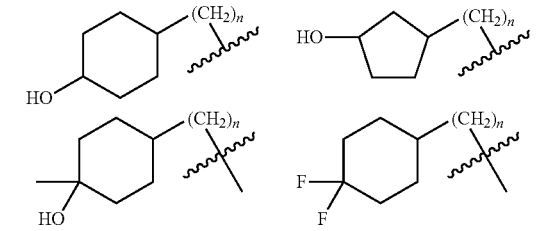
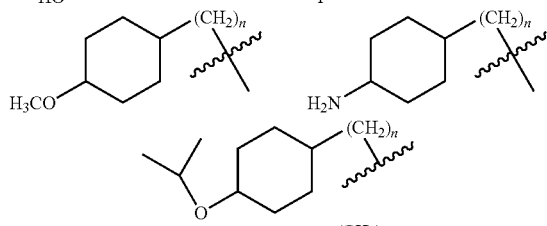
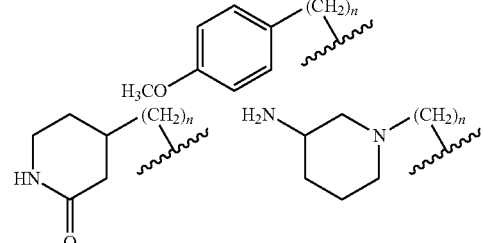
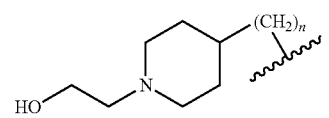
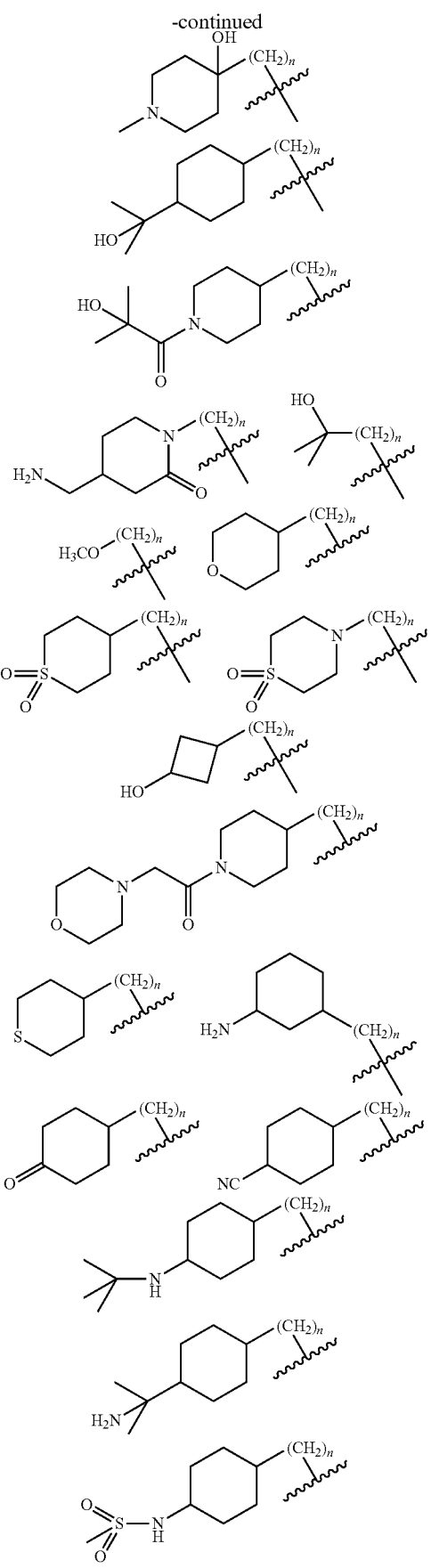

-continued

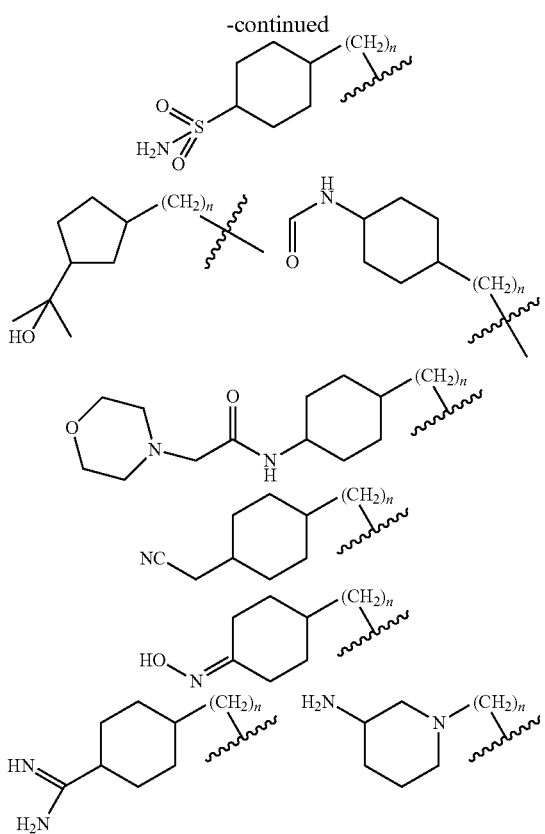

where W is —O—, —S(O)$_z$— or >C(R$^9$)[(CR$^{10}$R$^{11}$)$_y$R$^{12}$]; R$^3$, R$^4$, R$^7$, R$^9$, R$^{10}$ and R$^{11}$ are, at each occurrence, independently H or alkyl; R$^{12}$ is —OH, —CN or alkoxy; m is 1, 2, 3, 4, 5 or 6; n is 0, 1, 2, 3 or 4; y and z are each independently 0, 1 or 2 and unless otherwise specified, each of the above moieties are optionally substituted with one or more substituents.

In other certain embodiments of structures (I) and (II) above, R$_2$ is —(CH$_2$)$_n$-cyclohexyl In a more specific aspect of structures (I), (II) and (III) above, R$_2$ is

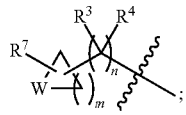

—(CH$_2$)$_n$-cyclobutyl, —(CH$_2$)$_n$-piperidin-2-onyl, —(CH$_2$)$_n$-thiomorpholinylsulfone, —(CH$_2$)$_n$-unsubstituted phenyl, —(CH$_2$)$_n$-tetrahydropyranyl, —(CH$_2$)$_n$-tetrahydrothiopyranyl, —(CH$_2$)$_n$-tetrahydrothiopyranylsulfone, or —(CH$_2$)$_n$C (CH$_3$)$_2$OH, where W is —O—, —S(O)$_z$— or >C(R$^9$)[(CR$^{10}$R$^{11}$)$_y$R$^{12}$]; R$^3$, R$^4$, R$^7$, R$^9$, R$^{10}$ and R$^{11}$ are, at each occurrence, independently H or alkyl; R$^{12}$ is —OH, —CN or alkoxy; m is 1, 2, 3, 4, 5 or 6; n is 0, 1, 2, 3 or 4; y and z are each independently 0, 1 or 2 and unless otherwise specified, each of the above moieties are optionally substituted with one or more substituents.

In other embodiments of structures (I), (II) and (III) above, R$_2$ is —(CH$_2$)$_n$-cyclobutyl, —(CH$_2$)$_n$-piperidin-2-onyl, —(CH$_2$)$_n$-thiomorpholinylsulfone, —(CH$_2$)$_n$-unsubstituted phenyl, —(CH$_2$)$_n$-tetrahydropyranyl, —(CH$_2$)$_n$-tetrahydrothiopyranyl, —(CH$_2$)$_n$-tetrahydrothiopyranylsulfone, or —(CH$_2$)$_n$C (CH$_3$)$_2$OH, n is 0, 1, 2, 3 or 4; and unless otherwise specified, each of the above moieties are optionally substituted with one or more substituents In still other embodiments of structures (I), (II) and (III) above, R$_2$ has a structure selected from one of the following structures:

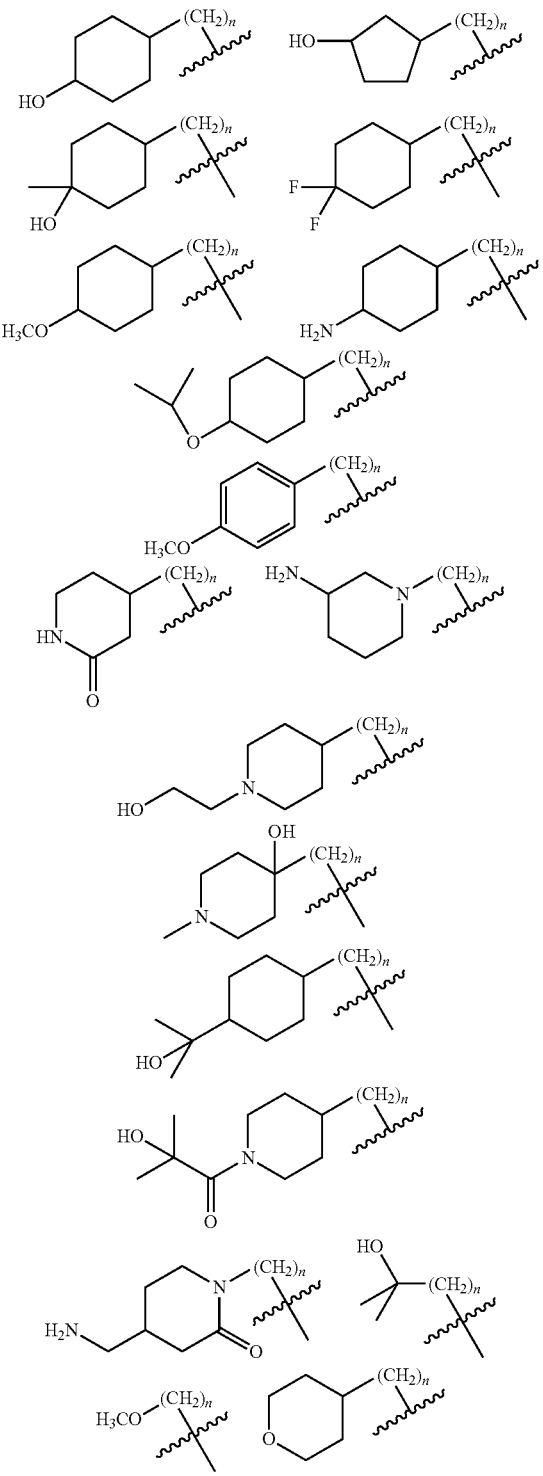

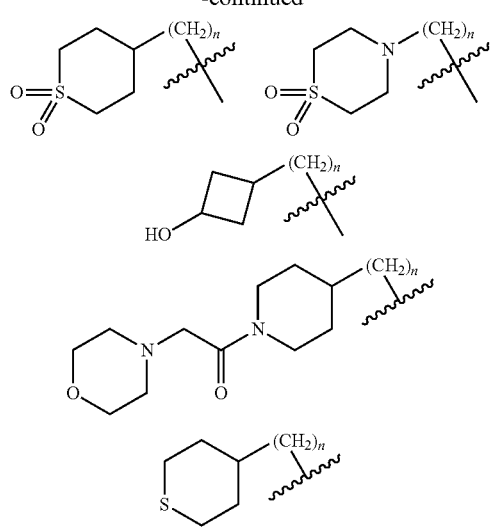

where n is 0, 1, 2, 3 or 4 and each of the above moieties are optionally substituted with one or more substituents.

In still other embodiments of structures (I), (II) and (III) above, $R_2$ has a structure selected from one of the following structures:

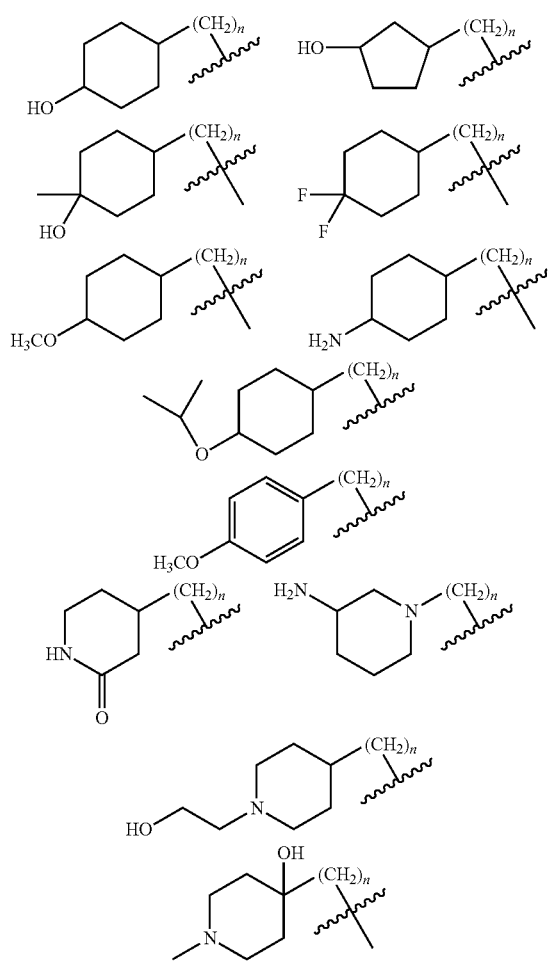

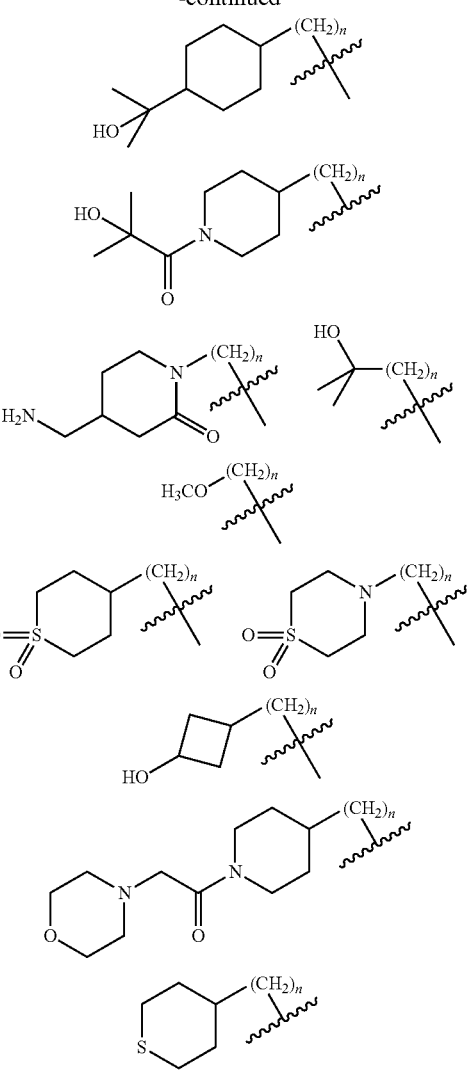

where n is 0, 1, 2, 3 or 4 and each of the above moieties are optionally substituted with one or more substituents.

In still other embodiments of structures (I), (II) and (III) above, $R_2$ has a structure selected from one of the following structures:

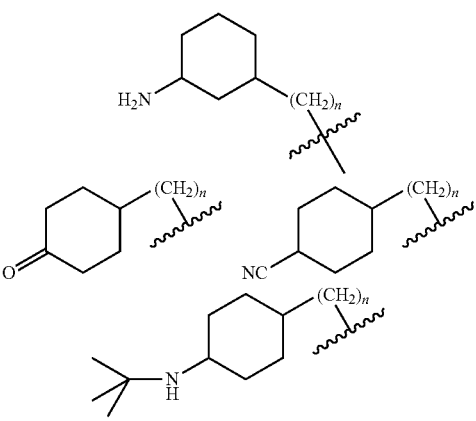

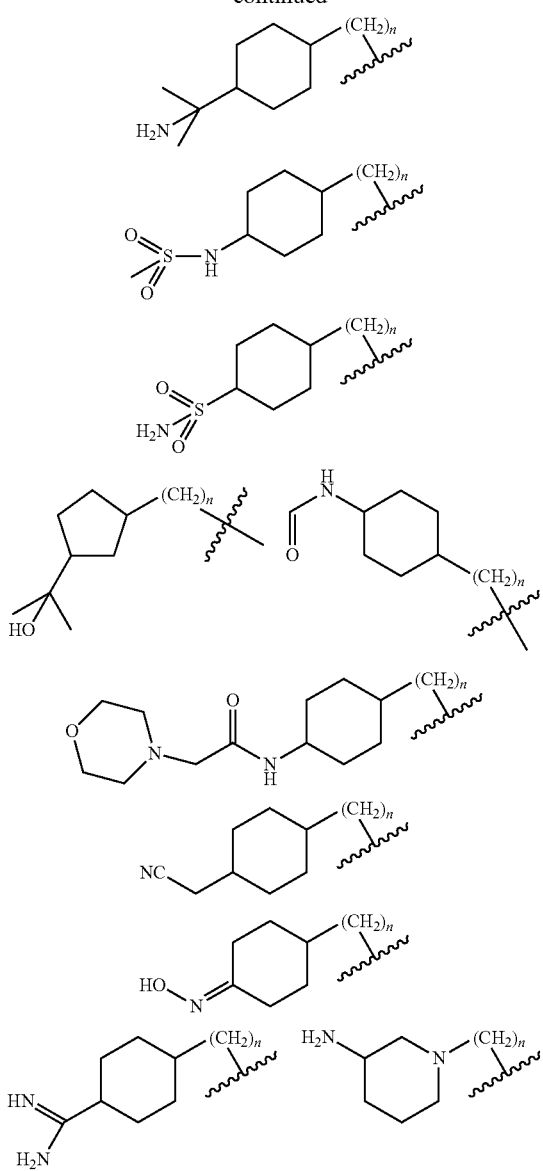

where n is 0, 1, 2, 3 or 4 and each of the above moieties are optionally substituted with one or more substituents. In further specific embodiments of structures (I) and (II), X is NH and R₁ is a substituted or unsubstituted phenyl (where R is as defined above and R₁' is absent or represents one or more substituents), and the compounds have the following structures (I-A) and (II-A), respectively:

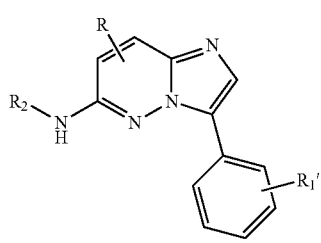
(I-A)

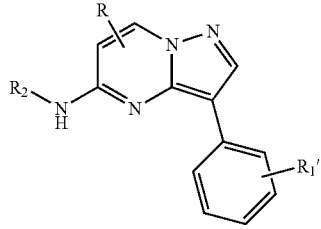
(II-A)

or a stereoisomer, prodrug or pharmaceutically acceptable salt thereof.

In some specific embodiments of (I-A) and (II-A), R is H. In other specific embodiments of (I-A) and (III-A), R is alky, such as methyl, and the compounds have the following structures (I-Aa) and (II-Aa):

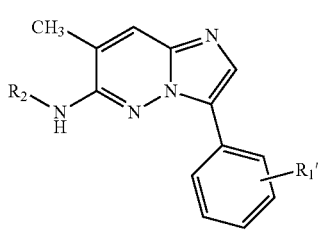
(I-Aa)

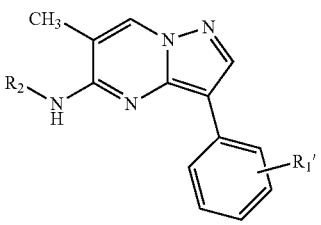
(II-Aa)

or a stereoisomer, prodrug or pharmaceutically acceptable salt thereof.

In more specific embodiments of (I-A), (II-A), (I-Aa) and (II-Aa), $R_1'$ is a p, o or m substituent selected from cyano, halo, —OCF₃, —OCHF₂, —CF₃, —OCH₃, —NH₂, —NO₂, —OH, —COCH₃, —NHSO₂CH₃ and —N(CH₃)₂, and in a more specific embodiment $R_1'$ is a p, o or m substituent selected from cyano, —OCF₃, —OCHF₂, —CF₃, —OCH₃ and —OH. In some embodiments R1' is cyano. In some embodiments R1' is chloro. In some embodiments R1' is —OCF₃. In some embodiments R1' is —CF₃. In certain more specific embodiments of the foregoing, R1' is in the meta position.

In some embodiments of (I-A), (II-A), (I-Aa) and (II-Aa), $R_1$ is selected from one of the following structures:

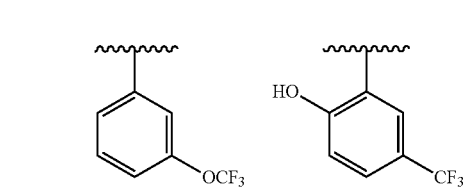

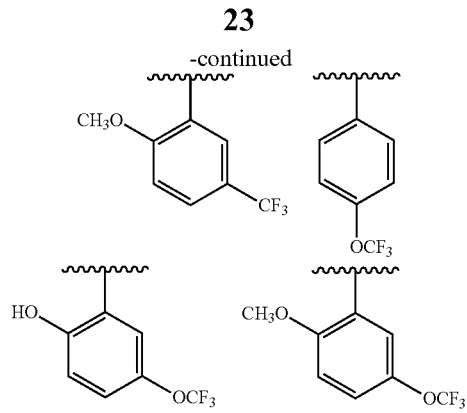

In more specific embodiments of (I-A), (II-A), (I-Aa) and (II-Aa), $R_1$ has a structure selected from one of the following structures:

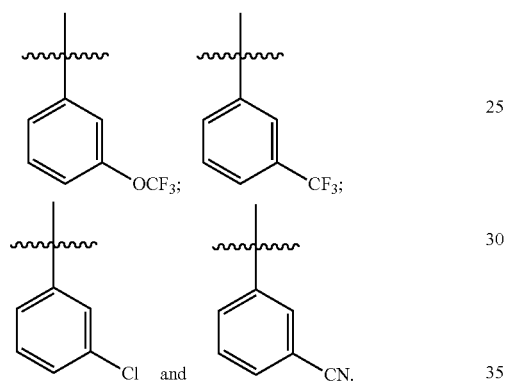

In more specific embodiments of structures (I-A), (II-A), (I-Aa) and (II-Aa), $R_2$ is

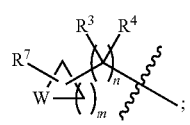

—$(CH_2)_n$-cyclobutyl, —$(CH_2)_n$-piperidin-2-onyl, —$(CH_2)_n$-thiomorpholinylsulfone, —$(CH_2)_n$-unsubstituted phenyl, —$(CH_2)_n$-tetrahydropyranyl, —$(CH_2)_n$-tetrahydrothiopyranyl, —$(CH_2)_n$-tetrahydrothiopyranylsulfone, or —$(CH_2)_nC(CH_3)_2OH$, where W is —O—, —S(O)$_z$— or >C(R$^9$)[(CR$^{10}$R$^{11}$)$_y$R$^{12}$]; R$^3$, R$^4$, R$^7$, R$^9$, R$^{10}$ and R$^{11}$ are, at each occurrence, independently H or alkyl; R$^{12}$ is —OH, —CN or alkoxy; m is 1, 2, 3, 4, 5 or 6; n is 0, 1, 2, 3 or 4; y and z are each independently 0, 1 or 2 and each of the above moieties are optionally substituted with one or more substituents.

In some embodiments $R_2$ is selected from one of the following structures:

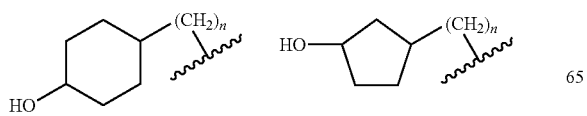

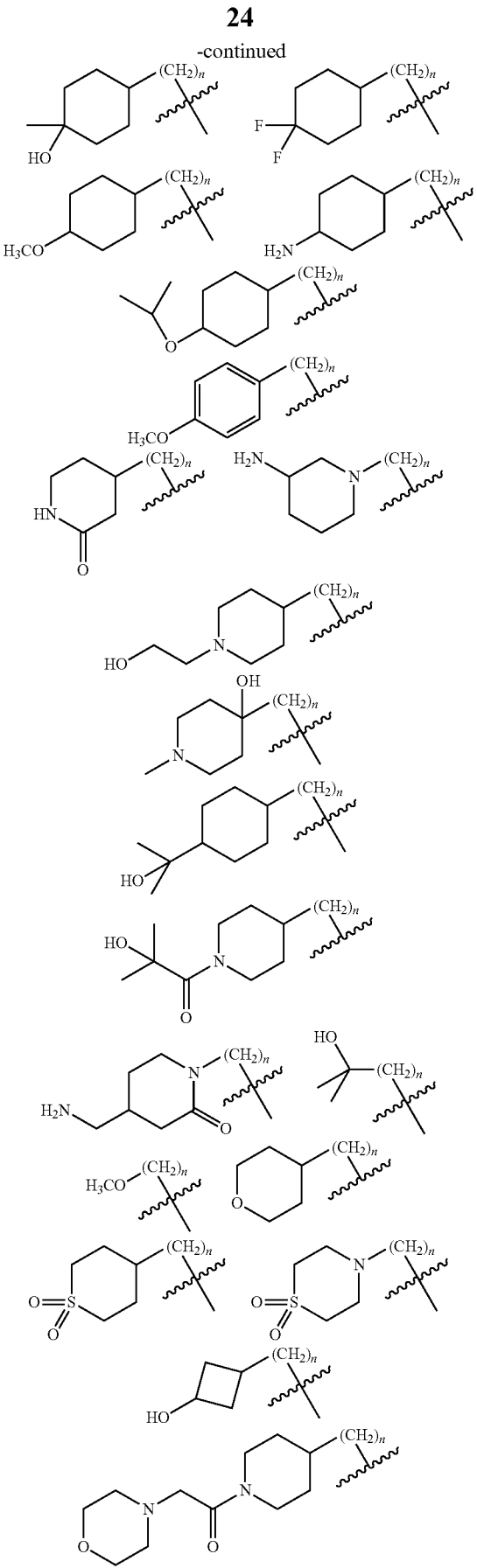

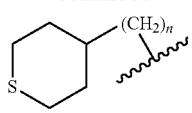

where n is 0, 1, 2, 3 or 4 and each of the above moieties are optionally substituted with one or more substituents.

In other embodiments of structures (I-A), (II-A), (I-Aa) and (II-Aa), R$_2$ has a structure selected from one of the following structures:

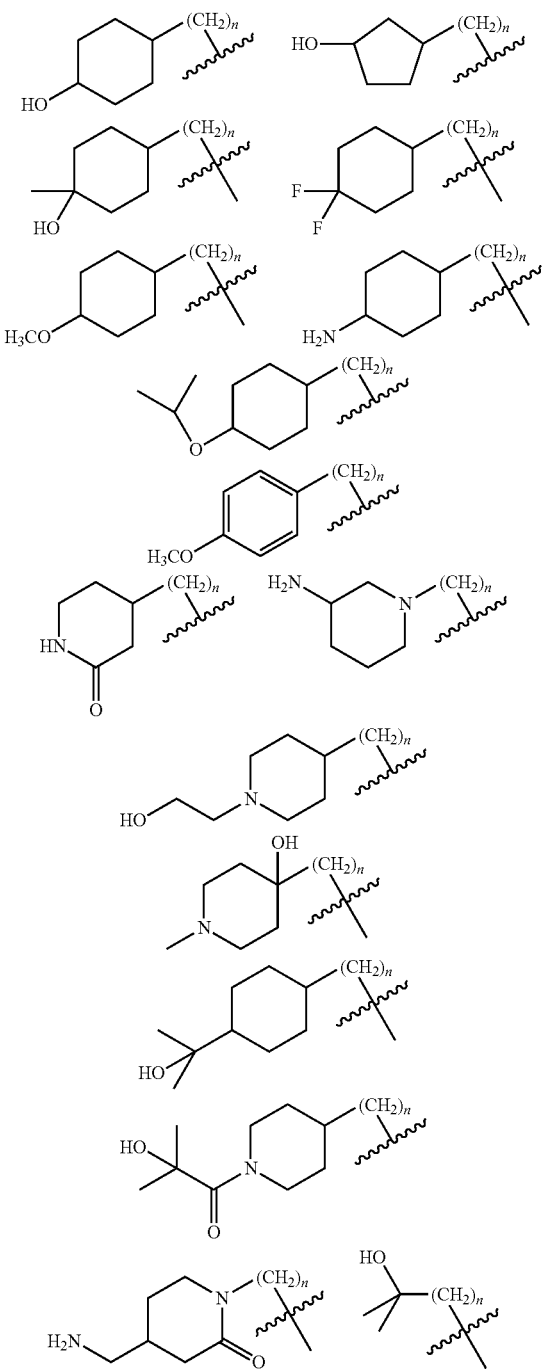

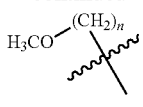

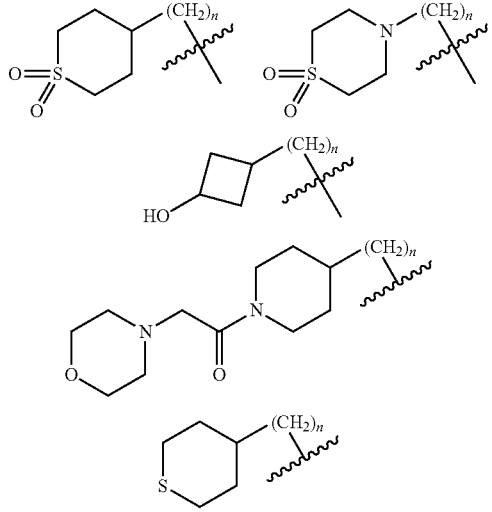

where n is 0, 1, 2, 3 or 4 and each of the above moieties are optionally substituted with one or more substituents.

In other embodiments of structures (I-A), (II-A), (I-Aa) and (II-Aa), R$_2$ has a structure selected from one of the following structures:

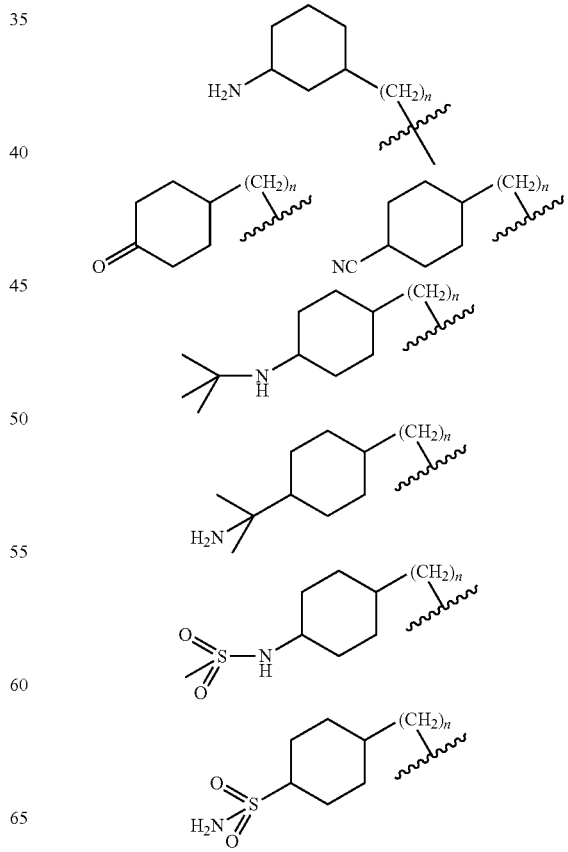

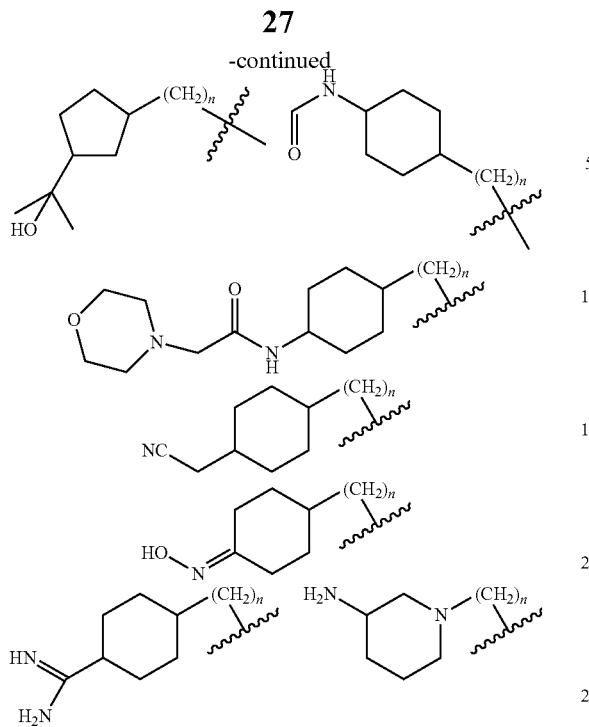

where n is 0, 1, 2, 3 or 4 and each of the above moieties are optionally substituted with one or more substituents.

In other embodiments of structures (I-A), (II-A), (I-Aa) and (II-Aa), $R_2$ is —$(CH_2)_n$-cyclobutyl, —$(CH_2)_n$-piperidin-2-onyl, —$(CH_2)_n$-thiomorpholinylsulfone, —$(CH_2)_n$-unsubstituted phenyl, —$(CH_2)_n$-tetrahydropyranyl, —$(CH_2)_n$-tetrahydrothiopyranyl, —$(CH_2)_n$-tetrahydrothiopyranylsulfone, or —$(CH_2)_nC(CH_3)_2OH$, where W is —O—, —$S(O)_z$— or >$C(R^9)[(CR^{10}R^{11})_yR^{12}]$; $R^3$, $R^4$, $R^7$, $R^9$, $R^{10}$ and $R^{11}$ are, at each occurrence, independently H or alkyl; $R^{12}$ is —OH, —CN or alkoxy; m is 1, 2, 3, 4, 5 or 6; n is 0, 1, 2, 3 or 4; y and z are each independently 0, 1 or 2 and each of the above moieties are optionally substituted with one or more substituents.

In more specific embodiments of structures (I-A), (II-A), (I-Aa) and (II-Aa) (II-Aa), in a more specific embodiment, p is 1 and $R_1'$ is a p, o or m substituent selected from cyano, —$OCF_3$, —$OCHF_2$, —$CF_3$, —$OCH_3$ and —OH and $R_2$ is

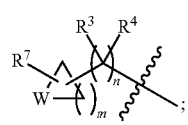

—$(CH_2)_n$-cyclobutyl, —$(CH_2)_n$-piperidin-2-onyl, —$(CH_2)_n$-thiomorpholinylsulfone, —$(CH_2)_n$-unsubstituted phenyl, —$(CH_2)_n$-tetrahydropyranyl, —$(CH_2)_n$-tetrahydrothiopyranyl, —$(CH_2)_n$-tetrahydrothiopyranylsulfone, —$(CH_2)_nC(CH_3)_2OH$, or a structure selected from one of the following structures:

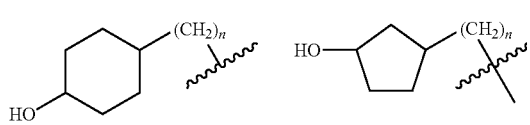

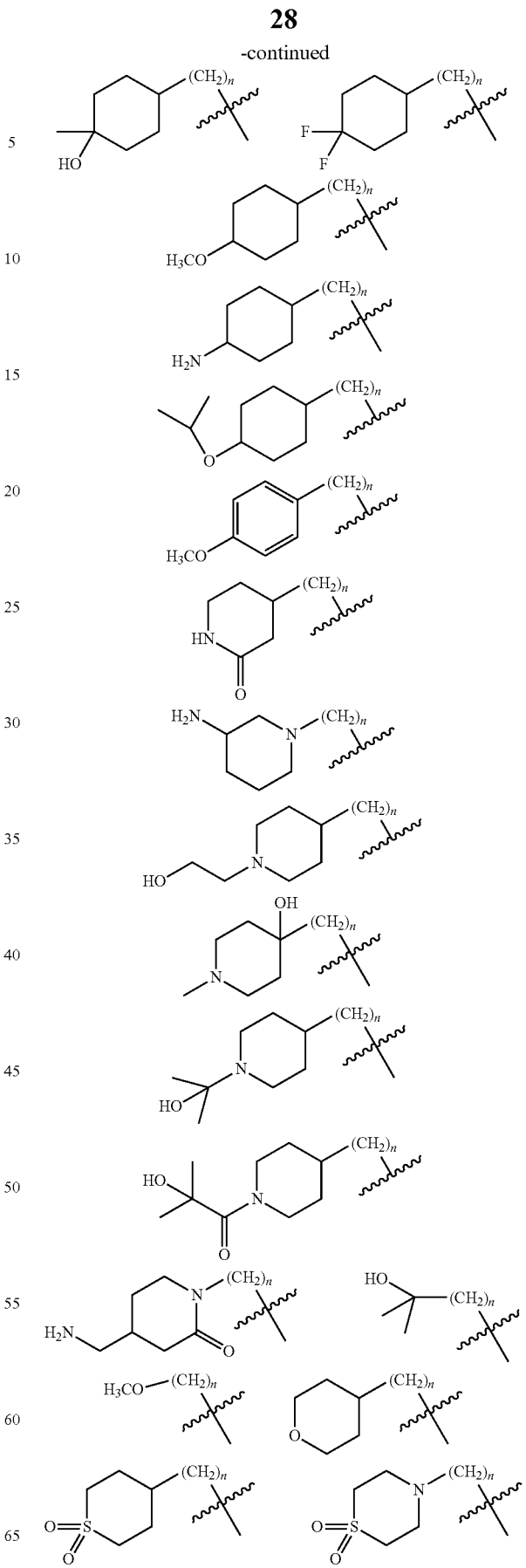

-continued

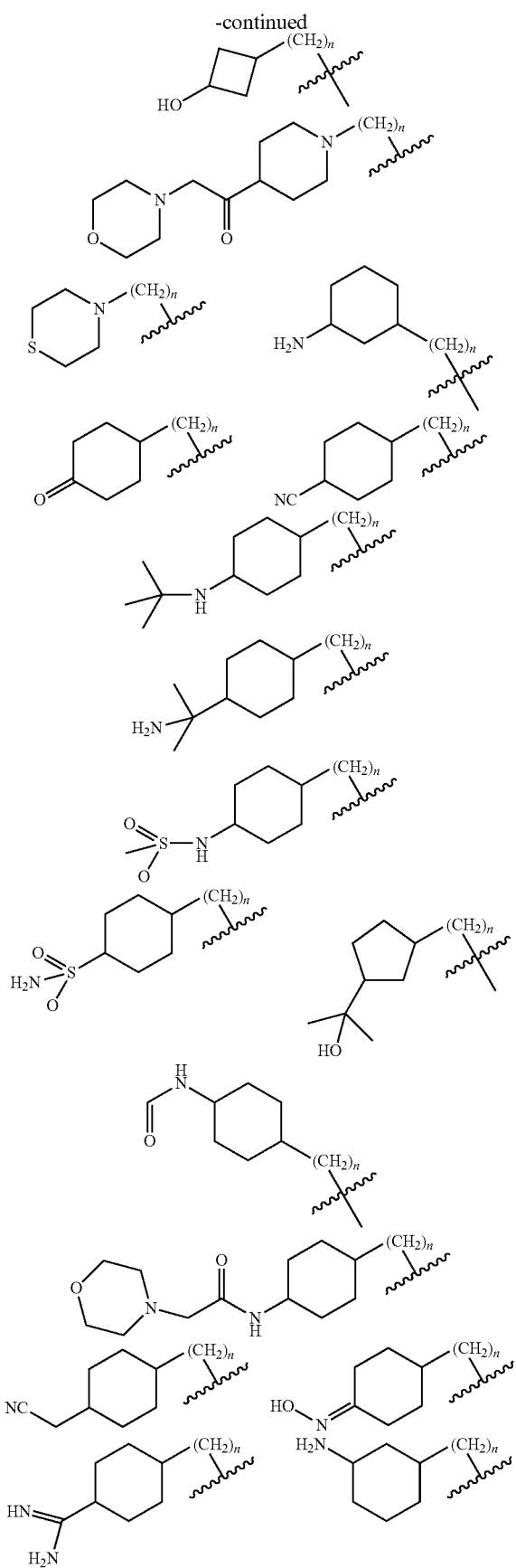

where n is 0, 1, 2, 3 or 4 and each of the above moieties are optionally substituted with one or more substituents, W is —O—, —S(O)$_z$— or >C(R$^9$)[(CR$^{10}$R$^{11}$)$_y$R$^{12}$]; R$^3$, R$^4$, R$^7$, R$^9$, R$^{10}$ and R$^{11}$ are, at each occurrence, independently H or alkyl; R$^{12}$ is —OH, —CN or alkoxy; m is 1, 2, 3, 4, 5 or 6; y and z are each independently 0, 1 or 2 and each of the above moieties are optionally substituted with one or more substituents.

In still further specific embodiments of structures (I) and (II), X is O and R$_1$ is a substituted or unsubstituted phenyl (where R is as defined above and R$_1$' is absent or represents one or more substituents), and the compounds have the following structures (I-B) and (II-B), respectively:

(I-B)
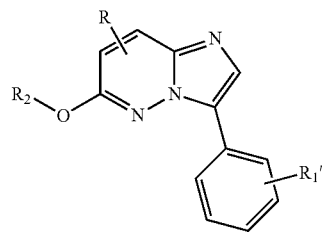

(II-B)
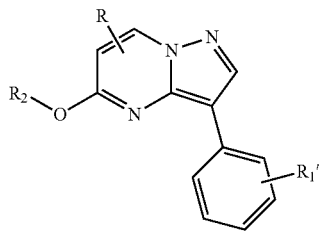

or a stereoisomer, prodrug or pharmaceutically acceptable salt thereof.

In some specific embodiments of (I-B) and (II-B), R is H. In other specific embodiments of (I-B) and (II-B), R is alky, such as methyl, and the compounds have the following structures (I-Bb) and (II-Bb):

(I-Bb)

(II-Bb)
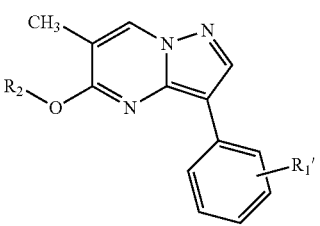

or a stereoisomer, prodrug or pharmaceutically acceptable salt thereof.

In more specific embodiments of (I-B), (II-B), (I-Bb) and (IIB-b), R$_1$ is substituted phenyl having at least one p, o or m substituent selected from cyano, halo, —OCF$_3$, —OCHF$_2$, —CF$_3$, —OCH$_3$, —NH$_2$, —NO$_2$, —OH, —COCH$_3$, —NHSO$_2$CH$_3$ and —N(CH$_3$)$_2$, and in a more specific embodiment R$_1$ is substituted phenyl having at least one p, o or m substituent selected from cyano —OCF$_3$, —OCHF$_2$, —CF$_3$, —OCH$_3$ and —OH. In some embodiments R1' is cyano. In some embodiments R1' is chloro. In some embodiments R1' is —OCF$_3$. in some embodiments R1' is —CF$_3$. In certain more specific embodiments of the foregoing, R1' is in the meta position.

In some embodiments of (I-B), (II-B), (I-Bb) and (II-Bb), R$_1$ is selected from one of the following structures:

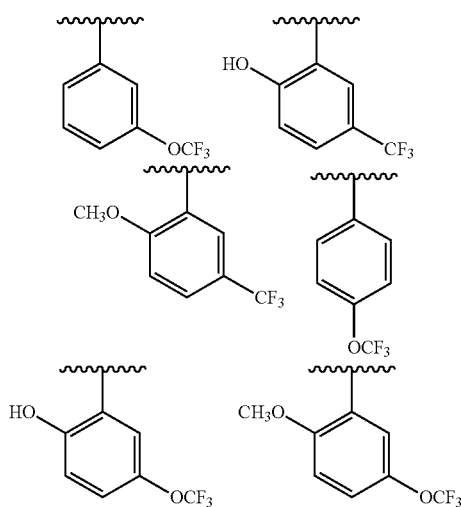

In more specific embodiments of (I-B), (II-B), (I-Bb) and (II-Bb), R$_1$ has a structure selected from one of the following structures:

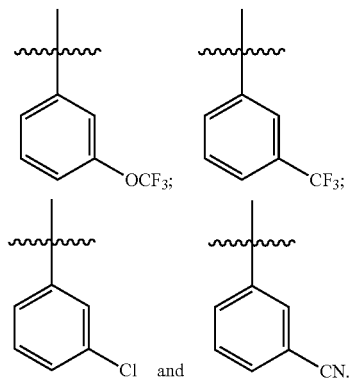

In more specific embodiments of structures (I-B), (II-B), (I-Bb) and (II-Bb), R$_2$ is

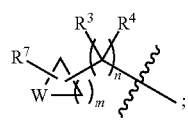

—(CH$_2$)$_n$-cyclobutyl, —(CH$_2$)$_n$-piperidin-2-onyl, —(CH$_2$)$_n$-thiomorpholinylsulfone, —(CH$_2$)$_n$-unsubstituted phenyl, —(CH$_2$)$_n$-tetrahydropyranyl, —(CH$_2$)$_n$-tetrahydrothiopyranyl, —(CH$_2$)$_n$-tetrahydrothiopyranylsulfone, or —(CH$_2$)$_n$C (CH$_3$)$_2$OH, where W is —O—, —S(O)$_z$— or >C(R$^9$)[(CR$^{10}$R$^{11}$), R$^{12}$]; R$^3$, R$^4$, R$^7$, R$^9$, R$^{10}$ and R$^{11}$ are, at each occurrence, independently H or alkyl; R$^{12}$ is —OH, —CN or alkoxy; m is 1, 2, 3, 4, 5 or 6; n is 0, 1, 2, 3 or 4; y and z are each independently 0, 1 or 2 and each of the above moieties are optionally substituted with one or more substituents. For example, in some embodiments R$_2$ is selected from one of the following structures:

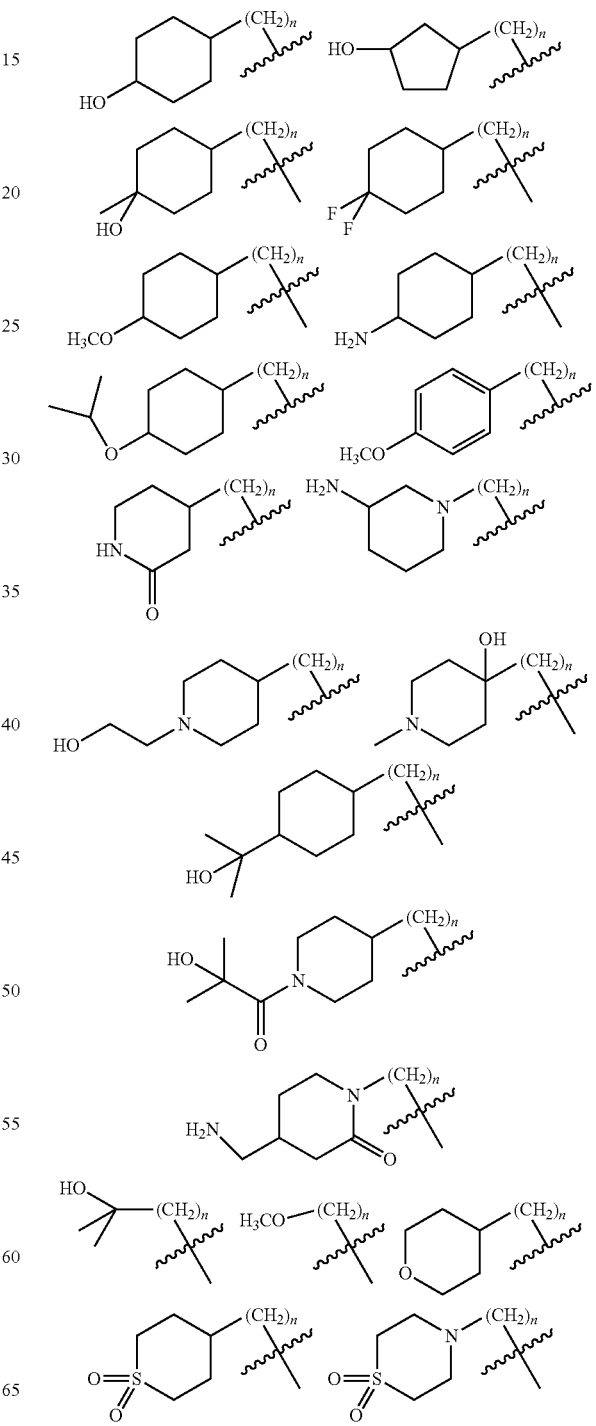

-continued

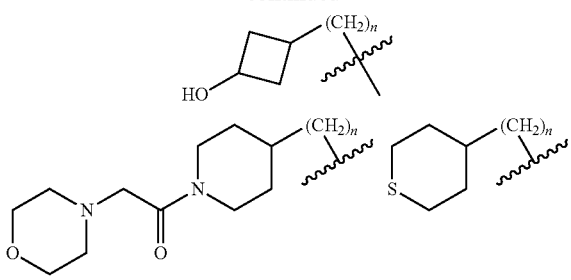

where n is 0, 1, 2, 3 or 4 and each of the above moieties are optional substituted with one or more substituents.

In other embodiments of structures (I-B), (II-B), (I-Bb) and (II-Bb), $R_2$ is selected from one of the following structures:

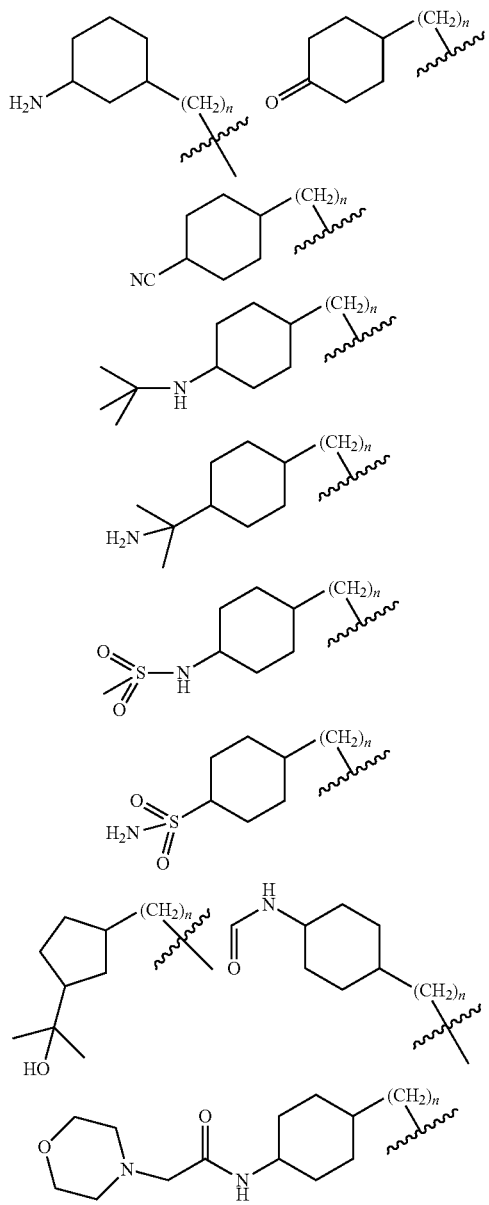

-continued

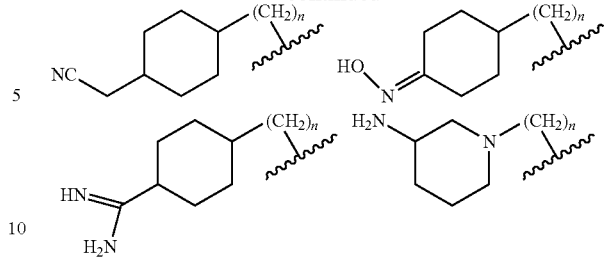

where n is 0, 1, 2, 3 or 4 and each of the above moieties are optionally substituted with one or more substituents.

In other embodiments of structures (I-B), (II-B), (I-Bb) and (II-Bb), $R_2$ is —$(CH_2)_n$-cyclobutyl, —$(CH_2)_n$-piperidin-2-onyl, —$(CH_2)_n$-thiomorpholinylsulfone, —$(CH_2)_n$-unsubstituted phenyl, —$(CH_2)_n$-tetrahydropyranyl, —$(CH_2)_n$-tetrahydrothiopyranyl, —$(CH_2)_n$-tetrahydrothiopyranylsulfone, or —$(CH_2)_nC(CH_3)_2OH$, where W is —O—, —$S(O)_z$— or >$C(R^9)[(CR^{10}R^{11})_yR^{12}]$; $R^3$, $R^4$, $R^7$, $R^{10}$ and $R^{11}$ are, at each occurrence, independently H or alkyl; $R^{12}$ is —OH, —CN or alkoxy; m is 1, 2, 3, 4, 5 or 6; n is 0, 1, 2, 3 or 4; y and z are each independently 0, 1 or 2 and each of the above moieties are optionally substituted with one or more substituents.

In more specific embodiments of structures (I-B), (II-B), (I-Bb) and (II-Bb), p is 1, $R_1$ is a p, o or m substituent selected from cyano, —$OCF_3$, —$OCHF_2$, —$CF_3$, —$OCH_3$ and —OH and $R_2$ is

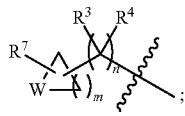

—$(CH_2)_n$-cyclobutyl, —$(CH_2)_n$-piperidin-2-onyl, —$(CH_2)_n$-thiomorpholinylsulfone, —$(CH_2)_n$-unsubstituted phenyl, —$(CH_2)_n$-tetrahydropyranyl, —$(CH_2)_n$-tetrahydrothiopyranyl, —$(CH_2)_n$-tetrahydrothiopyranylsulfone, —$(CH_2)_nC(CH_3)_2OH$, or a structure selected from one of the following structures:

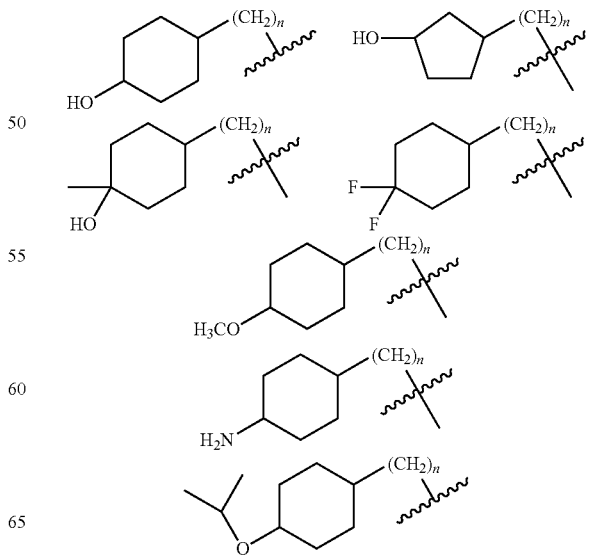

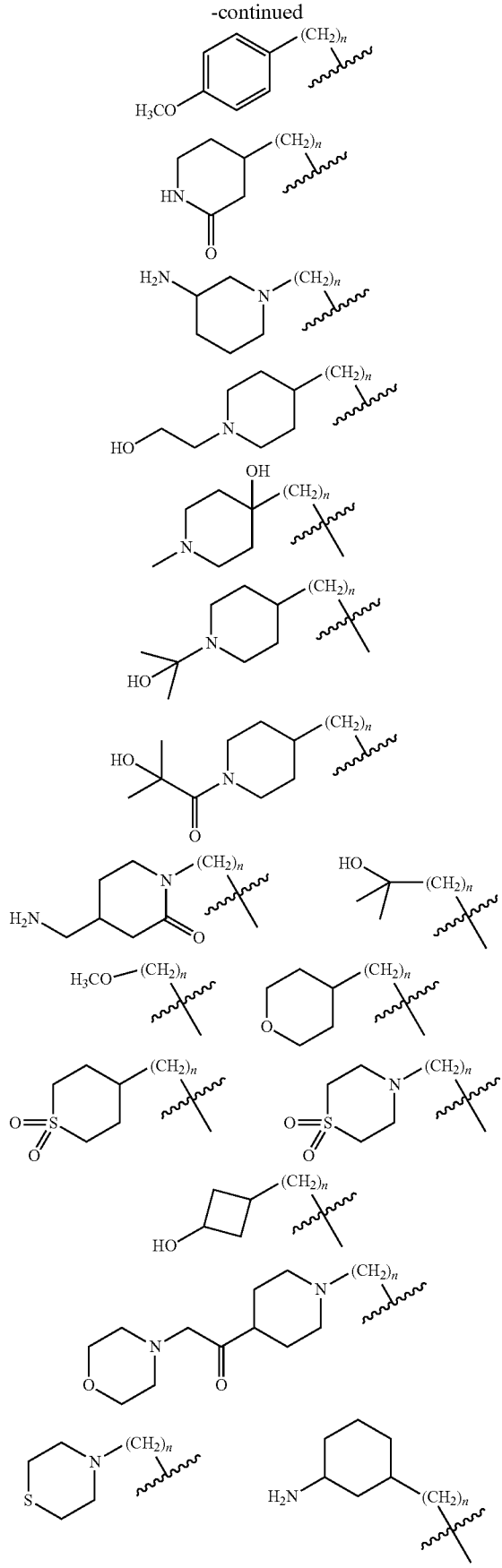
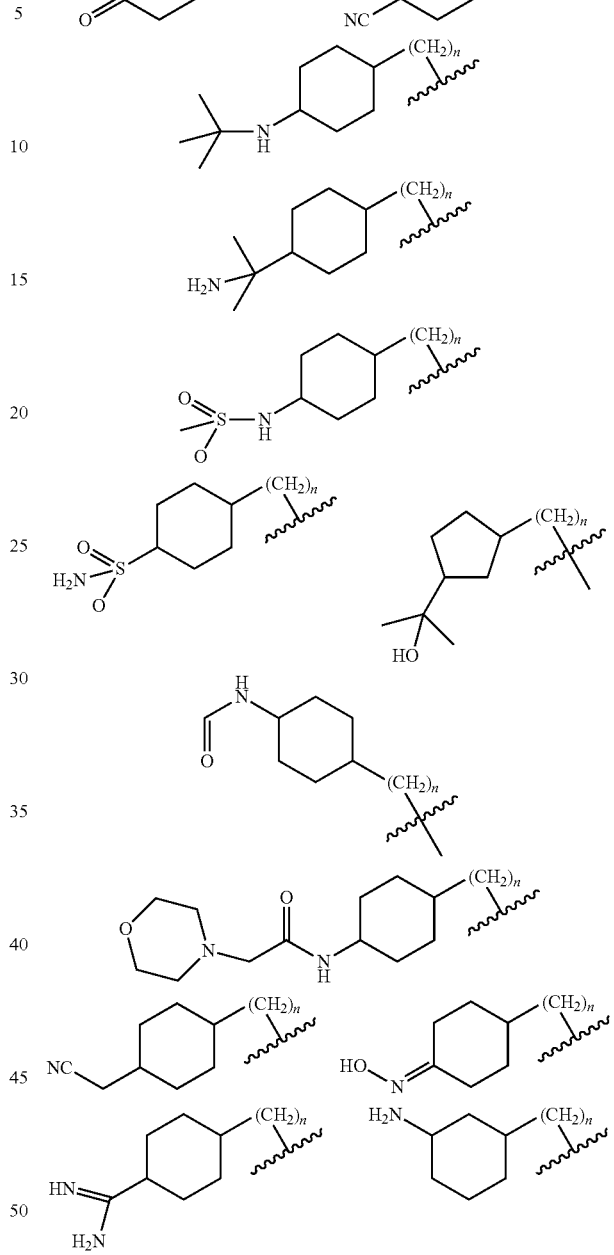

where n is 0, 1, 2, 3 or 4 and each of the above moieties are optionally substituted with one or more substituents, W is —O—, —S(O)$_z$— or >C(R$^9$)[(CR$^{10}$R$^{11}$)$_y$R$^{12}$]; R$^3$, R$^4$, R$^7$, R$^9$, R$^{10}$ and R$^{11}$ are, at each occurrence, independently H or alkyl; R$^{12}$ is —OH, —CN or alkoxy; m is 1, 2, 3, 4, 5 or 6; y and z are each independently 0, 1 or 2 and each of the above moieties are optionally substituted with one or more substituents.

In yet further specific embodiments of structures (I) and (II), X is S, SO or SO$_2$ and R$_1$ is a substituted or unsubstituted phenyl (where R$_1$' below is absent or represents one or more substituents), and the compounds have the following structures (I-C) and (II-C), respectively:

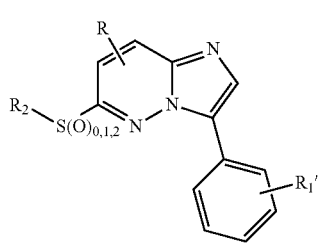

(I-C)

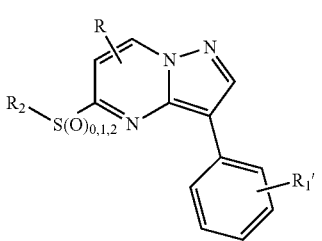

(II-C)

or a stereoisomer, prodrug or pharmaceutically acceptable salt thereof.

In some specific embodiments of (I-A) and (II-A), R is H. In other specific embodiments of (I-C) and (II-C), R is alky, such as methyl, and the compounds have the following structures (I-Cc) and (III-Cc):

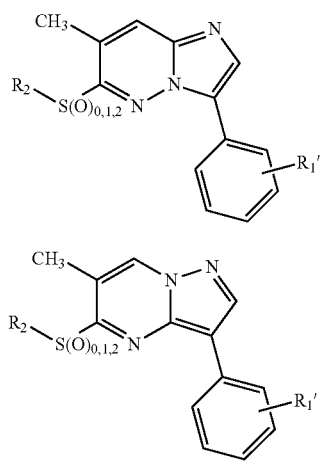

(I-Cc)

(II-Cc)

or a stereoisomer, prodrug or pharmaceutically acceptable salt thereof.

In more specific embodiments of (I-C), (II-C), (I-Cc) and (III-Cc), $R_1$ is substituted phenyl having at least one p, o or m substituent selected from cyano, halo. —$OCF_3$, —$OCHF_2$, —$CF_3$, —$OCH_3$, —$NH_2$, —$NO_2$, —OH, —$COCH_3$, —$NHSO_2CH_3$ and —$N(CH_3)_2$, and in an more specific embodiment $R_1$ is substituted phenyl having at least one p, o or m substituent selected from cyano, —$OCF_3$, —$OCHF_2$, —$CF_3$, —$OCH_3$ and —OH. In some embodiments $R1'$ is cyano. In some embodiments $R1'$ is chloro. In some embodiments $R1'$ is —$OCF_3$. in some embodiments $R1'$ is —$CF_3$. In certain more specific embodiments of the foregoing, $R1'$ is in the meta position.

In other embodiments of (I-C), (II-C), (I-Cc) and (II-Cc) $R_1$ is selected from one of the following structures:

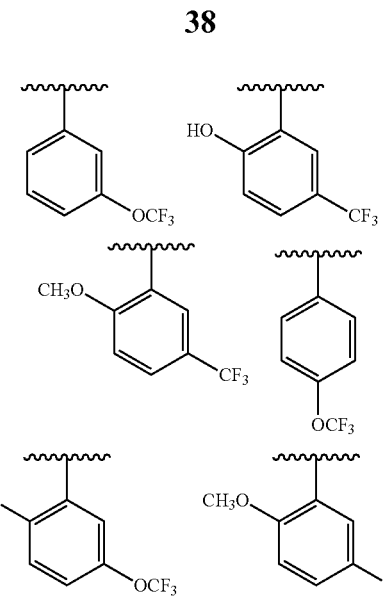

In more specific embodiments of (I-C), (II-C), (I-Cc) and (II-Cc), $R_1$ has a structure selected from one of the following structures:

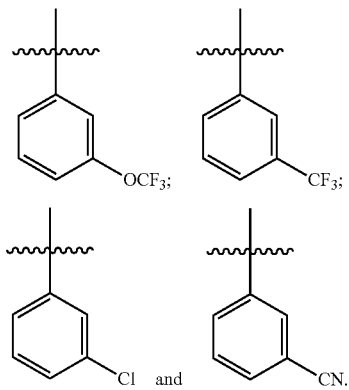

In more specific embodiments of (I-C), (II-C), (I-Cc) and (III-Cc), $R_2$ is

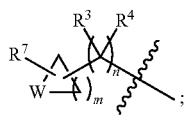

—$(CH_2)_n$-cyclobutyl, —$(CH_2)_n$-piperidin-2-onyl, —$(CH_2)_n$-thiomorpholinylsulfone, —$(CH_2)_n$-unsubstituted phenyl, —$(CH_2)_n$-tetrahydropyranyl, —$(CH_2)_n$-tetrahydrothiopyranyl, —$(CH_2)_n$-tetrahydrothiopyranylsulfone, or —$(CH_2)_nC(CH_3)_2OH$, where W is —O—, —$S(O)_z$— or >$C(R^9)[(CR^{10}R^{11})_yR^{12}]$; $R^3$, $R^4$, $R^7$, $R^9$, $R^{10}$ and $R^{11}$ are, at each occurrence, independently H or alkyl; $R^{12}$ is —OH, —CN or alkoxy; m is 1, 2, 3, 4, 5 or 6; n is 0, 1, 2, 3 or 4; y and z are each independently 0, 1 or 2 and each of the above moieties are optionally substituted with one or more substituents. For example, in some embodiments $R_2$ is selected from one of the following structures:

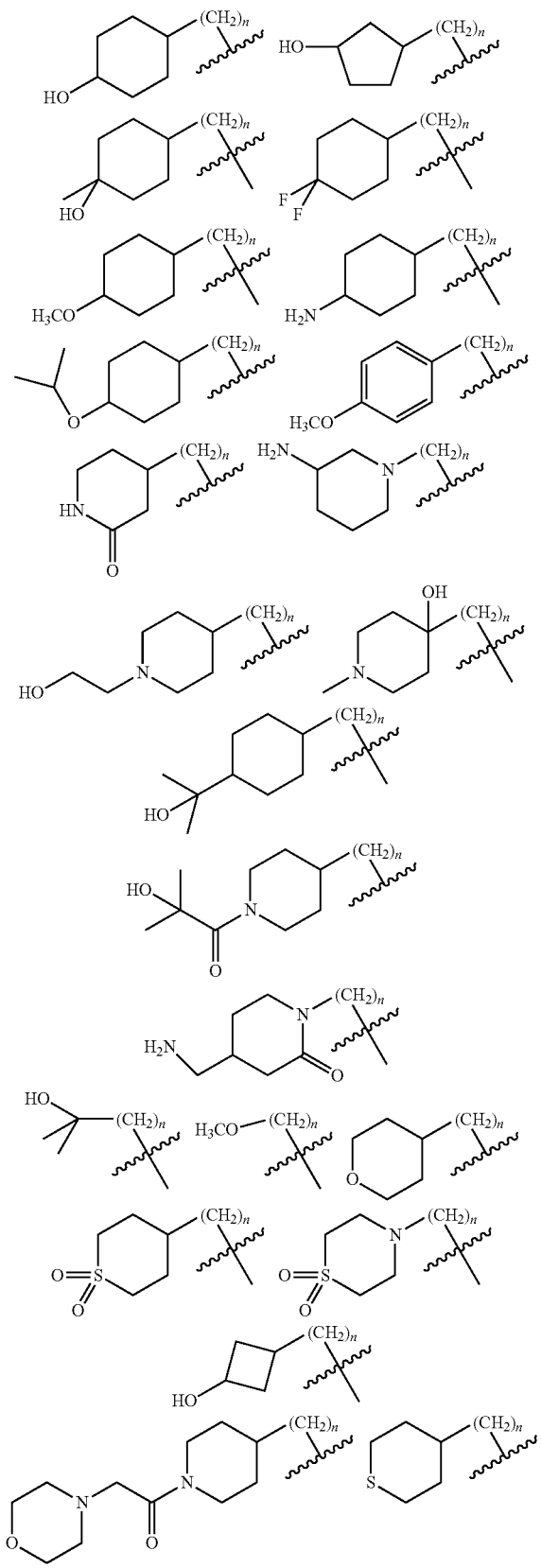

where n is 0, 1, 2, 3 or 4 and each of the above moieties are optionally substituted with one or more substituents.

In other embodiments of structures (I-C), (II-C), (I-Cc) and (III-Cc), $R_2$ is selected from one of the following structures:

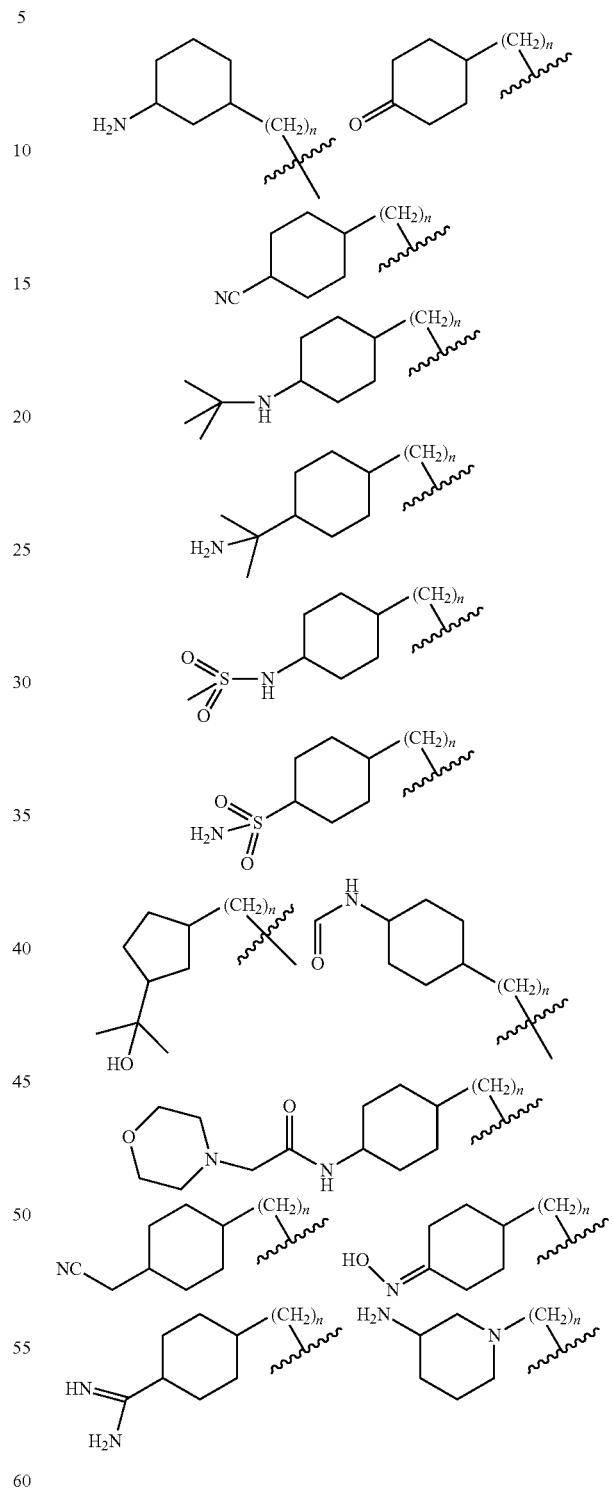

where n is 0, 1, 2, 3 or 4 and each of the above moieties are optionally substituted with one or more substituents.

In other embodiments of structures (I-C), (II-C), (I-Cc) and (II-Cc), $R_2$ is —$(CH_2)_n$-cyclobutyl, —$(CH_2)_n$-piperidin-2-onyl, —$(CH_2)_n$-thiomorpholinylsulfone, —$(CH_2)_n$-unsubstituted phenyl, —$(CH_2)_n$-tetrahydropyranyl, —$(CH_2)_n$-tetrahydrothiopyranyl, —$(CH_2)_n$- tetrahydrothiopyranylsulfone, or —(CH$_2$)$_n$C (CH$_3$)$_2$OH, where W is —O—, —S(O)$_z$— or >C(R$^9$)[(CR$^{10}$R$^{11}$)$_y$R$^{12}$]; R$^3$, R$^4$, R$^7$, R$^{10}$ and R$^{11}$ are, at each occurrence, independently H or alkyl; R$^{12}$ is —OH, —CN or alkoxy; m is 1, 2, 3, 4, 5 or 6; n is 0, 1, 2, 3 or 4; y and z are each independently 0, 1 or 2 and each of the above moieties are optionally substituted with one or more substituents.

In other embodiments of structures (I-B), (II-B), (I-Bb) and (II-Bb), R$_2$ is —(CH$_2$)$_n$-cyclobutyl, —(CH$_2$)$_n$-piperidin-2-onyl, —(CH$_2$)$_n$-thiomorpholinylsulfone, —(CH$_2$)$_n$-unsubstituted phenyl, —(CH$_2$)$_n$-tetrahydropyranyl, —(CH$_2$)$_n$-tetrahydrothiopyranyl, —(CH$_2$)$_n$-tetrahydrothiopyranylsulfone, or —(CH$_2$)$_n$C (CH$_3$)$_2$OH, where W is —O—, —S(O)$_z$— or >C(R$^9$)[(CR$^{10}$R$^{11}$)$_y$R$^{12}$]; R$^3$, R$^4$, R$^7$, R$^9$, R$^{10}$ and R$^{11}$ are, at each occurrence, independently H or alkyl; R$^{12}$ is —OH, —CN or alkoxy; m is 1, 2, 3, 4, 5 or 6; n is 0, 1, 2, 3 or 4; y and z are each independently 0, 1 or 2 and each of the above moieties are optionally substituted with one or more substituents.

In more specific embodiments of structures (I-C), (II-C), (I-Cc) and (II-Cc), p is 1, R$_1$' is a p, o or m substituent selected from cyano, —OCF$_3$, —OCHF$_2$, —CF$_3$, —OCH$_3$ and —OH and R$_2$ is

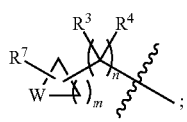

—(CH$_2$)$_n$-cyclobutyl, —(CH$_2$)$_n$-piperidin-2-onyl, —(CH$_2$)$_n$-thiomorpholinylsulfone, —(CH$_2$)$_n$-unsubstituted phenyl, —(CH$_2$)$_n$-tetrahydropyranyl, —(CH$_2$)$_n$-tetrahydrothiopyranyl, —(CH$_2$)$_n$-tetrahydrothiopyranylsulfone, —(CH$_2$)$_n$C (CH$_3$)$_2$OH, or a structure selected from one of the following structures:

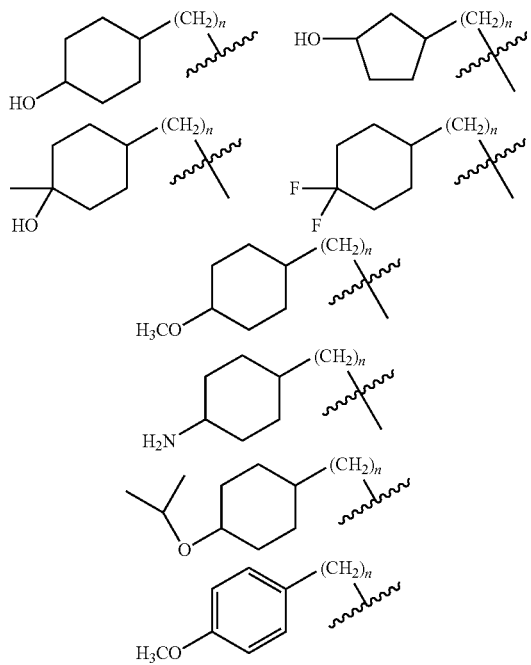

-continued

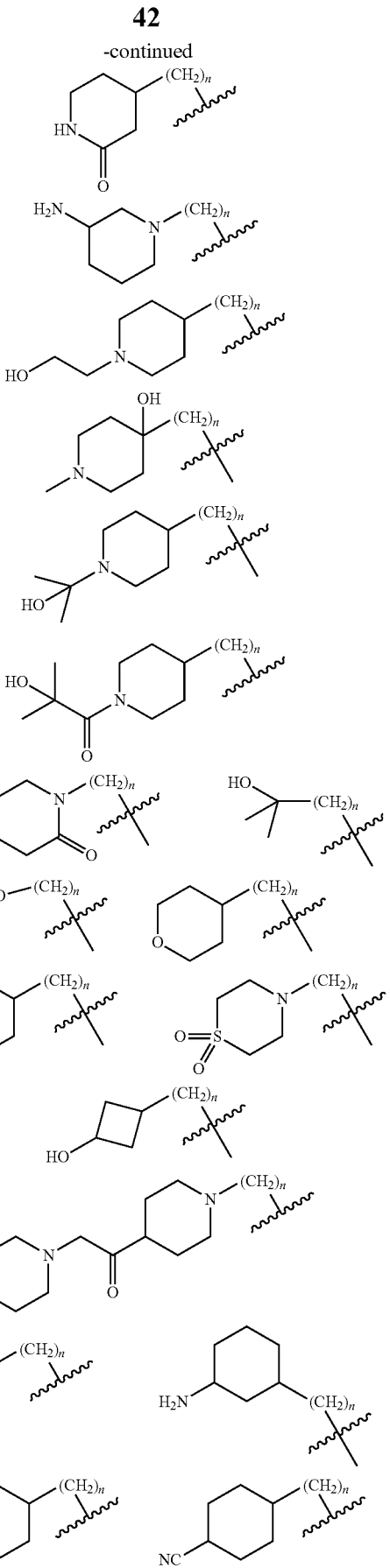

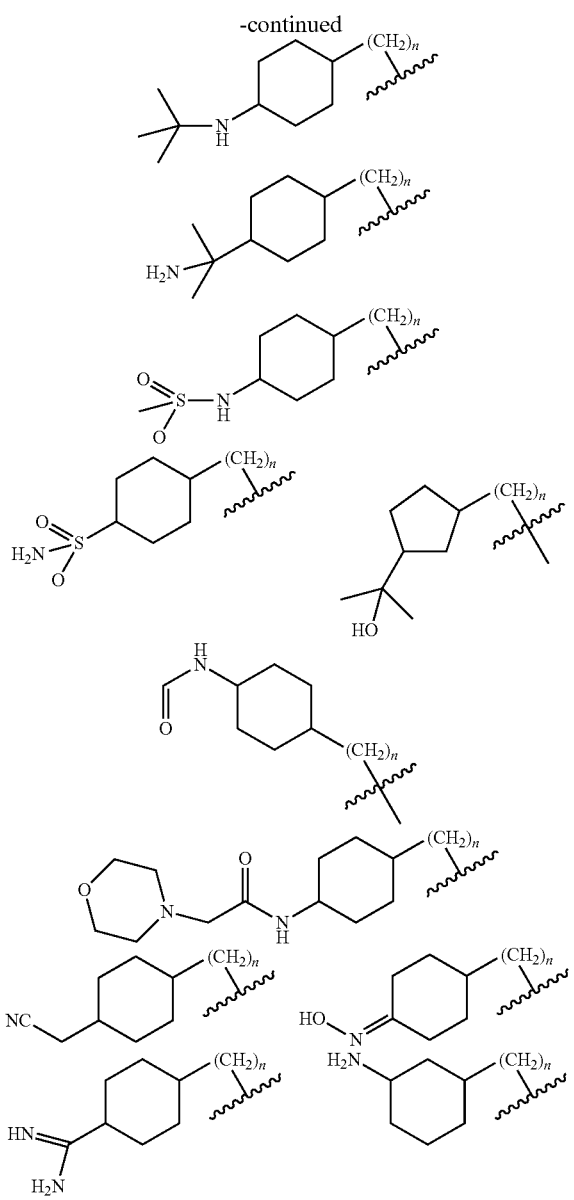

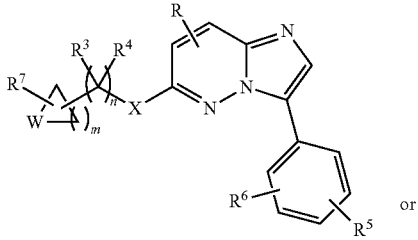

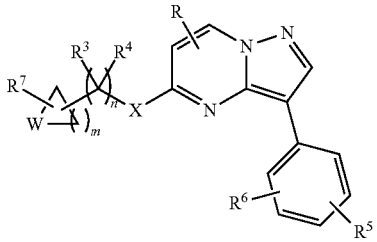

where n is 0, 1, 2, 3 or 4 and each of the above moieties are optionally substituted with one or more substituents, W is —O—, —S(O)$_z$— or >C(R$^9$)[(CR$^{10}$R$^{11}$)$_y$R$^{12}$]; R$^3$, R$^4$, R$^7$, R$^9$, R$^{10}$ and R$^{11}$ are, at each occurrence, independently H or alkyl; R$^{12}$ is —OH, —CN or alkoxy; m is 1, 2, 3, 4, 5 or 6; y and z are each independently 0, 1 or 2 and each of the above moieties are optionally substituted with one or more substituents.

In still other embodiments, R$_2$ is

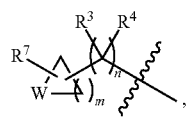

and the present invention is directed to a compound having a structure according to structure (I-D) or structure (II-D) below:

or a stereoisomer, tautomer or pharmaceutically acceptable salt thereof, wherein:

X is —N(R$^8$)— or —O—;

W is —O—, —S(O)$_z$— or

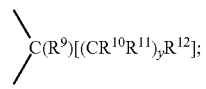

R is H, —OH, halo, alkyl, haloalkyl, alkoxy, haloalkoxy, —N(R$^8$)$_2$, or —CN;

R$^3$, R$^4$, R$^7$, R$^8$, R$^9$, R$^{10}$ and R$^{11}$ are, at each occurrence, independently H or alkyl;

R$^5$ is halo, haloalkyl or haloalkoxy;

R$^6$ is H, —OH, alkyl or alkoxy;

R$^{12}$ is —OH, —CN or alkoxy;

m is 1, 2, 3, 4, 5 or 6;

n is 0, 1, 2, 3 or 4; and y and z are each independently 0, 1 or 2.

In certain embodiments of the foregoing compounds of structure (I-D) or (II-D), R$^6$ is H, and in other embodiments R is H or methyl. In still other embodiments, R$^5$ is at the meta position, and the compound has one of the following structures (I-Da) or (II-Da):

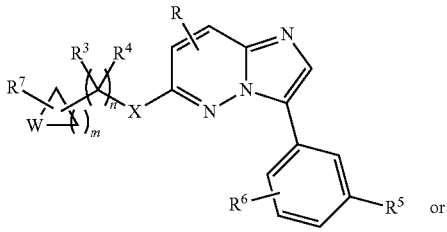

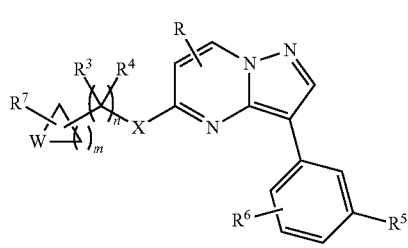

(II-Da)

In some embodiments of structures (I-Da) or (II-Da), $R^6$ is H, and in other embodiments R is H or methyl.

In some other embodiments, m is 3 or 4, for example is some embodiments m is 4. In certain embodiments where M is 4, the compound has one of the following structures (IDb) or (IIDb):

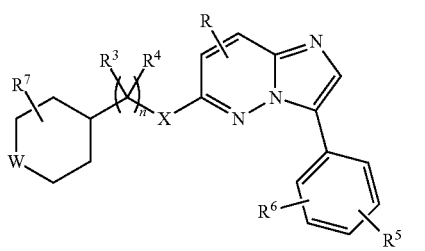

(I-Db)

or

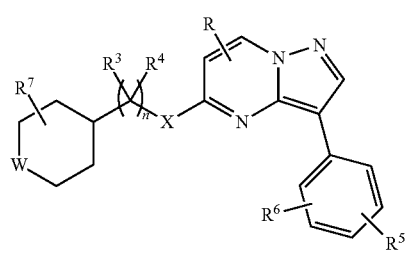

(II-Db)

In various embodiments of the foregoing compounds of structure (I-D) or (II-D), $R^7$ is H. In other various embodiments n is 0 or 1, for example in some specific embodiments of any of the foregoing n is 0.

In still other various embodiments of the foregoing compounds of structure (I-D) or (II-D), at least one of $R^3$ or $R^4$ is H, for example in certain embodiments each of $R^3$ and $R^4$ is H.

In some embodiments of the foregoing compounds of structure (I-D) or (II-D), $R^5$ is —OCF$_3$, —CF$_3$, Cl or F. For example, in some of these embodiments R5 is in the meta position and $R^6$ is H.

In still other embodiments of the foregoing compounds of structure (I-D) or (II-D), $R^{12}$ is —OH, —CN or —OCH$_3$. In some embodiments $R^9$ is H and in other embodiments $R^9$ is methyl. In yet other embodiments, at least one of $R^{10}$ or $R^{11}$ is methyl, for example in some embodiments each of $R^{10}$ and $R^{11}$ is methyl. In some embodiments y is 0 or 1.

In some other embodiments of the foregoing compounds of structure (I-D) or (II-D), The W is —O—, —S(O)$_2$—, —CH(OH)—, —CH(CN)—, —C(CH$_3$)(OH)—, —CH(OCH$_3$)— or —CH[C(CH$_3$)$_2$OH]—. In other embodiments X is —NH—, and in some other embodiments X is —O—.

In still other embodiments of the foregoing compounds of structure (I-D) or (II-D), $R_1$ is selected from the following structure one of the following structures:

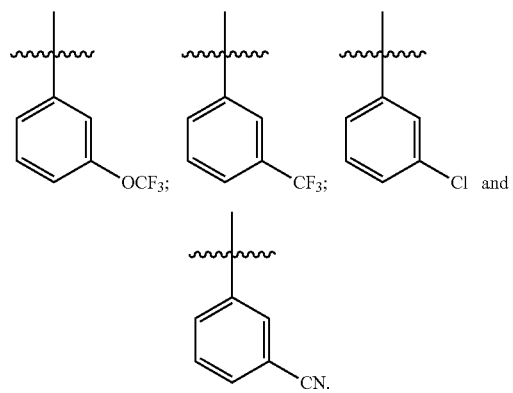

Still other embodiments include compounds of structure (I-D) or (II-D) wherein the compound has a hERG IC$_{50}$ activity of 10 µM or more, for example 30 µM or more.

In still other embodiments of structures (I), (II), (I-A), (II-A), (I-B), (II-B), (I-C) or (II-C) above, R$_2$ is

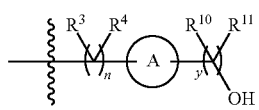

wherein A represents an optionally substituted 3 to 8-membered carbocyclic ring and $R^3$, $R^4$, $R^{10}$, $R^{11}$, n and y are as defined above.

In other embodiments of the foregoing, n is 0, and in other embodiments y is 0 or 1. In some other embodiments, at least one of $R^3$ or $R^4$ is H. In some other embodiments, $R^3$ and $R^4$ are each H. In some other embodiments, at least one of $R^{10}$ or $R^{11}$ is methyl. In some other embodiments, $R^{10}$ and $R^{11}$ are each methyl. In yet other embodiments, A is an optionally substituted 6-membered carbocyclic ring and $R^2$ has the following structure:

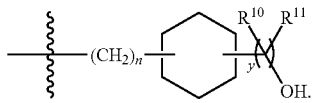

In some other embodiments of the foregoing, at least one of $R^{10}$ or $R^{11}$ is methyl. In some other embodiments, $R^{10}$ and $R^{11}$ are each methyl. In some embodiments y is 0 and in other embodiments y is 1.

In more specific embodiments R$_2$ has one of the following structures:

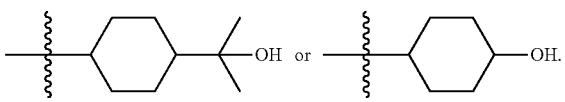

In even other embodiments, R$_2$ has one of the following structures:

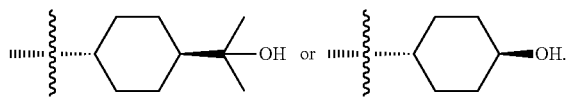

In still other embodiments of structures (I), (II), (I-A), (II-A), (I-B), (II-B), (I-C) or (II-C) above, $R_2$ is a 3, 4 or 5 membered carbocyclic ring and has one of the following structures:

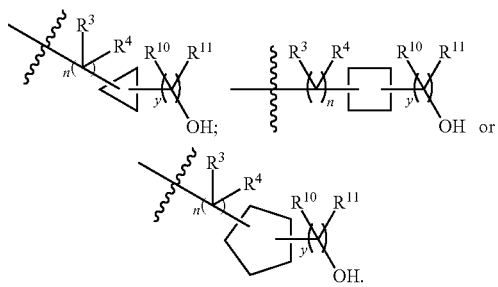

wherein $R^3$, $R^4$, $R^{10}$, $R^{11}$, n and y are as defined above.

In other embodiments of the foregoing, n is 0, and in other embodiments y is 0 or 1. In some other embodiments, at least one of $R^3$ or $R^4$ is H. In some other embodiments, $R^3$ and $R^4$ are each H. In some other embodiments, at least one of $R^{10}$ or $R^{11}$ is methyl. In some other embodiments, $R^{10}$ and $R^1$ are each methyl.

In still other embodiments, the present invention is directed to a compound of structure (III), wherein:

X is a direct bond, NH, N(alkyl), S, O, SO or $SO_2$;

R is H, —OH, —CN, halo, alkyl, haloalkyl, alkoxy or haloalkoxy;

$R_1$ is carbocycle, substituted carbocycle, heterocycle, or substituted heterocycle; or a structure selected from:

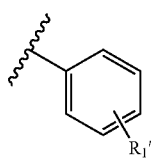

where $R_1'$ is a p, o or m substitution with one or more occurrences of cyano, halo, —$OCF_3$, —$OCHF_2$, —$CF_3$, —$OCH_3$, —$NH_2$, —$NO_2$, —OH, —$COCH_3$, —$NHSO_2CH_3$, —$CONH_2$, —CO—NH-alkyl, —CO—N-alkyl$_2$ or —$N(CH_3)_2$.

$R_2$ is —$(CH_2)_n$-cyclopropyl, —$(CH_2)_n$-cyclobutyl, —$(CH_2)_n$-cyclopentyl, —$(CH_2)_n$-cyclohexyl, —$SO_2$—$CH_3$, —$SO_2$—$(CH_2)_nCH_3$, —$(CH_2)_n$-piperonyl, —$(CH_2)_n$-piperidyl, —$(CH_2)$-piperidin-2-only, —$(CH_2)_n$-piperazinyl, —$(CH_2)_n$-furyl, —$(CH_2)_n$-thiophene, —$(CH_2)_n$-pyridyl, —$(CH_2)_n$-pyrimidyl, —$(CH_2)_n$-thiomorpholinylsulfone, —$(CH_2)_n$-phenyl, —$(CH_2)_n$-tetrahydropyranyl, —$(CH_2)_n$-tetrahydrothiopyranyl, —$(CH_2)_n$-tetrahydrothiopyranylsulfone, —$(CH_2)_nOCH_3$, —$(CH_2)_nOH$, —$(CH_2)_nN(CH_3)_2$, —$(CH_2)_nCH(CH_3)_2OH$ or —$(CH_2)_nN(CH_3)_2$, where n is 0, 1, 2, 3 or 4 and each of the above moieties are optionally substituted with one or more substituents; or $R_2$ is a structure selected from one of the following structures:

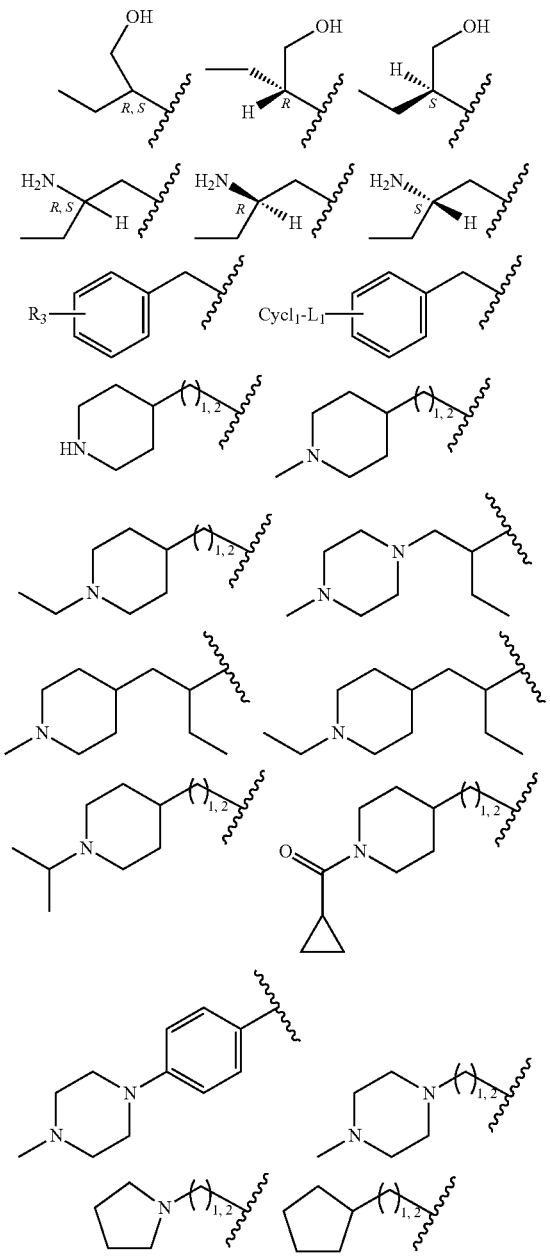

where L is optional and, if present, NH, N(alkyl), S, O, SO or $SO_2$; $R_3$ is one or more optional substituents; and $Cycl_1$ is a carbocycle, substituted carbocycle, heterocycle or substituted heterocycle; or $R_2$ is a structure selected from one of the following structures:

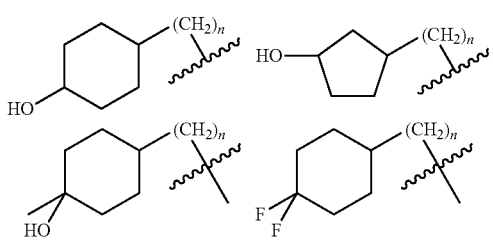

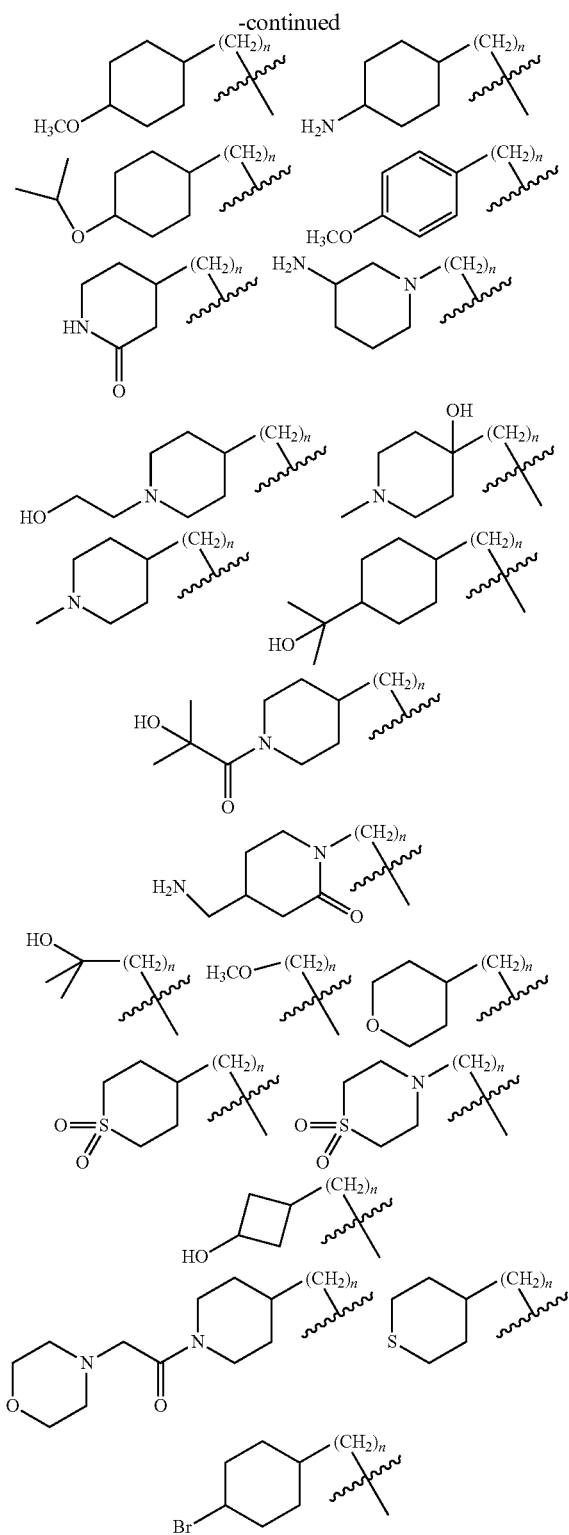

where n is 0, 1, 2, 3 or 4 and each of the above moieties are optional substituted with one or more substituents.

In a more specific aspect of structure (III) above, R₁ is a 5-6 membered saturated, partially unsaturated, or fully unsaturated monocyclic ring having 0-3 heteroatoms, where the heteroatoms are selected from nitrogen, oxygen and sulfur.

In a more specific aspect of structure (III) above, R₁ is p, o or m substituted phenyl with one or more occurrences of cyano, —F, —Cl, —Br, —CF₃, —OCF₃, —OCH₃, —CH₃, NO₂, —N(CH₃)₂, —NH₂, —NHSO₂CH₃, —NHSO₂CH₂CH₃, —COCH₃, —COOH, —CH₂NH₂, —OH, —SO₂NH₂, —SCH₃, piperazine or morpholine.

In a more specific aspect of structure (III) above, R₁ is an optionally substituted pyrazolyl, furyl, thiophene, pyridyl, pyrimidyl, or indolyl group.

In a more specific aspect of structure (III) above, R₁ has the structure:

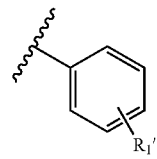

where R₁' represents one or more optional substituents or, in a more specific embodiment, is a p, o or m substitution with one or more occurrences of cyano, halo, —OCF₃, —CF₃, —OCH₃, —OCHF₂, NH₂, NO₂, OH, —COCH₃, —NHSO₂CH₃, —CONH₂, —CO—NH-alkyl, —CO—N-alkyl₂ or —N(CH₃)₂.

In a more specific aspect of structure (III) above, R₁ has a structure selected from:

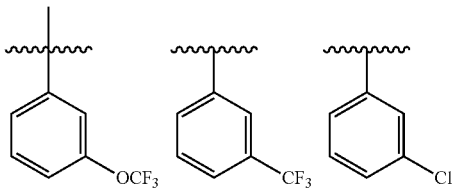

In a more specific aspect of structure (III) above, R₂ is 2-butane-1-ol, —SO₂CH₃, —SO₂CH₂CH₃, —CH₂CH₂OCH₃, —CH₂CH₂CH₂OH, or —CH₂CH₂N(CH₃)₂.

In a more specific aspect of structure (III) above, R₂ is optionally substituted —(CH₂)ₙ-cyclopropyl, —(CH₂)ₙ-cyclopentyl, —(CH₂)ₙ-cyclohexyl, —(CH₂)ₙ-piperonyl, —(CH₂)ₙ-piperidyl, —(CH₂)ₙ-piperazinyl, —(CH₂)ₙ-furyl, —(CH₂)ₙ-thiophene, —(CH₂)ₙ-pyridyl, or —(CH₂)ₙ-pyrimidyl.

In a more specific aspect of structure (III) above, R₂ has a structure selected from one of the following structures:

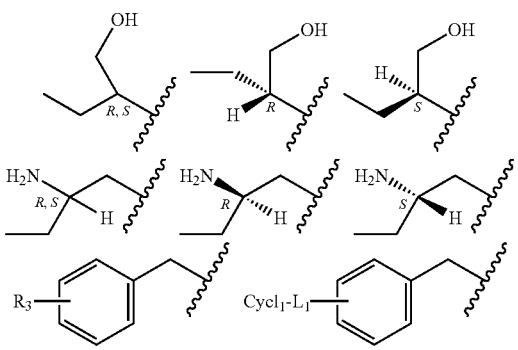

-continued

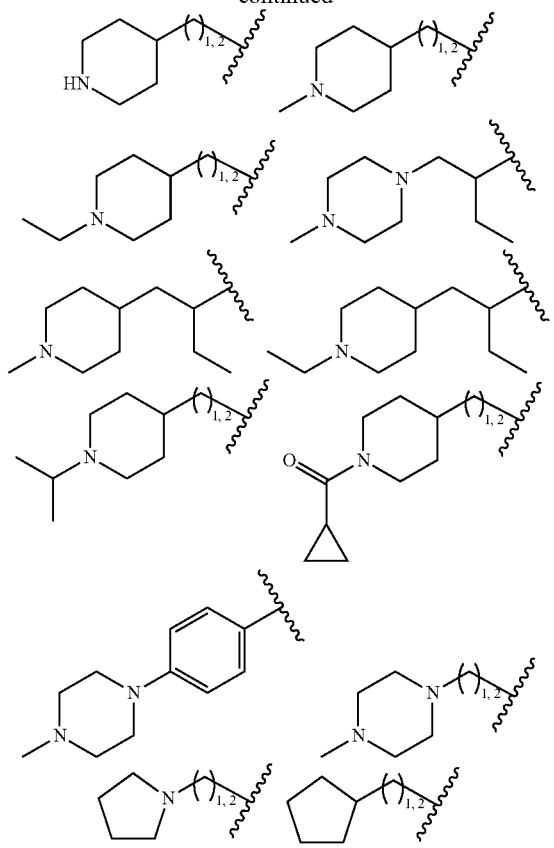

where L is optional and, if present, NH, N(alkyl), S, O, SO or SO$_2$; R$_3$ is one or more optional substituents; and Cycl$_1$ is a carbocycle, substituted carbocycle, heterocycle or substituted heterocycle.

In a more specific aspect of structure (III) above, R$_2$ has the following structure:

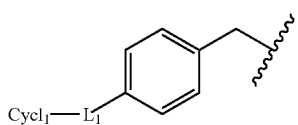

where L is optional and, if present, NH, N(alkyl), S, O, SO or SO$_2$; and Cycl$_1$ is a carbocycle, substituted carbocycle, heterocycle or substituted heterocycle, and in a more specific embodiment Cycl$_1$ is a 5-6 membered saturated, partially unsaturated, or fully unsaturated monocyclic ring having 0-3 heteroatoms, where the heteroatoms are selected from nitrogen, oxygen and sulfur.

In a more specific aspect of structure (III) above, R$_2$ has a structure selected from:

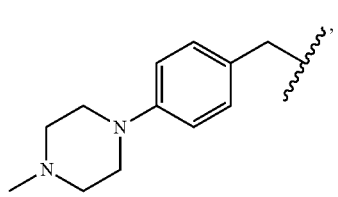

-continued

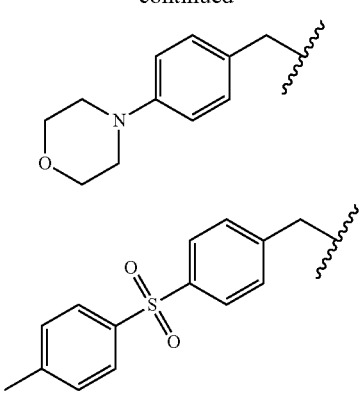

In a more specific aspect of structure (III) above, R$_2$ is —(CH$_2$)$_n$-cyclobutyl, —(CH$_2$)$_n$-cyclopentyl, —(CH$_2$)$_n$-cyclohexyl, —(CH$_2$)$_n$-piperidyl, —(CH$_2$)$_n$-piperidin-2-onyl, —(CH$_2$)$_n$-thiomorpholinylsulfone, —(CH$_2$)$_n$-phenyl, —(CH$_2$)$_n$-tetrahydropyranyl, —(CH$_2$)$_n$-tetrahydrothiopyranyl, —(CH$_2$)$_n$-tetrahydrothiopyranylsulfone, —(CH$_2$)$_n$OCH$_3$ or —(CH$_2$)$_n$CH(CH$_3$)$_2$OH where n is 0, 1, 2, 3 or 4 and each of the above moieties are optionally substituted with one or more substituents. For example, in some embodiments R$_2$ has a structure selected from one of the following structures:

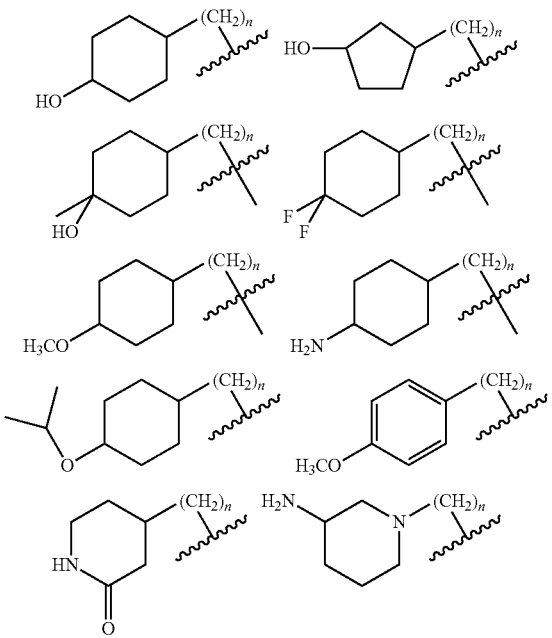

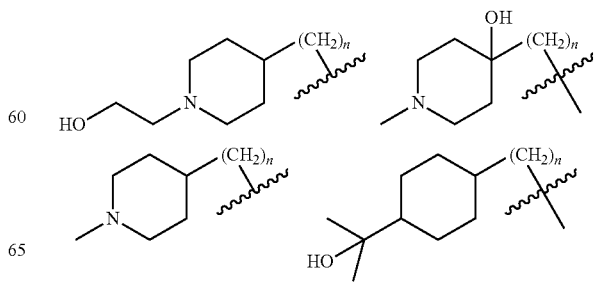

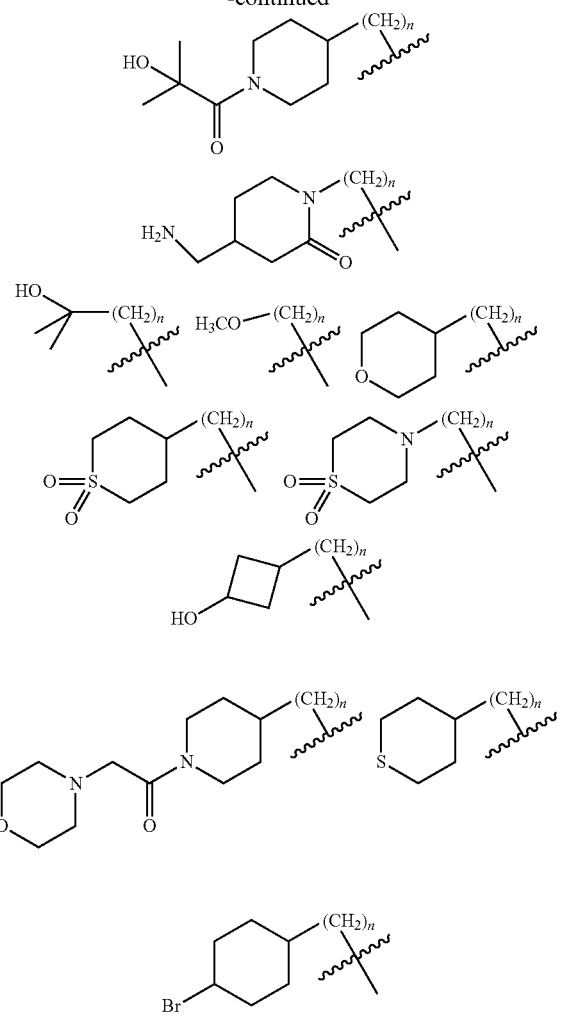

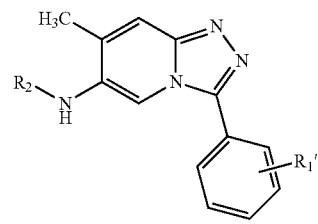

or a stereoisomer, prodrug or pharmaceutically acceptable salt thereof.

In more specific embodiments of (III-A) and (II-Aa), $R_1$ is substituted phenyl having at least one p, o or m substituent selected from cyano, halo, —OCF$_3$, —OCHF$_2$, —CF$_3$, —OCH$_3$, —NH$_2$, —NO$_2$, —OH, —COCH$_3$, —NHSO$_2$CH$_3$ and —N(CH$_3$)$_2$, and in an more specific embodiment $R_1$ is substituted phenyl having at least one p, o or m substituent selected from —OCF$_3$, —OCHF$_2$, —CF$_3$, —OCH$_3$ and —OH, and in a more specific embodiment $R_1$ is selected from one of the following structures:

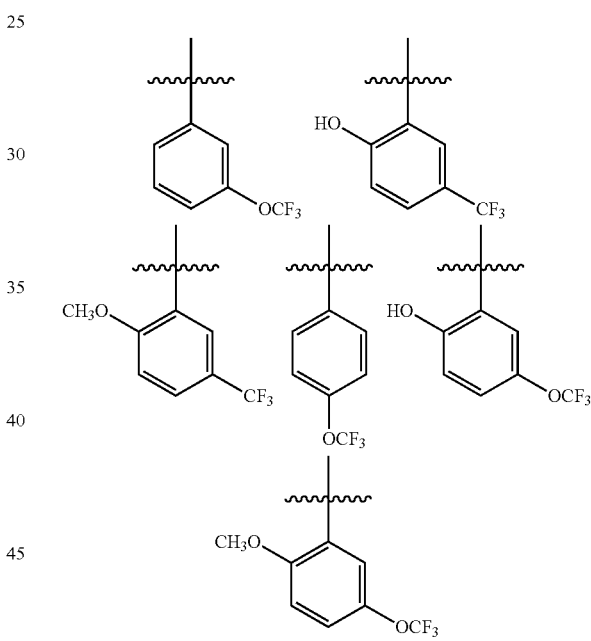

In more specific embodiments of (III-A) and (II-Aa), $R_1$ has a structure selected from one of the following structures:

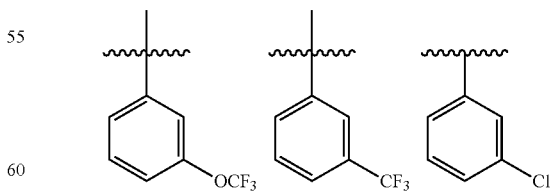

where n is 0, 1, 2, 3 or 4 and each of the above moieties are optional substituted with one or more substituents.

In further specific embodiments of structure (III), X is NH and $R_1$ is a substituted or unsubstituted phenyl (where R is as defined above and $R_1'$ is absent or represents one or more substituents), and the compounds have the following structure (III-A):

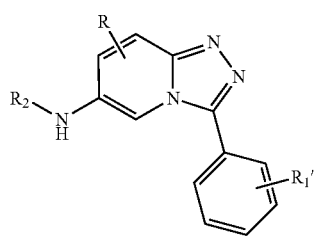

or a stereoisomer, prodrug or pharmaceutically acceptable salt thereof.

In more specific embodiments of (III-A), R is alky, such as methyl, and the compounds have the following structure (II-Aa):

In more specific embodiments of (III-A) and (II-Aa), $R_2$ is —(CH$_2$)$_{1,2}$-piperid-4-yl, substituted —(CH$_2$)$_{1,2}$-piperid-4-yl, —(CH$_2$)$_{1,2}$-piperazin-1-yl, or substituted —(CH$_2$)$_{1,2}$-piperazin-1-yl, such as a moiety selected from one of the following structures:

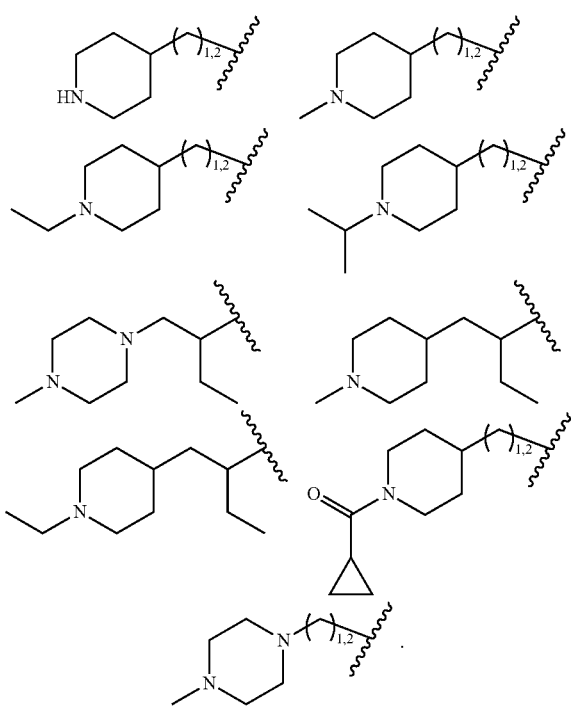

More specifically, in some embodiments R₂ may be selected from one of the following structures:

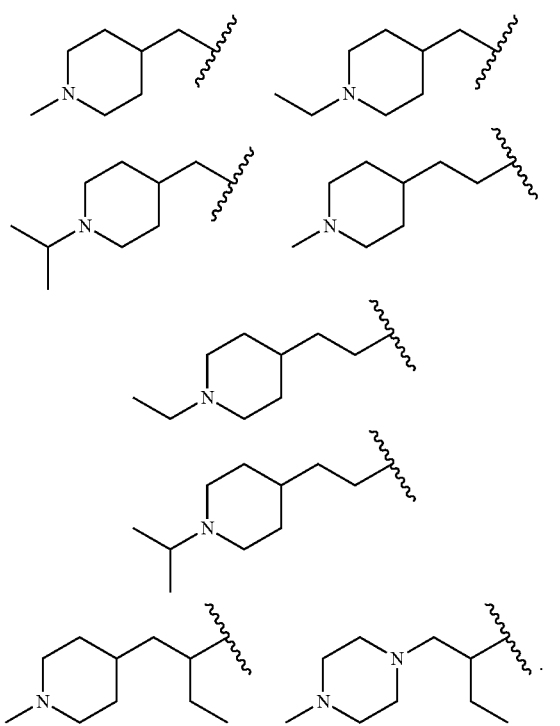

In more specific embodiments of structures (III-A) and (III-Aa), R₂ is —(CH₂)$_n$-cyclobutyl, —(CH₂)$_n$-cyclopentyl, —(CH₂)$_n$-cyclohexyl, —(CH₂)$_n$-piperidyl, —(CH₂)$_n$-piperidin-2-onyl, —(CH₂)$_n$-thiomorpholinylsulfone, —(CH₂)$_n$-phenyl, —(CH₂)$_n$-tetrahydropyranyl, —(CH₂)$_n$-tetrahydrothiopyranyl, —(CH₂)$_n$-tetrahydrothiopyranylsulfone, —(CH₂)$_n$OCH₃ or —(CH₂)$_n$CH(CH₃)₂OH where n is 0, 1, 2, 3 or 4 and each of the above moieties are optionally substituted with one or more substituents. For example, in some embodiments R₂ has a structure selected from one of the following structures:

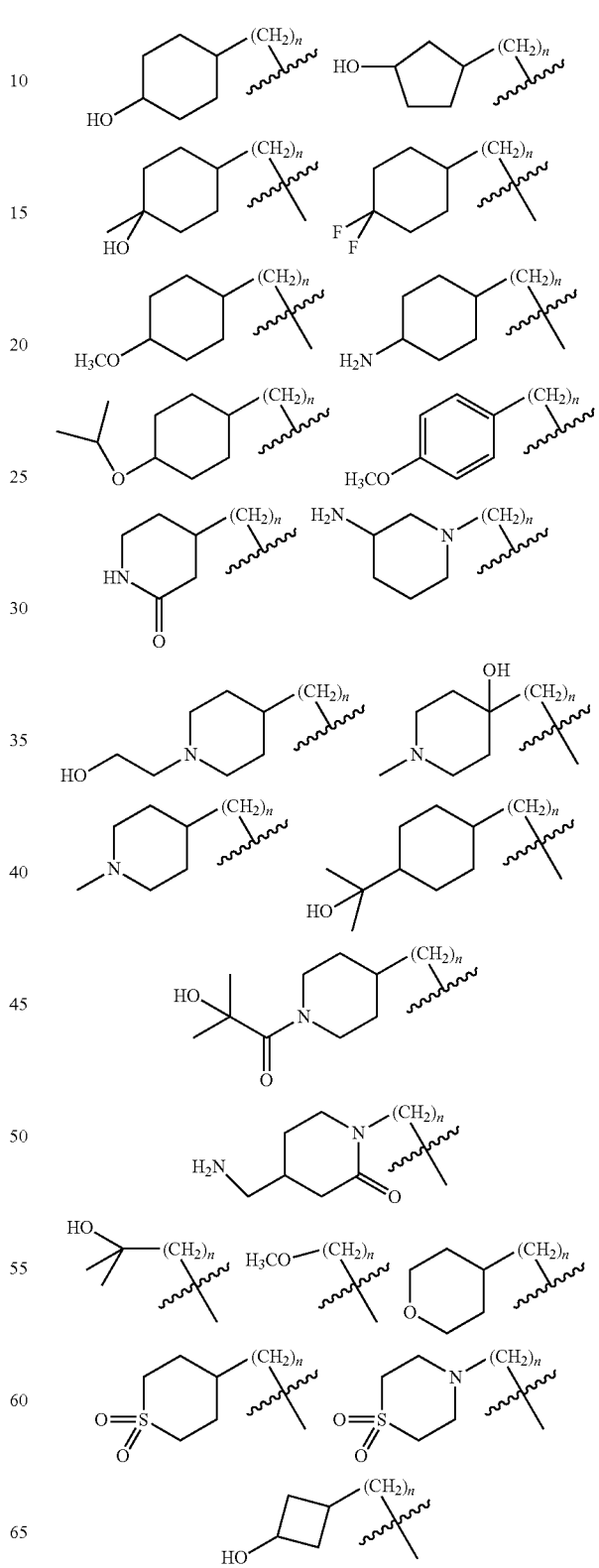

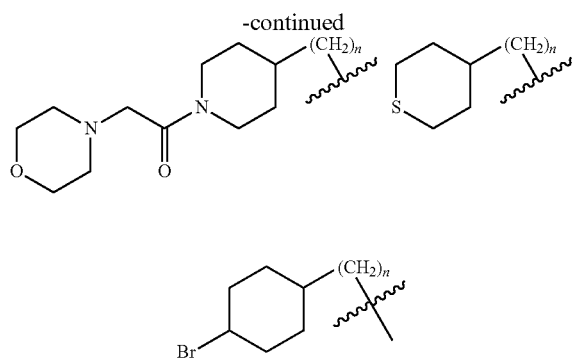

where n is 0, 1, 2, 3 or 4 and each of the above moieties are optional substituted with one or more substituents.

In still further specific embodiments of structure (III), X is O and $R_1$ is a substituted or unsubstituted phenyl (where R is as defined above and $R_1'$ is absent or represents one or more substituents), and the compounds have the following structure (III-B):

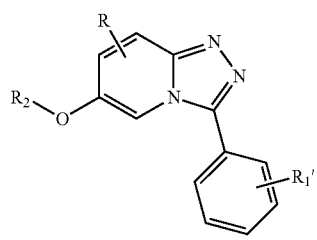

(III-B)

or a stereoisomer, prodrug or pharmaceutically acceptable salt thereof.

In more specific embodiments of (III-B), R is alky, such as methyl, and the compounds have the following structure (III-Bb):

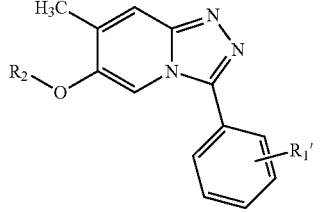

(III-Bb)

or a stereoisomer, prodrug or pharmaceutically acceptable salt thereof.

In more specific embodiments of (III-B) and (III-Bb), $R_1$ is substituted phenyl having at least one p, o or m substituent selected from cyano, halo, —OCF$_3$, —OCHF$_2$, —CF$_3$, —OCH$_3$, —NH$_2$, —NO$_2$, —OH, —COCH$_3$, —NHSO$_2$CH$_3$, —CONH$_2$, —CO—NH-alkyl, —CO—N-alkyl$_2$ and —N(CH$_3$)$_2$, and in an more specific embodiment $R_1$ is substituted phenyl having at least one p, o or m substituent selected from —OCF$_3$, —OCHF$_2$, —CF$_3$, —OCH$_3$ and —OH, and in a more specific embodiment $R_1$ is selected from one of the following structures:

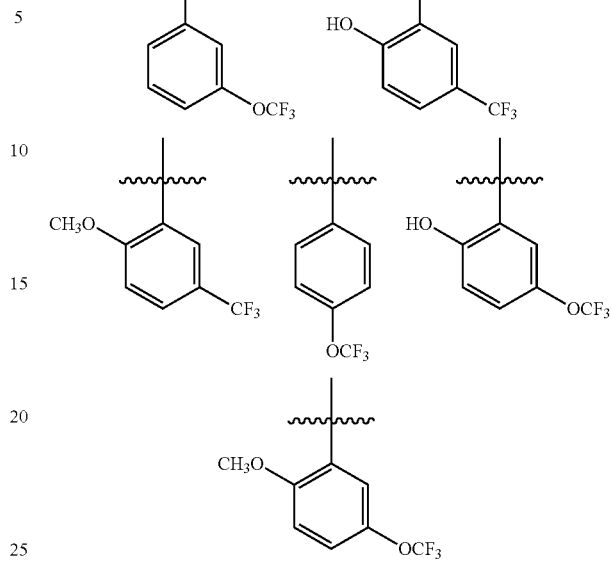

In more specific embodiments of (III-B) and (III-Bb), $R_1$ has a structure selected from one of the following structures:

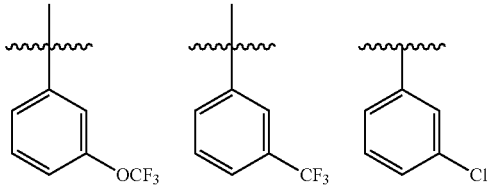 [SMILES: *c1cccc(OC(F)(F)F)c1 ; *c1cccc(C(F)(F)F)c1 ; *c1cccc(Cl)c1]

In more specific embodiments of structures (III-B) and (III-Bb), $R_2$ is —(CH$_2$)$_n$-cyclopropyl, —(CH$_2$)$_n$-cyclopentyl, —(CH$_2$)$_n$-cyclohexyl, —SO$_2$—CH$_3$, —SO$_2$—(CH$_2$)$_n$CH$_3$, —(CH$_2$)$_n$-piperonyl, —(CH$_2$)$_n$-piperidyl, —(CH$_2$)$_n$-piperazinyl, —(CH$_2$)$_n$-furyl, —(CH$_2$)$_n$-thiophene, —(CH$_2$)$_n$-pyridyl, —(CH$_2$)$_n$-pyrimidyl, —(CH$_2$)$_n$OCH$_3$, —(CH$_2$)$_n$OH, or —(CH$_2$)$_n$N(CH$_3$)$_2$, where n is 0, 1, 2, 3 or 4 and each of the above moieties are optionally substituted with one or more substituents; or a structure selected from one of the following structures:

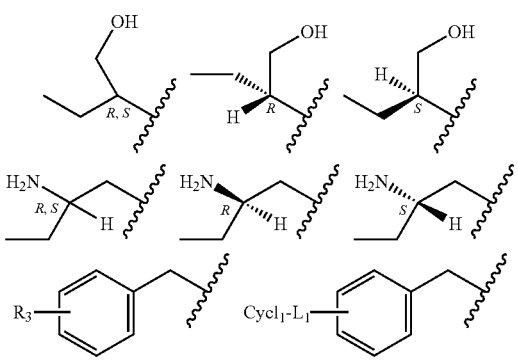

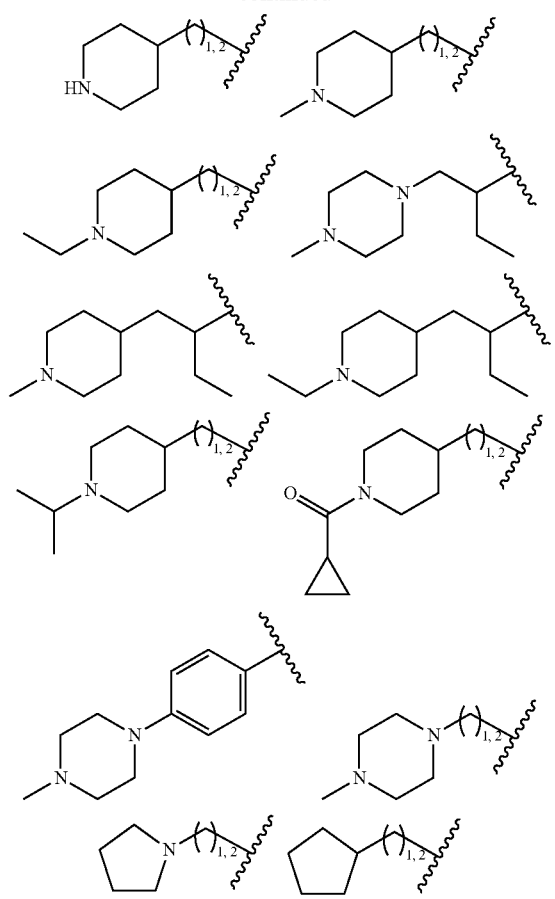

In more specific embodiments of (III-B) and (III-Bb), R$_2$ is —(CH$_2$)$_{1,2}$-piperid-4-yl, substituted —(CH$_2$)$_{1,2}$-piperid-4-yl, —(CH$_2$)$_{1,2}$-piperazin-1-yl, or substituted —(CH$_2$)$_{1,2}$-piperazin-1-yl, such as moiety selected from one of the following structures:

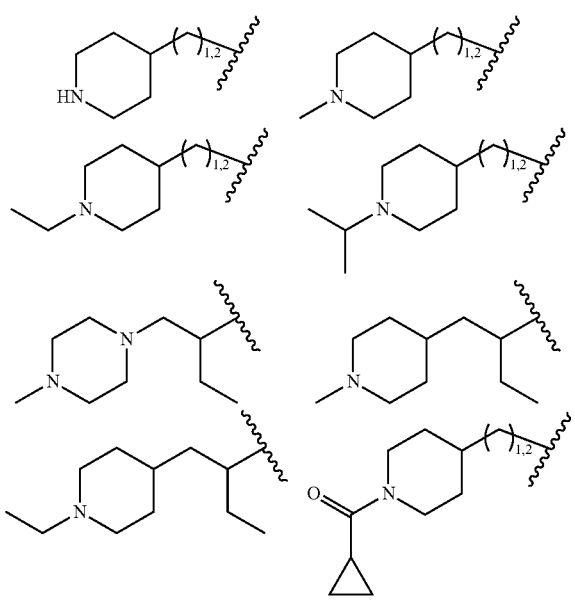

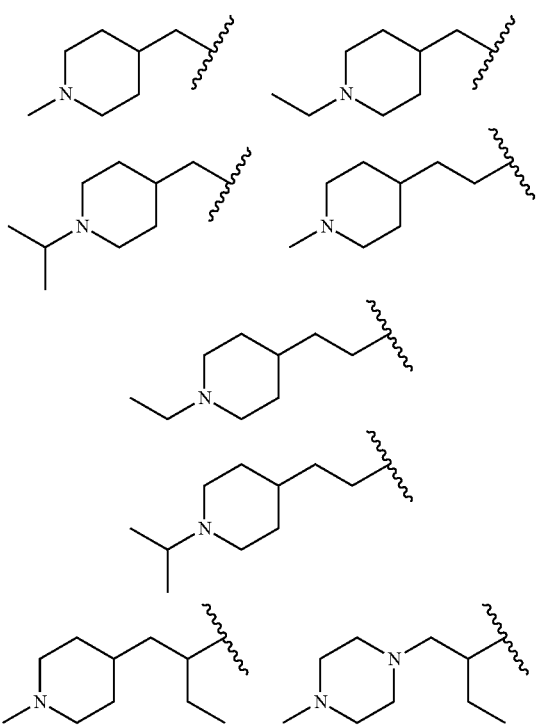

More specifically, in some embodiments R$_2$ is selected from one of the following structures:

In more specific embodiments of structures (III-B) and (III-Bb), R$_2$ is —(CH$_2$)$_n$-cyclobutyl, —(CH$_2$)$_n$-cyclopentyl, —(CH$_2$)$_n$-cyclohexyl, —(CH$_2$)$_n$-piperidyl, —(CH$_2$)$_n$-piperidin-2-onyl, —(CH$_2$)$_n$-thiomorpholinylsulfone, —(CH$_2$)$_n$-phenyl, —(CH$_2$)$_n$-tetrahydropyranyl, —(CH$_2$)$_n$-tetrahydrothiopyranyl, —(CH$_2$)$_n$-tetrahydrothiopyranylsulfone, —(CH$_2$)$_n$OCH$_3$ or —(CH$_2$)$_n$CH(CH$_3$)$_2$OH where n is 0, 1, 2, 3 or 4 and each of the above moieties are optionally substituted with one or more substituents. For example, in some embodiments R$_2$ has a structure selected from one of the following structures:

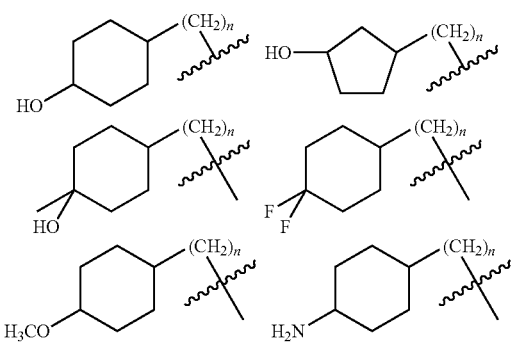

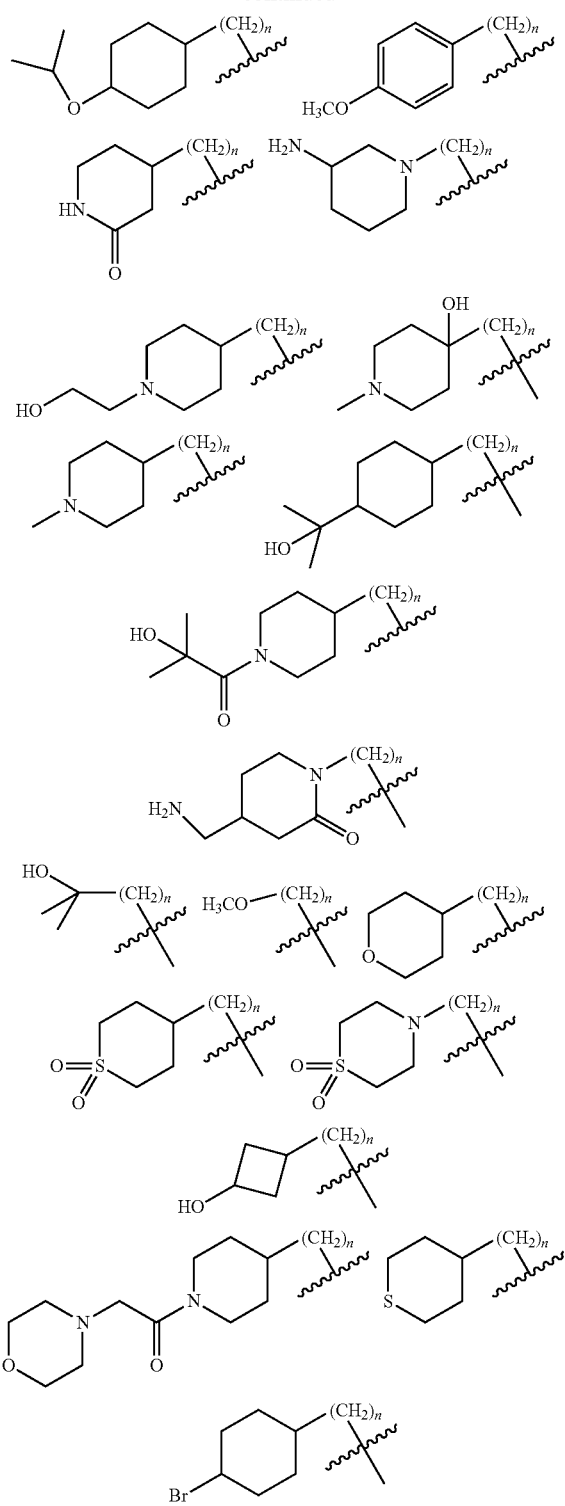

where n is 0, 1, 2, 3 or 4 and each of the above moieties are optional substituted with one or more substituents.

In yet further specific embodiments of structure (III), X is S, SO or $SO_2$ and $R_1$ is a substituted or unsubstituted phenyl (where $R_1'$ below is absent or represents one or more substituents), and the compounds have the following structure (III-C):

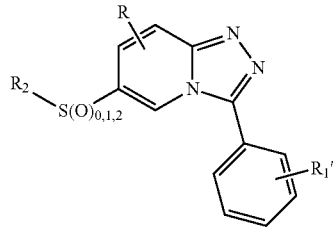

(III-C)

or a stereoisomer, prodrug or pharmaceutically acceptable salt thereof.

In more specific embodiments of (III-C), R is alky, such as methyl, and the compounds have the following structure (III-Cc):

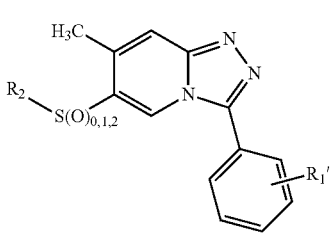

(III-Cc)

or a stereoisomer, prodrug or pharmaceutically acceptable salt thereof.

In more specific embodiments of (III-C) and (III-Cc), $R_1$ is substituted phenyl having at least one p, o or m substituent selected from cyano, halo, —$OCF_3$, —$OCHF_2$, —$CF_3$, —$OCH_3$, —$NH_2$, —$NO_2$, —OH, —$COCH_3$, —$NHSO_2CH_3$, —$CONH_2$, —CO—NH-alkyl, —CO—N-alkyl$_2$ and —N($CH_3$)$_2$, and in an more specific embodiment $R_1$ is substituted phenyl having at least one p, o or m substituent selected from —$OCF_3$, —$OCHF_2$, —$CF_3$, —$OCH_3$ and —OH, and in a more specific embodiment $R_1$ is selected from one of the following structures:

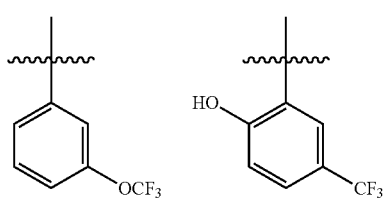

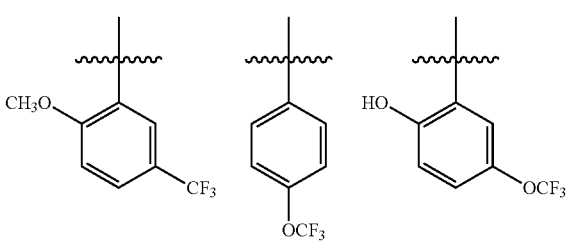

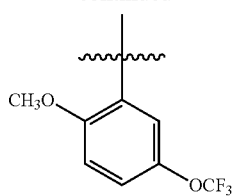

In more specific embodiments of (III-C) and (III-Cc), R₁ has a structure selected from one of the following structures:

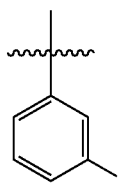 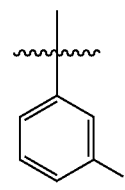 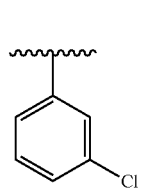

In more specific embodiments of structures (III-C) and (III-Cc), R₂ is —(CH₂)ₙ-cyclopropyl, —(CH₂)ₙ-cyclopentyl, —(CH₂)ₙ-cyclohexyl, —SO₂—CH₃, —SO₂—(CH₂)ₙCH₃, —(CH₂)ₙ-piperonyl, —(CH₂)ₙ-piperidyl, —(CH₂)ₙ-piperazinyl, —(CH₂)ₙ-furyl, —(CH₂)ₙ-thiophene, —(CH₂)ₙ-pyridyl, —(CH₂)ₙ-pyrimidyl, —(CH₂)ₙOCH₃, —(CH₂)ₙOH, or —(CH₂)ₙN(CH₃)₂, where n is 0, 1, 2, 3 or 4 and each of the above moieties are optionally substituted with one or more substituents; or a structure selected from one of the following structures:

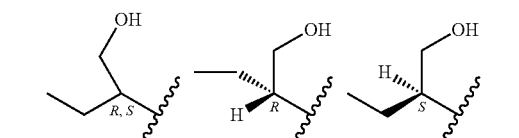
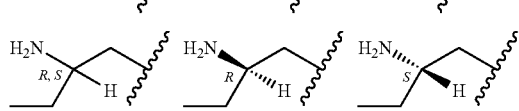
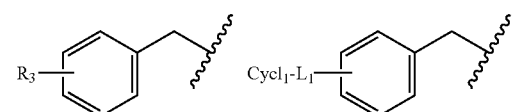
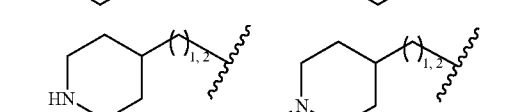
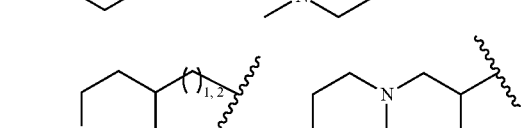
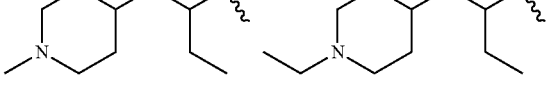

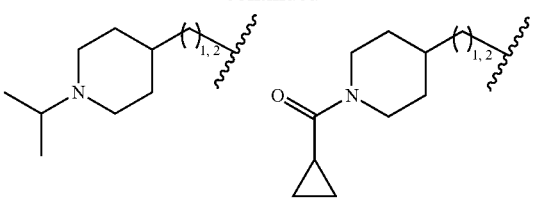

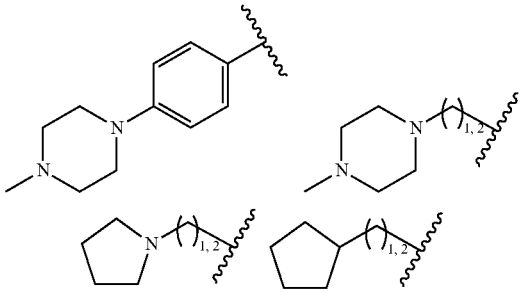

In more specific embodiments of (III-C) and (III-Cc), R₂ is —(CH₂)₁,₂-piperid-4-yl, substituted —(CH₂)₁,₂-piperid-4-yl, —(CH₂)₁,₂-piperazin-1-yl, or substituted —(CH₂)₁,₂-piperazin-1-yl, such as moiety selected from one of the following structures:

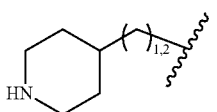 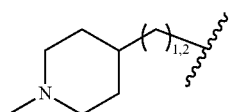
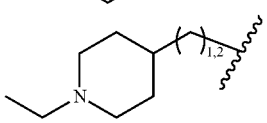 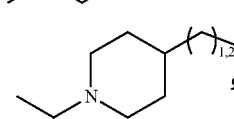
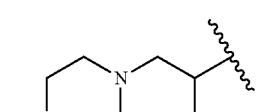 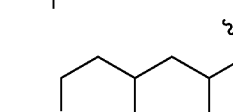
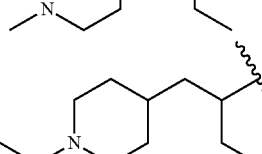 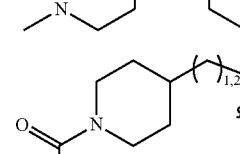
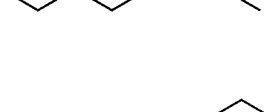 
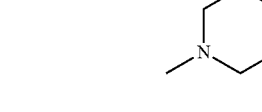 

More specifically, in some embodiments R₂ is selected from one of the following structures:

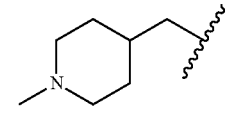 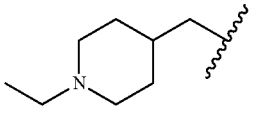

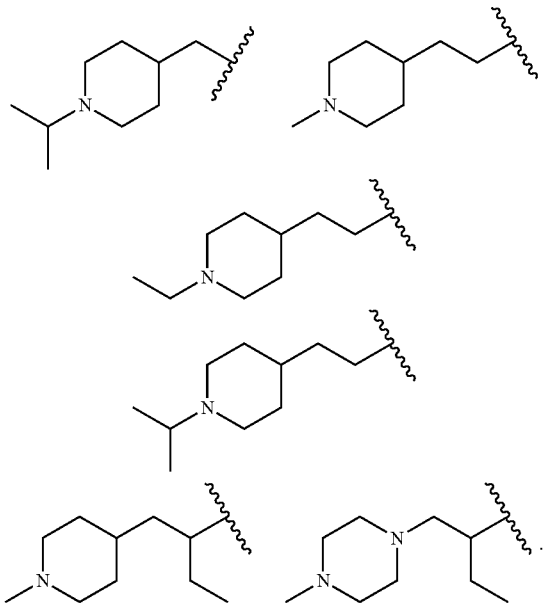

In more specific embodiments of (III-C) and (III-Cc), $R_2$ is —$(CH_2)_n$-cyclobutyl, —$(CH_2)_n$-cyclopentyl, —$(CH_2)_n$-cyclohexyl, —$(CH_2)_n$-piperidyl, —$(CH_2)_n$-piperidin-2-onyl, —$(CH_2)_n$-thiomorpholinylsulfone, —$(CH_2)_n$-phenyl, —$(CH_2)_n$-tetrahydropyranyl, —$(CH_2)_n$-tetrahydrothiopyranyl, —$(CH_2)_n$-tetrahydrothiopyranylsulfone, —$(CH_2)_nOCH_3$ or —$(CH_2)_nCH(CH_3)_2OH$ where n is 0, 1, 2, 3 or 4 and each of the above moieties are optionally substituted with one or more substituents. For example, in some embodiments $R_2$ has a structure selected from one of the following structures:

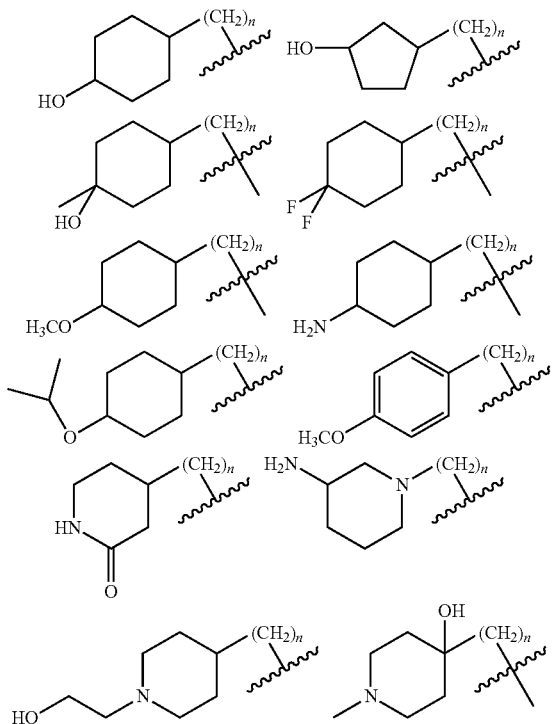

where n is 0, 1, 2, 3 or 4 and each of the above moieties are optional substituted with one or more substituents.

In still other embodiments of the compound of structure (III), $R_2$ is

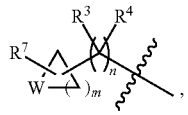

and the present invention is directed to a compound having a structure according to structure (III-D) below:

(III-D)

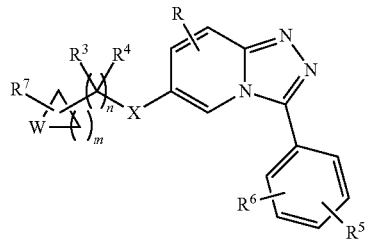

or a stereoisomer, tautomer or pharmaceutically acceptable salt thereof, wherein:

X is —N(R$^8$)— or —O—;

W is —O—, —S(O)$_z$— or

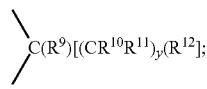

R is H, —OH, halo, alkyl, haloalkyl, alkoxy, haloalkoxy, —N(R$^8$)$_2$, or —CN;

R$^3$, R$^4$, R$^7$, R$^8$, R$^9$, R$^{10}$ and R$^{11}$ are, at each occurrence, independently H or alkyl;

R$^5$ is halo, haloalkyl or haloalkoxy;

R$^6$ is H, —OH, alkyl or alkoxy;

R$^{12}$ is —OH, —CN or alkoxy;

m is 1, 2, 3, 4, 5 or 6;

n is 0, 1, 2, 3 or 4; and y and z are each independently 0, 1 or 2.

In certain embodiments of the foregoing compounds of structure (III-D) or (II-D), R$^6$ is H, and in other embodiments R is H or methyl. In still other embodiments, R$^5$ is at the meta position, and the compound has the following structure (III-Da):

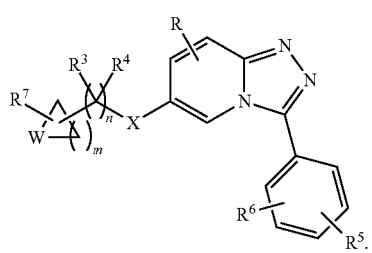

(III-Da)

In some embodiments of structure (III-Da), R$^6$ is H, and in other embodiments R is H or methyl.

In some other embodiments, m is 3 or 4, for example is some embodiments m is 4. In certain embodiments where M is 4, the compound has the following structure (III-Db):

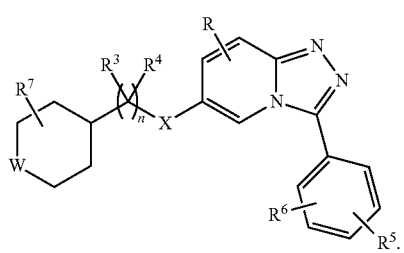

(III-Db)

In various embodiments of the foregoing compounds of structure (III-D), R$^7$ is H. In other various embodiments n is 0 or 1, for example in some specific embodiments of any of the foregoing n is 0.

In still other various embodiments of the foregoing compounds of structure (III-D), at least one of R$^3$ or R$^4$ is H, for example in certain embodiments each of R$^3$ and R$^4$ is H.

In some embodiments of the foregoing compounds of structure (III-D), R$^5$ is —OCF$_3$, —CF$_3$, Cl or F. For example, in some of these embodiments R5 is in the meta position and R$^6$ is H.

In still other embodiments of the foregoing compounds of structure (III-D), R$^{12}$ is —OH, —CN or —OCH$_3$. In some embodiments R$^9$ is H and in other embodiments R$^9$ is methyl. In yet other embodiments, at least one of R$^{10}$ or R$^{11}$ is methyl, for example in some embodiments each of R$^{10}$ and R$^{11}$ is methyl. In some embodiments y is 0 or 1.

In some other embodiments of the foregoing compounds of structure (III-D), The W is —O—, —S(O)$_2$—, —CH(OH)—, —CH(CN)—, —C(CH$_3$)(OH)—, —CH(OCH$_3$)— or —CH[C(CH$_3$)$_2$OH]—. In other embodiments X is —NH—, and in some other embodiments X is —O—.

In still other embodiments of the foregoing compounds of structure (III-D), R$_1$ is selected from one of the following structures:

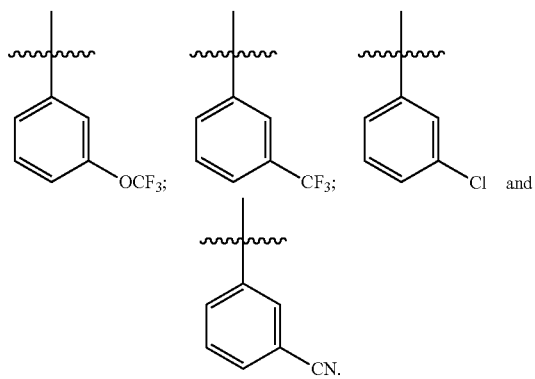

Still other embodiments include compounds of structure (III-D) wherein the compound has a hERG IC$_{50}$ activity of 10 μM or more, for example 30 μM or more.

In still other embodiments of structures (III), (III-A), (III-B) or (III-C) above, R$_2$ is

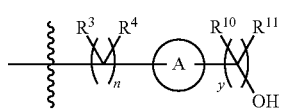

wherein A represents an optionally substituted 3 to 8-membered carbocyclic ring and R$^3$, R$^4$, R$^{10}$, R$^{11}$, n and y are as defined above.

In other embodiments of the foregoing, n is 0, and in other embodiments y is 0 or 1. In some other embodiments, at least one of R$^3$ or R$^4$ is H. In some other embodiments, R$^3$ and R$^4$ are each H. In some other embodiments, at least one of R$^{10}$ or R$^{11}$ is methyl. In some other embodiments, R$^{10}$ and R$^{11}$ are each methyl. In yet other embodiments, A is an optionally substituted 6-membered carbocyclic ring and R$^2$ has the following structure:

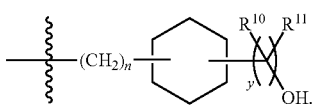

In some other embodiments of the foregoing, at least one of $R^{10}$ or $R^{11}$ is methyl. In some other embodiments, $R^{10}$ and $R^{11}$ are each methyl. In some embodiments y is 0 and in other embodiments y is 1.

In more specific embodiments $R_2$ has one of the following structures:

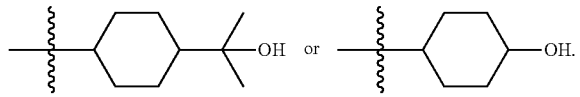

In even other embodiments, $R_2$ has one of the following structures:

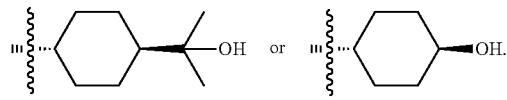

In still other embodiments of structures (III), (III-A), (III-B) or (III-C) above, $R_2$ is a 3, 4 or 5 membered carbocyclic ring and has one of the following structures:

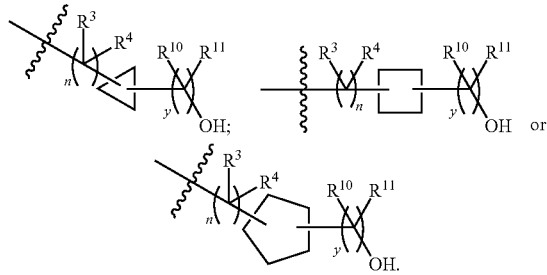

wherein $R^3$, $R^4$, $R^{10}$, $R^{11}$, n and y are as defined above.

In other embodiments of the foregoing, n is 0, and in other embodiments y is 0 or 1. In some other embodiments, at least one of $R^3$ or $R^4$ is H. In some other embodiments, $R^3$ and $R^4$ are each H. In some other embodiments, at least one of $R^{10}$ or $R^{11}$ is methyl. In some other embodiments, $R^{10}$ and $R^{11}$ are each methyl. In more specific aspects of structure (I) above, compounds are provided having structures set forth in Table I below (Compounds 8-1 to 8-45 and 8-70 to 8-93).

In more specific aspects of structure (II) above, compounds are provided having structures set forth in Table II below (Compounds 8-46 to 8-69 and 8-95 to 8-98).

In more specific aspects of structure (III) above, compounds are provided having structures set forth in Table III below (Compounds 8-99 to 8-113).

TABLE I

Illustrative Pim inhibitors.

| EX. | Structure |
| --- | --- |
| 8-1 | 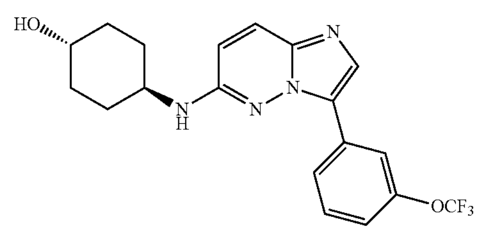 [SMILES: O[C@H]1CC[C@H](Nc2ccc3ncc(-c4cccc(OC(F)(F)F)c4)n3n2)CC1] |
| 8-2 | 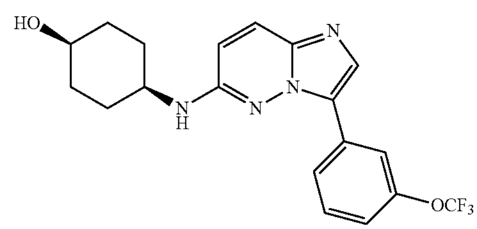 [SMILES: O[C@H]1CC[C@@H](Nc2ccc3ncc(-c4cccc(OC(F)(F)F)c4)n3n2)CC1] |
| 8-3 | 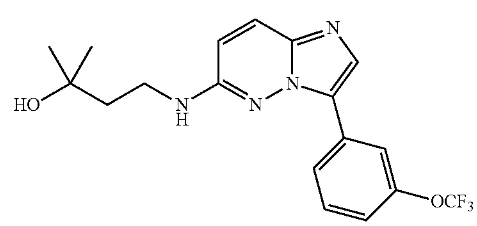 [SMILES: CC(C)(O)CCNc1ccc2ncc(-c3cccc(OC(F)(F)F)c3)n2n1] |

TABLE I-continued

Illustrative Pim inhibitors.

| EX. | Structure |
|---|---|
| 8-4 | 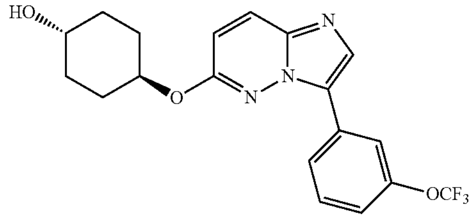 [SMILES: O[C@H]1CC[C@H](Oc2ccc3ncc(-c4cccc(OC(F)(F)F)c4)n3n2)CC1] |
| 8-5 | 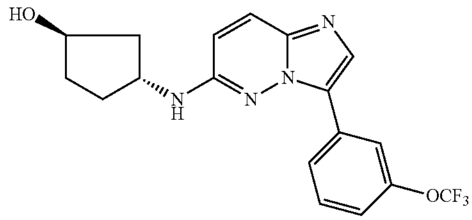 [SMILES: O[C@@H]1CC[C@@H](Nc2ccc3ncc(-c4cccc(OC(F)(F)F)c4)n3n2)C1] |
| 8-6 | 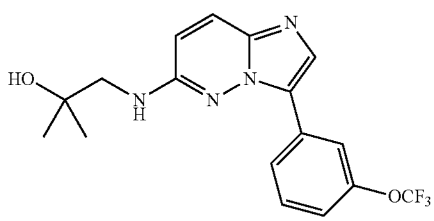 [SMILES: CC(C)(O)CNc1ccc2ncc(-c3cccc(OC(F)(F)F)c3)n2n1] |
| 8-7 | 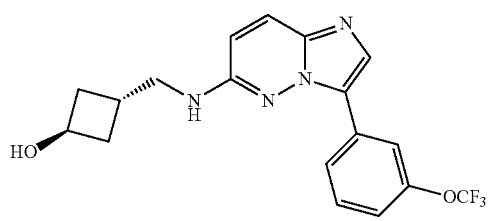 [SMILES: O[C@H]1C[C@H](CNc2ccc3ncc(-c4cccc(OC(F)(F)F)c4)n3n2)C1] |
| 8-8 | 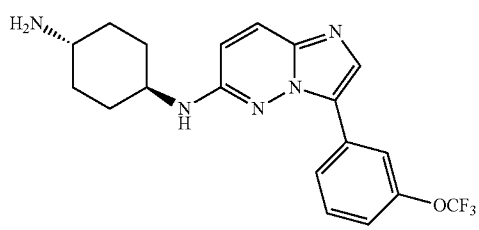 [SMILES: N[C@H]1CC[C@H](Nc2ccc3ncc(-c4cccc(OC(F)(F)F)c4)n3n2)CC1] |
| 8-9 | 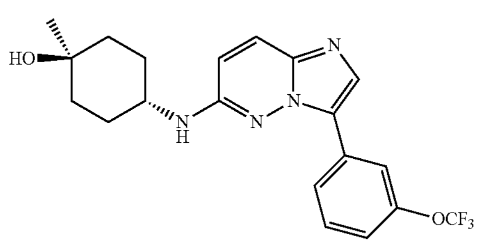 [SMILES: C[C@]1(O)CC[C@H](Nc2ccc3ncc(-c4cccc(OC(F)(F)F)c4)n3n2)CC1] |

TABLE I-continued

Illustrative Pim inhibitors.

| EX. | Structure |
|---|---|
| 8-10 | 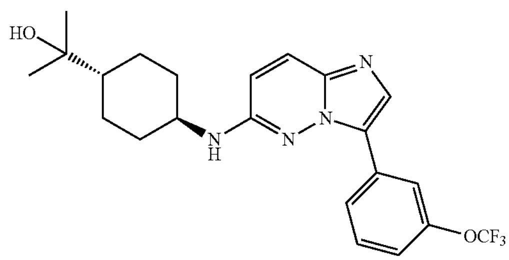 [SMILES: CC(C)(O)[C@H]1CC[C@H](Nc2ccc3ncc(-c4cccc(OC(F)(F)F)c4)n3n2)CC1] |
| 8-11 | 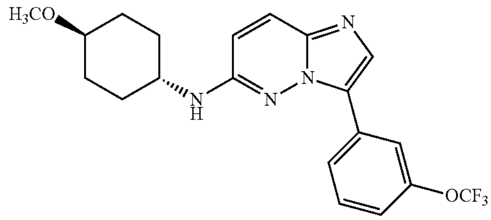 [SMILES: CO[C@H]1CC[C@H](Nc2ccc3ncc(-c4cccc(OC(F)(F)F)c4)n3n2)CC1] |
| 8-12 | 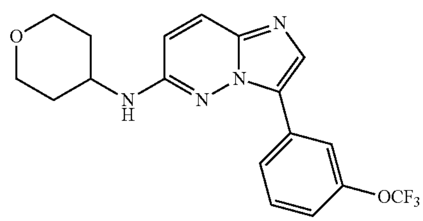 [SMILES: FC(F)(F)Oc1cccc(-c2cnc3ccc(NC4CCOCC4)nn23)c1] |
| 8-13 | 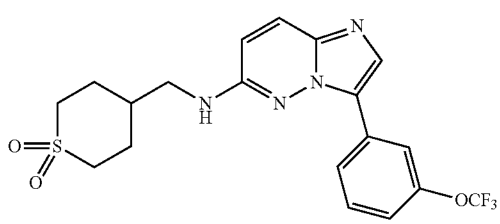 [SMILES: O=S1(=O)CCC(CNc2ccc3ncc(-c4cccc(OC(F)(F)F)c4)n3n2)CC1] |
| 8-14 | 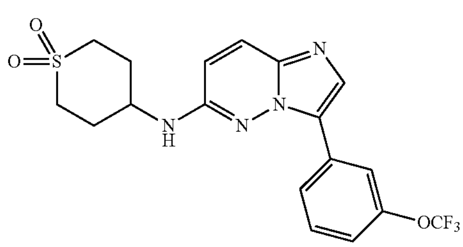 [SMILES: O=S1(=O)CCC(Nc2ccc3ncc(-c4cccc(OC(F)(F)F)c4)n3n2)CC1] |
| 8-15 | 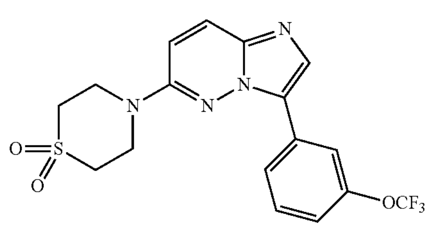 [SMILES: O=S1(=O)CCN(c2ccc3ncc(-c4cccc(OC(F)(F)F)c4)n3n2)CC1] |

TABLE I-continued

Illustrative Pim inhibitors.

| EX. | Structure |
|---|---|
| 8-16 | 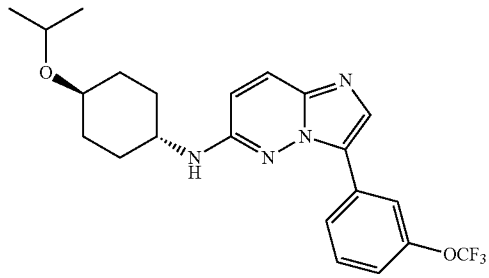 [SMILES: CC(C)O[C@H]1CC[C@H](Nc2ccc3ncc(-c4cccc(OC(F)(F)F)c4)n3n2)CC1] |
| 8-17 | 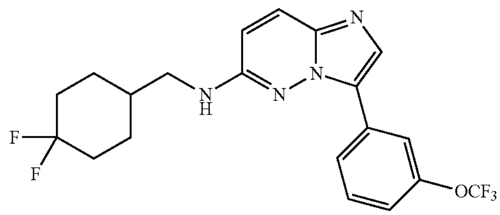 [SMILES: FC1(F)CCC(CNc2ccc3ncc(-c4cccc(OC(F)(F)F)c4)n3n2)CC1] |
| 8-18 | 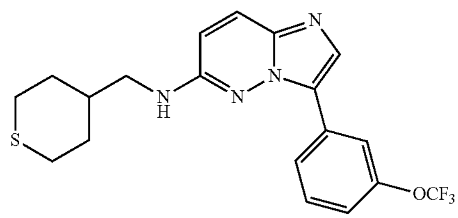 [SMILES: FC(F)(F)Oc1cccc(-c2cnc3ccc(NCC4CCSCC4)nn23)c1] |
| 8-19 | 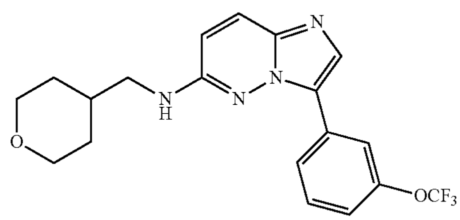 |
| 8-20 | 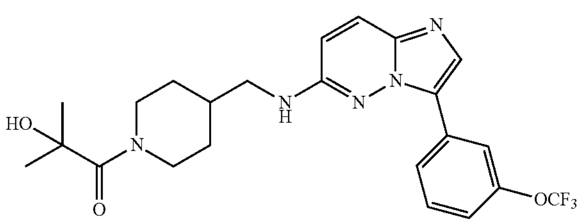 [SMILES: CC(C)(O)C(=O)N1CCC(CNc2ccc3ncc(-c4cccc(OC(F)(F)F)c4)n3n2)CC1] |
| 8-21 | 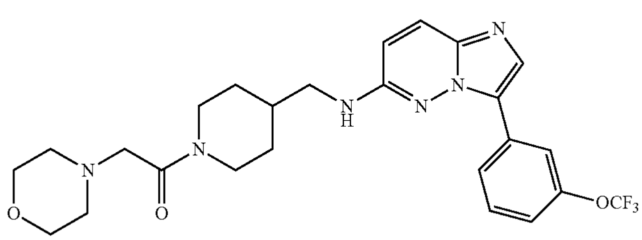 [SMILES: O=C(CN1CCOCC1)N1CCC(CNc2ccc3ncc(-c4cccc(OC(F)(F)F)c4)n3n2)CC1] |

TABLE I-continued

Illustrative Pim inhibitors.

| EX. | Structure |
|---|---|
| 8-22 | (1-methylpiperidin-4-ol with CH2-NH linker to imidazo[1,2-b]pyridazine bearing 3-(3-trifluoromethoxyphenyl)) |
| 8-23 | (2-oxopiperidin-4-yl)methyl-NH-imidazo[1,2-b]pyridazine-3-(3-trifluoromethoxyphenyl) |
| 8-24 | 4-(aminomethyl)-2-oxopiperidin-1-yl-imidazo[1,2-b]pyridazine-3-(3-trifluoromethoxyphenyl) |
| 8-25 | (3R)-3-aminopiperidin-1-yl-imidazo[1,2-b]pyridazine-3-(3-trifluoromethoxyphenyl) |
| 8-26 | trans-4-hydroxycyclohexyl-NH-imidazo[1,2-b]pyridazine-3-(3-cyanophenyl) |
| 8-27 | [1-(2-hydroxyethyl)piperidin-4-yl]methyl-NH-imidazo[1,2-b]pyridazine-3-(3-trifluoromethoxyphenyl) |
| 8-28 | (tetrahydro-2H-pyran-4-yl)methoxy-imidazo[1,2-b]pyridazine-3-(3-trifluoromethoxyphenyl) |

TABLE I-continued

Illustrative Pim inhibitors.

| EX. | Structure |
|---|---|
| 8-29 | 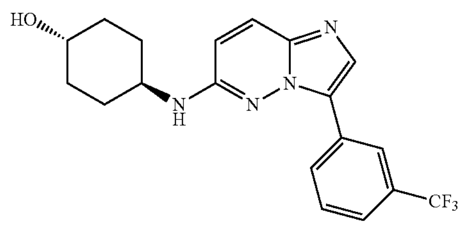 [SMILES: O[C@H]1CC[C@H](Nc2ccc3ncc(-c4cccc(C(F)(F)F)c4)n3n2)CC1] |
| 8-30 | 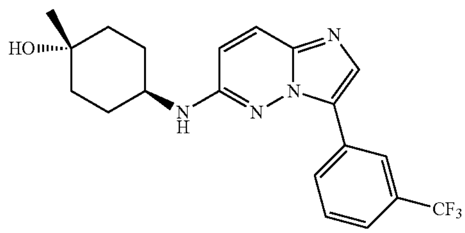 [SMILES: C[C@]1(O)CC[C@H](Nc2ccc3ncc(-c4cccc(C(F)(F)F)c4)n3n2)CC1] |
| 8-31 | 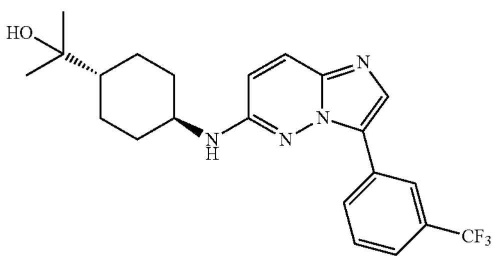 [SMILES: CC(C)(O)[C@H]1CC[C@H](Nc2ccc3ncc(-c4cccc(C(F)(F)F)c4)n3n2)CC1] |
| 8-32 | 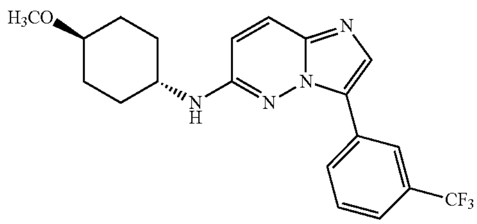 [SMILES: CO[C@H]1CC[C@H](Nc2ccc3ncc(-c4cccc(C(F)(F)F)c4)n3n2)CC1] |
| 8-33 | 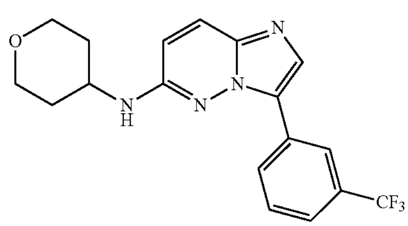 [SMILES: FC(F)(F)c1cccc(-c2cnc3ccc(NC4CCOCC4)nn23)c1] |
| 8-34 | 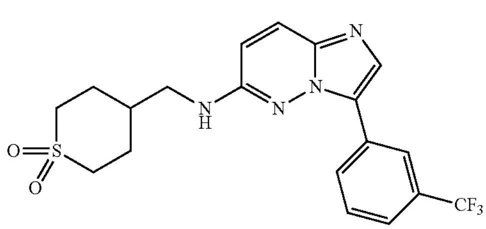 [SMILES: O=S1(=O)CCC(CNc2ccc3ncc(-c4cccc(C(F)(F)F)c4)n3n2)CC1] |

TABLE I-continued

Illustrative Pim inhibitors.

| EX. | Structure |
|---|---|
| 8-35 | 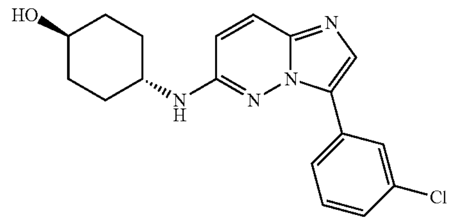 |
| 8-36 | 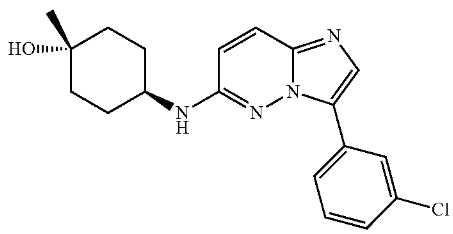 [SMILES: C[C@]1(O)CC[C@H](Nc2ccc3ncc(-c4cccc(Cl)c4)n3n2)CC1] |
| 8-37 | 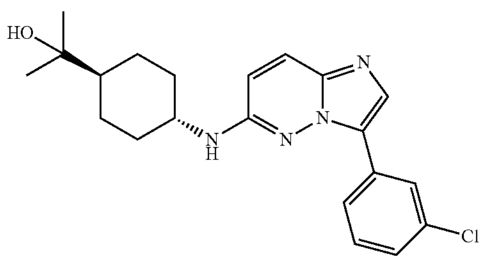 [SMILES: CC(C)(O)[C@H]1CC[C@H](Nc2ccc3ncc(-c4cccc(Cl)c4)n3n2)CC1] |
| 8-38 | 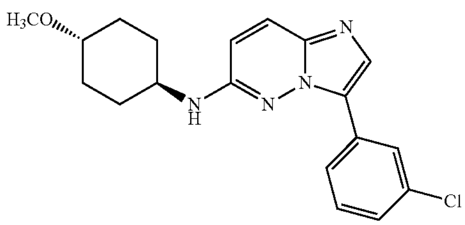 [SMILES: CO[C@H]1CC[C@H](Nc2ccc3ncc(-c4cccc(Cl)c4)n3n2)CC1] |
| 8-39 | 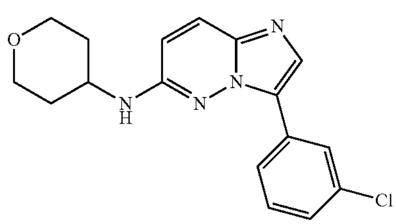 [SMILES: Clc1cccc(-c2cnc3ccc(NC4CCOCC4)nn23)c1] |
| 8-40 | 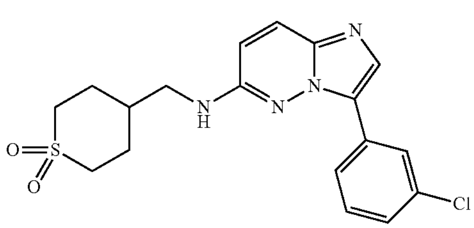 [SMILES: O=S1(=O)CCC(CNc2ccc3ncc(-c4cccc(Cl)c4)n3n2)CC1] |

TABLE I-continued

Illustrative Pim inhibitors.

| EX. | Structure |
|---|---|
| 8-41 | 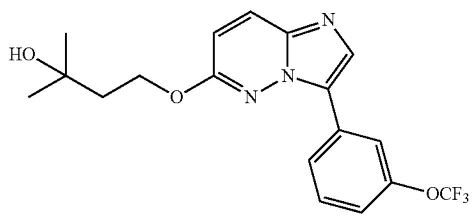 [SMILES: CC(C)(O)CCOc1ccc2ncc(-c3cccc(OC(F)(F)F)c3)n2n1] |
| 8-42 | 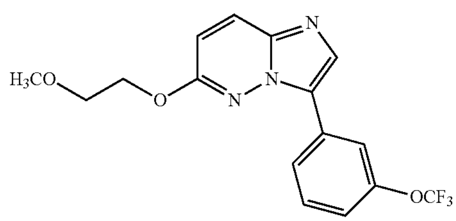 [SMILES: COCCOc1ccc2ncc(-c3cccc(OC(F)(F)F)c3)n2n1] |
| 8-43 | 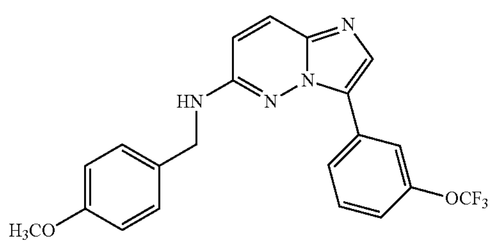 [SMILES: COc1ccc(CNc2ccc3ncc(-c4cccc(OC(F)(F)F)c4)n3n2)cc1] |
| 8-44 | 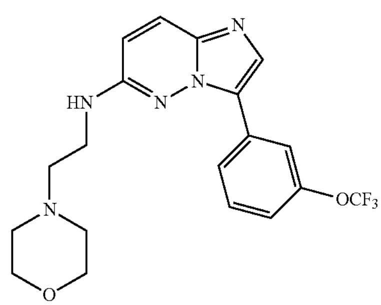 [SMILES: FC(F)(F)Oc1cccc(-c2cnc3ccc(NCCN4CCOCC4)nn23)c1] |
| 8-45 | 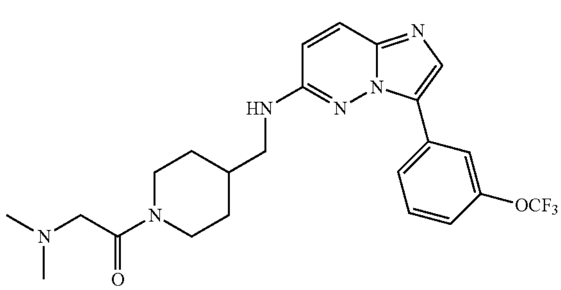 [SMILES: CN(C)CC(=O)N1CCC(CNc2ccc3ncc(-c4cccc(OC(F)(F)F)c4)n3n2)CC1] |
| 8-68 | 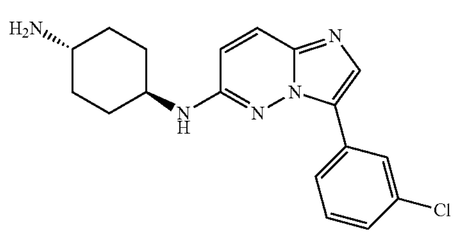 [SMILES: N[C@H]1CC[C@H](Nc2ccc3ncc(-c4cccc(Cl)c4)n3n2)CC1] |

TABLE I-continued

Illustrative Pim inhibitors.

| EX. | Structure |
|---|---|
| 8-70 | 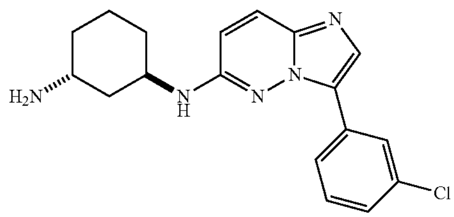 [SMILES: N[C@@H]1CCC[C@@H](Nc2ccc3ncc(-c4cccc(Cl)c4)n3n2)C1] |
| 8-71 | 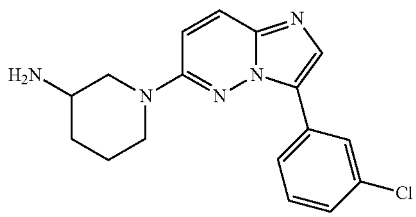 [SMILES: NC1CCCN(c2ccc3ncc(-c4cccc(Cl)c4)n3n2)C1] |
| 8-72 | 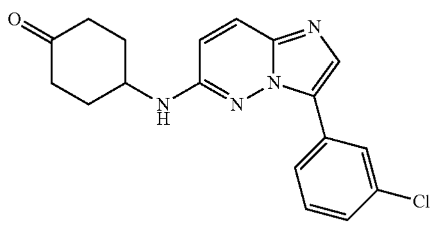 [SMILES: O=C1CCC(Nc2ccc3ncc(-c4cccc(Cl)c4)n3n2)CC1] |
| 8-73 | 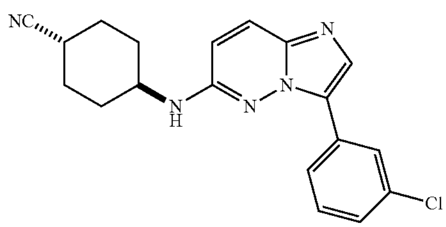 [SMILES: N#C[C@H]1CC[C@H](Nc2ccc3ncc(-c4cccc(Cl)c4)n3n2)CC1] |
| 8-75 | 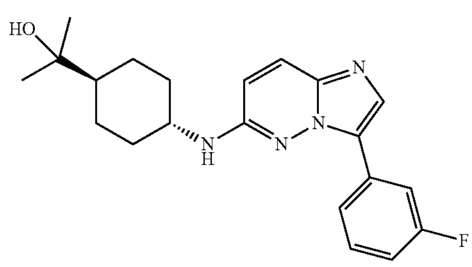 [SMILES: CC(C)(O)[C@H]1CC[C@H](Nc2ccc3ncc(-c4cccc(F)c4)n3n2)CC1] |
| 8-76 | 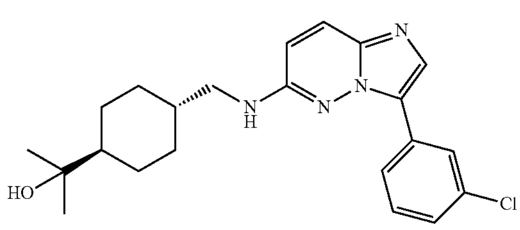 [SMILES: CC(C)(O)[C@H]1CC[C@H](CNc2ccc3ncc(-c4cccc(Cl)c4)n3n2)CC1] |

TABLE I-continued

Illustrative Pim inhibitors.

| EX. | Structure |
|---|---|
| 8-77 | 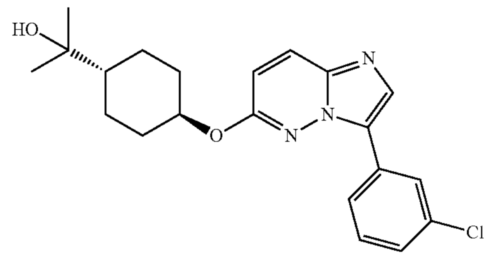 [SMILES: CC(C)(O)[C@H]1CC[C@H](Oc2ccc3ncc(-c4cccc(Cl)c4)n3n2)CC1] |
| 8-78 | 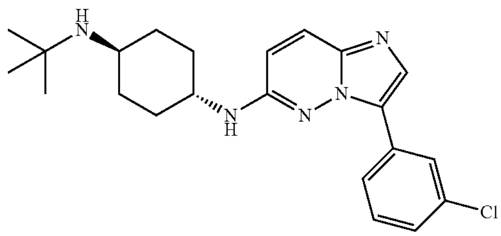 [SMILES: CC(C)(C)N[C@H]1CC[C@H](Nc2ccc3ncc(-c4cccc(Cl)c4)n3n2)CC1] |
| 8-79 | 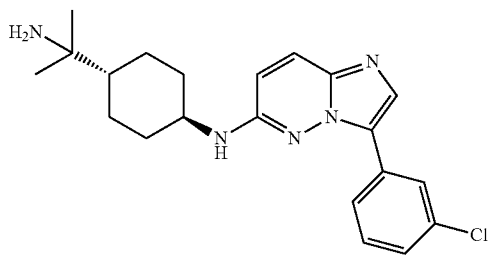 [SMILES: CC(C)(N)[C@H]1CC[C@H](Nc2ccc3ncc(-c4cccc(Cl)c4)n3n2)CC1] |
| 8-80 | 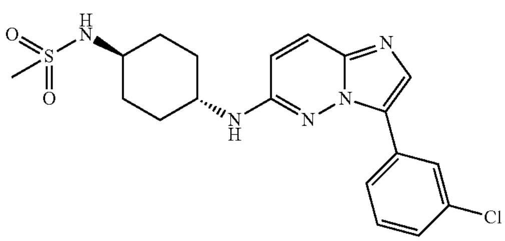 [SMILES: CS(=O)(=O)N[C@H]1CC[C@H](Nc2ccc3ncc(-c4cccc(Cl)c4)n3n2)CC1] |
| 8-81 | 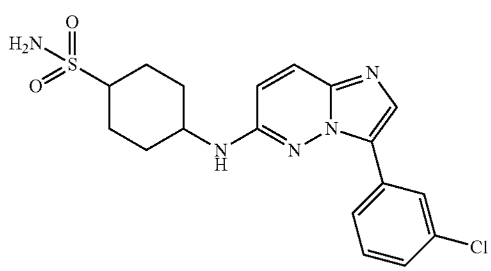 [SMILES: NS(=O)(=O)C1CCC(Nc2ccc3ncc(-c4cccc(Cl)c4)n3n2)CC1] |
| 8-82 | 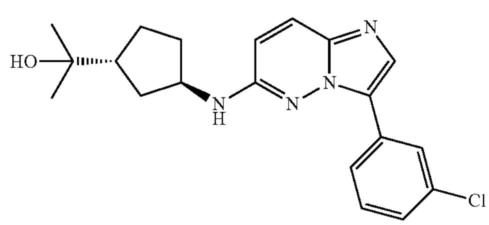 [SMILES: CC(C)(O)[C@@H]1CC[C@@H](Nc2ccc3ncc(-c4cccc(Cl)c4)n3n2)C1] |

TABLE I-continued

Illustrative Pim inhibitors.

| EX. | Structure |
|---|---|
| 8-83 | 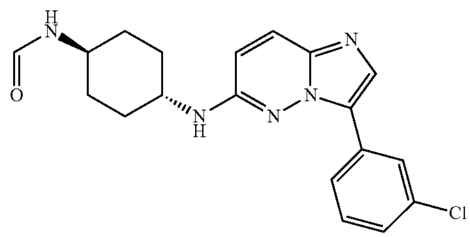 [SMILES: O=CN[C@H]1CC[C@H](Nc2ccc3ncc(-c4cccc(Cl)c4)n3n2)CC1] |
| 8-84 | 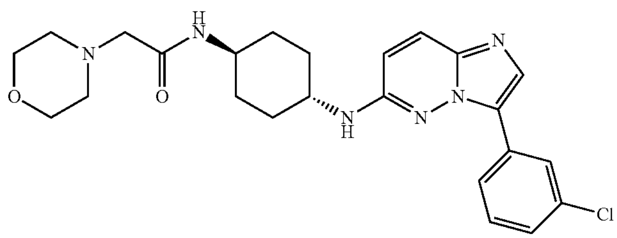 [SMILES: O=C(CN1CCOCC1)N[C@H]1CC[C@H](Nc2ccc3ncc(-c4cccc(Cl)c4)n3n2)CC1] |
| 8-85 | 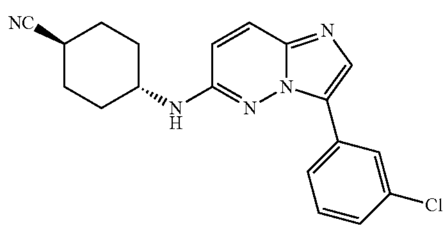 [SMILES: N#C[C@H]1CC[C@H](Nc2ccc3ncc(-c4cccc(Cl)c4)n3n2)CC1] |
| 8-86 | 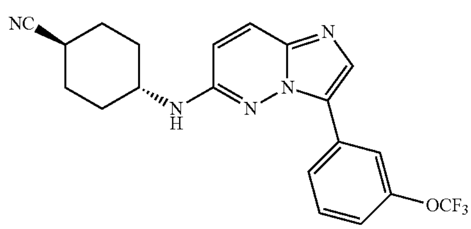 [SMILES: N#C[C@H]1CC[C@H](Nc2ccc3ncc(-c4cccc(OC(F)(F)F)c4)n3n2)CC1] |
| 8-87 | 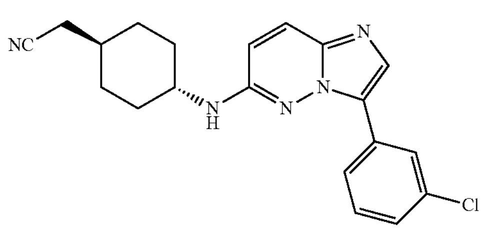 [SMILES: N#CC[C@H]1CC[C@H](Nc2ccc3ncc(-c4cccc(Cl)c4)n3n2)CC1] |
| 8-88 | 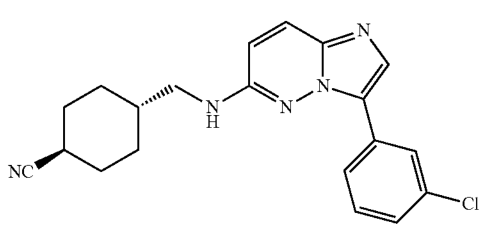 [SMILES: N#C[C@H]1CC[C@H](CNc2ccc3ncc(-c4cccc(Cl)c4)n3n2)CC1] |

TABLE I-continued

Illustrative Pim inhibitors.

| EX. | Structure |
|---|---|
| 8-89 | *(structure: N-(4-((3-(3-fluorophenyl)imidazo[1,2-b]pyridazin-6-yl)amino)cyclohexyl)methanesulfonamide)* |
| 8-90 | *(structure: N-(4-((3-(3-(trifluoromethyl)phenyl)imidazo[1,2-b]pyridazin-6-yl)amino)cyclohexyl)methanesulfonamide)* |
| 8-91 | *(structure: N-(4-((3-(3-(trifluoromethoxy)phenyl)imidazo[1,2-b]pyridazin-6-yl)amino)cyclohexyl)methanesulfonamide)* |
| 8-92 | *(structure: 4-((3-(3-chlorophenyl)imidazo[1,2-b]pyridazin-6-yl)amino)cyclohexan-1-one oxime)* |
| 8-93 | *(structure: 4-((3-(3-chlorophenyl)imidazo[1,2-b]pyridazin-6-yl)amino)cyclohexane-1-carboximidamide)* |

TABLE II

Illustrative Pim inhibitors.

| EX. | Structure |
|---|---|
| 8-46 | (4-hydroxycyclohexyl)amino-pyrazolo[1,5-a]pyrimidine with 3-(3-OCF₃-phenyl) |
| 8-47 | [4-(2-hydroxypropan-2-yl)cyclohexyl]amino-pyrazolo[1,5-a]pyrimidine with 3-(3-OCF₃-phenyl) |
| 8-48 | (4-hydroxy-4-methylcyclohexyl)amino-pyrazolo[1,5-a]pyrimidine with 3-(3-OCF₃-phenyl) |
| 8-49 | (4-methoxycyclohexyl)amino-pyrazolo[1,5-a]pyrimidine with 3-(3-OCF₃-phenyl) |
| 8-50 | (tetrahydropyran-4-yl)amino-pyrazolo[1,5-a]pyrimidine with 3-(3-OCF₃-phenyl) |
| 8-51 | [(1,1-dioxidotetrahydro-2H-thiopyran-4-yl)methyl]amino-pyrazolo[1,5-a]pyrimidine with 3-(3-OCF₃-phenyl) |

TABLE II-continued

Illustrative Pim inhibitors.

| EX. | Structure |
|---|---|
| 8-52 | (4-aminocyclohexyl)amino-pyrazolo[1,5-a]pyrimidine with 3-(3-OCF₃-phenyl) |
| 8-53 | (3-aminopiperidin-1-yl)-pyrazolo[1,5-a]pyrimidine with 3-(3-OCF₃-phenyl) |
| 8-54 | (4-hydroxycyclohexyl)amino-pyrazolo[1,5-a]pyrimidine with 3-(3-CF₃-phenyl) |
| 8-55 | (4-hydroxy-4-methylcyclohexyl)amino-pyrazolo[1,5-a]pyrimidine with 3-(3-CF₃-phenyl) |
| 8-56 | [4-(2-hydroxypropan-2-yl)cyclohexyl]amino-pyrazolo[1,5-a]pyrimidine with 3-(3-CF₃-phenyl) |
| 8-57 | (4-methoxycyclohexyl)amino-pyrazolo[1,5-a]pyrimidine with 3-(3-CF₃-phenyl) |

TABLE II-continued
Illustrative Pim inhibitors.
| EX. | Structure |
|---|---|
| 8-58 | 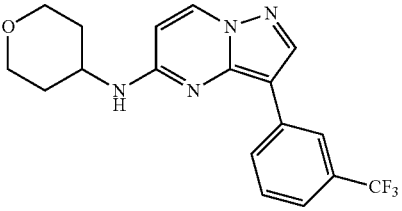 [SMILES: FC(F)(F)c1cccc(-c2cnn3ccc(NC4CCOCC4)nc23)c1] |
| 8-59 | 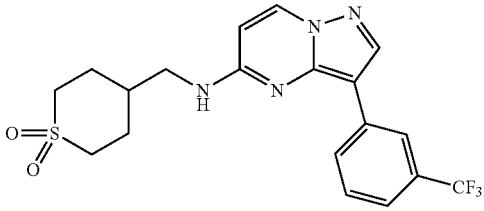 [SMILES: O=S1(=O)CCC(CNc2ccn3ncc(-c4cccc(C(F)(F)F)c4)c3n2)CC1] |
| 8-60 | 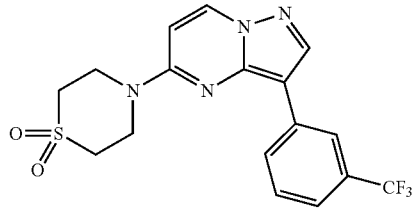 [SMILES: O=S1(=O)CCN(c2ccn3ncc(-c4cccc(C(F)(F)F)c4)c3n2)CC1] |
| 8-61 | 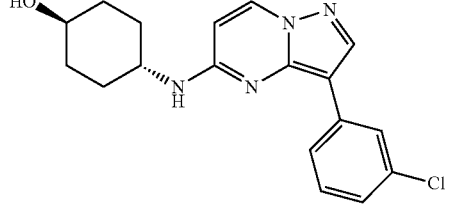 |
| 8-62 | 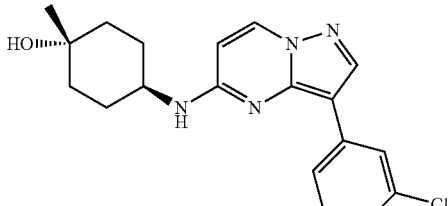 |
| 8-63 | 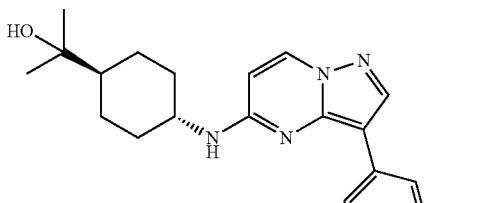 |
| 8-64 | 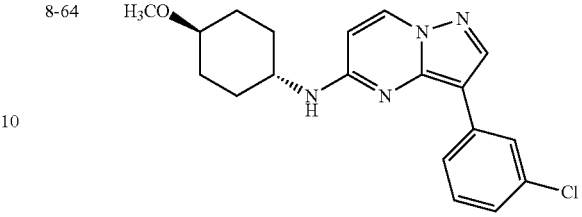 |
| 8-65 | 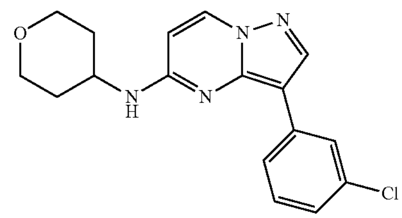 [SMILES: Clc1cccc(-c2cnn3ccc(NC4CCOCC4)nc23)c1] |
| 8-66 | 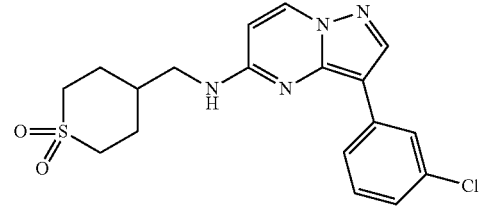 [SMILES: O=S1(=O)CCC(CNc2ccn3ncc(-c4cccc(Cl)c4)c3n2)CC1] |
| 8-67 | 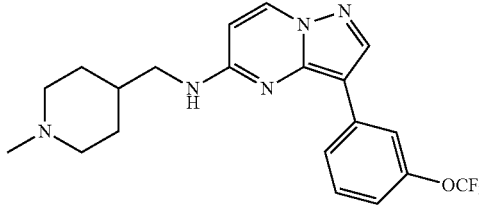 |
| 8-69 | 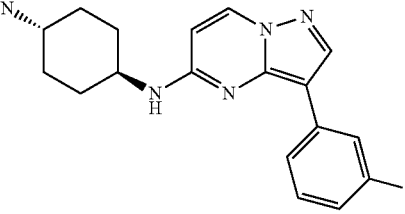 |
| 8-95 | 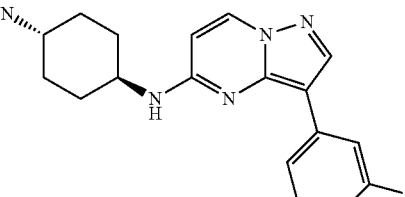 |
| 8-96 | 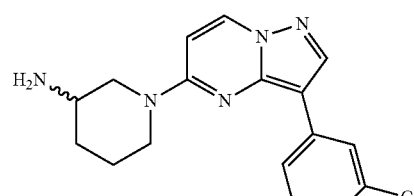 |

TABLE II-continued
Illustrative Pim inhibitors.
| EX. | Structure |
|---|---|
| 8-97 | 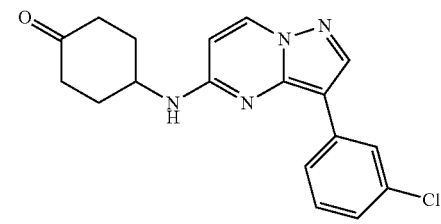 [SMILES: O=C1CCC(Nc2ccn3ncc(-c4cccc(Cl)c4)c3n2)CC1] |
| 8-98 | 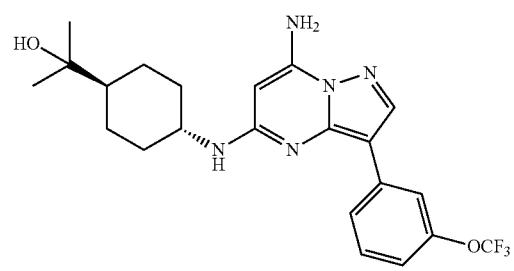 [SMILES: CC(C)(O)[C@H]1CC[C@H](Nc2cc(N)n3ncc(-c4cccc(OC(F)(F)F)c4)c3n2)CC1] |
TABLE III
Illustrative Pim inhibitors.
| EX. | Structure |
|---|---|
| 8-99 | 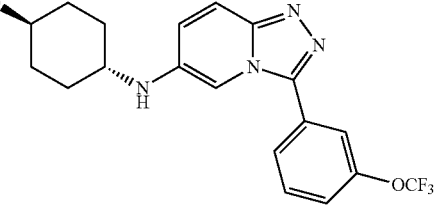 |
| 8-100 | 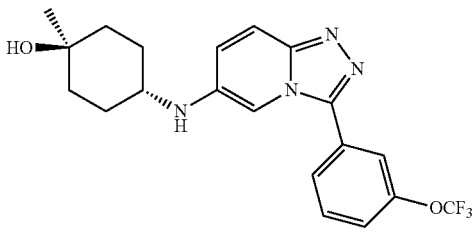 [SMILES: C[C@]1(O)CC[C@H](Nc2ccc3nnc(-c4cccc(OC(F)(F)F)c4)n3c2)CC1] |
| 8-101 | 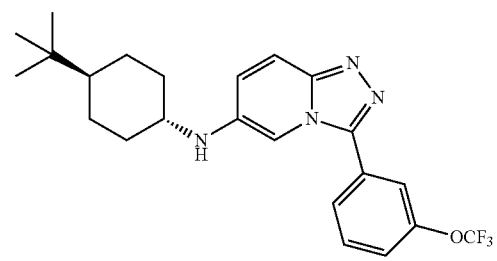 [SMILES: CC(C)(C)[C@H]1CC[C@H](Nc2ccc3nnc(-c4cccc(OC(F)(F)F)c4)n3c2)CC1] |
TABLE III-continued
Illustrative Pim inhibitors.
| EX. | Structure |
|---|---|
| 8-102 | 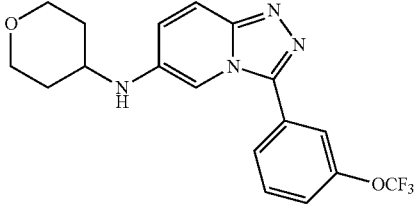 [SMILES: FC(F)(F)Oc1cccc(-c2nnc3ccc(NC4CCOCC4)cn23)c1] |
| 8-103 | 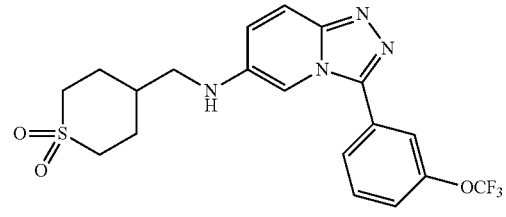 [SMILES: O=S1(=O)CCC(CNc2ccc3nnc(-c4cccc(OC(F)(F)F)c4)n3c2)CC1] |
| 8-104 | 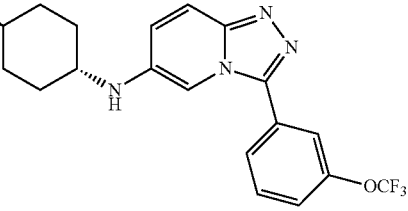 |
| 8-105 | 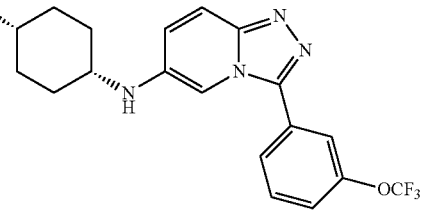 |
| 8-106 | 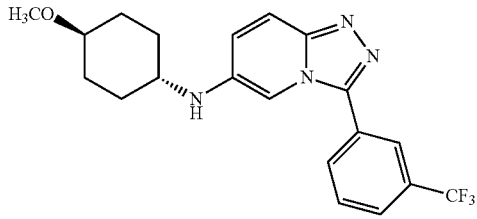 [SMILES: CO[C@H]1CC[C@H](Nc2ccc3nnc(-c4cccc(C(F)(F)F)c4)n3c2)CC1] |
| 8-107 | 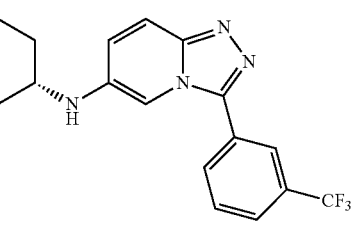 |

TABLE III-continued
Illustrative Pim inhibitors.
| EX. | Structure |
|---|---|
| 8-108 | 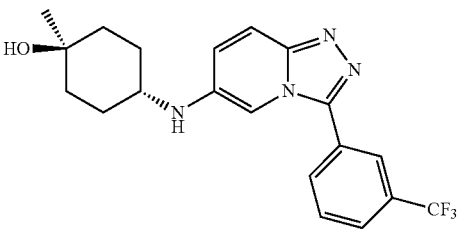 [SMILES: C[C@]1(O)CC[C@H](Nc2ccc3nnc(-c4cccc(C(F)(F)F)c4)n3c2)CC1] |
| 8-109 | 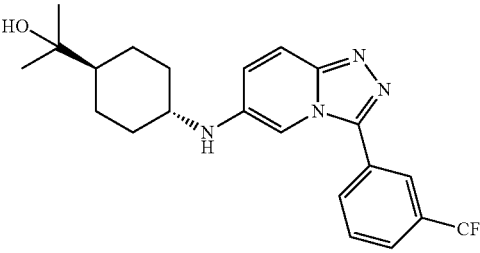 |
| 8-110 | 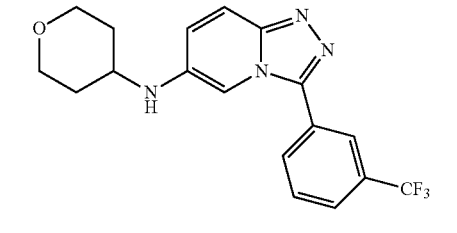 [SMILES: FC(F)(F)c1cccc(-c2nnc3ccc(NC4CCOCC4)cn23)c1] |
| 8-111 | 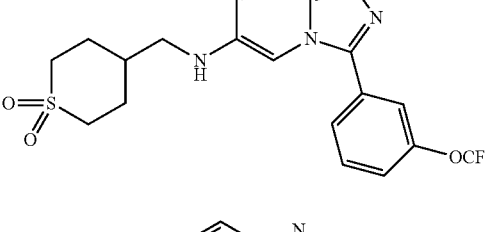 |
| 8-112 | 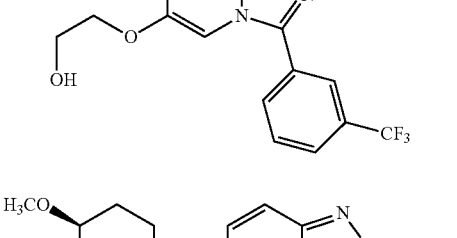 |
| 8-113 | 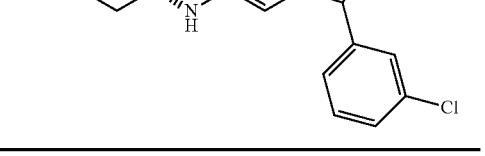 |
In certain embodiments, the compound of structure (I-D) or (II-D) has one of the following structures:
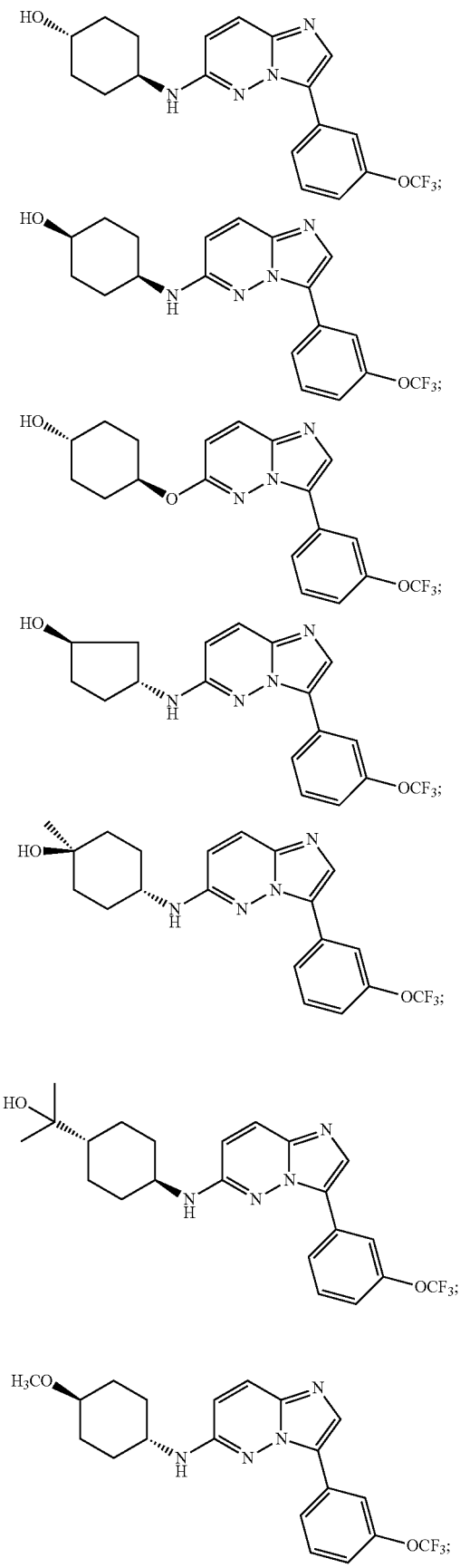

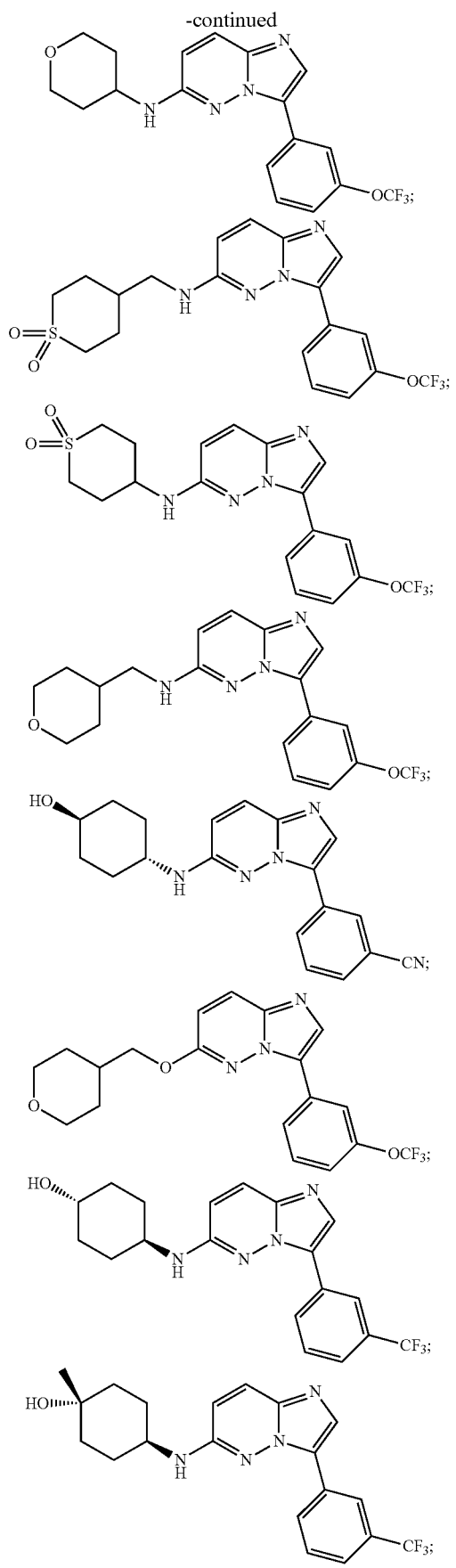
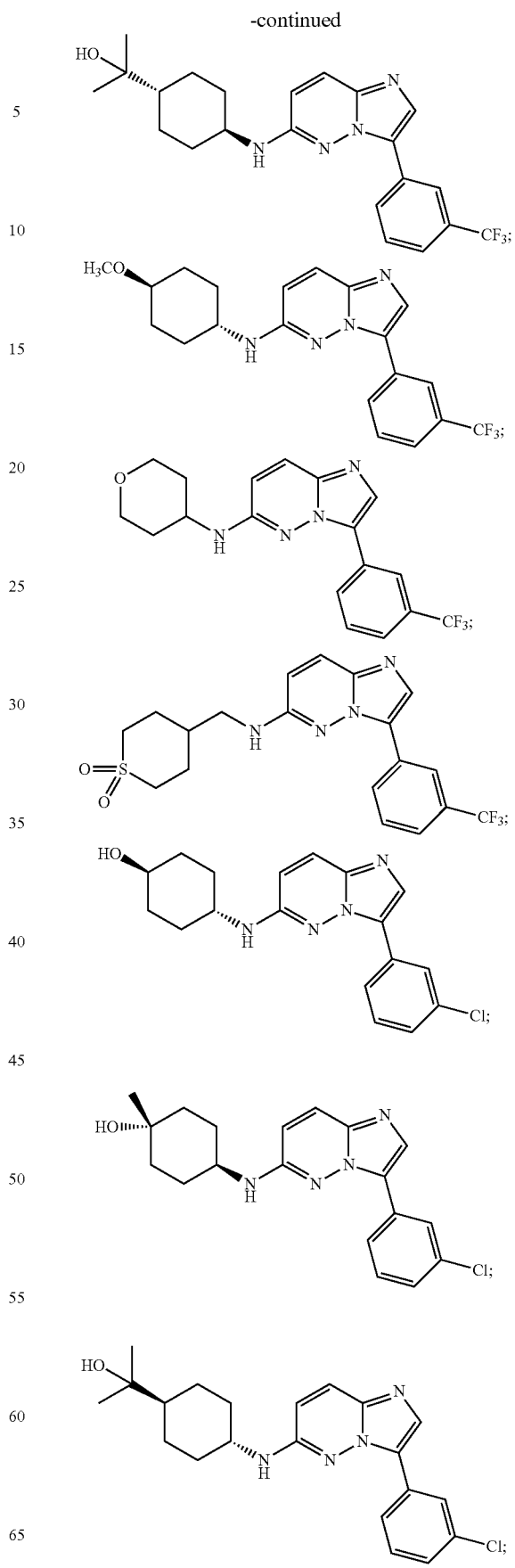

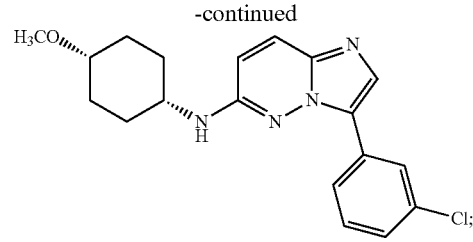
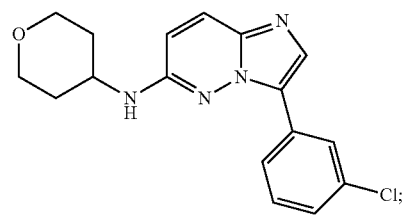
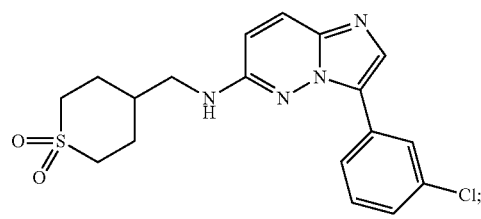 [SMILES: O=S1(=O)CCC(CNc2ccn3ncc(-c4cccc(Cl)c4)c3n2)CC1]
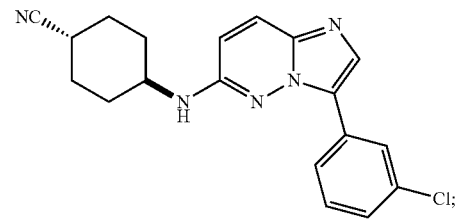
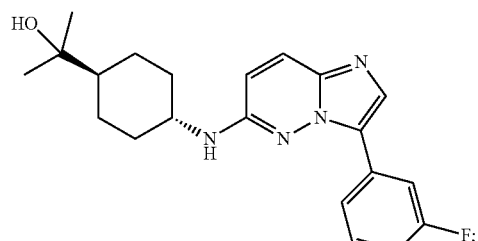
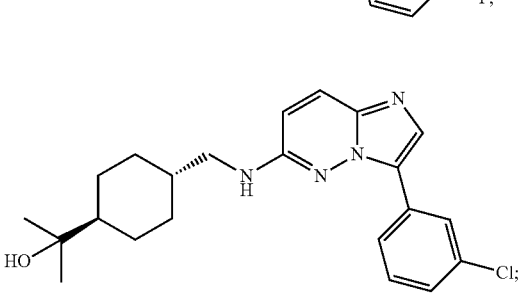
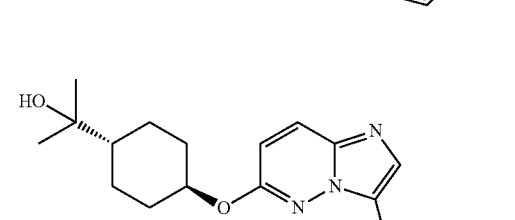
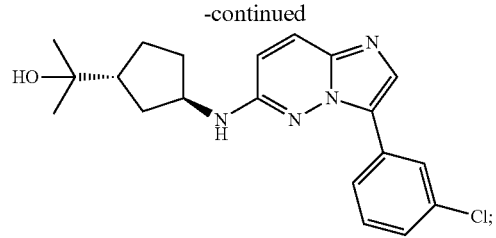
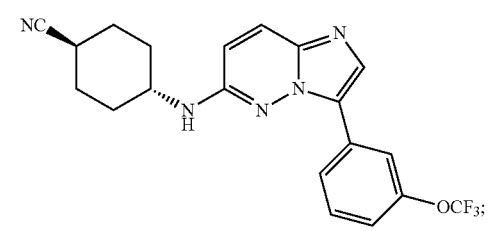
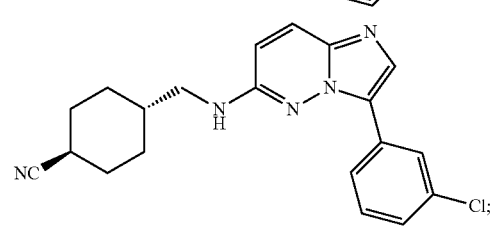
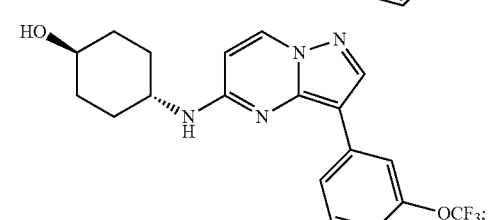
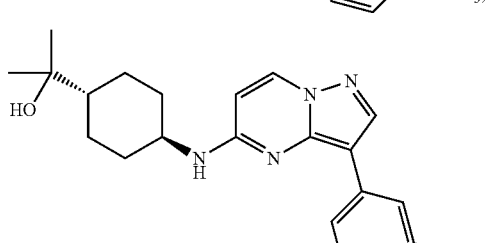
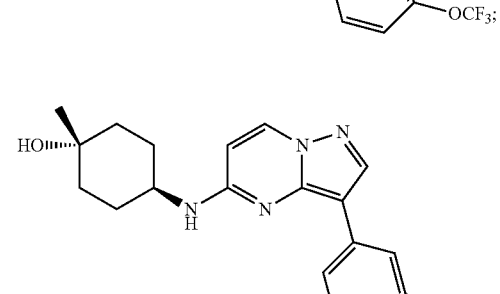
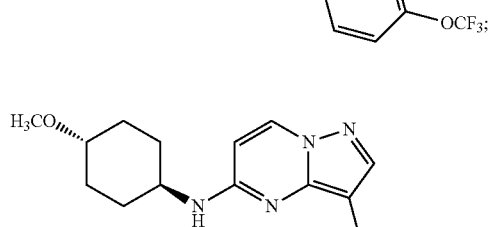

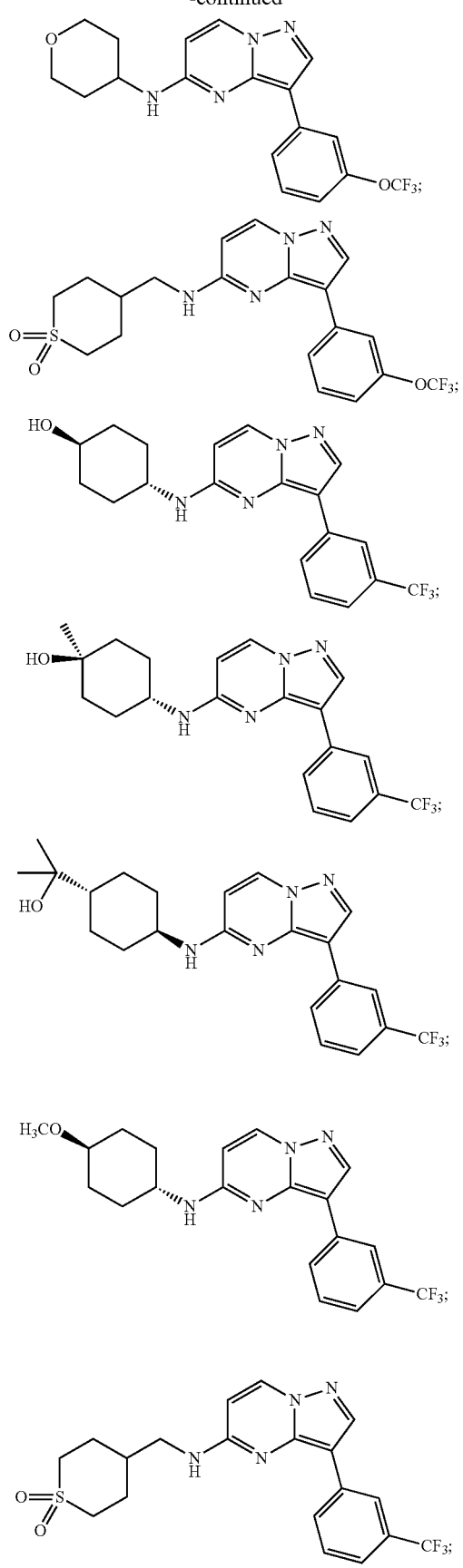
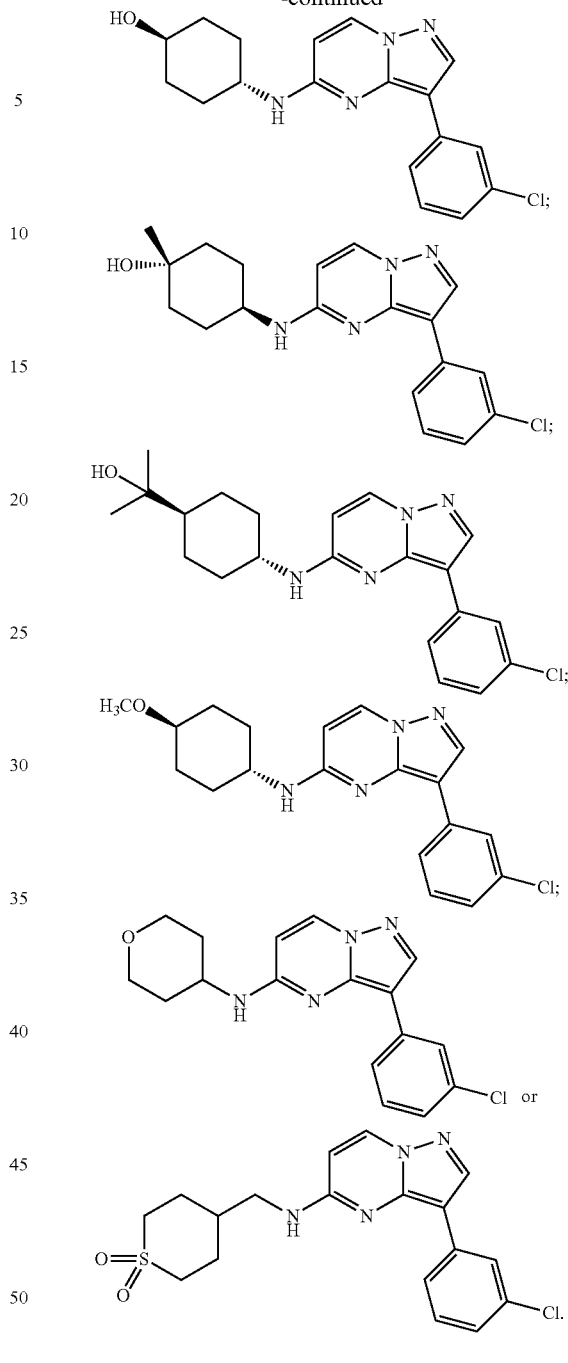

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog (Cahn, R., Ingold, C., and Prelog, V. Angew. Chem. 78:413-47, 1966; Angew.

Chem. Internat. Ed. Eng. 5:385-415, 511, 1966), or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Ch. 4 of ADVANCED ORGANIC CHEMISTRY, 4$^{th}$ edition, March, J., John Wiley and Sons, New York City, 1992).

The compounds of the present invention may exhibit the phenomena of tautomerism and structural isomerism. For example, the compounds described herein may adopt an E or a Z configuration about the double bond connecting the 2-indolinone moiety to the pyrrole moiety or they may be a mixture of E and Z. This invention encompasses any tautomeric or structural isomeric form and mixtures thereof which possess the ability to modulate aurora-2 kinase activity and is not limited to, any one tautomeric or structural isomeric form.

It is contemplated that a compound of the present invention would be metabolized by enzymes in the body of the organism such as human being to generate a metabolite that can modulate the activity of the protein kinases. Such metabolites are within the scope of the present invention.

Compounds of the present invention can be prepared according to methods known to those of ordinary skill in the art, including the methods exemplified in the examples. In a general sense, compounds of structure (I) can be prepared according to General Reaction Scheme I.

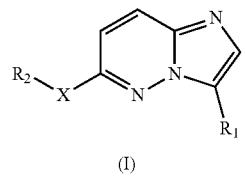

(I)

Referring to General Reaction Scheme I, compounds of structure (a), wherein R is as defined above and LG represents an appropriate leaving groups (e.g., chloro, bromo and the like) can be purchased or prepared according to methods known in the art. Reaction of (a) with an activated aldehyde, such as 2-bromoacetaldehyde, yields fused bycyclic compounds of structure (b). Activation of an aryl carbon of (b), for example by treatment with bromine, results in (c), wherein "Act" is an activating group such as bromine. Arylation of (c) with R1-Y, wherein Y is an appropriate activating group) under appropriate conditions (e.g., Suzuki coupling, wherein Y is boronic acid) yields (d). Finally, treatment of (d) with $R_2$—XH, wherein R2 and X are as defined herein, results in compounds of structure (I). In certain embodiments, a catalyst, such as palladium (e.g., Buchwald catalysts and the like), may be useful to effect the coupling of $R_2$—Z and (d). Optional oxidation or alkylation using methods known in the art are used to produce compounds having various X moieties.

Compounds of structure (II) can be prepared according to methods known to those of ordinary skill in the art, including the methods exemplified in the examples. A general preparation method for compounds of structure (II) is depicted in General Reaction Scheme II.

General Reaction Scheme I

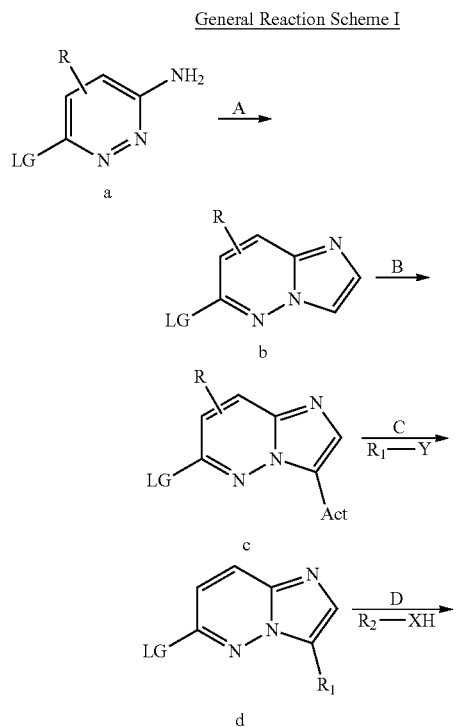

General Reaction Scheme II

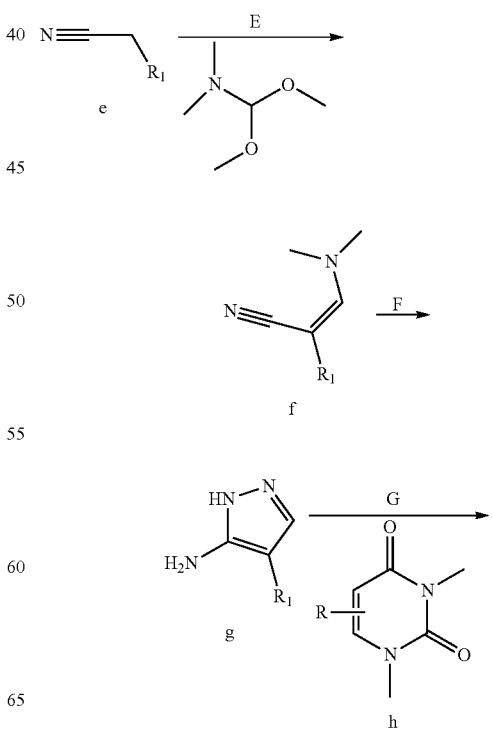

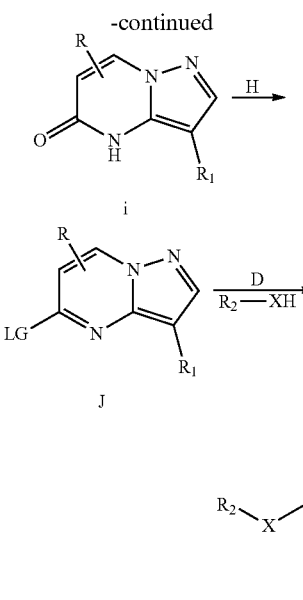

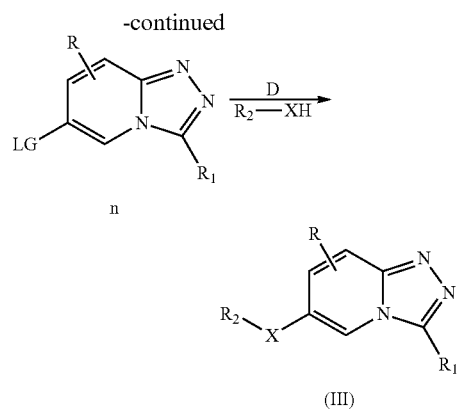

One skilled in the art will recognize that the above General Reaction Schemes I, II and III may be modified at any number of steps and the order of steps may be changed. In addition, protecting groups and other strategies well known to one of ordinary skill in the art may be employed, even if not specifically described herein.

In reference to General reaction Scheme II, nitriles of structure (e) can be treated with amino acetals under basic conditions to yield (f). Compounds of structure (f) may then be reacted with hydrazine under acidic conditions (e.g., acetic acid) to yield pyrazoles of structure (g). (g) can then be cyclized by treatment with h in the presence of a base (e.g., sodium ethoxide) to yield (i). Reduction of (i) with an appropriate reagent (e.g., POCl3) yields (j), wherein LG is an appropriate leaving group (e.g., halogen such as chloro or bromo). Finally, compounds of structure (II) are prepared as described for step D in General Reaction Scheme (I).

Compounds of structure (III) may be prepared according to General Reaction Scheme III. Compounds of structure k, wherein LG represents an appropriate leaving group such as bromine, may be purchased from commercial sources or prepared according to methods known in the art and/or described herein. Reaction of k with an appropriate halo acid (e.g., acid chloride) results in compounds of structure m. Cyclization of m by treatment under dehydrating conditions (e.g., acetic acid/HCl) results in compounds of structure n. Finally, compounds of structure (III) are obtained as described for step D in General Reaction Scheme (I).

The present inventors have discovered that compounds of the present invention may be prepared at large scales (e.g., greater than 50 g) according to the general procedures described above. Accordingly, in some specific embodiments, the present invention is directed to a method for preparing a compound having the following structure (ID):

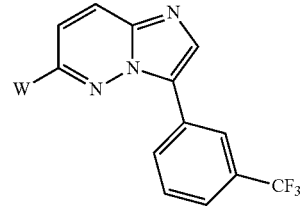

or a salt thereof, wherein W is

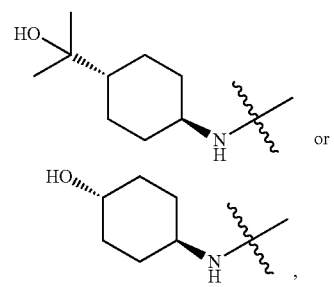

the method comprising:
a) reacting W—H with a compound of structure (A):

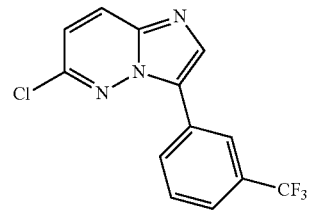

in the presence of CsF; and
b) isolating (ID) as a solid,
wherein W—H indicates a W radical (as defined above) having a hydrogen atom completing its valence.

General Reaction Scheme III

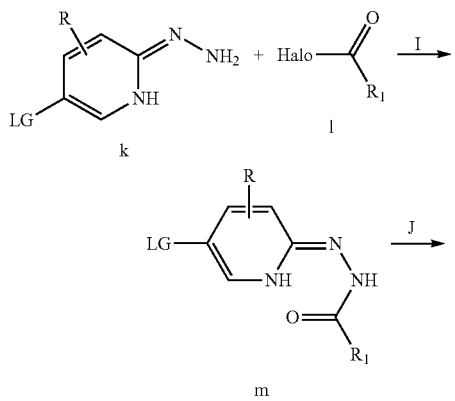

In certain embodiments of the foregoing method, W—H and (A) are reacted in the presence of a base. For example, in some embodiments the base is Diisopropylethylamine.

In other embodiments, (A) has been prepared by reaction of (B) and (C):

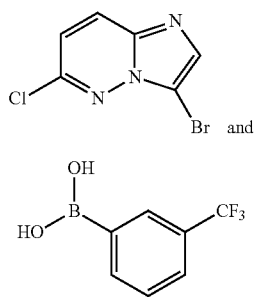

in the presence of a palladium catalyst and a base. For example, the palladium catalyst may be Pd(PPh$_3$)$_4$ and/or the base may be potassium carbonate.

In certain other embodiments, the method further comprises treating the solid with an acid to obtain a salt of (ID). In some embodiments, the acid is HCl, maleic acid or methane sulfonic acid.

Some embodiments of the foregoing method further comprise recrystallizing the solid in a solvent, for example methanol.

In certain specific embodiments, wherein W is H

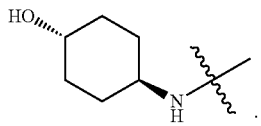 [SMILES: *N[C@H]1CC[C@H](O)CC1]

In other embodiments, W is H

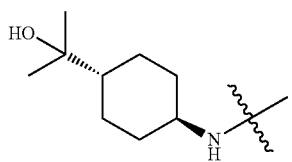

In still other embodiments, W—H is prepared by a method comprising alkylation of

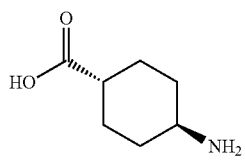

or a carboxy or amino protected derivative or a salt thereof. For example, alkylation may comprise reaction with a methylmagnesium halide compound such as methylmagnesium chloride, methylmagnesium bromide or methylmagnesium iodide.

In even other embodiments, (ID) is prepared at scales of 50 grams or higher.

A compound of the present invention or a pharmaceutically acceptable salt thereof, can be administered as such to a human patient or can be administered in pharmaceutical compositions in which the foregoing materials are mixed with suitable carriers or excipient(s). Techniques for formulation and administration of drugs may be found, for example, in REMINGTON'S PHARMACOLOGICAL SCIENCES, Mack Publishing Co., Easton, Pa., latest edition.

A "pharmaceutical composition" refers to a mixture of one or more of the compounds described herein, or pharmaceutically acceptable salts or prodrugs thereof, with other chemical components, such as pharmaceutically acceptable excipients. The purpose of a pharmaceutical composition is to facilitate administration of a compound to an organism.

"Pharmaceutically acceptable excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

"Pharmaceutically acceptable salt" refers to those salts which retain the biological effectiveness and properties of the parent compound. Such salts may include: (1) acid addition salt which is obtained by reaction of the free base of the parent compound with inorganic acids such as hydrochloric acid, hydrobromic acid, nitric acid, phosphoric acid, sulfuric acid, and perchloric acid and the like, or with organic acids such as acetic acid, oxalic acid, (D)- or (L)-malic acid, maleic acid, methanesulfonic acid, ethanesulfonic acid, p-toluenesulfonic acid, salicylic acid, tartaric acid, citric acid, succinic acid, glutamic acid or malonic acid and the like, preferably hydrochloric acid or (L)-malic acid; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

The compounds of the present invention (I.e., compounds (I), (II) and/or (III) may also act, or be designed to act, as a prodrug. A "prodrug" refers to an agent, which is converted into the parent drug in vivo. Prodrugs are often useful because, in some situations, they may be easier to administer than the parent drug. They may, for instance, be bioavailable by oral administration whereas the parent drug is not. The prodrug may also have improved solubility in pharmaceutical compositions over the parent drug. An example, without limitation, of a prodrug would be a compound of the present invention, which is, administered as an ester (the "prodrug"), phosphate, amide, carbamate or urea.

"Therapeutically effective amount" refers to that amount of the compound being administered which will relieve to some extent one or more of the symptoms of the disorder being treated. In reference to the treatment of cancer, a therapeutically effective amount refers to that amount which has the effect of: (1) reducing the size of the tumor; (2) inhibiting tumor metastasis; (3) inhibiting tumor growth; and/or (4) relieving one or more symptoms associated with the cancer.

The term "protein kinase-mediated condition" or "disease", as used herein, means any disease or other deleterious condition in which a protein kinase is known to play a role. The term "protein kinase-mediated condition" or "disease" also means those diseases or conditions that are alleviated by treatment with a protein kinase inhibitor. Such conditions include, without limitation, cancers which express Pim kinases, particularly Pim-1 kinase, and other hyperproliferative disorders associated with Pim kinase expression. In certain embodiments, the cancer is a cancer of colon, breast, stomach, prostate, pancreas, or ovarian tissue.

The term "Pim kinase-mediated condition" or "disease", as used herein, means any disease or other deleterious condition in which Pim 1 kinase, Pim 2 Kinase and/or Pim 3 kinase is known to be expressed and/or play a role. The term "Pim kinase-mediated condition" or "disease" also means those diseases or conditions that are alleviated by treatment with an Pim kinase inhibitor.

As used herein, "administer" or "administration" refers to the delivery of an inventive compound or of a pharmaceutically acceptable salt thereof or of a pharmaceutical composition containing an inventive compound or a pharmaceutically acceptable salt thereof of this invention to an organism for the purpose of prevention or treatment of a protein kinase-related disorder.

Suitable routes of administration may include, without limitation, oral, rectal, transmucosal or intestinal administration or intramuscular, subcutaneous, intramedullary, intrathecal, direct intraventricular, intravenous, intravitreal, intraperitoneal, intranasal, or intraocular injections. In certain embodiments, the preferred routes of administration are oral and intravenous.

Alternatively, one may administer the compound in a local rather than systemic manner, for example, via injection of the compound directly into a solid tumor, often in a depot or sustained release formulation.

Furthermore, one may administer the drug in a targeted drug delivery system, for example, in a liposome coated with tumor-specific antibody. In this way, the liposomes may be targeted to and taken up selectively by the tumor.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention may be formulated in any conventional manner using one or more physiologically acceptable carriers comprising excipients and auxiliaries which facilitate processing of the active compounds into preparations which can be used pharmaceutically. Proper formulation is dependent upon the route of administration chosen.

For injection, the compounds of the invention may be formulated in aqueous solutions, preferably in physiologically compatible buffers such as Hanks' solution, Ringer's solution, or physiological saline buffer. For transmucosal administration, penetrants appropriate to the barrier to be permeated are used in the formulation. Such penetrants are generally known in the art.

For oral administration, the compounds can be formulated by combining the active compounds with pharmaceutically acceptable carriers well known in the art. Such carriers enable the compounds of the invention to be formulated as tablets, pills, lozenges, dragees, capsules, liquids, gels, syrups, slurries, suspensions and the like, for oral ingestion by a patient. Pharmaceutical preparations for oral use can be made using a solid excipient, optionally grinding the resulting mixture, and processing the mixture of granules, after adding other suitable auxiliaries if desired, to obtain tablets or dragee cores. Useful excipients are, in particular, fillers such as sugars, including lactose, sucrose, mannitol, or sorbitol, cellulose preparations such as, for example, maize starch, wheat starch, rice starch and potato starch and other materials such as gelatin, gum tragacanth, methyl cellulose, hydroxypropylm ethyl-cellulose, sodium carboxymethylcellulose, and/or polyvinyl-pyrrolidone (PVP). If desired, disintegrating agents may be added, such as cross-linked polyvinyl pyrrolidone, agar, or alginic acid. A salt such as sodium alginate may also be used.

Dragee cores are provided with suitable coatings. For this purpose, concentrated sugar solutions may be used which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical compositions which can be used orally include push-fit capsules made of gelatin, as well as soft, sealed capsules made of gelatin and a plasticizer, such as glycerol or sorbitol. The push-fit capsules can contain the active ingredients in admixture with a filler such as lactose, a binder such as starch, and/or a lubricant such as talc or magnesium stearate and, optionally, stabilizers. In soft capsules, the active compounds may be dissolved or suspended in suitable liquids, such as fatty oils, liquid paraffin, or liquid polyethylene glycols. Stabilizers may be added in these formulations, also. Pharmaceutical compositions which may also be used include hard gelatin capsules. The capsules or pills may be packaged into brown glass or plastic bottles to protect the active compound from light. The containers containing the active compound capsule formulation are preferably stored at controlled room temperature (15-30° C.).

For administration by inhalation, the compounds for use according to the present invention may be conveniently delivered in the form of an aerosol spray using a pressurized pack or a nebulizer and a suitable propellant, e.g., without limitation, dichlorodifluoromethane, trichlorofluoromethane, dichlorotetra-fluoroethane or carbon dioxide. In the case of a pressurized aerosol, the dosage unit may be controlled by providing a valve to deliver a metered amount. Capsules and cartridges of, for example, gelatin for use in an inhaler or insufflator may be formulated containing a powder mix of the compound and a suitable powder base such as lactose or starch.

The compounds may also be formulated for parenteral administration, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulating materials such as suspending, stabilizing and/or dispersing agents.

Pharmaceutical compositions for parenteral administration include aqueous solutions of a water soluble form, such as, without limitation, a salt, of the active compound. Additionally, suspensions of the active compounds may be prepared in a lipophilic vehicle. Suitable lipophilic vehicles include fatty oils such as sesame oil, synthetic fatty acid esters such as ethyl oleate and triglycerides, or materials such as liposomes. Aqueous injection suspensions may contain substances which increase the viscosity of the suspension, such as sodium carboxymethyl cellulose, sorbitol, or dextran. Optionally, the suspension may also contain suitable stabilizers and/or agents that increase the solubility of the compounds to allow for the preparation of highly concentrated solutions.

Alternatively, the active ingredient may be in powder form for constitution with a suitable vehicle, e.g., sterile, pyrogen-free water, before use.

The compounds may also be formulated in rectal compositions such as suppositories or retention enemas, using, e.g., conventional suppository bases such as cocoa butter or other glycerides.

In addition to the formulations described previously, the compounds may also be formulated as depot preparations. Such long acting formulations may be administered by implantation (for example, subcutaneously or intramuscularly) or by intramuscular injection. A compound of this invention may be formulated for this route of administration with suitable polymeric or hydrophobic materials (for instance, in an emulsion with a pharmacologically acceptable oil), with ion exchange resins, or as a sparingly soluble derivative such as, without limitation, a sparingly soluble salt.

A non-limiting example of a pharmaceutical carrier for the hydrophobic compounds of the invention is a cosolvent system comprising benzyl alcohol, a nonpolar surfactant, a water-miscible organic polymer and an aqueous phase such as the VPD cosolvent system. VPD is a solution of 3% w/v benzyl alcohol, 8% w/v of the nonpolar surfactant polysorbate 80, and 65% w/v polyethylene glycol 300, made up to volume in absolute ethanol. The VPD cosolvent system (VPD:D5W) consists of VPD diluted 1:1 with a 5% dextrose in water solution. This cosolvent system dissolves hydrophobic compounds well, and itself produces low toxicity upon systemic administration. Naturally, the proportions of such a cosolvent system may be varied considerably without destroying its solubility and toxicity characteristics. Furthermore, the identity of the cosolvent components may be varied: for example, other low-toxicity nonpolar surfactants may be used instead of polysorbate 80, the fraction size of polyethylene glycol may be varied, other biocompatible polymers may replace polyethylene glycol, e.g., polyvinyl pyrrolidone, and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. In addition, certain organic solvents such as dimethylsulfoxide also may be employed, although often at the cost of greater toxicity.

Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions herein also may comprise suitable solid or gel phase carriers or excipients. Examples of such carriers or excipients include, but are not limited to, calcium carbonate, calcium phosphate, various sugars, starches, cellulose derivatives, gelatin, and polymers such as polyethylene glycols.

Many of the protein kinase-modulating compounds of the invention may be provided as physiologically acceptable salts wherein the claimed compound may form the negatively or the positively charged species. Examples of salts in which the compound forms the positively charged moiety include, without limitation, quaternary ammonium (defined elsewhere herein), salts such as the hydrochloride, sulfate, carbonate, lactate, tartrate, malate, maleate, succinate wherein the nitrogen atom of the quaternary ammonium group is a nitrogen of the selected compound of this invention which has reacted with the appropriate acid. Salts in which a compound of this invention forms the negatively charged species include, without limitation, the sodium, potassium, calcium and magnesium salts formed by the reaction of a carboxylic acid group in the compound with an appropriate base (e.g. sodium hydroxide (NaOH), potassium hydroxide (KOH), calcium hydroxide ($Ca(OH)_2$), etc.).

Pharmaceutical compositions suitable for use in the present invention include compositions wherein the active ingredients are contained in an amount sufficient to achieve the intended purpose, e.g., the modulation of protein kinase activity and/or the treatment or prevention of a protein kinase-related disorder.

More specifically, a therapeutically effective amount means an amount of compound effective to prevent, alleviate or ameliorate symptoms of disease or prolong the survival of the subject being treated.

Determination of a therapeutically effective amount is well within the capability of those skilled in the art, especially in light of the detailed disclosure provided herein.

For any compound used in the methods of the invention, the therapeutically effective amount or dose can be estimated initially from cell culture assays. Then, the dosage can be formulated for use in animal models so as to achieve a circulating concentration range that includes the $IC_{50}$ as determined in cell culture (i.e., the concentration of the test compound which achieves a half-maximal inhibition of the protein kinase activity). Such information can then be used to more accurately determine useful doses in humans.

Toxicity and therapeutic efficacy of the compounds described herein can be determined by standard pharmaceutical procedures in cell cultures or experimental animals, e.g., by determining the $IC_{50}$ and the $LD_{50}$ (both of which are discussed elsewhere herein) for a subject compound. The data obtained from these cell culture assays and animal studies can be used in formulating a range of dosage for use in humans. The dosage may vary depending upon the dosage form employed and the route of administration utilized. The exact formulation, route of administration and dosage can be chosen by the individual physician in view of the patient's condition. (See, e.g., GOODMAN & GILMAN'S THE PHARMACOLOGICAL BASIS OF THERAPEUTICS, Ch. 3, $9^{th}$ ed., Ed. by Hardman, J., and Limbard, L., McGraw-Hill, New York City, 1996, p. 46.)

Dosage amount and interval may be adjusted individually to provide plasma levels of the active species which are sufficient to maintain the kinase modulating effects. These plasma levels are referred to as minimal effective concentrations (MECs). The MEC will vary for each compound but can be estimated from in vitro data, e.g., the concentration necessary to achieve 50-90% inhibition of a kinase may be ascertained using the assays described herein. Dosages necessary to achieve the MEC will depend on individual characteristics and route of administration. HPLC assays or bioassays can be used to determine plasma concentrations.

Dosage intervals can also be determined using MEC value. Compounds should be administered using a regimen that maintains plasma levels above the MEC for 10-90% of the time, preferably between 30-90% and most preferably between 50-90%.

At present, the therapeutically effective amounts of compounds of the present invention may range from approximately 2.5 mg/m² to 1500 mg/m² per day. Additional illustrative amounts range from 0.2-1000 mg/qid, 2-500 mg/qid, and 20-250 mg/qid.

In cases of local administration or selective uptake, the effective local concentration of the drug may not be related to plasma concentration, and other procedures known in the art may be employed to determine the correct dosage amount and interval.

The amount of a composition administered will, of course, be dependent on the subject being treated, the severity of the affliction, the manner of administration, the judgment of the prescribing physician, etc.

The compositions may, if desired, be presented in a pack or dispenser device, such as an FDA approved kit, which may contain one or more unit dosage forms containing the active ingredient. The pack may for example comprise metal or plastic foil, such as a blister pack. The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions or of human or veterinary administration. Such notice, for example, may be of the labeling approved by the U.S. Food and Drug Administration for prescription drugs or of an approved product insert. Compositions comprising a compound of the invention formulated in a compatible pharmaceutical carrier may also be prepared, placed in an appropriate container, and labeled for treatment of an indicated condition. Suitable conditions indicated on the label may include treatment of a tumor, inhibition of angiogenesis, treatment of fibrosis, diabetes, and the like.

Certain embodiments of the compounds of the present invention are small molecule PIM kinase inhibitors that reduce the growth of solid tumor xenografts where the tumorigenicity is mediated by over-expression of either PIM-1 or PIM-2, as well as human bladder carcinoma tumors, androgen-independent prostate tumors, and AML models harboring either wild-type FLT3 or the FLT3-ITD mutation. While not wishing to be bound by theory, the combination of inhibiting all three PIM family members together in one compound may promote the observed anti-tumor activity.

Previous work evaluating bladder carcinoma indicated that PIM-1 was expressed in over 80% of malignant tissues compared with normal epithelia, and expression was enhanced when comparing specimens derived from bladder cancer patients with invasive versus with non-invasive tumors (Guo, S (2010) J Exp Clin Cancer Res 29:161). Further, it was shown that shRNA knockdown of PIM-1 in bladder carcinoma cell lines reduced the growth of the cells in vitro, indicating a prominent role for PIM-1 in bladder carcinoma (Guo, S (2010) J Exp Clin Cancer Res 29:161). As demonstrated in the examples, a representative compound of the invention in the bladder cancer model UM-UC-3 in vitro showed an effective phenocopy by the compound compared to shRNA-mediated knockdown. The compound reduced the growth of established UM-UC-3 xenografts, suggesting that PIM-1 over-expression in patient bladder tumors may be sensitive to perturbation. The examples also demonstrate that PC3 prostate cancer xenografts were inhibited by a representative compound. While not wishing to be bound by theory, certain embodiments of the present compounds may advantageously inhibit PIM kinase function in the solid tumor setting by inhibition of all three PIM kinases for an anti-tumor effect.

AML also represents an important indication of interest for targeting with PIM kinase inhibitors based on over-expression of PIM-1 and PIM-2 (Brault, L (2010) Haematologica 95:1004; Magnuson, N S (2010) Future Oncol 6:1461; Nawijn, M C (2011) Nature Rev Cancer 11:23; Alvarado, Y (2012) Expert. Rev. Hematol 5:81), as well as FLT3 kinase, where approximately 25% of patients with AML have tumor cells expressing the FLT3-ITD driver mutation (Kottaridis PD (2001) Blood 98:1752). In evaluations of AML cell line models for effects of PIM kinase inhibitors, several groups reported sensitivity in models expressing the FLT3-ITD mutation (Chen, L S (2011) Blood 118:693; Pierre, F (2012) BMCL 22:3327; Blanco-Aparicio, C (2011) Cancer Lett 300:145; Fathi, A T (2012) Leuk Res 36:224). PIM-2 over-expression in AML patient specimens suggests a link between malignancy and expression (Tamburini, J (2009) Blood 114:1618).

As shown in the examples, a representative compound demonstrated a 5-fold enhancement in cell cytotoxicity in vitro in the FLT3-ITD mutant cells compared to the wild-type FLT3-expressing cells correlated with xenograft regression versus a partial antitumor effect. Accordingly, it is believed that both populations of AML patients, based on FLT3 status, may benefit from treatment with a PIM kinase inhibitor according to the present invention.

As mentioned above, the compounds and compositions of the invention will find utility in a broad range of diseases and conditions mediated by protein kinases, including diseases and conditions mediated by PIM kinase. Such diseases may include by way of example and not limitation, cancers such as lung cancer, NSCLC (non small cell lung cancer), oat-cell cancer, bone cancer, pancreatic cancer, skin cancer, dermatofibrosarcoma protuberans, cancer of the head and neck, cutaneous or intraocular melanoma, uterine cancer, ovarian cancer, colo-rectal cancer, cancer of the anal region, stomach cancer, colon cancer, breast cancer, gynecologic tumors (e.g., uterine sarcomas, carcinoma of the fallopian tubes, carcinoma of the endometrium, carcinoma of the cervix, carcinoma of the vagina or carcinoma of the vulva), Hodgkin's Disease, hepatocellular cancer, cancer of the esophagus, cancer of the small intestine, cancer of the endocrine system (e.g., cancer of the thyroid, pancreas, parathyroid or adrenal glands), sarcomas of soft tissues, cancer of the urethra, cancer of the penis, prostate cancer (particularly hormone-refractory), chronic or acute leukemia, solid tumors of childhood, hypereosinophilia, lymphocytic lymphomas, cancer of the bladder, cancer of the kidney or ureter (e.g., renal cell carcinoma, carcinoma of the renal pelvis), pediatric malignancy, neoplasms of the central nervous system (e.g., primary CNS lymphoma, spinal axis tumors, medulloblastoma, brain stem gliomas or pituitary adenomas), Barrett's esophagus (pre-malignant syndrome), neoplastic cutaneous disease, psoriasis, mycoses fungoides, and benign prostatic hypertrophy, diabetes related diseases such as diabetic retinopathy, retinal ischemia, and retinal neovascularization, hepatic cirrhosis, angiogenesis, cardiovascular disease such as atherosclerosis, immunological disease such as autoimmune disease and renal disease.

In some embodiments, the compounds and compositions of the invention can be used in methods for treating cancers such as hematological malignancies. For example, in some embodiments the compounds and compositions of the invention can be used in methods for treating acute myeloid leukemia (AML). Other methods include treatment of bladder cancer, or treatment of prostate cancer.

The inventive compounds (i.e., compounds (I), (II) and (III)) can be used in combination with one or more other chemotherapeutic agents. The dosage of the inventive compounds may be adjusted for any drug-drug reaction. In one embodiment, the chemotherapeutic agent is selected from the group consisting of mitotic inhibitors, alkylating agents, anti-metabolites, cell cycle inhibitors, enzymes, topoisomerase inhibitors such as CAMPTOSAR (irinotecan), biological response modifiers, anti-hormones, antiangiogenic agents such as MMP-2, MMP-9 and COX-2 inhibitors, anti-androgens, platinum coordination complexes (cisplatin, etc.), substituted ureas such as hydroxyurea; methylhydrazine derivatives, e.g., procarbazine; adrenocortical suppressants, e.g., mitotane, aminoglutethimide, hormone and hormone antagonists such as the adrenocorticosteriods (e.g., prednisone), progestins (e.g., hydroxyprogesterone caproate), estrogens (e.g., diethylstilbesterol), antiestrogens such as tamoxifen, androgens, e.g., testosterone propionate, and aromatase inhibitors, such as anastrozole, and AROMASIN (exemestane).

Examples of alkylating agents that the above method can be carried out in combination with include, without limitation, fluorouracil (5-FU) alone or in further combination with leukovorin; other pyrimidine analogs such as UFT, capecitabine, gemcitabine and cytarabine, the alkyl sulfonates, e.g., busulfan (used in the treatment of chronic granulocytic leukemia), improsulfan and piposulfan; aziridines, e.g., benzodepa, carboquone, meturedepa and uredepa; ethyleneimines and methylmelamines, e.g., altretamine, triethylenemelamine, triethylenephosphoramide, triethylenethiophosphoramide and trimethylolmelamine; and the nitrogen mustards, e.g., chlorambucil (used in the treatment of chronic lymphocytic leukemia, primary macroglobulinemia and non-Hodgkin's lymphoma), cyclophosphamide (used in the treatment of Hodgkin's disease, multiple myeloma, neuroblastoma, breast cancer, ovarian cancer, lung cancer, Wilm's tumor and rhabdomyosarcoma), estramustine, ifosfamide, novembrichin, prednimustine and uracil mustard (used in the treatment of primary thrombocytosis, non-Hodgkin's lymphoma, Hodgkin's disease and ovarian cancer); and triazines, e.g., dacarbazine (used in the treatment of soft tissue sarcoma).

Examples of antimetabolite chemotherapeutic agents that the above method can be carried out in combination with include, without limitation, folic acid analogs, e.g., methotrexate (used in the treatment of acute lymphocytic leukemia, choriocarcinoma, mycosis fungiodes, breast cancer, head and neck cancer and osteogenic sarcoma) and pteropterin; and the purine analogs such as mercaptopurine and thioguanine which find use in the treatment of acute granulocytic, acute lymphocytic and chronic granulocytic leukemias.

Examples of natural product-based chemotherapeutic agents that the above method can be carried out in combination with include, without limitation, the vinca alkaloids, e.g., vinblastine (used in the treatment of breast and testicular cancer), vincristine and vindesine; the epipodophyllotoxins, e.g., etoposide and teniposide, both of which are useful in the treatment of testicular cancer and Kaposi's sarcoma; the antibiotic chemotherapeutic agents, e.g., daunorubicin, doxorubicin, epirubicin, mitomycin (used to treat stomach, cervix, colon, breast, bladder and pancreatic cancer), dactinomycin, temozolomide, plicamycin, bleomycin (used in the treatment of skin, esophagus and genitourinary tract cancer); and the enzymatic chemotherapeutic agents such as L-asparaginase.

Examples of useful COX-II inhibitors include Vioxx, CELEBREX (celecoxib), valdecoxib, paracoxib, rofecoxib, and Cox 189.

Examples of useful matrix metalloproteinase inhibitors are described in WO 96/33172 (published Oct. 24, 1996), WO 96/27583 (published Mar. 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13, 1994), European Patent Publication 931,788 (published Jul. 28, 1999), WO 90/05719 (published May 31, 1990), WO 99/52910 (published Oct. 21, 1999), WO 99/52889 (published Oct. 21, 1999), WO 99/29667 (published Jun. 17, 1999), PCT International Application No. PCT/IB98/01113 (filed Jul. 21, 1998), European Patent Application No. 99302232.1 (filed Mar. 25, 1999), Great Britain patent application number 9912961.1 (filed Jun. 3, 1999), U.S. Pat. No. 5,863,949 (issued Jan. 26, 1999), U.S. Pat. No. 5,861,510 (issued Jan. 19, 1999), and European Patent Publication 780,386 (published Jun. 25, 1997), all of which are incorporated herein in their entireties by reference. Preferred MMP-2 and MMP-9 inhibitors are those that have little or no activity inhibiting MMP-1. More preferred are those that selectively inhibit MMP-2 and/or MMP-9 relative to the other matrix-metalloproteinases (i.e., MMP-1, MMP-3, MMP-4, MMP-5, MMP-6, MMP-7, MMP-8, MMP-10, MMP-11, MMP-12, and MMP-13).

Some specific examples of MMP inhibitors useful in the present invention are AG-3340, RO 32-3555, RS 13-0830, and compounds selected from: 3-[[4-(4-fluoro-phenoxy)-benzenesulfonyl]-(1-hydroxycarbamoyl-cyclopentyl)-amino]-propionic acid; 3-exo-3-[4-(4-fluoro-phenoxy)-benzenesulfonylamino]-8-oxa-bicyclo[3.2.1]octane-3-carboxylic acid hydroxyamide; (2R,3R) 1-[4-(2-chloro-4-fluoro-benzyloxy)-benzenesulfonyl]-3-hydroxy-3-methyl-piperidine-2-carboxylic acid hydroxyamide; 4-[4-(4-fluoro-phenoxy)-benzenesulfonylamino]-tetrahydro-pyran-4-carboxylic acid hydroxyamide; 3-[[4-(4-fluoro-phenoxy)-benzenesulfonyl]-(1-hydroxycarbamoyl-cyclobutyl)-amino]-propionic acid; 4-[4-(4-chloro-phenoxy)-benzenesulfonylamino]-tetrahydro-pyran-4-carboxylic acid hydroxyamide; (R) 3-[4-(4-chloro-phenoxy)-benzenesulfonylamino]-tetrahydro-pyran-3-carboxylic acid hydroxyamide; (2R,3R) 1-[4-(4-fluoro-2-methylbenzyloxy)-benzenesulfonyl]-3-hydroxy-3-methyl-piperidine-2-carboxylic acid hydroxyamide; 3-[[(4-(4-fluoro-phenoxy)-benzenesulfonyl]-(1-hydroxycarbamoyl-1-methyl-ethyl)-amino]-propionic acid; 3-[[4-(4-fluoro-phenoxy)-benzenesulfonyl]-(4-hydroxycarbamoyl-tetrahydro-pyran-4-yl)-amino]-propionic acid; 3-exo-3-[4-(4-chloro-phenoxy)-benzenesulfonylamino]-8-oxa-bicyclo[3.2.1]octane-3-carboxylic acid hydroxyamide; 3-endo-3-[4-(4-fluoro-phenoxy)-benzenesulfonylamino]-8-oxa-bicyclo[3.2.1]octane-3-carboxylic acid hydroxyamide; and (R) 3-[4-(4-fluoro-phenoxy)-benzenesulfonylamino]-tetrahydro-furan-3-carboxylic acid hydroxyamide; and pharmaceutically acceptable salts and solvates of these compounds.

Other anti-angiogenesis agents, other COX-II inhibitors and other MMP inhibitors, can also be used in the present invention.

An inventive compound can also be used with other signal transduction inhibitors, such as agents that can inhibit EGFR (epidermal growth factor receptor) responses, such as EGFR antibodies, EGF antibodies, and molecules that are EGFR inhibitors; VEGF (vascular endothelial growth factor) inhibitors; and erbB2 receptor inhibitors, such as organic molecules or antibodies that bind to the erbB2 receptor, such as HERCEPTIN (Genentech, Inc., South San Francisco, Calif.). EGFR inhibitors are described in, for example in WO 95/19970 (published Jul. 27, 1995), WO 98/14451 (published Apr. 9, 1998), WO 98/02434 (published Jan. 22, 1998), and U.S. Pat. No. 5,747,498 (issued May 5, 1998), and such substances can be used in the present invention as described herein.

EGFR-inhibiting agents include, but are not limited to, the monoclonal antibodies C225 and anti-EGFR 22Mab (ImClone Systems, Inc., New York, N.Y.), the compounds ZD-1839 (AstraZeneca), BIBX-1382 (Boehringer Ingelheim), MDX-447 (Medarex Inc., Annandale, N.J.), and OLX-103 (Merck & Co., Whitehouse Station, N.J.), and EGF fusion toxin (Seragen Inc., Hopkinton, Mass.).

These and other EGFR-inhibiting agents can be used in the present invention. VEGF inhibitors, for example SU-5416 and SU-6668 (Sugen Inc., South San Francisco, Calif.), can also be combined with an inventive compound. VEGF inhibitors are described in, for example, WO 01/60814 A3 (published Aug. 23, 2001), WO 99/24440 (published May 20, 1999), PCT International Application PCT/IB99/00797 (filed May 3, 1999), WO 95/21613 (published Aug. 17, 1995), WO 99/61422 (published Dec. 2, 1999), U.S. Pat. No. 5,834,504 (issued Nov. 10, 1998), WO 01/60814, WO 98/50356 (published Nov. 12, 1998), U.S. Pat. No. 5,883,113 (issued Mar. 16, 1999), U.S. Pat. No. 5,886,020 (issued Mar. 23, 1999), U.S. Pat. No. 5,792,783 (issued Aug. 11, 1998), WO 99/10349 (published Mar. 4, 1999), WO 97/32856 (published Sep. 12, 1997), WO 97/22596 (published Jun. 26, 1997), WO 98/54093 (published Dec. 3, 1998), WO 98/02438 (published Jan. 22, 1998), WO 99/16755 (published Apr. 8, 1999), and WO 98/02437 (published Jan. 22, 1998), all of which are incorporated herein in their entireties by reference. Other examples of some specific VEGF inhibitors useful in the present invention are IM862 (Cytran Inc., Kirkland, Wash.); anti-VEGF monoclonal antibody of Genentech, Inc.; and angiozyme, a synthetic ribozyme from Ribozyme (Boulder, Colo.) and Chiron (Emeryville, Calif.). These and other VEGF inhibitors can be used in the present invention as described herein. pErbB2 receptor inhibitors, such as GW-282974 (Glaxo Wellcome plc), and the monoclonal antibodies AR-209 (Aronex Pharmaceuticals Inc., The Woodlands, Tex.) and 2B-1 (Chiron), can furthermore be combined with an inventive compound, for example, those indicated in WO 98/02434 (published Jan. 22, 1998), WO 99/35146 (published Jul. 15, 1999), WO 99/35132 (published Jul. 15, 1999), WO 98/02437 (published Jan. 22, 1998), WO 97/13760 (published Apr. 17, 1997), WO 95/19970 (published Jul. 27, 1995), U.S. Pat. No. 5,587,458 (issued Dec. 24, 1996), and U.S. Pat. No. 5,877,305 (issued Mar. 2, 1999), which are all hereby incorporated herein in their entireties by reference. ErbB2 receptor inhibitors useful in the present invention are also described in U.S. Pat. No. 6,284,764 (issued Sep. 4, 2001), incorporated in its entirety herein by reference. The erbB2 receptor inhibitor compounds and substance described in the aforementioned PCT applications, U.S. patents, and U.S. provisional applications, as well as other compounds and substances that inhibit the erbB2 receptor, can be used with an inventive compound, in accordance with the present invention.

An inventive compound can also be used with other agents useful in treating cancer, including, but not limited to, agents capable of enhancing antitumor immune responses, such as CTLA4 (cytotoxic lymphocyte antigen 4) antibodies, and other agents capable of blocking CTLA4; and anti-proliferative agents such as other farnesyl protein transferase inhibitors, for example the farnesyl protein transferase inhibitors described in the references cited in the "Background" section, of U.S. Pat. No. 6,258,824 B1.

The above method can also be carried out in combination with radiation therapy, wherein the amount of an inventive compound in combination with the radiation therapy is effective in treating the above diseases.

Techniques for administering radiation therapy are known in the art, and these techniques can be used in the combination therapy described herein. The administration of the compound of the invention in this combination therapy can be determined as described herein.

Pim kinases also play a role in immune regulation and inflammatory states. Accordingly, one embodiment of the invention is directed to methods for treatment of an autoimmune or inflammatory disorder, disease or condition mediated by Pim kinase. The disclosed methods comprise administering an effective amount of any of the disclosed compounds to a mammal, for example a mammal in need of treatment for an autoimmune or inflammatory disease, disorder or condition. Inflammatory diseases, disorders or conditions treatable according to the disclosed methods include, but are not limited to: osteoarthritis, rheumatoid arthritis, pain, inflammatory bowel diseases, respiratory disorders, skin disorders or combinations thereof.

In some embodiments, the inflammatory bowel diseases are selected from Crohn's disease, ulcerative colitis, irritable bowel syndrome and combinations thereof.

In some other embodiments, the respiratory disorders are selected from asthma, rhinitis, chronic obstructive pulmonary disease, bronchitis, nasal polyposis, nasal congestion, farmer's lung, fibroid lung, cough and combinations thereof.

In yet other embodiments, the skin disorders are selected from dermatitis, cutaneous eosinophilias, Lichen planus, urticaria, psoriasis, pruritus, angiodermas, corneal ulcers, chronic skin ulcers, conjunctivitis, vasculitides, uveitis, erythemas and combinations thereof.

While the compounds and compositions of the invention find utility in a broad range of diseases and conditions, including those described above, some embodiments include compounds which have reduced side effects compared to other known therapeutics. One such side effect may include hERG inhibition. hERG (the human Ether-à-go-go-Related Gene) is a gene that encodes a protein which contribiutes to the electrical activity of the heart. Some clinically successful drug candidates have the tendency to inhibit hERG which may compromise the electrical ativity of the heart and can result in a potentially fatal disorder called long QT syndrome. Thus, drugs capable of treating any of the diseases, conditions or disorders described herein, without substanatial concomitant inhibition of hERG, may be advantageous in certain methods of treatment. Accordingly, certain embodiments of the present invention include compounds which have a hERG inhibition $IC_{50}$ of greater than 1 μM, greater than 10 μM, greater than 30 μM or even greater than 50 μM (as determined by the Fast Patch assay available from WuXiApptec (Shanghai China)). In further embodiments of the foregoing, the compound is also effective for treatment of the Pim kinase mediated diseases described above.

The invention will be further understood upon consideration of the following non-limiting Examples.

EXAMPLES

Representative compounds of the present invention were synthesized according the synthetic procedures detailed herein.

All solvents and reagents were available from Aldrich or VWR chemicals and used as supplied or purified by standard laboratory methods as required. NMR spectra were recorded on a Varian Unity at 400 MHz ($^1$H) at 25° C. Chemical shifts are reported in ppm and referenced internally to residual CHCl$_3$ for (d 7.26) or CH$_3$OH for (d 3.33). Low resolution mass spectrometry was performed by The Mass Spectrometry and Proteomics Core facility at the University of Utah. Flash chromatography was performed on Combifalsh (Yamazen) with normal phase silica gel column (RediSep) and CH$_2$Cl$_2$/CH$_3$OH solvent system. TLC used pre-coated silica gel aluminum sheets.

Antibodies and Reagents

PIM-1, PIM-2 and actin antibodies were purchased from Cell Signaling Technology (Danvers, Mass.) (Cat #3247, 4730 and 3700). IRDye 800CW goat anti-rabbit and IRDye 680 goat anti-mouse secondary antibodies were purchased from LI-COR (Lincoln, Nebr.). HEK-293, NIH-3T3, 22RV-1, UM-UC-3, PC-3 MV-4-11, GDM-1, RPMI-8226, NCI-H929, Pfeiffer, SU-DHL-6, Toledo, Z-138, Jeko-1, Maver-1, Mino, MC116, JM-1, SupT1, U937 and K562 cell lines were purchased from ATCC (Manassas, Va.), while the MOLM-13, ML-2 and PL-21 cell lines were purchased from DSMZ (Braunschweig, Germany), and the 22RV1/PIM-1 over-expression cell line was licensed from the lab of Anjali Jain, Ph.D. (Cedars Sinai, Calif.). The NIH-3T3/PIM-2 over-expression cell lines were generated at Epoch Life Science (Missouri City, Tex.) by transfecting the NIH-3T3 cell line with a PIM-2 over-expression plasmid encoding a neomycin resistance gene and selecting a stable pool resistant to G418. PIM-1, PIM-2 and BAD plasmids were purchased from Origene (Rockville, Md.). Human shRNA lentiviral particles were purchased from the Sigma-Aldrich MISSION collection (St. Louis, Mo.). For cell culture, RPMI 1640 and EMEM media with glutamine were supplemented with 10% fetal bovine serum and 1× Penicillin-Streptomycin (Life Technologies, Grand Island N.Y.). ATPlite was purchased from Perkin Elmer (Shelton, Conn.).

Cell-based Assays

HEK-293 cells (1×10$^4$) were seeded in a 96-well plate using EMEM media with serum and incubated overnight at 37° C. in 5% CO$_2$. Adherent cells were transfected the next day using Effectene (Qiagen) with 0.1 µg BAD+300 pg of PIM-1 or PIM-1 KD (K67M) overexpression plasmids for 18 hours. Cells were serum starved for an additional 18 hours, then treated 2 hours with various concentrations of SGI-9481 or 0.5% carrier DMSO control. Media was removed and cells were lysed using 25 µl 1× lysis buffer from the AlphaScreen SureFire Phospho-BAD (Ser112) kit from Perkin Elmer. Lysates (4 µl) were transferred to a 384-well proxiplate, and 5 µl of acceptor mix was added to each well and incubated for 2 hours at room temperature. Donor mix (2 µl) was added to each well, and samples incubated for 2 hours at room temperature and reactions measured on an Envision plate reader (PerkinElmer) with AlphaScreen capabilities. Non-specific phosphorylation of BAD was subtracted using values from PIM-1 KD transfected cells, and the remaining wells were normalized to the DMSO control wells. EC$_{50}$ values were calculated using GraphPad Prism software (La Jolla, Calif.).

Western Blot Analysis

Protein lysates were prepared from cells using an NP-40 based cell lysis buffer (30 mM Tris-HCl pH 7.4, 120 mM NaCl, 1% NP-40, 1× protease inhibitor cocktail, 1× phosphatase inhibitor cocktail I and II (Sigma)). Cells were incubated with lysis buffer for 20 minutes on ice, centrifuged at 13000×g for 5 min at 4° C., and clarified lysate was quantified using the BCA protein assay kit (Thermo Scientific, Rockford, Ill.). Protein (10 µg) from PIM-1 and PIM-2 overexpressing cells and matching parental controls or 50 µg of protein from UM-UC-3 cells 48 hours post-transduction were loaded onto a 4-12% Bis-Tris NuPAGE Novex gel, transferred to nitrocellulose membrane using an iBlot transfer system. Membranes were probed with antibodies against PIM-1, PIM-2 or actin, then probed with rabbit or mouse IRDye secondary antibodies and imaged on an Odyssey fluorescence imaging system (LI-COR).

shRNA Transduction

UM-UC-3 cells (2.5×10$^5$) were seeded in a 6-well plate in complete RPMI 1640 media, and allowed to adhere overnight at 37° C. in 5% CO$_2$. Cells were transduced with 8 µg/mL polybrene (Sigma-Aldrich) and Lentiviral particles at an MOI of 50 based on titer values pre-determined by Sigma-Aldrich using a p24 ELISA for each batch of shRNA. Following overnight transduction, viral particle containing media was removed and replaced with fresh complete media, and cells were cultured for an additional 48 hours at 37° C. in 5% CO$_2$. Cells were trypsinized and fractions of the transduced cells were collected for colony formation growth assays, while the remaining cells were collected for RNA and protein isolation.

RT-PCR

RNA from 0.5×10$^6$ cells was isolated on a QIAcube (Qiagen, Santa Clarita, Calif.) using the protocol for purification of total RNA from animal cells (QIAshredder homogenization and on-column DNase digest), and quantified using a Nanodrop 8000 spectrophotometer (Thermo Electron, West Palm Beach, Fla.). Total RNA (1 µg) was converted to cDNA in a 20 µl reaction using the iScript cDNA synthesis kit (Bio-Rad, Hercules, Calif.) by incubating the reaction components for 5 minutes at 25° C., 30 minutes at 42° C., followed by 5 minutes at 85° C. The cDNA reaction (2 µl) was used in a 20 µl PCR multiplex reaction using 1×FAM-labeled PIM-1, VIC-labeled actin Taqman primer sets and the Taqman gene expression master mix from Life Technologies on an iQ5 Real-Time PCR machine (Bio-Rad). An 8-point, half-log standard curve was generated for PIM-1 and actin messages using RNA from untreated cells. A linear trendline (with an R squared value >0.99) was generated by plotting log concentrations of standard vs. Ct values generated from the real-time PCR reactions. Relative message levels from shRNA treated samples were calculated based on the standard curve, normalized to actin and compared to the non-target shRNA control.

Colony Formation Assay

For shRNA growth experiments, 500 UM-UC-3 cells were seeded in a 12-well plate 48 hours post-transduction and cultured for 8-10 days at 37° C. in 5% CO$_2$. Cells were fixed with 4% paraformaldehyde in PBS, washed twice with PBS, and stained with a crystal violet solution (1% crystal violet, 10% ethanol in water). Stained cells were washed thrice with water, and imaged after drying on a GelCount colony counter (Oxford Optronix Ltd., Oxford, UK). Total staining intensity per well was determined by lysis of cells with 200 µl of Triton X-100 lysis buffer (1% Triton X-100, 50 mM Tris-HCl pH 7.4, 150 mM NaCl, 1 mM EDTA). Lysates (100 µl) from each well were transferred to a clear 96-well plate and absorbance at 560 nm was determined on an Envision microplate reader. IC$_{50}$ values were determined using GraphPad Prism software. For compound treated PC-3 and UM-UC-3, cells were seeded and stained as above, but were incubated with various concentrations of test compound or DMSO one day after seeding.

Proliferation Assay

Adherent or suspension cancer cell lines were seeded at 2000-5000 cells/well in a 96-well plate, or 1000-2000 cells/well in a 384-well plate. Suspension cells were treated with drug the same day as seeding, while adherent cells were incubated overnight at 37° C. in 5% $CO_2$ prior to drug treatment. All cells were treated for 72 hours, then lysed with ATPlite (Perkin Elmer) and measured on an Envision microplate reader. $IC_{50}$ values were determined using GraphPad Prism software.

Tumor Xenograft Studies

Male and female Nu/Nu mice were purchased from Harlan Sprague Dawley (Indianapolis, Ind.). Female Nu/Nu mice were used for all xenograft evaluations with the exception of the PC-3 xenografts where male Nu/Nu mice were used. Cell lines were expanded in vitro in complete media, and if adherent were harvested by trypsin-EDTA, centrifuged and resuspended in PBS 1:1 with Matrigel (BD Biosciences). Cells were inoculated subcutaneously in the right hind flank of mice. When tumors reached 100-200 $mm^3$ by caliper measurement, mice were randomized and dosing of SGI-9481 or vehicle control began and continued every day for 5 days (QDx5) with 2 days off for 18-21 days. Tumor volumes and body weights were determined twice a week, and tumor weights were measured at the completion of the translational xenograft studies.

Statistical Analyses

All statistical analyses were performed by parametric ANOVA test.

Example 1

Synthesis of Illustrative Pim-1 Kinase Inhibitors 1. 4-((3-(3-(Trifluoromethoxy)phenyl)imidazo[1,2-b]pyridazin-6-yl)amino)-trans-cyclohexanol (EX. 8-1)

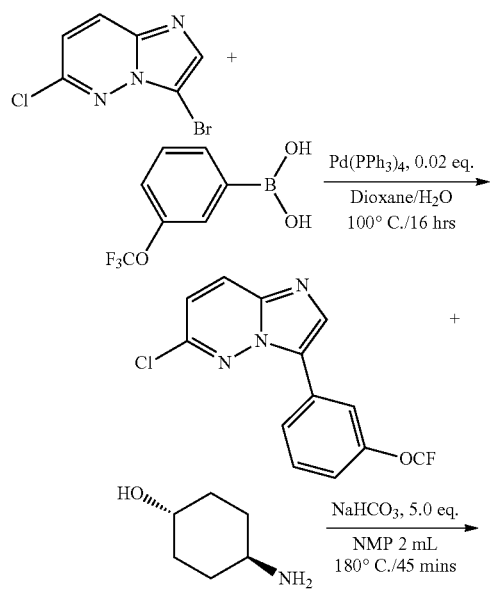

-continued

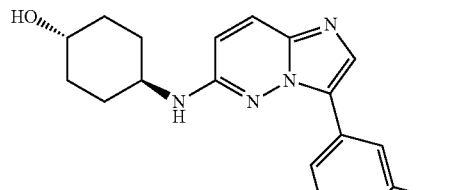

EX. 8-1

3-bromo-6-chloroimidazo[1,2-b]pyridazine was prepared according to procedures described in U.S. Pat. No. 7,750,007, which is hereby incorporated by reference in its entirety. To a solution of 3-bromo-6-chloroimidazo[1,2-b]pyridazine (5 g, 21.5 mmol) and 3-(trifluoromethoxy)phenylboronic acid (4.43 g, 21.5 mmol) in dioxane/$H_2O$ (100 mL, 4:1) was added $K_2CO_3$ (6.8 g, 64.5 mmol) and $Pd(PPh_3)_4$ (1.9 g, 2.58 mmol), the mixture was stirred at 110° C. for 3 h. The solution was concentrated, partitioned in EtOAc/$H_2O$. The aqueous layer was washed with EtOAc (50 mL) for 3 times. The collected organic layers were dried over $Na_2SO_4$, concentrated and purified by column chromatography to give compound 6-chloro-3-(3-(trifluoromethoxy)phenyl)imidazo[1,2-b]pyridazine (3.2 g, with 63% purity, yield 30%) as a brown solid.

To a solution of 6-chloro-3-(3-(trifluoromethoxy)phenyl)imidazo[1,2-b]pyridazine (200 mg, 0.64 mmol) and trans-4-aminocyclohexanol hydrogenchloride (184 mg, 1.59 mmol) in NMP (2.0 mL) was added $NaHCO_3$ (161 mg, 1.91 mmol), the mixture was stirred at 180° C. for 45 mins under microwave irridiation. The mixture was purified by flash chromatograph to give 4-((3-(3-(trifluoromethoxy)phenyl)imidazo[1,2-b]pyridazin-6-yl)amino)cyclohexanol (50 mg, 0.127 mmol, 16%) as a pale yellow solid.

$^1$H-NMR (DMSO-$d_6$/400 MHz): δ 8.49 (s, 1H), 8.34 (brs, 1H), 8.07 (d, J=8 Hz, 1H), 7.99 (d, J=10 Hz, 1H), 7.67 (m, 2H), 7.45 (d, J=7.6 Hz, 1H), 7.12 (m, J=10 Hz, 1H), 3.54 (s, 2H), 2.05 (d, J=9.6 Hz, 2H), 1.87 (d, J=9.6 Hz, 2H), 1.25 (m, 4H). MS (ES$^+$, m/z): (M+H)$^+$: 393.4.

2. 4-((3-(3-(Trifluoromethoxy)phenyl)imidazo[1,2-b]pyridazin-6-yl)amino)-cis-cyclohexanol (EX 8-2)

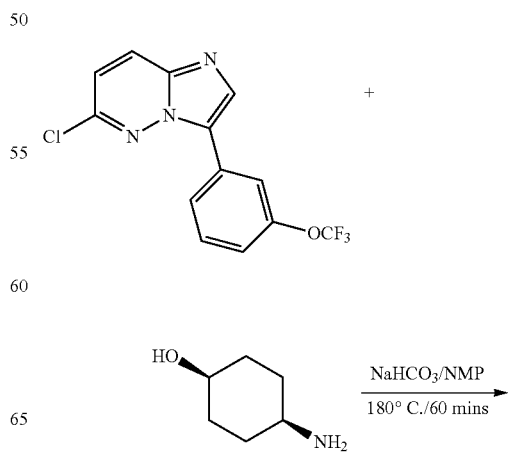

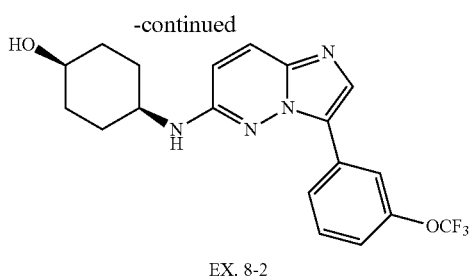

EX. 8-2

To a solution of 6-chloro-3-(3-(trifluoromethoxy)phenyl)imidazo[1,2-b]pyridazine (200 mg, 0.64 mmol) and cis-4-aminocyclohexanol hydrogenchloride (367 mg, 3.19 mmol) in NMP (2.0 mL) was added NaHCO$_3$ (268 mg, 3.19 mmol), the mixture was stirred at 180° C. for 45 mins under microwave irradiation. The mixture was purified by flash chromatograph to give 4-((3-(3-(trifluoromethoxy)phenyl)imidazo[1,2-b]pyridazin-6-yl)amino)cyclohexanol (80 mg, 32%) as a pale yellow solid.

$^1$H-NMR (CD$_3$OD/400 MHz): δ 8.40 (s, 1H), 7.97 (d, J=8.0 Hz, 1H), 7.84 (s, 1H), 7.58 (d, J=8.0 Hz, 1H), 7.51 (m, 1H), 7.21 (d, J=8.4 Hz, 1H), 6.75 (d, J=9.6 Hz, 1H), 3.88 (m, 2H), 1.79 (m, 8H). MS (ES$^+$, m/z): (M+H)$^+$: 393.4.

3. 2-Methyl-4-((3-(3-(trifluoromethoxy)phenyl)imidazo[1,2-b]pyridazin-6-yl)amino)butan-2-ol (EX. 8-3)

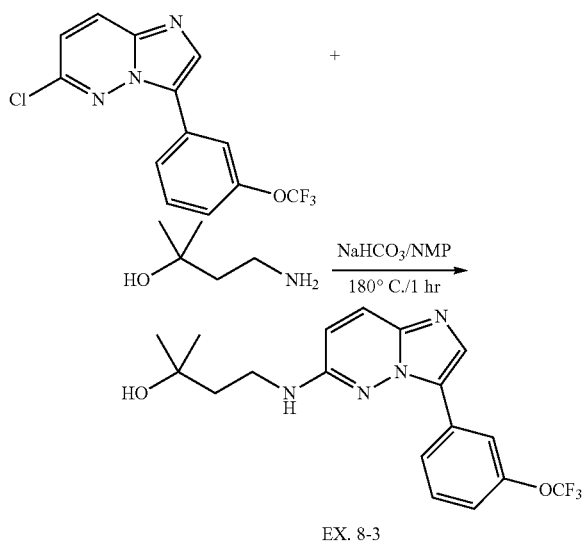

EX. 8-3

To a solution of 6-chloro-3-(3-(trifluoromethoxy)phenyl)imidazo[1,2-b]pyridazine (300 mg, 0.96 mmol) and 4-amino-2-methylbutan-2-ol hydrogenchloride (493 mg, 4.78 mmol) in NMP (2.0 mL) was added NaHCO$_3$ (516 mg, 4.78 mmol), the mixture was stirred at 180° C. for 45 mins under microwave irradiation. The mixture was purified by flash chromatograph to give 2-methyl-4-((3-(3-(trifluoromethoxy)phenyl)imidazo[1,2-b]pyridazin-6-yl)amino)butan-2-ol (175 mg, 48%) as a pale yellow solid.

$^1$H-NMR (CD$_3$OD/400 MHz): δ 9.30 (s, 1H), 8.05 (d, J=8.0 Hz, 1H), 7.83 (s, 1H), 7.61 (d, J=10.0 Hz, 1H), 7.51 (t, J=8.4 Hz, 1H), 7.20 (d, J=8.0 Hz, 1H), 6.71 (d, J=10.0 Hz, 1H), 3.88 (t, J=7.6 Hz, 1H), 1.89 (t, J=7.6 Hz, 1H), 1.26 (s, 6H). MS (ES$^+$, m/z): (M+H)$^+$: 381.5.

4. 4-((3-(3-(Trifluoromethoxy)phenyl)imidazo[1,2-b]pyridazin-6-yl)oxy)-trans-cyclohexanol (EX. 8-4)

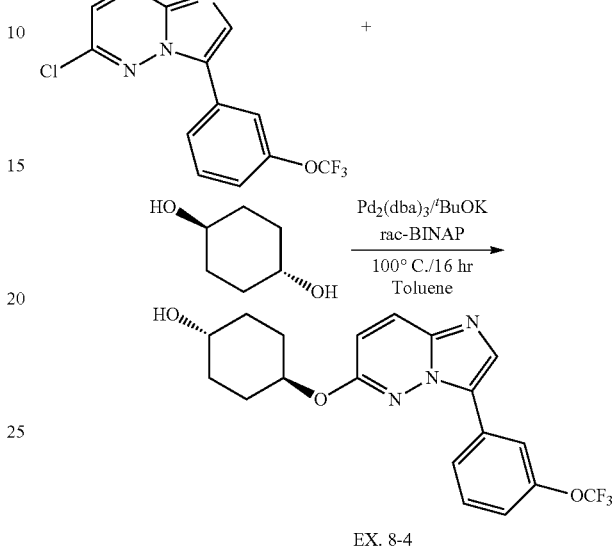

EX. 8-4

A solution of 6-chloro-3-(3-(trifluoromethoxy)phenyl)imidazo[1,2-b]pyridazine (0.3 g, 0.96 mmol) and cyclohexanediol (0.11 g, 0.96 mmol) in toluene 5 mL was added potassium tertiary butoxide (0.165 g, 1.72 mmol), rac-BINAP (36 mg, 0.057 mmol) and Pd$_2$(dba)$_3$ (26 mg, 0.029 mmol) and the mixture was heated at 120° C. for 4 h under microwave irridiation. The resulting dark brown solution was cooled down and was concentrated under reduced pressure. The solid was further purified by using combiflash chromatography (12 g column), eluent: 0-10% methanol/DCM and obtained product 4-((3-(3-(trifluoromethoxy)phenyl)imidazo[1,2-b]pyridazin-6-yl)oxy)cyclohexanol (50 mg, 0.127 mmol, 13% yield).

$^1$H-NMR (CD$_3$OD/400 MHz): δ 8.12 (s, 1H), 7.93 (s, 1H), 7.89 (m, 1H), 7.87 (s, 1H), 7.87 (m, 1H), 7.54 (t, J=8.0 Hz, 1H), 7.25 (d, J=9.2 Hz, 1H), 6.85 (d, J=9.6 Hz, 1H), 4.98 (m, 1H), 3.69 (m, 1H), 2.22 (m, 2H), 2.02 (m, 2H), 1.62 (m, 2H), 1.45 (m, 2H). MS (ES$^+$, m/z): (M+H)$^+$: 394.5.

5. (1R,3R)3-((3-(3-(Trifluoromethoxy)phenyl)imidazo[1,2-b]pyridazin-6-yl)amino)cyclopentanol (EX. 8-5)

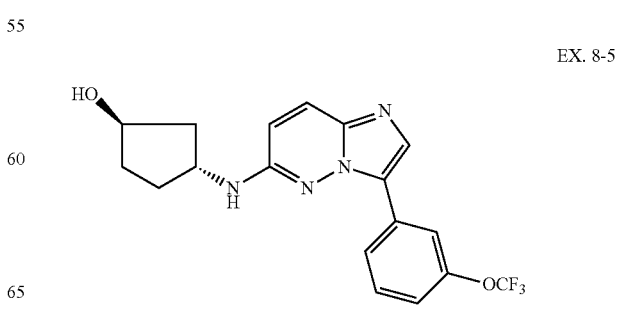

EX. 8-5

EX. 8-5 was prepared by similar procedures as in EX. 8-1 using trans-3-aminocyclopentanol.

¹H-NMR (CD₃OD/400 MHz): δ 8.40 (s, 1H), 7.98 (d, J=8.8 Hz, 1H), 7.80 (s, 1H), 7.58 (d, J=8.0 Hz, 1H), 7.50 (m, 1H), 7.19 (m, 1H), 6.72 (d, J=8.0 Hz, 1H), 4.28 (m, 1H), 4.21 (m, 1H), 2.43 (m, 1H), 2.15 (m, 1H), 1.83 (m, 3H), 1.58 (m, 1H). MS (ES⁺, m/z): (M+H)⁺: 379.5.

6. 2-Methyl-1-((3-(3-(trifluoromethoxy)phenyl)imidazo[1,2-b]pyridazin-6-yl)amino)propan-2-ol (EX 8-6)

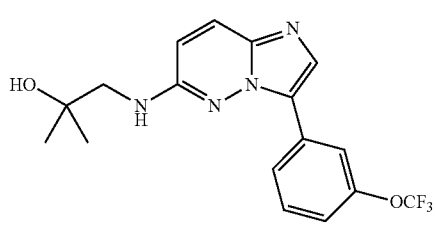

EX. 8-6

To the solution of compound 1-amino-2-methylpropan-2-ol (55 mg, 0.57 mmol) and compound 6-chloro-3-(3-(trifluoromethoxy)phenyl)imidazo[1,2-b]pyridazine (150 mg, 0.48 mmol) in 3 mL DMSO was added DIEA (0.21 mL, 0.96 mmol) and 10 mg CsF, the solvent was stirred for 5 h at 120° C., Then the mixture was purified by HPLC to afford the compound 2-methyl-1-((3-(3-(trifluoromethoxy)phenyl)imidazo[1,2-b]pyridazin-6-yl)amino)propan-2-ol (25 mg, 12%) as a white solid.

¹H-NMR (CD₃OD/400 MHz): δ 8.28-8.24 (d, J=15.2 Hz, 2H), 7.99-7.92 (m, 2H), 7.66-7.62 (t, J=8.4 Hz, 1H), 7.41-7.39 (m, 1H), 7.34-7.31 (d, J=9.6 Hz, 1H), 3.42 (d, 2H), 1.28-1.27 (d, J=6 Hz, 6H). MS (ES⁺, m/z): (M+H)⁺: 367.4.

7. 3-(((3-(3-(Trifluoromethoxy)phenyl)imidazo[1,2-b]pyridazin-6-yl)amino)methyl)-trans-cyclobutanol (EX. 8-7)

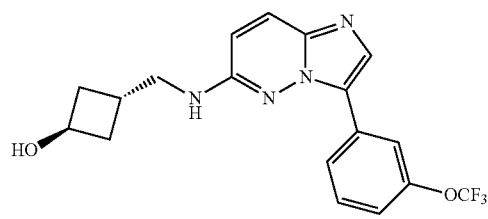

EX. 8-7

EX. 8-5 was prepared by similar procedures as in EX. 8-1 using trans-3-(aminomethyl)cyclobutanol.

¹H-NMR (CD₃OD/400 MHz): δ 8.43 (s, 1H), 7.94 (d, J=8.8 Hz, 1H), 7.83 (s, 1H), 7.59 (d, J=8.0 Hz, 1H), 7.48 (m, 1H), 7.19 (m, 1H), 6.70 (d, J=8.0 Hz, 1H), 4.38 (m, 1H), 3.40 (m, 1H), 2.57 (m, 1H), 2.10 (m, 5H). MS (ES⁺, m/z): (M+H)⁺: 379.5.

8. (3-(3-(Trifluoromethoxy)phenyl)imidazo[1,2-b]pyridazin-6-yl)cyclohexane-trans-1,4-diamine (EX. 8-8)

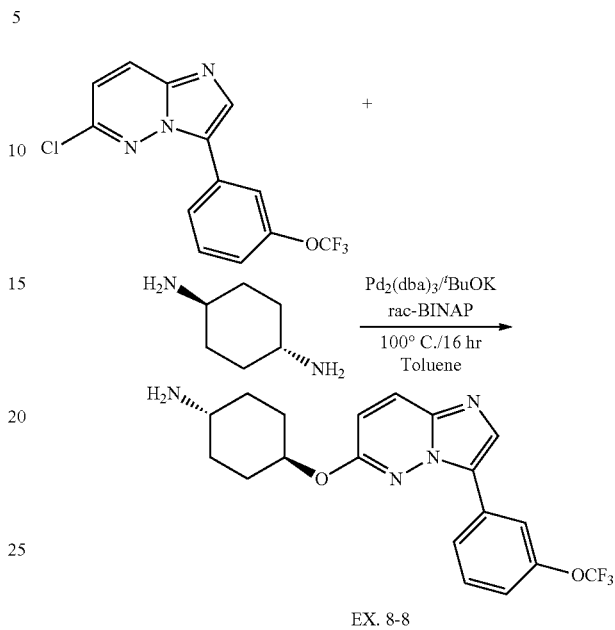

EX. 8-8

A solution of pyridazine (0.3 g, 0.96 mmol) and 1,4-trans-cyclohexanediamine (0.11 g, 0.96 mmol) in toluene 5 mL was added potassium tertiary butoxide (0.165 g, 1.72 mmol), rac-BINAP (36 mg, 0.057 mmol) and Pd₂(dba)₃ (26 mg, 0.029 mmol) and the mixture was heated at 100° C. for 16 h under microwave irradiation. The resulting dark brown solution was cooled down and was concentrated under reduced pressure. The solid was further purified by using combiflash chromatography (12 g column), eluent: 0-10% methanol/DCM and obtained product 4-((3-(3-(trifluoromethoxy)phenyl)imidazo[1,2-b]pyridazin-6-yl)oxy)cyclohexanol (170 mg, 0.434 mmol, 45% yield.).

¹H-NMR (CD₃OD/400 MHz): δ 8.30 (s, 1H), 8.00 (m, 1H), 7.83 (s, 1H), 7.60 (d, J=9.2 Hz, 1H), 7.50 (t, J=8.0 Hz, 1H), 7.21 (d, J=9.2 Hz, 1H), 6.68 (d, J=9.6 Hz, 1H), 3.68 (m, 1H), 2.70 (m, 1H), 2.24 (m, 2H), 1.98 (m, 2H), 1.33 (m, 4H). MS (ES⁺, m/z): (M+H)⁺: 375.4.

9. 1-Methyl-4-((3-(3-(trifluoromethoxy)phenyl)imidazo[1,2-b]pyridazin-6-yl)amino)-trans-cyclohexanol (EX. 8-9)

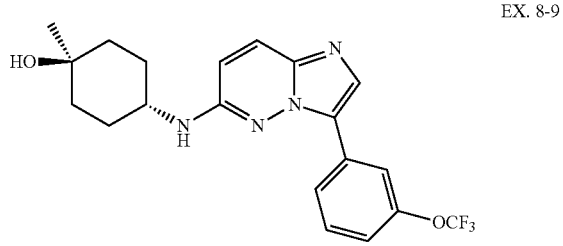 [SMILES: C[C@]1(O)CC[C@H](Nc2ccc3ncc(-c4cccc(OC(F)(F)F)c4)n3n2)CC1]

EX. 8-9

EX. 8-9 was prepared by similar procedures as in EX. 8-1 using trans-4-amino-1-methylcyclohexanol.

¹H-NMR (CD₃OD/400 MHz): δ 8.23 (s, 1H), 7.93 (d, J=8.8 Hz, 1H), 7.76 (s, 1H), 7.54 (d, J=8.0 Hz, 1H), 7.42 (m, 1H), 7.16 (m, 1H), 6.60 (d, J=8.0 Hz, 1H), 3.77 (m, 1H), 2.09 (m, 2H), 1.72 (m, 2H), 1.45 (m, 4H), 1.30 (s, 3H). MS (ES⁺, m/z): (M+H)⁺: 407.5.

10. 4-((3-(3-(Trifluoromethoxy)phenyl)imidazo[1,2-b]pyridazin-6-yl)amino)-trans-cyclohexyl)propan-2-ol (EX. 8-10)

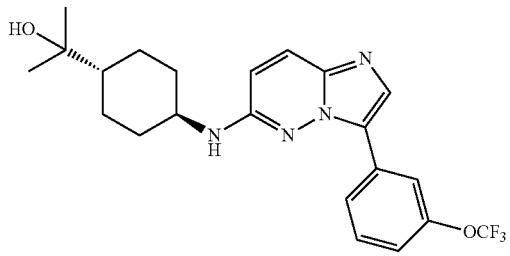

EX. 8-10

EX. 8-10 was prepared by similar procedures as in EX. 8-1 using 2-(trans-4-aminocyclohexyl)propan-2-ol.

¹H-NMR (CD₃OD/400 MHz): δ 8.45 (s, 1H), 7.95 (d, J=8.0 Hz, 1H), 7.82 (s, 1H), 7.59 (d, J=8.0 Hz, 1H), 7.50 (t, J=8.0 Hz, 1H), 7.21 (d, J=7.6 Hz, 1H), 6.68 (d, J=10.0 Hz, 1H), 3.50 (m, 1H), 2.09 (m, 2H), 2.27 (m, 2H), 1.95 (m, 2H), 1.40 (m, 1H), 1.26 (m, 2H), 1.14 (s, 6H). MS (ES⁺, m/z): (M+H)⁺: 435.6.

11. 4-(trans-Methoxycyclohexyl-3-(3-(trifluoromethoxy)phenyl)imidazo[1,2-b]pyridazin-6-amine (EX. 8-11)

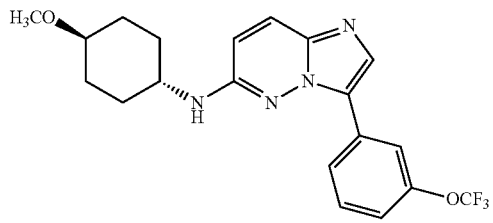

EX. 8-11

EX. 8-11 was prepared by similar procedures as in EX. 8-1 using trans-4-methoxycyclohexanamine.

¹H-NMR (CD₃OD/400 MHz): δ 8.40 (s, 1H), 8.02 (d, J=8.0 Hz, 1H), 7.87 (s, 1H), 7.63 (d, J=8.0 Hz, 1H), 7.54 (s, 1H), 7.26 (s, 1H), 6.72 (d, J=10.0 Hz, 1H), 3.76 (m, 1H), 3.39 (s, 6H), 3.30 (m, 1H), 2.27 (m, 2H), 2.15 (m, 2H), 1.40 (m, 4H). MS (ES⁺, m/z): (M+H)⁺: 407.6.

12. N-(Tetrahydro-2H-pyran-4-yl)-3-(3-(trifluoromethoxy)phenyl)imidazo[1,2-b]pyridazin-6-amine (EX. 8-12)

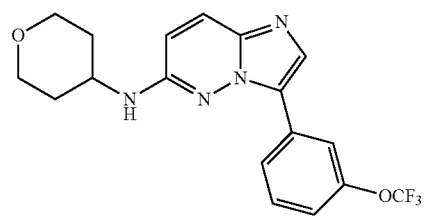

EX. 8-12

EX. 8-12 was prepared by similar procedures as in EX. 8-1 using tetrahydro-2H-pyran-4-amine.

¹H-NMR (CD₃OD/400 MHz): δ 8.37 (s, 1H), 7.95 (d, J=8.0 Hz, 1H), 7.87 (s, 1H), 7.63 (d, J=8.0 Hz, 1H), 7.52 (t, J=8.0 Hz, 1H), 7.23 (m, 1H), 6.72 (d, J=10.0 Hz, 1H), 3.98 (m, 5H), 2.11 (m, 2H), 1.59 (m, 2H). MS (ES⁺, m/z): (M+H)⁺: 379.5.

13. 4-(((3-(3-(Trifluoromethoxy)phenyl)imidazo[1,2-b]pyridazin-6-yl)amino)methyl)tetrahydro-2H-thiopyran 1,1-dioxide (EX. 8-13)

A mixture of compound dihydro-2H-thiopyran-4(3H)-one (0.75 g, 6.46 mmol) and TosMIC (0.138 g, 7.11 mmol) in DME (25 mL) was cooled to 0° C. and a solution of potassium tert-butoxide (0.145 g, 12.9 mmol) in tert-butanol (13 mL) added dropwise. The mixture was then allowed to warm to room temperature and stirred for 3 h before dilution with DCM, washing with Sat. sodium bicarbonate and dried over Na$_2$SO$_4$. Removal of the solvent in vacuo to afford the compound tetrahydro-2H-thiopyran-4-carbonitrile (1 g, crude) as pale brown oil.

$^1$H-NMR (CDCl$_3$/400 MHz): δ 7.98-7.94 (m, 1H), 7.44-7.43 (d, J=1.6 Hz, 1H), 7.37-7.34 (m, 1H).

LiAlH$_4$ (45 mg, 11.8 mmol) in 15 mL THF was cooled to 0° C. under N$_2$. The addition funnel was charged with 10 mL compound tetrahydro-2H-thiopyran-4-carbonitrile (1 g, 8 mmol) in 5 mL THF, the rate of addition was set to maintain the temperature below 10° C. The reaction mixture was allowed to gradually warm to room temperature and stirred for overnight. The reaction mixture was then cooled to about 5° C. and Na$_2$SO$_4$.10H$_2$O was added in portions to maintain the temperature at about 10° C. The reaction mixture was filtered and the salts were washed with warm THF. The filtrate was combined and concentrated to afford the compound (tetrahydro-2H-thiopyran-4-yl)methanamine (150 mg, crude) as yellow oil.

To the solution of compound (tetrahydro-2H-thiopyran-4-yl)methanamine (150 mg, 1.14 mmol) and compound 6-chloro-3-(3-(trifluoromethoxy)phenyl)imidazo[1,2-b]pyridazine (358 mg, 1.14 mmol) in 3 mL DMSO was added DIEA (0.22 mL, 2.28 mmol) and 10 mg CsF, the solvent was stirred for 5 h at 120° C., Then the mixture was purified by HPLC to afford the compound N-((tetrahydro-2H-thiopyran-4-yl)methyl)-3-(3-(trifluoromethoxy)phenyl)imidazo[1,2-b]pyridazin-6-amine (26 mg, 30%) as yellow oil.

$^1$H-NMR (CDCl$_3$/400 MHz): δ 8.29 (s, 1H), 8.23 (s, 1H), 7.98-7.95 (m, 2H), 7.64-7.60 (t, J=8 Hz, 1H), 7.41-7.39 (d, J=8 Hz, 1H), 7.25-7.23 (d, J=10 Hz, 1H), 3.24-3.22 (d, J=6.8 Hz, 2H), 2.68-2.55 (m, 4H), 2.14-2.10 (m, 2H), 1.80-1.78 (t, J=3.2 Hz, 1H), 1.44-1.37 (m, 2H). MS (ES$^+$, m/z): (M+H)$^+$: 409.5.

The compound N-((tetrahydro-2H-thiopyran-4-yl)methyl)-3-(3-(trifluoromethoxy)phenyl)imidazo[1,2-b]pyridazin-6-amine (70 mg, 0.171 mmol) was dissolved in CH$_3$OH (10 mL). A solution of (NH$_4$)Mo$_7$O$_{24}$ (84 mg, 0.07 mmol) in H$_2$O$_2$ (290 mg, 2.56 mmol) was added to the mixture dropwise. After stirred for 30 min, the solvent was removed and purified by column to afford the compound 4-(((3-(3-(trifluoromethoxy)phenyl)imidazo[1,2-b]pyridazin-6-yl)amino)methyl)tetrahydro-2H-thiopyran 1,1-dioxide (23 mg, 30%) as a yellow solid.

$^1$H-NMR (CD$_3$OD/400 MHz): δ 8.20 (s, 1H), 7.90-7.87 (m, 1H), 7.75 (s, 1H), 7.56-7.53 (d, J=9.6 Hz, 1H), 7.44-7.40 (t, J=8.4 Hz, 1H), 7.14-7.12 (m, 1H), 6.65-6.62 (d, J=9.6 Hz, 1H), 3.25-3.20 (m, 2H), 3.02-2.95 (m, 4H), 2.15-2.11 (d, J=12.8 Hz, 2H), 2.08-1.95 (m, 1H), 1.81-1.69 (m, 2H). MS (ES$^+$, m/z): (M+H)$^+$: 441.5.

14. 4-((3-(3-(Trifluoromethoxy)phenyl)imidazo[1,2-b]pyridazin-6-yl)amino)tetrahydro-2H-thiopyran 1,1-dioxide (EX 8-14)

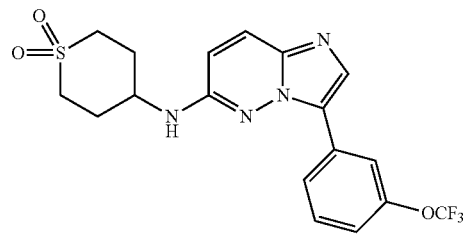

EX. 8-14

EX. 8-14 was prepared by similar procedures as in EX. 8-1 using 4-aminotetrahydro-2H-thiopyran 1,1-dioxide.

$^1$H-NMR (CD$_3$OD/400 MHz): δ 8.20 (s, 1H), 8.01 (d, J=7.6 Hz, 1H), 7.82 (s, 1H), 7.67 (d, J=7.6 Hz, 1H), 7.55 (t, J=8.0 Hz, 1H), 7.23 (d, J=8.0 Hz, 1H), 6.75 (d, J=10.0 Hz, 1H), 4.01 (m, 1H), 3.20 (m, 4H), 2.48 (m, 2H), 2.24 (m, 2H). MS (ES$^+$, m/z): (M+H)$^+$: 441.5.

15. 4-(3-(3-(Trifluoromethoxy)phenyl)imidazo[1,2-b]pyridazin-6-yl)thiomorpholine 1,1-dioxide (EX. 8-15)

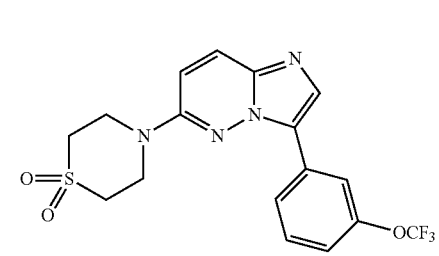

EX. 8-15

EX. 8-15 was prepared by similar procedures as in EX. 8-1 using thiomorpholine 1,1-dioxide.

$^1$H-NMR (CD$_3$OD/400 MHz): δ 8.10 (s, 1H), 7.98 (m, 2H), 7.89 (d, J=7.6 Hz, 1H), 7.57 (t, J=8.0 Hz, 1H), 7.31 (d, J=10.0 Hz, 1H), 7.26 (d, J=8.4 Hz, 1H), 4.18 (t, J=6.4 Hz, 4H), 3.21 (t, J=6.4 Hz, 4H). MS (ES$^+$, m/z): (M+H)$^+$: 413.4.

16. 4-(trans-isopropoxycyclohexyl)-3-(3-(trifluoromethoxy)phenyl)imidazo[1,2-b]pyridazin-6-amine (EX. 8-16)

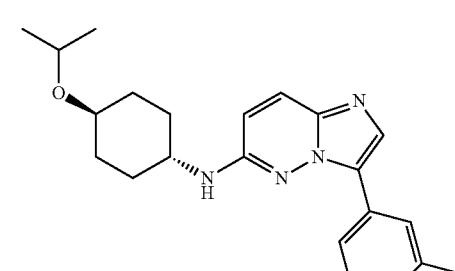

EX. 8-16

EX. 8-16 was prepared by similar procedures as in EX. 8-1 using trans-4-isopropoxycyclohexanamine.
¹H-NMR (CD₃OD/400 MHz): δ 8.35 (s, 1H), 7.98 (d, J=9.6 Hz, 1H), 7.84 (s, 1H), 7.59 (d, J=9.6 Hz, 1H), 7.51 (t, J=8.0 Hz, 1H), 7.20 (d, J=7.0 Hz, 1H), 6.68 (d, J=9.6 Hz, 1H), 3.45 (m, 1H), 3.42 (m, 2H), 2.02 (m, 2H), 1.33 (m, 2H), 1.14 (d, J=6.0 Hz, 6H). MS (ES⁺, m/z): (M+H)⁺: 435.5.

17. N-((4,4-difluorocyclohexyl)methyl)-3-(3-(trifluoromethoxy)phenyl)imidazo[1,2-b]pyridazin-6-amine (EX. 8-17)

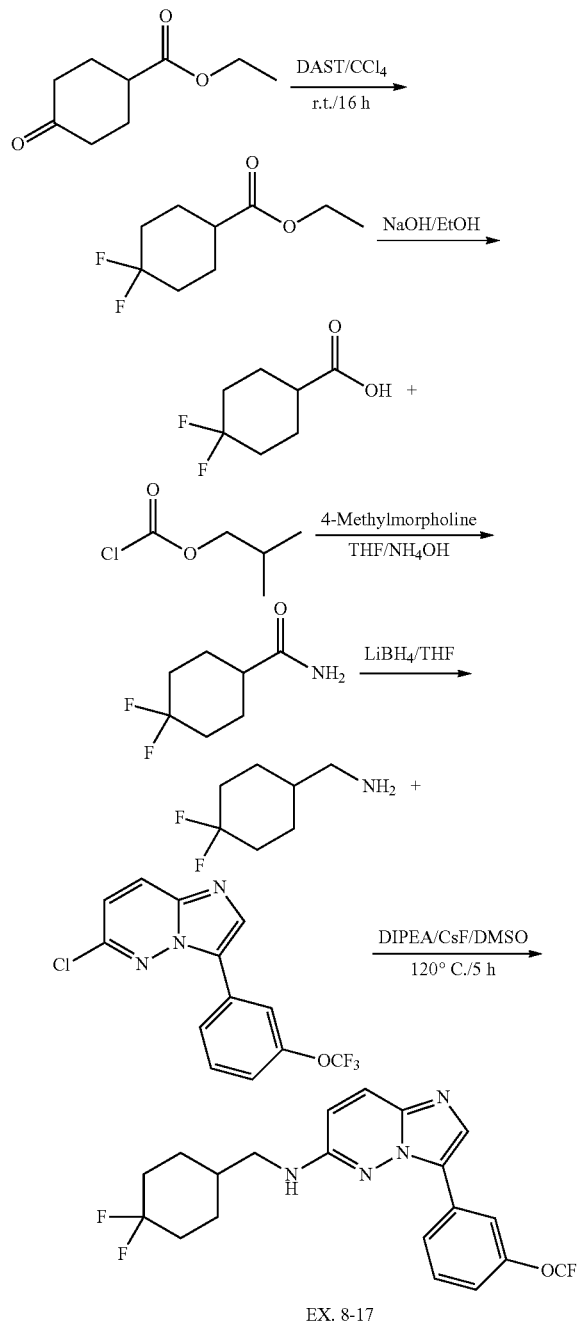

EX. 8-17

To a solution of DAST (7.7 mL) in 75 mL CCl₄ was added the compound ethyl 4-oxocyclohexanecarboxylate (5 g, 29 mmol) dropwise at 0° C., then the mixture was stirred for 16 h at r.t, water was added slowly and the organic phase washed with water, dried over Na₂SO₄, distilled to afford the compound ethyl 4,4-difluorocyclohexanecarboxylate (4.2 g, 71%) as a colorless oil.

To a solution of compound ethyl 4,4-difluorocyclohexanecarboxylate (4.2 g, 21.8 mmol) in 40 mL EtOH was treated with 2N NaOH (1.34 g, 32.8 mmol) at 0° C., and the mixture was allowed to warm to r.t. and stirred for 18 h. The mixture was diluted with water and the pH was adjusted to 3-4 with 6N HCl. The mixture was extracted with toluene, dried and concentrated to give the title compound 4,4-difluorocyclohexanecarboxylic acid (3.4 g, 94%) as a white solid.
¹H-NMR (CDCl₃/400 MHz): δ 2.28-2.27 (m, 1H), 2.22-2.20 (m, 1H), 2.08-2.02 (m, 3H), 1.99-1.94 (m, 3H), 1.19 (s, 1H).

To a solution of compound 4,4-difluorocyclohexanecarboxylic acid (3.5 g, 21 mmol) in 80 mL THF, 4-methylmorpholine (2.51 g, 21 mmol) was added at −70° C., followed by isobutyl chloridocarbonate (2.85 g, 21 mmol). 30 min later, 10 mL ammonium hydroxide was added. The resulting mixture was allowed to warm up to 0° C. After removal of all solvents, the residue was washed with water, PE to afford the compound 4,4-difluorocyclohexanecarboxamide (1.82 g, 40%) as a white solid.
¹H-NMR (DMSO-d₆/400 MHz): δ 7.26 (s, 1H), 6.77 (s, 1H), 2.25-2.15 (m, 1H), 2.05-1.95 (m, 2H), 1.80-1.75 (m, 4H), 1.57-1.53 (m, 2H).

To a solution of compound 4,4-difluorocyclohexanecarboxamide (1.8 g, 13 mmol) in 100 mL THF was added LiBH₄ (1.1 g, 50 mmol) under N₂ stirred for overnight. Then the reaction mixture was refluxed for 4 h. After cooled to r.t, it was poured into ice-water slowly. After filtration, the product was extracted with DCM from filtrate. Combined organic layers washed with water, brine, dried over Na₂SO₄, filtered and condensed to afford compound (4,4-difluorocyclohexyl)methanamine (0.8 g, crude) as a colorless oil.

To the solution of compound (4,4-difluorocyclohexyl)methanamine (100 mg, 6 mmol) and compound 6-chloro-3-(3-(trifluoromethoxy)phenyl)imidazo[1,2-b]pyridazine (190 mg, 6 mmol) in 3 mL DMSO was added DIEA (0.21 mL, 12 mmol) and 10 mg CsF, the solvent was stirred for 5 h at 120° C., Then the mixture was purified by HPLC to afford the compound N-((4,4-difluorocyclohexyl)methyl)-3-(3-(trifluoromethoxy)phenyl)imidazo[1,2-b]pyridazin-6-amine (21 mg, 10%) as a white solid.
¹H-NMR (CD3OD/400 MHz): δ 8.35 (s, 1H), 7.94-7.91 (t, J=13.2 Hz, 1H), 7.93-7.82 (d, J=4 Hz, 1H), 7.62-7.60 (t, J=4.8 Hz, 1H), 7.49-7.46 (m, 1H), 7.20-7.18 (t, J=2.8 Hz, 1H), 7.73-7.69 (d, 1H), 3.26-3.22 (t, J=6.4 Hz, 2H), 2.05 (s, 1H), 2.02 (s, 2H), 1.93-1.65 (m, 4H), 1.38-1.22 (m, 2H). MS (ES⁺, m/z): (M+H)⁺: 427.4.

18. N-((tetrahydro-2H-thiopyran-4-yl)methyl)-3-(3-(trifluoromethoxy)phenyl)imidazo[1,2-b]pyridazin-6-amine (EX. 8-18)

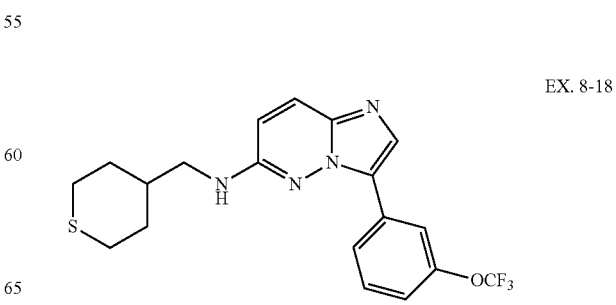

EX. 8-18

To the solution of compound (tetrahydro-2H-thiopyran-4-yl)methanamine (150 mg, 1.14 mmol) and compound 6-chloro-3-(3-(trifluoromethoxy)phenyl)imidazo[1,2-b]pyridazine (358 mg, 1.14 mmol) in 3 mL DMSO was added DIEA (0.22 mL, 2.28 mmol) and 10 mg CsF, the solvent was stirred for 5 h at 120° C., Then the mixture was purified by HPLC to afford the compound N-((tetrahydro-2H-thiopyran-4-yl)methyl)-3-(3-(trifluoromethoxy)phenyl)imidazo[1,2-b]pyridazin-6-amine (26 mg, 30%) as yellow oil.

$^1$H-NMR (CDCl$_3$/400 MHz): δ 8.29 (s, 1H), 8.23 (s, 1H), 7.98-7.95 (m, 2H), 7.64-7.60 (t, J=8 Hz, 1H), 7.41-7.39 (d, J=8 Hz, 1H), 7.25-7.23 (d, J=10 Hz, 1H), 3.24-3.22 (d, J=6.8 Hz, 2H), 2.68-2.55 (m, 4H), 2.14-2.10 (m, 2H), 1.80-1.78 (t, J=3.2 Hz, 1H), 1.44-1.37 (m, 2H). MS (ES$^+$, m/z): (M+H)$^+$: 409.5.

19. N-((tetrahydro-2H-pyran-4-yl)methyl)-3-(3-(trifluoromethoxy)phenyl)imidazo[1,2-b]pyridazin-6-amine (EX. 8-19)

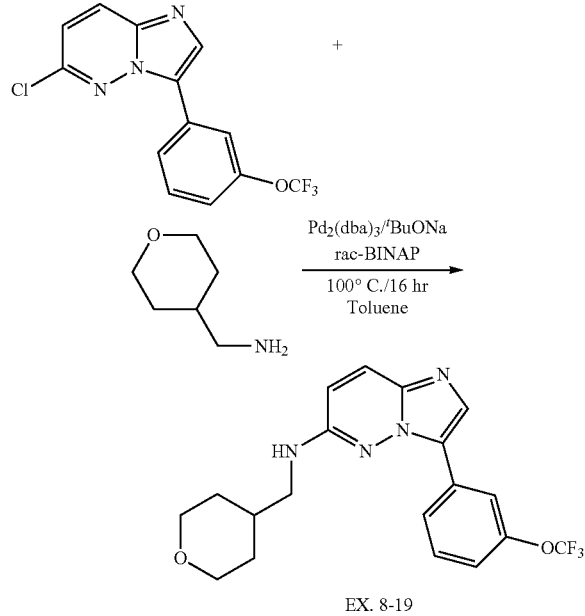

EX. 8-19

Compound 6-chloro-3-(3-(trifluoromethoxy)phenyl)imidazo[1,2-b]pyridazine (0.2 g, 0.638 mmol), 4-aminomethyltetrahydropyran (0.145 g, 0.956 mmol), Sodium tertiary-butyloxide (0.172 g, 1.785 mmol), rac-BINAP (0.024 g, 0.038 mmol) and Pd2(dba)3 (0.018 g, 0.019 mmol) were combined in a 20 ml vial. Toluene (5 mL) was added and nitrogen was bubbled through the mixture for 5 minutes. The reaction mixture was then heated to 100° C. overnight. Silica gel was added to the reaction mixture and the solvent stripped off. The product was isolated via column chromatography (hexanes:EtOAc) with the Compound N-((tetrahydro-2H-pyran-4-yl)methyl)-3-(3-(trifluoromethoxy)phenyl)imidazo[1,2-b]pyridazin-6-amine eluting at 100% EtOAc.

$^1$H-NMR (CDCl$_3$/400 MHz): δ 8.50 (s, 1H), 8.07 (d, J=7.6 Hz, 1H), 8.03 (s, 1H), 7.77 (d, J=9.2 Hz, 1H), 7.58 (t, J=8.0 Hz, 1H), 7.29 (d, J=8.4 Hz, 1H), 7.24 (bs, 1H), 6.76 (d, J=10.0 Hz, 1H), 3.87 (d, J=11.2 Hz, 2H), 3.30 (m, 3H), 3.20 (m, 2H), 1.97 (bs, 1H), 1.69 (d, J=12.8 Hz, 2H), 1.26 (m, 2H). MS (ES$^+$, m/z): (M+H)$^+$: 393.3

20. 2-Hydroxy-2-methyl-1-(4-(((3-(3-(trifluoromethoxy)phenyl)imidazo[1,2-b]pyridazin-6-yl)amino)methyl)piperidin-1-yl)propan-1-one (EX. 8-20)

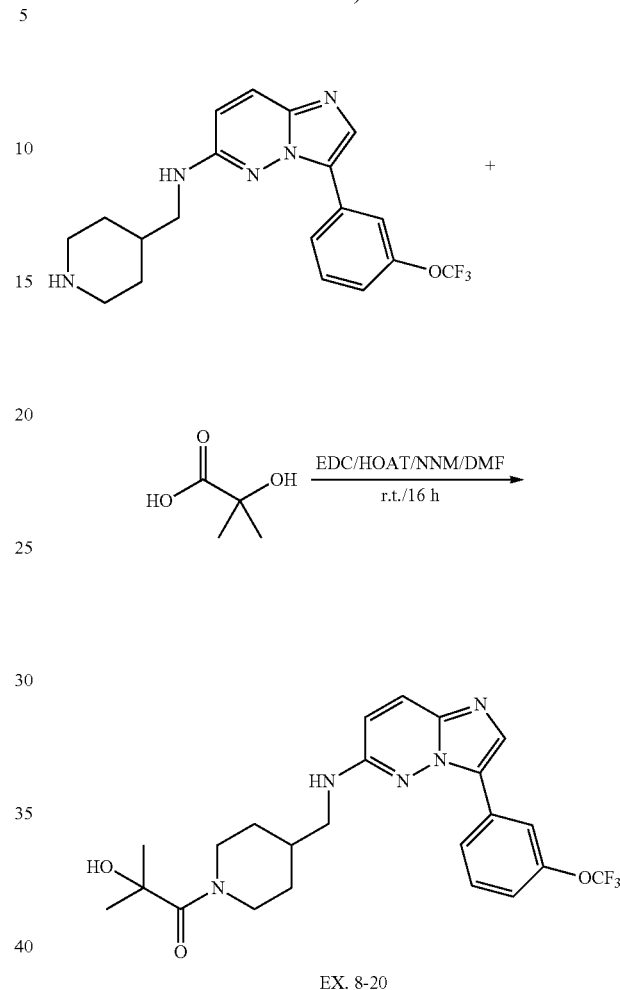

EX. 8-20

Compound N-(piperidin-4-ylmethyl)-3-(3-(trifluoromethoxy)phenyl)imidazo[1,2-b]pyridazin-6-amine (200 mg, 0.47 mmol) was combined with 2-hydroxy-2-methylpropanoic acid (49 mg, 0.47 mmol), EDC (99 mg, 0.51 mmol) and HOAT (64 mg, 0.47 mmol). The mixture was then taken up in DMF (2 mL) and NMM (257 uL, 2.34 mmol) was added. The mixture was then stirred overnight at room temperature. The DMF solution was then poured into an excess of water (20 mL) causing a precipitate to form. The precipitate was collected by filtration and purified via column chromatography (DCM/MeOH 0-15%) to give Compound 2-hydroxy-2-methyl-1-(4-(((3-(3-(trifluoromethoxy)phenyl)imidazo[1,2-b]pyridazin-6-yl)amino)methyl)piperidin-1-yl)propan-1-one.

$^1$H-NMR (CDCl$_3$/400 MHz): δ 8.46 (s, 1H), 8.14 (s, 1H) 8.08 (d, J=7.6 Hz, 1H), 7.83 (d, J=9.2 Hz, 1H), 7.60 (t, J=8.0 Hz, 1H), 7.42 (bs, 1H), 7.32 (d, J=8.0 Hz, 1H), 6.85 (d, J=9.2 Hz, 1H), 4.62 (m, 1H), 3.19 (s, 2H), 2.99 (m, 1H), 2.76 (d, J=15.6 Hz, 2H), 2.66 (d, J=15.6 Hz, 2H), 1.99 (m, 1H), 1.80 (d, J=13.2 Hz, 2H), 1.30 (s, 6H), 1.14 (m, 2H). MS (ES$^+$, m/z): (M+H)$^+$: 478.3

21. 2-Morpholino-1-(4-(((3-(3-(trifluoromethoxy)phenyl)imidazo[1,2-b]pyridazin-6-yl)amino)methyl)piperidin-1-yl)ethanone (EX. 8-21)

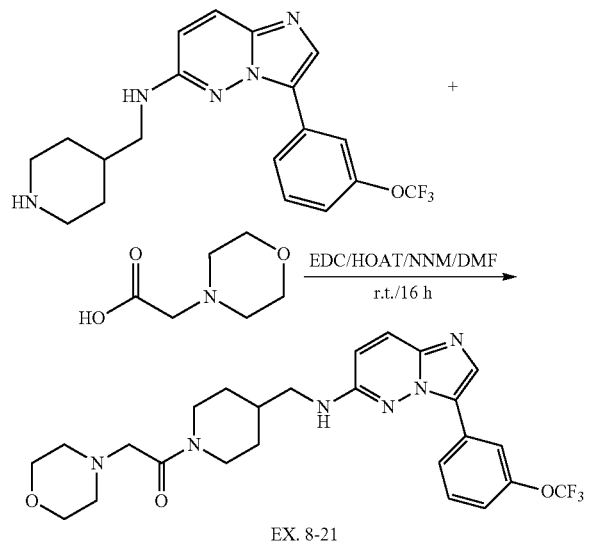

EX. 8-21

Compound N-(piperidin-4-ylmethyl)-3-(3-(trifluoromethoxy)phenyl)imidazo[1,2-b]pyridazin-6-amine (200 mg, 0.47 mmol) was combined with 2-morpholinoacetic acid (68 mg, 0.47 mmol), EDC (99 mg, 0.51 mmol) and HOAT (64 mg, 0.47 mmol). The mixture was taken up in DMF (2 mL) and NMM (257 uL, 2.34 mmol) was added. The mixture was then stirred overnight at room temperature. The DMF solution was then poured into an excess of water (20 mL) causing a precipitate to form. The precipitate was collected by filtration and purified via column chromatography (DCM/MeOH 0-15%) The crude product was then dissolved in methanolic HCl and precipitated with diethyl ether to give 2-morpholino-1-(4-(((3-(3-(trifluoromethoxy)phenyl)imidazo[1,2-b]pyridazin-6-yl)amino)methyl)piperidin-1-yl)ethanone as the HCl salt.

$^1$H-NMR (CDCl$_3$/400 MHz): δ 10.26 (bs, 1H), 8.60 (s, 1H), 8.38 (m, 2H) 8.09 (m, 2H), 7.69 (t, J=8.0 Hz, 1H), 7.48 (d, J=8.0 Hz, 1H), 7.39 (d, J=13.6 Hz, 1H), 4.62 (m, 4H), 3.90 (m, 5H), 3.68 (d, J=12.8 Hz, 1H), 3.38 (m, 3H), 3.05 (t, J=12.0 Hz, 1H), 2.68 (t, J=12.0 Hz, 1H), 2.03 (m, 1H), 1.86 (d, J=11.6 Hz, 2H), 1.26 (m, 1H), 1.09 (m, 2H). MS (ES$^+$, m/z): (M+H)$^+$: 519.3

22. 1-Methyl-4-(((3-(3-(trifluoromethoxy)phenyl)imidazo[1,2-b]pyridazin-6-yl)amino)methyl)piperidin-4-ol (EX. 8-22)

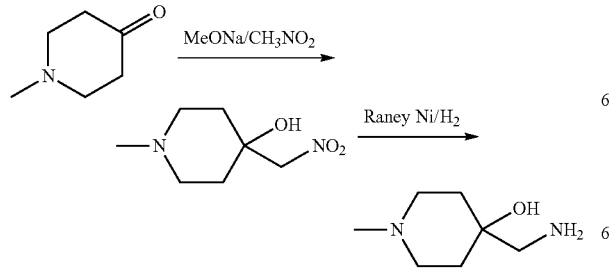

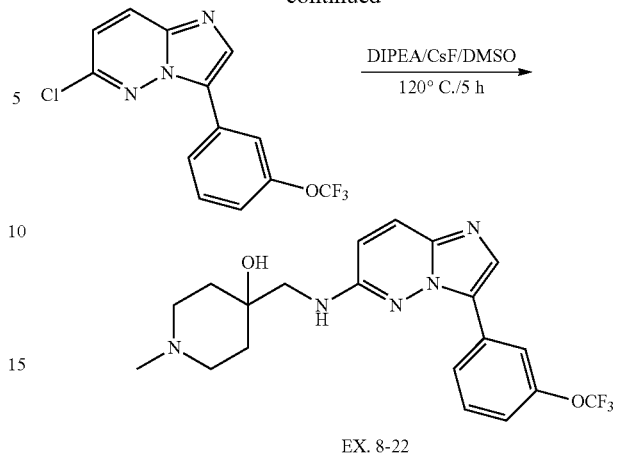

EX. 8-22

CH$_3$NO$_2$ (6.6 mL, 122 mmol) and MeONa (221 mg, 4.1 mmol) was added to a solution of compound 1-methylpiperidin-4-one (10 mL, 81.3 mmol) in EtOH (10 mL). After 30 min more ethanol (15 mL) was added to facilitate stirring. The reaction mixture was stirred at room temperature for 2 days and then filtered through celite. The isolated solid was washed with ether to give the product 1-methyl-4-(nitromethyl)piperidin-4-ol (5.7 g, yield 40.4%). $^1$H-NMR (DMSO-d$_6$/400 MHz): δ 5.01 (s, 1H), 4.47 (s, 2H), 2.41-2.40 (m, 2H), 2.21-2.15 (m, 2H), 2.12 (s, 3H), 1.64-1.53 (m, 4H).

A mixture of 1-methyl-4-(nitromethyl)piperidin-4-ol (0.6 g, 3.5 mmol) and Raney Ni (0.1 g) in methanol (25 ml) was stirred for 16 hrs at room temperature under ambient pressure of hydrogen gas. The mixture was filtered through celite and evaporated under reduced pressure. The residue was used without further purification 4-(aminomethyl)-1-methylpiperidin-4-ol (0.4 g, 74%).

CsF (50 mg, 0.33 mmol) was added to the mixture of 6-chloro-3-(3-(trifluoromethoxy)phenyl)imidazo[1,2-b]pyridazine (150 mg, 0.48 mmol) and 4-(aminomethyl)-1-methylpiperidin-4-ol (150 mg, 1.04 mmol) in DMSO (1.5 mL). The mixture was heated to 120° C. over night and partitioned with EtOAc (10 mL) and water (10 mL). The organic layer was washed with brine (8 mL×3), dried with Na$_2$SO$_4$ and concentrated under reduced pressure. The residue was purified by pre-HPLC to give the product 1-methyl-4-(((3-(3-(trifluoromethoxy)phenyl)imidazo[1,2-b]pyridazin-6-yl)amino)methyl)piperidin-4-ol (22 mg, 10%)

$^1$H-NMR (CD$_3$OD/400 MHz): δ 8.28 (s, 1H), 8.02 (d, J=8.0 Hz, 1H), 7.84 (s, 1H), 7.64 (d, J=5.6 Hz, 1H), 7.55 (t, J=8.0 Hz, 1H), 7.22 (d, J=8.0 Hz, 1H), 6.84 (d, J=10.0 Hz, 1H), 3.47 (s, 2H), 2.58-2.60 (brs, 2H), 2.48-2.47 (brs, 2H), 2.25 (s, 3H), 1.79-1.69 (m, 4H). MS (ES$^+$, m/z): (M+H)$^+$: 422.0.

23. 4-(((3-(3-(Trifluoromethoxy)phenyl)imidazo[1,2-b]pyridazin-6-yl)amino)methyl)piperidin-2-one (EX. 8-23)

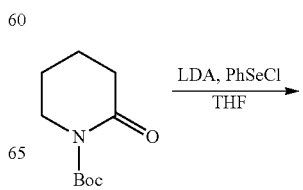

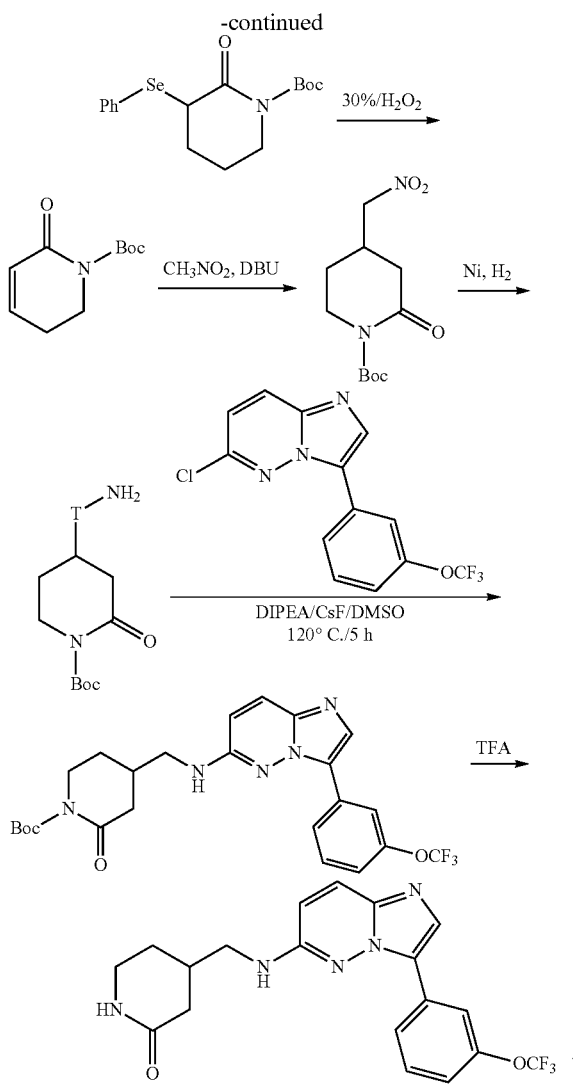

EX. 8-23

A solution of tert-butyl 2-oxopiperidine-1-carboxylate (5.4 g, 27 mmol) in THF (100 mL) was added LDA (16.2 mL, 32.4 mmol) at −78° C. After stirring for 0.5 h, phenyl selenisum chloride (7.94 g, 41.5 mmol) was added. The mixture was stirred at −78° C. for 4.5 hrs and then quenched with H₂O (30 mL), diluted with brine (200 mL). The aqueous layer was extracted with CH₂Cl₂ (200 mL×2). The combined organic phase was dried, filtered and condensed. The residue was purified by flash chromatography (100% petroleum ether to petroleum ether/EtOAc=5:1) to give compound tert-butyl 2-oxo-3-(phenylselanyl)piperidine-1-carboxylate (4.27 g, 45%) as an orange solid.

A solution of 30% H₂O₂ (2.2 mL, 36 mmol) was added to a stirring solution of tert-butyl 2-oxo-3-(phenylselanyl)piperidine-1-carboxylate (4.27 g, 12 mmol) in THF (20 mL) at 0° C. The reaction mixture was stirred 15 min at 0° C. and allowed to warm up to room temperature and kept for 30 min. The reaction mixture was then dissolved in CH₂Cl₂ (200 mL) and washed with a saturated NaHCO₃. The organic phase was dried and condensed to compound tert-butyl 2-oxo-5,6-dihydropyridine-1 (2H)-carboxylate (2.1 g, 88.6%).

A solution of tert-butyl 2-oxo-5,6-dihydropyridine-1(2H)-carboxylate (2.1 g, 11 mmol) in CH₃NO₂ (22.7 g, 372 mmol) under N₂ was added DBU (2.52 g, 16.5 mmol). The mixture was stirred at room temperature overnight and then condensed and purified by flash chromatography to give compound tert-butyl 4-(nitromethyl)-2-oxopiperidine-1-carboxylate (0.6 g, 22%) as a white solid.

A solution of compound tert-butyl 4-(nitromethyl)-2-oxopiperidine-1-carboxylate (0.3 g, 1.2 mmol), Ni (0.1 g) and ammonia (2 mL) in MeOH (30 mL) was stirred under H₂ at room temperature for 7 hrs. The mixture was filtered and condensed to compound tert-butyl 4-(aminomethyl)-2-oxopiperidine-1-carboxylate (0.13 g, 49%) as a white solid.

A mixture of compound tert-butyl 4-(aminomethyl)-2-oxopiperidine-1-carboxylate (37 mg, 0.16 mmol), DIEA (0.6 mL, 3.5 mmol), 6-chloro-3-(3-(trifluoromethoxy)phenyl)imidazo[1,2-b]pyridazine (50 mg) and CsF (17 mg, 0.11 mmol) in DMSO (2 mL) was stirred at 120° C. overnight. The mixture was diluted with H₂O (20 mL) and CH₂Cl₂ (20 mL). The organic phase was separated and condensed to give crude compound tert-butyl 2-oxo-4-(((3-(3-(trifluoromethoxy)phenyl)imidazo[1,2-b]pyridazin-6-yl)amino)methyl)piperidine-1-carboxylate (60 mg).

A solution of compound tert-butyl 2-oxo-4-(((3-(3-(trifluoromethoxy)phenyl)imidazo[1,2-b]pyridazin-6-yl)amino)methyl)piperidine-1-carboxylate (114 mg, 0.23 mmol) in CH₂Cl₂ (10 mL) was added TFA (2 mL). The mixture was stirred at room temperature for 30 min and condensed. The residue was purified by prep-HPLC to give 4-(((3-(3-(trifluoromethoxy)phenyl)imidazo[1,2-b]pyridazin-6-yl)amino)methyl)piperidin-2-one (6 mg, 6.6%) as white solid.

¹H-NMR (CD₃OD/400 MHz): δ 9.06 (d, J=10 Hz, 2H), 8.59 (s, 1H), 8.45 (d, J=10 Hz, 1H), 8.19 (s, 1H), 8.03-8.01 (m, 1H), 7.69 (t, J=8 Hz, 1H), 7.51-7.48 (m, 1H), 4.36-4.32 (m, 1H), 3.79-3.74 (m, 1H), 3.06-3.01 (m, 2H), 2.69-2.63 (m, 1H), 2.59-2.53 (m, 1H), 2.02-1.97 (m, 1H), 1.95-1.89 (m, 1H). MS (ES⁺, m/z): 406.3.

24. 4-(Aminomethyl)-1-(3-(3-(trifluoromethoxy)phenyl)imidazo[1,2-b]pyridazin-6-yl)piperidin-2-one (EX. 8-24)

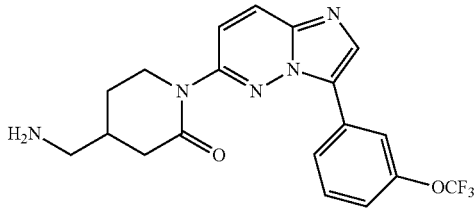

EX. 8-24

A solution of compound tert-butyl 2-oxo-4-(((3-(3-(trifluoromethoxy)phenyl)imidazo[1,2-b]pyridazin-6-yl)amino)methyl)piperidine-1-carboxylate (114 mg, 0.23 mmol) in CH₂Cl₂ (10 mL) was added TFA (2 mL). The mixture was stirred at room temperature for 30 min and condensed. The residue was purified by prep-HPLC to give 4-(aminomethyl)-1-(3-(3-(trifluoromethoxy)phenyl)imidazo[1,2-b]pyridazin-6-yl)piperidin-2-one as white solid.

¹H-NMR (CD₃OD/400 MHz): δ 8.33 (s, 1H), 8.22 (s, 1H), 7.99 (m, 2H), 7.69 (t, J=8.0 Hz, 1H), 7.44 (d, J=8.0 Hz, 1H), 7.25 (d, J=8.0 Hz, 1H), 3.52 (m, 2H), 3.44 (m, 2H), 3.07 (m, 1H), 2.60 (m, 1H), 2.49 (m, 1H), 2.08 (m, 1H), 1.86 (m, 1H). MS (ES⁺, m/z): 406.3.

25. (S)-1-(3-(3-(Trifluoromethoxy)phenyl)imidazo[1,2-b]pyridazin-6-yl)piperidin-3-amine (EX. 8-25)

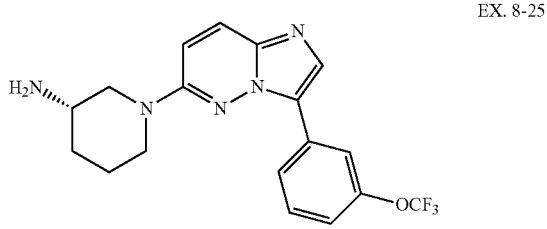 [SMILES: N[C@H]1CCCN(c2ccc3ncc(-c4cccc(OC(F)(F)F)c4)n3n2)C1]

EX. 8-25

EX. 8-25 was prepared by similar procedures as in EX. 8-1 using (S)-tert-butyl piperidin-3-ylcarbamate, and then deprotected with HCl in dioxane.

$^1$H-NMR (CD$_3$OD/400 MHz): δ 8.22 (s, 1H), 7.96 (d, J=8.0 Hz, 1H), 7.89 (s, 1H), 7.74 (d, J=8.0 Hz, 1H), 7.52 (t, J=8.0 Hz, 1H), 7.20 (m, 2H), 3.98 (m, 2H), 3.07 (m, 1H), 2.88 (m, 2H), 2.00 (m, 1H), 1.88 (m, 1H), 1.69 (m, 1H), 1.43 (m, 1H). MS (ES$^+$, m/z): (M+H)$^+$: 378.5.

26. 4-(trans-Hydroxycyclohexyl)amino)imidazo[1,2-b]pyridazin-3-yl)benzonitrile (EX. 8-26)

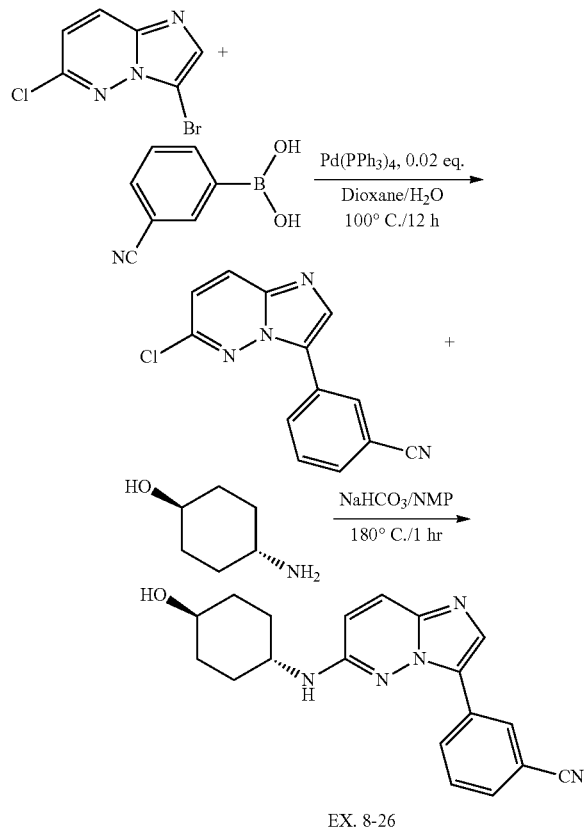

EX. 8-26

To a solution of 3-bromo-6-chloroimidazo[1,2-b]pyridazine (2 g, 8.6 mmol) and 3-(cyano)phenylboronic acid (1.26 g, 8.6 mmol) in dioxane/H$_2$O (100 mL, 4:1) was added K$_2$CO$_3$ (2.38 g, 17.2 mmol) and Pd(PPh$_3$)$_4$ (0.19 g, 0.172 mmol), the mixture was stirred at 110° C. for 3 h. The solution was concentrated and partitioned in EtOAc/H$_2$O. The aqueous layer was washed with EtOAc (50 mL) 3 times. The collected organic layers were dried over Na$_2$SO$_4$, concentrated and purified by column chromatography to give compound 3-(6-chloroimidazo[1,2-b]pyridazin-3-yl)benzonitrile (1.2 g, 4.71 mmol, yield 55%) as a brown solid.

$^1$H-NMR (CDCl$_3$/400 MHz): δ 8.39 (s, 1H), 8.24 (m, 1H), 8.10 (s, 1H), 7.99 (d, J=9.6 Hz, 1H), 7.65 (m, 2H), 7.15 (d, J=9.6 Hz, 1H). MS (ES$^+$, m/z): (M+H)$^+$: 264.3.

To a solution of 3-(6-chloroimidazo[1,2-b]pyridazin-3-yl)benzonitrile (300 mg, 1.18 mmol) and trans-4-aminocyclohexanol hydrogenchloride (678 mg, 5.89 mmol) in NMP (2.0 mL) was added NaHCO$_3$ (496 mg, 5.89 mmol), the mixture was stirred at 180° C. for 45 mins under microwave irradiation. The mixture was purified by flash chromatograph to give 4-((3-(3-cyano phenyl)imidazo[1,2-b]pyridazin-6-yl)amino)cyclohexanol (110 mg, 28%) as a pale yellow solid.

$^1$H-NMR (CD$_3$OD/400 MHz): δ 8.72 (s, 1H), 8.33 (m, 1H), 7.87 (s, 1H), 7.64 (m, 3H), 6.70 (d, J=9.6 Hz, 1H), 3.61 (m, 2H), 2.23 (d, J=8.8 Hz, 2H), 2.02 (d, J=8.8 Hz, 2H), 1.49 (m, 2H), 1.34 (m, 2H). MS (ES$^+$, m/z): (M+H)$^+$: 334.5.

27. 2-(4-(((3-(3-(Trifluoromethoxy)phenyl)imidazo[1,2-b]pyridazin-6-yl)amino)methyl)piperidin-1-yl)ethanol (EX 8-27)

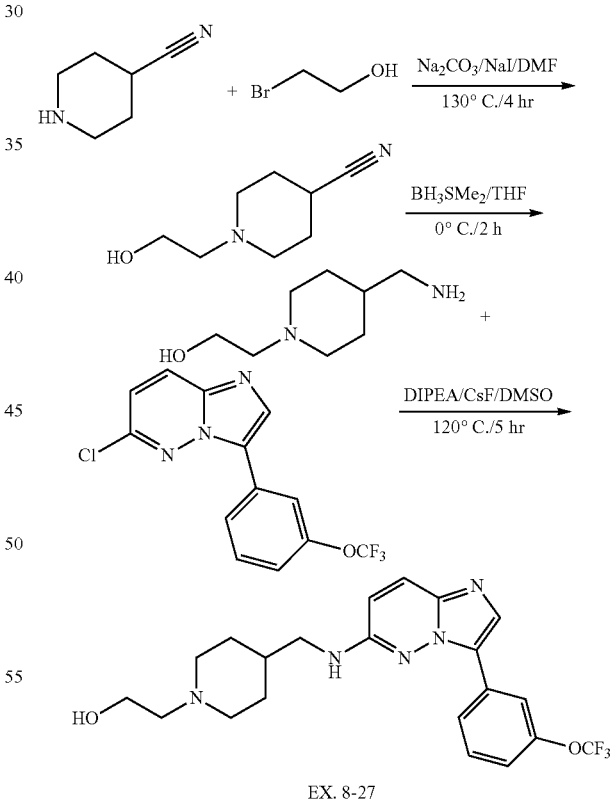

EX. 8-27

Bromoethanol (1.36 g, 11 mmol) and piperidine-4-carbonitrile (1.0 g, 9.1 mmol) 5 mL of dimethylformamide. After this, 4.0 g of anhydrous sodium carbonate and 0.08 g of sodium iodide were added to the resulting solution, and the mixture was stirred for 4 hours at 130° C. Then the mixture was poured into ice water and extracted with ethyl acetate.

The oily extract obtained was purified by silica gel chromatography 1-(2-hydroxyethyl)piperidine-4-carbonitrile (300 mg, 18%).

$^1$H-NMR (CDCl$_3$/400 MHz): δ 3.58 (t, J=4.6 Hz, 2H), 2.60-2.75 (m, 4 H), 2.50-2.60 (m, 2H), 2.31-2.46 (m, 2H), 1.70-2.00 (m, 4 H).

To the solution of compound 1-(2-hydroxyethyl)piperidine-4-carbonitrile (300 mg, 2 mmol) in dry THF (5 mL) at 0° C., BH$_3$.SMe$_2$ (220 mg, 2.4 mmol) was added dropwise. The mixture was stirred at 0° C. for 2 hrs. Water was added then K$_2$CO$_3$. The mixture was filtered and concentrated to give compound 2-(4-(aminomethyl)piperidin-1-yl)ethanol (150 mg, 47%).

$^1$H-NMR (CDCl$_3$/400 MHz): δ 3.61-3.70 (m, 1 H), 3.59 (t, J=5.6 Hz, 2 H), 2.91 (d, J=11.6 Hz, 2 H), 2.57 (d, J=6.4 Hz, 2 H), 2.50 (t, J=5.6 Hz, 2 H), 1.97-2.10 (m, 2 H), 1.63-1.70 (m, 2 H), 1.15-1.35 (m, 2 H).

To the solution of compound 2-(4-(aminomethyl)piperidin-1-yl)ethanol (150 mg, 0.95 mmol) and compound 6-chloro-3-(3-(trifluoromethoxy)phenyl)imidazo[1,2-b]pyridazine (200 mg, 0.64 mmol) in 3 mL DMSO was added DIEA (0.3 mL, 1.37 mmol) and 10 mg CsF, the solvent was stirred for 5 h at 120° C., Then the mixture was purified by HPLC to afford the compound 2-(4-(((3-(3-(trifluoromethoxy)phenyl)imidazo[1,2-b]pyridazin-6-yl)amino)methyl)cyclohexyl)ethanol (34 mg, 8.2%) as a brown solid.

$^1$H-NMR (CDCl$_3$/400 MHz): δ 8.61 (s, 1 H), 8.20-8.25 (m, 1 H), 7.95-8.05 (m, 2 H), 7.66 (t, J=4.4 Hz, 1 H), 7.21-7.28 (m, 1 H), 3.80-3.90 (m, 2 H), 3.62-3.75 (m, 2 H), 3.37 (d, J=6.4 Hz, 2 H), 3.21 (t, J=5.2 Hz, 2 H), 2.91-3.09 (m, 2 H), 2.10 (d, J=14.0 Hz, 2 H), 1.51-1.69 (m, 2 H). MS (ES$^+$, m/z): (M+H)$^+$: 435.5.

28. 6-((Tetrahydro-2H-pyran-4-yl)methoxy)-3-(3-(trifluoromethoxy)phenyl)imidazo[1,2-b]pyridazine (EX. 8-28)

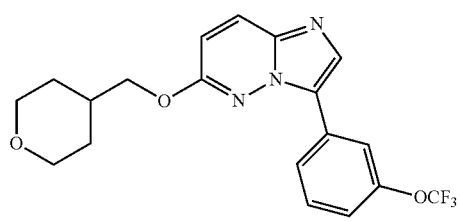

EX. 8-28

To the solution of compound (tetrahydro-2H-pyran-4-yl)methanol (100 mg, 0.86 mmol) and compound 6-chloro-3-(3-(trifluoromethoxy)phenyl)imidazo[1,2-b]pyridazine (270 mg, 0.86 mmol) in 10 mL dioxane was added t-BuOK (200 mg, 1.78 mmol). The mixture was stirred at 70° C. for 4 hrs. Then the mixture was purified by Pre-HPLC to afford the compound 6-((tetrahydro-2H-pyran-4-yl)methoxy)-3-(3-(trifluoromethoxy)phenyl)imidazo[1,2-b]pyridazine (25 mg, 12%) as a white solid.

$^1$H-NMR (CD$_3$OD/400 MHz): δ 8.18 (s, 1 H), 7.89 (s, 1 H), 7.82 (d, J=9.2 Hz, 1 H), 7.71-7.79 (m, 1 H), 7.42 (d, J=8.0 Hz, 1 H), 7.10-7.19 (m, 1H), 6.69 (d, J=9.6 Hz, 1H), 4.16 (d, J=6.8 Hz, 2H), 3.90-4.04 (m, 2 H), 3.30-3.45 (m, 2 H), 2.01-2.15 (m, 1 H), 1.63-1.75 (m, 2), 1.37-1.45 (m, 2 H). MS (ES$^+$, m/z): (M+H)$^+$: 334.5.

29. 4-((3-(3-(Trifluoromethyl)phenyl)imidazo[1,2-b]pyridazin-6-yl)amino)-trans-cyclohexanol (EX. 8-29)

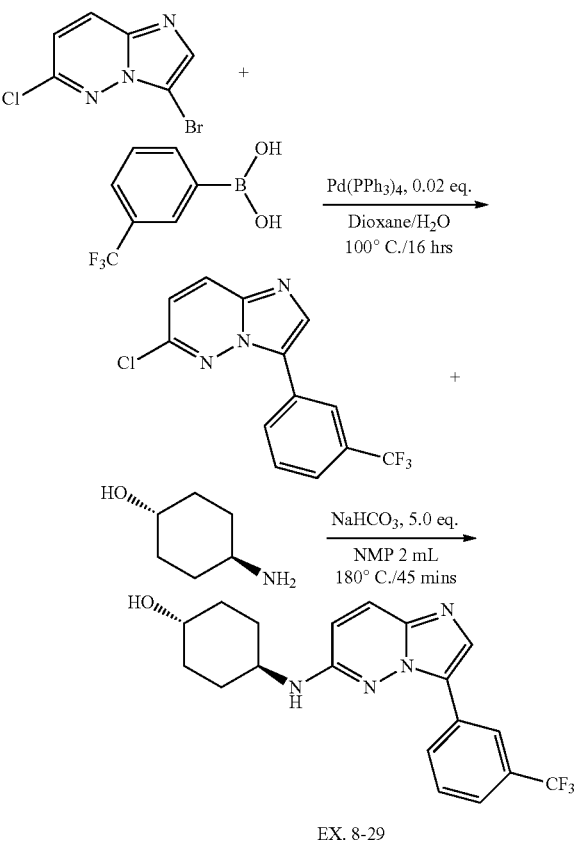

EX. 8-29

To a solution of 3-bromo-6-chloroimidazo[1,2-b]pyridazine (2 g, 8.6 mmol) and 3-(trifluoromethyl)phenylboronic acid (1.63 g, 8.6 mmol) in dioxane/H$_2$O (100 mL, 4:1) was added K$_2$CO$_3$ (2.4 g, 17.2 mmol) and Pd(PPh$_3$)$_4$ (0.497 g, 0.430 mmol), the mixture was stirred at 110° C. for 3 h. The solution was concentrated, partitioned in EtOAc/H$_2$O. The aqueous layer was washed with EtOAc (50 mL) for 3 times. The collected organic layers were dried over Na$_2$SO$_4$, concentrated and purified by column chromatography to give compound 6-chloro-3-(3-(trifluoromethyl)phenyl)imidazo[1,2-b]pyridazine (0.22 g, 0.739 mmol, yield 9%) as a brown solid.

$^1$H-NMR (CDCl$_3$/400 MHz): δ 8.28 (s, 1H), 8.24 (m, 1H), 8.11 (s, 1H), 7.99 (d, J=9.6 Hz, 1H), 7.64 (m, 2H), 7.13 (d, J=9.6 Hz, 1H).

To a solution of 6-chloro-3-(3-(trifluoromethyl)phenyl)imidazo[1,2-b]pyridazine (220 mg, 0.739 mmol) and trans-4-aminocyclohexanol hydrogenchloride (85 mg, 0.739 mmol) in NMP (2.0 mL) was added NaHCO$_3$ (79 mg, 0.739 mmol), the mixture was stirred at 180° C. for 45 mins under microwave irradiation. The mixture was purified by flash chromatograph to give 4-((3-(3-trifluoromethylphenyl)imidazo[1,2-b]pyridazin-6-yl)amino)cyclohexanol (40 mg, 0.106 mmol, 14%) as a pale yellow solid.

$^1$H-NMR (CD$_3$OD/400 MHz): δ 8.71 (s, 1H), 8.21 (m, 1H), 7.84 (s, 1H), 7.60 (m, 3H), 6.67 (m, 1H), 3.71 (m, 1H), 3.59 (m, 1H), 2.18 (m, 2H), 1.96 (m, 2H), 1.38 (m, 4H). MS (ES$^+$, m/z): (M+H)$^+$: 377.4.

EX. 8-29 free base and hydrochloride salt were prepared in 50 g scale according the following procedures.

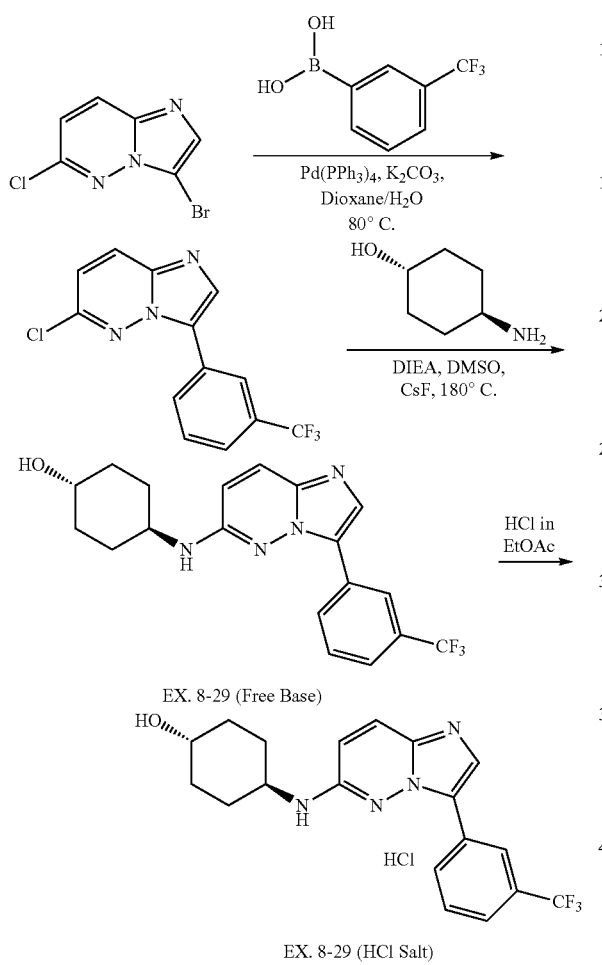

EX. 8-29 (Free Base)

EX. 8-29 (HCl Salt)

To a solution of 3-bromo-6-chloroimidazo[1,2-b]pyridazine (150 g, 0.65 mol) and 3-(trifluoromethyl)phenylboronic (143 g, 0.65 mol) in dioxane/H$_2$O (2.5 L: 4:1) was added K$_2$CO$_3$ (180 g, 1.3 mol) and Pd(PPh$_3$)$_4$ (10 g, 10 mmol). The mixture was stirred at 80° C. for 24 h. The solution was concentrated, partitioned with EA/H$_2$O. The aqueous layer was extracted with EA (500 mL) for 3 times. The collected organic layers was dried over Na$_2$SO$_4$, concentrated and purified by column chromatograph (PE:EA, 3:1 to 2:1) to give 6-chloro-3-(3-(trifluoromethyl)phenyl)imidazo[1,2-b]pyridazine (135.15 g, 70.3%) as yellow solid.

To a solution of 6-chloro-3-(3-(trifluoromethyl)phenyl)imidazo[1,2-b]pyridazine (90 g, 300 mmol) and trans-4-aminocyclohexanol (60 g, 522 mmol) in 300 mL of DMSO was added DIEA (90 g, 900 mmol) and CsF (45 g, 30 mmol). The mixture was stirred at 180° C. for 4 hour. After cooled to the room temperature, the reaction mixture was poured into 3 L of water. The solid precipitated was collected, washed with water and recrystallized with MeOH to give the EX. 8-29 (Free Base) (68.3 g, 63.06%) as a white solid. The product precipitated from MeOH generally contains 1 eq of MeOH. To remove the residue MeOH, the product was dissolved in EA, and then re-evaporated.

To a solution of EX. 8-29 (Free Base) (54 g, 144 mmol) in EA (3000 mL) was added HCl/EA until no further solid formed. The solid was collected and dried under vacuo to give EX. 8-29 (HCl Salt) (53 g, 98.13%) as a white solid.

$^1$H NMR (MeOD/400 MHz): δ 8.64 (s, 1H), 8.37 (s, 1H), 8.27 (d, J=8.0 Hz, 1H), 8.00 (d, J=9.6 Hz, 1H), 7.85 (d, J=8.0 Hz, 1H), 7.79 (t, J=8.0 Hz, 1H), 7.27 (d, J=9.6 Hz, 1H), 3.76-3.71 (m, 1H), 3.66-3.61 (m, 1H), 2.22-2.20 (m, 2H), 2.03-2.01 (m, 2H), 1.45-1.41 (m, 4H). MS (ES$^+$, m/z): (M+H)$^+$: 377.2.

30. 1-Methyl-4-((3-(3-(trifluoromethyl)phenyl)imidazo[1,2-b]pyridazin-6-yl)amino)-trans-cyclohexanol (EX. 8-30)

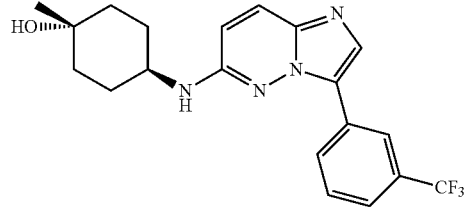

EX. 8-30 was prepared by similar procedures as in EX. 8-1 using trans-4-amino-1-methylcyclohexanol.

$^1$H-NMR (CD$_3$OD/400 MHz): δ 8.72 (s, 1H), 8.23 (d, J=7.6 Hz, 1H), 7.86 (s, 1H), 7.62 (m, 3H), 6.74 (d, J=9.6 Hz, 1H), 3.84 (m, 1H), 2.08 (m, 2H), 1.74 (m, 2H), 1.60 (m, 4H), 1.55 (s, 3H). MS (ES$^+$, m/z): (M+H)$^+$: 391.5.

31. 4-((3-(3-(Trifluoromethyl)phenyl)imidazo[1,2-b]pyridazin-6-yl)amino)-trans-cyclohexyl)propan-2-ol (EX. 8-31)

EX. 8-31 was prepared by similar procedures as in EX. 8-1 using 2-(trans-4-aminocyclohexyl)propan-2-ol.

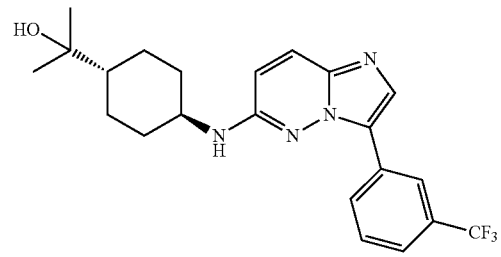 [SMILES: CC(C)(O)[C@H]1CC[C@H](Nc2ccc3ncc(-c4cccc(C(F)(F)F)c4)n3n2)CC1]

$^1$H-NMR (CD$_3$OD/400 MHz): δ 8.82 (s, 1H), 8.19 (m, 1H), 7.88 (s, 1H), 7.62 (m, 3H), 6.70 (d, J=9.6 Hz, 1H), 3.71 (m, 1H), 2.26 (m, 2H), 1.95 (m, 2H), 1.36 (m, 1H), 1.27 (m, 4H), 1.21 (s, 6H). MS (ES$^+$, m/z): (M+H)$^+$: 419.6.

Alternatively, EX. 8-31 was prepared in 50 g scale employing the following procedures.

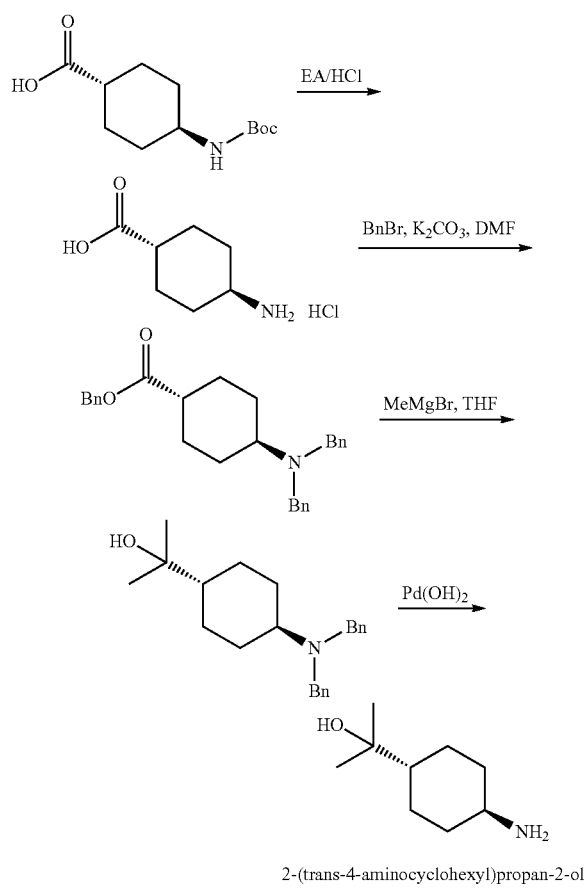

2-(trans-4-aminocyclohexyl)propan-2-ol

To a solution of trans-4-((tert-butoxycarbonyl)amino)cyclohexanecarboxylic acid (823 g, 3.38 mol) in EtOAc (4000 mL) was added EA/HCl (2500 mL). The mixture was stirred at 0° C. overnight. The reaction mixture was filtered and dried in vacuo to give a product of hydrochloride salt of trans-4-aminocyclohexanecarboxylic acid as white solid (604 g, 99.42% yield).

A mixture of hydrochloride salt of trans-4-aminocyclohexanecarboxylic acid (720 g), BnBr (1700 g, 2.5 eq) and $K_2CO_3$ in DMF (8000 mL) was stirred at rt overnight. More BnBr (100 g) was added and the reaction mixture was heated to 50° C. and kept for 3 hrs. The reaction mixture was then poured into water and extracted with EtOAc and combined organic phase washed with brine and concentrated in vacuo to give crude trans-benzyl 4-(dibenzylamino)cyclohexanecarboxylate as white solid (1495 g, 93.9% yield).

To a solution of trans-benzyl 4-(dibenzylamino)cyclohexanecarboxylate (290 g×5, 3.6 mol) in 2 L of THF under $N_2$ at 0° C., MeMgBr (800 mL) was added. The mixture was stirred at room temperature overnight and then quenched with 1.5 L of saturated $NH_4Cl$. The resulting mixture was extracted with EtOAc. The product was extracted with 1 M HCl to the aqueous phase, which was then wash with EtOAc. The aqueous phase was then neutralized with NaOH, extracted with EtOAc, washed with brine, dried with $Na_2SO_4$ and concentrated in vacuo to give the 2-(trans-4-(dibenzylamino)cyclohexyl)propan-2-ol as white solid (950 g, 78.3% yield).

A mixture of 2-(trans-4-(dibenzylamino)cyclohexyl)propan-2-ol (120 g×8, 356 mmol) and $Pd(OH)_2$ (15 g×8) in methanol (1000 mL) and $MeOH/NH_3$ (100 mL) was stirred under $H_2$ (50 psi) at 50° C. for 72 hrs, then the catalyst was removed and the filtrate was concentrated in vacuo and The crude product was chromatographed on silica gel (DCM/MeOH 20:1-DCM/MeOH/$NH_3$ 5:4:1) to give the 2-(trans-4-aminocyclohexyl)propan-2-ol as a pale yellow solid (210 g, 47.5% yield).

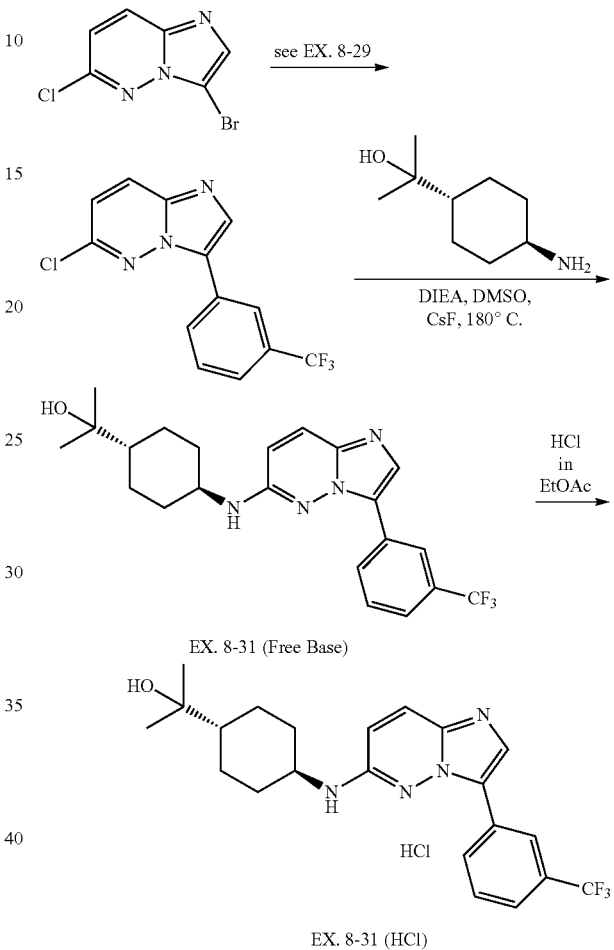

EX. 8-31 (Free Base)

EX. 8-31 (HCl)

6-chloro-3-(3-(trifluoromethyl)phenyl)imidazo[1,2-b]pyridazine was prepared according to procedure in EX. 8-29.

To a solution of 6-chloro-3-(3-(trifluoromethyl)phenyl)imidazo[1,2-b]pyridazine (100 g, 337 mmol) and 2-(trans-4-aminocyclohexyl)propan-2-ol (55 g, 350 mmol) in 400 mL of DMSO was added DIEA (90 g, 900 mmol) and CsF (45 g, 30 mmol). The mixture was stirred at 180° C. for 4 hour. The solid was removed and the filtrate was poured into a stirred solution of water (4 L) and EA (1 L), The solid formed was collected and recrystallized from EA to give EX. 8-31 (Free Base) as off white solid (70.58 g, 48.34%). From the mother liquid and the filtrate, a second batch of product was obtained after column chromatography (EA).

$^1$H NMR (MeOD/400 MHz): δ 8.80 (s, 1H), 8.17 (d, J=6.8 Hz, 1H), 7.85 (s, 1H), 7.62-7.58 (m, 3H), 6.68 (d, J=9.6 Hz, 1H), 3.72-3.65 (m, 1H), 2.30-2.24 (m, 2H), 1.95-1.90 (m, 2H), 1.37-1.22 (m, 5H), 1.16 (s, 6H). MS (ES$^+$, m/z): (M+H)$^+$: 419.3. Melting Point: 216.7° C.-219.3° C.

To a production of EX. 8-31 (Free Base) (57 g, 136 mmol) in EA (10 L) was added HCl/EA until no further solid formed (about 100 mL of HCl/EA). The mixture was stirred at room temperature for half an hour and the solid was collected, washed with EA and dried under vacuo to give EX. 8-31 (HCl) (52.06 g, 91.33%) as off white solid.

¹H NMR (MeOD/400 MHz): δ 8.69 (s, 1H), 8.34 (s, 1H), 8.21 (d, J=7.6 Hz, 1H), 7.96 (d, J=9.6 Hz, 1H), 7.81 (d, J=8.0 Hz, 1H), 7.75 (dd, J=7.6 Hz, 8.0 Hz, 1H), 7.23 (d, J=9.6 Hz, 1H), 3.73-3.66 (m, 1H), 2.24-2.20 (m, 2H), 1.97 (m, 2H), 1.37-1.25 (m, 5H), 1.16 (s, 6H). MS (ES⁺, m/z): (M+H)⁺: 419.2. Melting Point: 200.4° C.-201.6° C.

EX. 8-32 to EX. 8-34 were prepared by similar procedures as in EX. 8-1.

32. 4-(trans-Methoxycyclohexyl)-3-(3-(trifluoromethyl)phenyl)imidazo[1,2-b]pyridazin-6-amine (EX. 8-32)

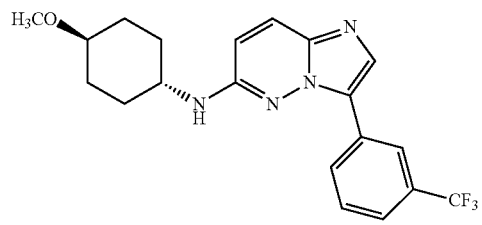

EX. 8-32

¹H-NMR (CD₃OD/400 MHz): δ 8.73 (s, 1H), 8.21 (d, J=8.0 Hz, 1H), 7.86 (s, 1H), 7.60 (m, 3H), 6.69 (d, J=8.0 Hz, 1H), 3.73 (m, 1H), 3.34 (s, 3H), 3.24 (m, 1H), 2.21 (m, 2H), 1.36 (m, 4H). MS (ES⁺, m/z): (M+H)⁺: 391.5.

33. N-(Tetrahydro-2H-pyran-4-yl)-3-(3-(trifluoromethyl)phenyl)imidazo[1,2-b]pyridazin-6-amine (EX. 8-33)

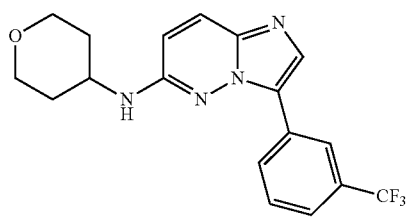

EX. 8-33

¹H-NMR (CD₃OD/400 MHz): δ 8.74 (s, 1H), 8.16 (d, J=6.8 Hz, 1H), 7.86 (s, 1H), 7.62 (m, 3H), 6.71 (d, J=9.6 Hz, 1H), 3.98 (m, 3H), 3.53 (m, 2H), 2.08 (m, 2H), 1.57 (m, 2H). MS (ES⁺, m/z): (M+H)⁺: 363.5.

34. 4-(((3-(3-(Trifluoromethyl)phenyl)imidazo[1,2-b]pyridazin-6-yl)amino)methyl)tetrahydro-2H-thiopyran 1,1-dioxide (EX. 8-34)

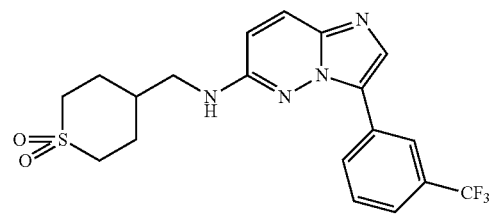

EX. 8-34

¹H-NMR (CD₃OD/400 MHz): δ 8.73 (s, 1H), 8.25 (d, J=8.0 Hz, 1H), 7.69 (s, 1H), 7.64 (m, 3H), 6.76 (d, J=10.0 Hz, 1H), 3.98 (m, 2H), 3.06 (m, 4H), 2.23 (m, 2H), 2.11 (m, 1H), 1.86 (m, 2H). MS (ES⁺, m/z): (M+H)⁺: 425.4.

35. 4-((3-(3-Chlorophenyl)imidazo[1,2-b]pyridazin-6-yl)amino)-trans-cyclohexanol (EX. 8-35)

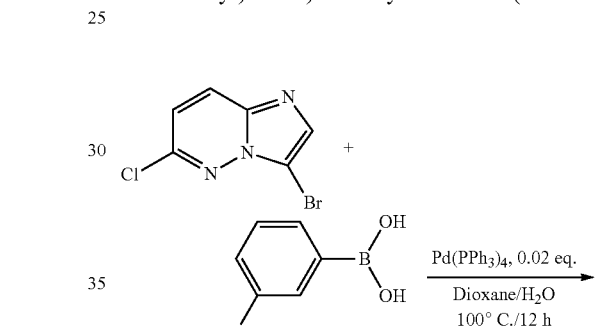

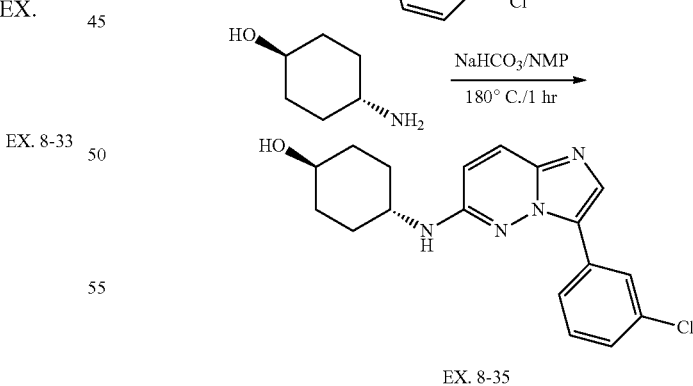

EX. 8-35

To a solution of 3-bromo-6-chloroimidazo[1,2-b]pyridazine (2 g, 8.6 mmol) and 3-(chloro)phenylboronic acid (1.35 g, 8.6 mmol) in dioxane/H₂O (100 mL, 4:1) was added K₂CO₃ (2.4 g, 17.2 mmol) and Pd(PPh₃)₄ (0.19 g, 0.172 mmol), the mixture was stirred at 110° C. for 3 h. The solution was concentrated, partitioned in EtOAc/H₂O. The aqueous layer was washed with EtOAc (50 mL) for 3 times.

The collected organic layers were dried over Na$_2$SO$_4$, concentrated and purified by column chromatography to give compound 6-chloro-3-(3-chlorophenyl)imidazo[1,2-b]pyridazine (1.2 g, 4.54 mmol, 53% yield) as a brown solid.

$^1$H-NMR (CDCl$_3$/400 MHz): δ 8.04 (d, J=13.2 Hz, 2H), 7.94 (m, 2H), 7.42 (m, 2H), 7.10 (d, J=9.2 Hz, 1H). MS (ES$^+$, m/z): (M+H)$^+$: 264.3.

To a solution of 6-chloro-3-(3-chlorophenyl)imidazo[1,2-b]pyridazine (300 mg, 1.14 mmol) and trans-4-aminocyclohexanol hydrogenchloride (327 mg, 2.84 mmol) in NMP (2.0 mL) was added NaHCO$_3$ (286 mg, 3.41 mmol), the mixture was stirred at 180° C. for 45 mins under microwave irradiation. The mixture was purified by flash chromatograph to give 4-((3-(3-chlorophenyl)imidazo[1,2-b]pyridazin-6-yl)amino)cyclohexanol (120 mg, 0.350 mmol, 31%) as a pale yellow solid.

$^1$H-NMR (CD$_3$OD/400 MHz): δ 8.47 (s, 1H), 7.90 (m, 1H), 7.80 (s, 1H), 7.58 (d, J=10.0 Hz, 1H), 7.41 (m, 2H), 7.30 (m, 1H), 6.66 (m, 1H), 3.61 (m, 2H), 2.20 (m, 2H), 2.00 (m, 2H), 1.50 (m, 2H), 1.45 (m, 2H). MS (ES$^+$, m/z): (M+H)$^+$: 343.5.

EX. 8-36 to EX. 8-40 were prepared by similar procedures as in EX. 8-35.

36. 4-((3-(3-Chlorophenyl)imidazo[1,2-b]pyridazin-6-yl)amino)-1-methyl-trans-cyclohexano (EX. 8-36)I

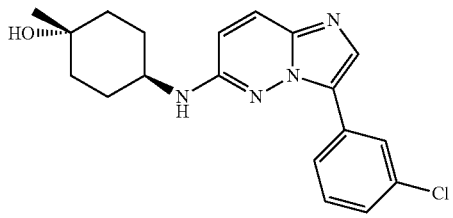

EX. 8-36

$^1$H-NMR (CD$_3$OD/400 MHz): δ 8.43 (s, 1H), 7.91 (d, J=8.0 Hz, 1H), 7.79 (s, 1H), 7.57 (d, J=8.0 Hz, 1H), 7.36 (m, 1H), 7.27 (d, J=8.0 Hz, 1H), 6.79 (d, J=10.0 Hz, 1H), 3.80 (m, 1H), 2.14 (m, 2H), 1.73 (m, 4H), 1.52 (m, 2H), 1.26 (s, 3H). MS (ES$^+$, m/z): (M+H)$^+$: 357.5.

37. 4-((3-(3-Chlorophenyl)imidazo[1,2-b]pyridazin-6-yl)amino)-trans-cyclohexyl)propan-2-ol (EX. 8-37)

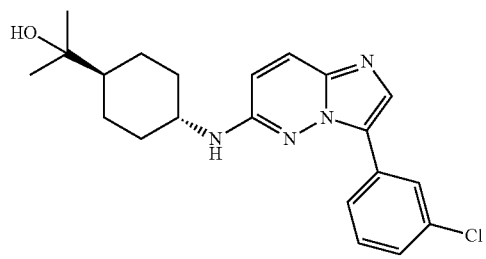

EX. 8-37

$^1$H-NMR (CD$_3$OD/400 MHz): δ 8.56 (s, 1H), 7.88 (d, J=8.0 Hz, 1H), 7.82 (s, 1H), 7.58 (d, J=9.6 Hz, 1H), 7.41 (m, 1H), 7.29 (d, J=6.8 Hz, 1H), 6.65 (d, J=10.0 Hz, 1H), 3.68 (m, 1H), 2.30 (m, 2H), 1.94 (m, 4H), 1.30 (m, 5H), 1.15 (s, 6H). MS (ES$^+$, m/z): (M+H)$^+$: 385.5.

38. 3-(3-Chlorophenyl)-N-(4-trans-methoxycyclohexyl)imidazo[1,2-b]pyridazin-6-amine (EX. 8-38)

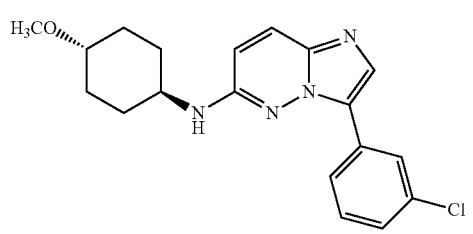

EX. 8-38

$^1$H-NMR (CD$_3$OD/400 MHz): δ 8.44 (s, 1H), 7.84 (d, J=9.6 Hz, 1H), 7.77 (s, 1H), 7.55 (d, J=9.6 Hz, 1H), 7.35 (m, 1H), 7.26 (d, J=6.8 Hz, 1H), 6.63 (d, J=10.0 Hz, 1H), 3.65 (m, 1H), 3.23 (m, 1H), 2.22 (m, 2H), 2.09 (m, 2H), 1.32 (m, 4H). MS (ES$^+$, m/z): (M+H)$^+$: 357.5.

39. 3-(3-Chlorophenyl)-N-(tetrahydro-2H-pyran-4-yl)imidazo[1,2-b]pyridazin-6-amine (EX. 8-39)

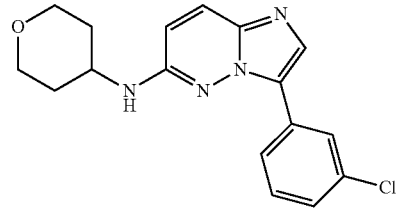

EX. 8-39

$^1$H-NMR (CDCl$_3$/400 MHz): δ 8.35 (s, 1H), 7.81 (m, 2H), 7.74 (d, J=9.6 Hz, 1H), 7.38 (m, 1H), 6.63 (d, J=9.6 Hz, 1H), 4.04 (m, 3H), 3.60 (m, 2H), 2.17 (m, 2H), 1.60 (m, 2H). MS (ES$^+$, m/z): (M+H)$^+$: 329.5.

40. 4-(((3-(3-Chlorophenyl)imidazo[1,2-b]pyridazin-6-yl)amino)methyl)tetrahydro-2H-thiopyran 1,1-dioxide (EX. 8-40)

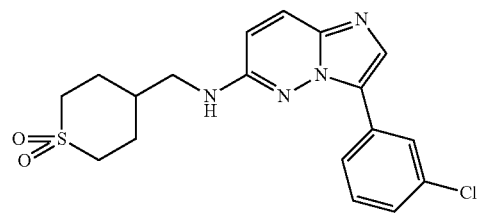

EX. 8-40

$^1$H-NMR (CD$_3$OD/400 MHz): δ 8.41 (s, 1H), 7.90 (d, J=8.0 Hz, 1H), 7.82 (s, 1H), 7.63 (d, J=8.0 Hz, 1H), 7.40 (m,

1H), 7.30 (d, J=8.0 Hz, 1H), 6.68 (d, J=8.0 Hz, 1H), 3.34 (m, 2H), 3.07 (m, 4H), 2.28 (m, 2H), 2.19 (m, 1H), 1.85 (m, 2H). MS (ES+, m/z): (M+H)+: 391.4.

EX. 8-41 to EX. 8-42 were prepared by similar procedures as in EX. 8-4.

41. 2-Methyl-4-((3-(3-(Trifluoromethoxy)phenyl)imidazo[1,2-b]pyridazin-6-yl)oxy)butan-2-ol (EX. 8-41)

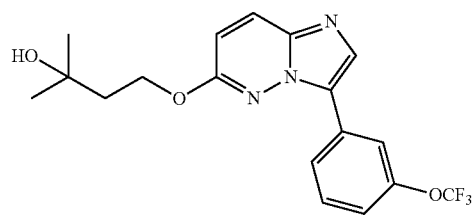

EX. 8-41

1H-NMR (CD3OD/400 MHz): δ 8.41 (s, 1H), 7.94 (m, 2H), 7.82 (d, J=8.0 Hz, 1H), 7.48 (t, J=8.0 Hz, 1H), 7.21 (d, J=9.6 Hz, 1H), 4.56 (t, J=6.4 Hz, 1H), 2.05 (t, J=6.4 Hz, 1H), 1.32 (s, 6H). MS (ES+, m/z): (M+H)+: 382.5.

42. 6-(2-Methoxyethoxy)-3-(3-(trifluoromethoxy)phenyl)imidazo[1,2-b]pyridazine (EX. 8-42)

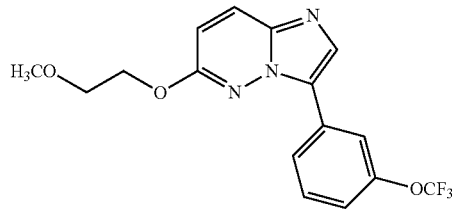

EX. 8-42

1H-NMR (CD3OD/400 MHz): δ 8.11 (s, 1H), 7.98 (d, J=10.0 Hz, 1H), 7.94 (s, 1H), 7.81 (d, J=8.0 Hz, 1H), 7.49 (t, J=7.6 Hz, 1H), 7.22 (d, J=9.6 Hz, 1H), 6.90 (d, J=9.6 Hz, 1H), 4.53 (t, J=4.8 Hz, 1H), 3.80 (t, J=4.8 Hz, 1H), 3.45 (s, 3H). MS (ES+, m/z): (M+H)+: 354.4.

43. N-(4-Methoxybenzyl)-3-(3-(trifluoromethoxy)phenyl)imidazo[1,2-b]pyridazin-6-amine (EX. 8-43)

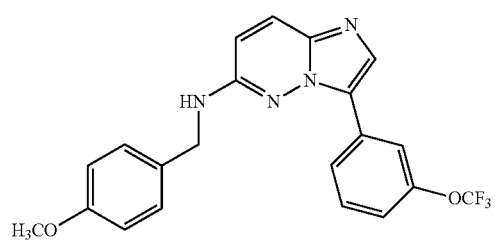

EX. 8-43

EX. 8-43 was prepared by similar procedures as in EX. 8-1.

1H-NMR (CD3OD/400 MHz): δ 8.21 (s, 1H), 7.92 (d, J=8.0 Hz, 1H), 7.82 (s, 1H), 7.64 (d, J=10.0 Hz, 1H), 7.48 (t, J=8.0 Hz, 1H), 7.32 (d, J=6.4 Hz, 2H), 7.20 (d, J=8.4 Hz, 1H), 6.87 (m, 2H), 6.78 (d, J=10.0 Hz, 1H), 4.48 (s, 2H), 3.75 (s, 3H). MS (ES+, m/z): (M+H)+: 415.5.

44. N-(2-morpholinoethyl)-3-(3-(trifluoromethoxy)phenyl)imidazo[1,2-b]pyridazin-6-amine (EX. 8-44)

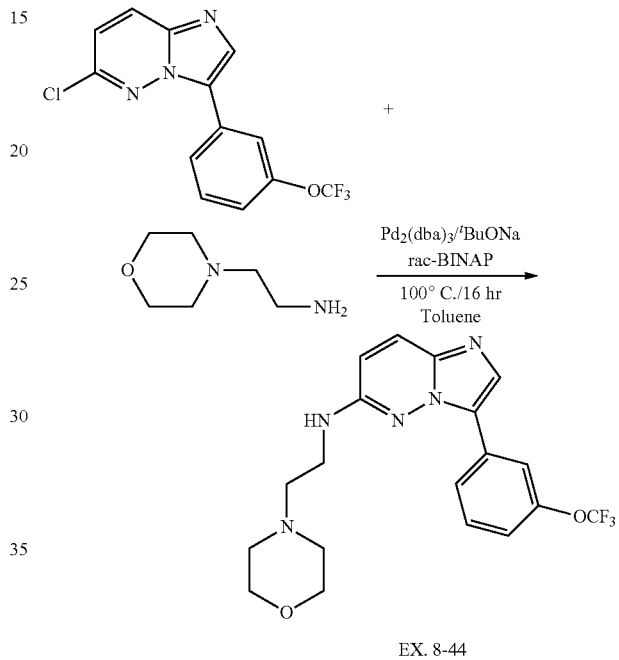

EX. 8-44

A solution of 6-chloro-3-(3-(trifluoromethoxy)phenyl)imidazo[1,2-b]pyridazine (200 mg, 0.638 mmol) and 2-morpholinoethanamine (83 mg, 0.638 mmol) in toluene (5 mL, 0.638 mmol) was added sodium tetiarybutyloxide (110 mg, 1.148 mmol), rac-BINAP (23.81 mg, 0.038 mmol) and the mixture was heated at 100° C. for overnight. After 16 h, the resulting dark brown solution was cooled down and was concentrated under reduced pressure. The solid was further purified by using combiflash chromatography (12 g, DCM to 10% MeOH/DCM) gave 252 mg of yellow solid N-(2-morpholinoethyl)-3-(3-(trifluoromethoxy)phenyl)imidazo[1,2-b]pyridazin-6-amine. 1HNMR (400 MHz, CD3OD) 8.28 (s, 1H), 8.00 (d, J=7.6 Hz, 1H), 7.82 (s, 1H), 7.63 (d, J=9.6 Hz, 1H), 7.52 (m, 1H), 7.21 (d, J=8.0 Hz, 1H), 6.74 (d, J=9.6 Hz, 1H), 3.67 (m, 4H), 3.53 (m, 2H), 2.68 (m, 2H), 2.52 (m, 4H) ESI: 408.4 (M+H)+

The free base of N-(2-morpholinoethyl)-3-(3-(trifluoromethoxy)phenyl)imidazo[1,2-b]pyridazin-6-amine (258 mg, 0.658 mmol) was suspended into methanol (2 ml). Concentrated HCl (137 uL, 12 M) was added and the solution was added drop wise into 30 mL of Ether, filtration and dry to give 247 mg off white powder as HCl salt. 1HNMR (400 MHz, CD3OD) 8.31 (s, 1H), 8.26 (s, 2H), 7.97 (m, 2H), 7.64 (m, 1H), 7.42 (d, J=8.21 Hz, 1H), 7.26 (m, 1H), 3.93 (m, 2H), 3.35 (m, 4H), 2.02 (m, 1H), 1.71 (m, 2H), 1.34 (m, 2H).

45. N-(2-morpholinoethyl)-3-(3-(trifluoromethoxy)phenyl)imidazo[1,2-b]pyridazin-6-amine (EX. 8-45)

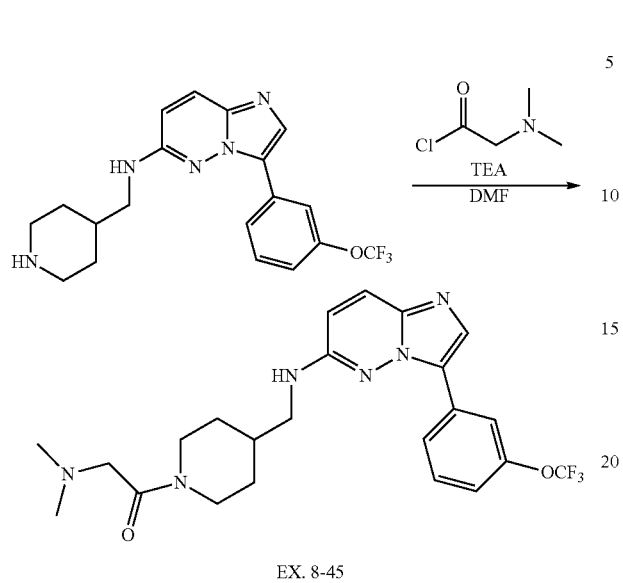

EX. 8-45

The reaction mixture of N-(piperidin-4-ylmethyl)-3-(3-(trifluoromethoxy)phenyl)imidazo[1,2-b]pyridazin-6-amine (100 mg 0.234 mmol), 2-(dimethylamino)acetyl chloride (43.5 mg, 0.234 mmol), TEA (81 uL, 2.5 eq) in DMF (1 mL) was stirred overnight. The residue was poured into water (20 mL). The precipitate was collected by filtration and purified by combiflash chromatography (12 g, DCM to 10% MeOH/DCM) gave 22 mg of solid 2-(dimethylamino)-1-(4-(((3-(3-(trifluoromethoxy)phenyl)imidazo[1,2-b]pyridazin-6-yl)amino)methyl)piperidin-1-yl)ethanone. $^1$HNMR (400 MHz, CD$_3$OD) 8.28 (m, 2H), 7.97 (m, 2H), 7.64 (t, J=8.02 Hz, 1H), 7.41 (d, J=8.21 Hz, 1H), 7.22 (d, J=9.0 Hz, 1H), 4.53 (d, J=13.5 Hz, 1H), 4.25 (m, 2H), 3.68 (d, J=13.5 Hz, 1H), 3.11 (m, 2H), 3.06 (s, 3H), 2.90 (s, 3H), 2.71 (t, J=12.5 Hz, 2H), 2.08 (m, 1H), 1.90 (d, J=12.5 Hz, 2H). ESI: 477.5 (M+H)$^+$ The free base 2-(dimethylamino)-1-(4-(((3-(3-(trifluoromethoxy)phenyl)imidazo[1,2-b]pyridazin-6-yl)amino)methyl)piperidin-1-yl)ethanone (247 mg, 0.517 mmol) was suspended into methanol (2 mL). Concentrated HCl (108 uL, 2.5 eq) was added. The solution was added dropwise into 30 mL of Ether, filtration and dry to give 205 mg off white powder as HCl salt. $^1$HNMR (400 MHz, CD$_3$OD) 8.29 (s, 1H), 8.25 (s, 1H), 7.96 (m, 2H), 7.64 (t, J=8.02 Hz, 1H), 7.41 (d, J=8.41 Hz, 1H), 7.24 (d, J=9.8 Hz, 1H), 2.02 (m, 1H), 1.87 (d, J=8.32 Hz, 2H), 1.39 (s, 6H).

46. 4-((3-(3-(Trifluoromethoxy)phenyl)pyrazolo[1,5-a]pyrimidin-5-yl)amino)-trans-cyclohexanol (EX. 8-46)

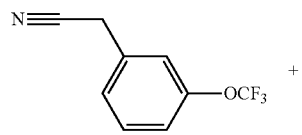

+

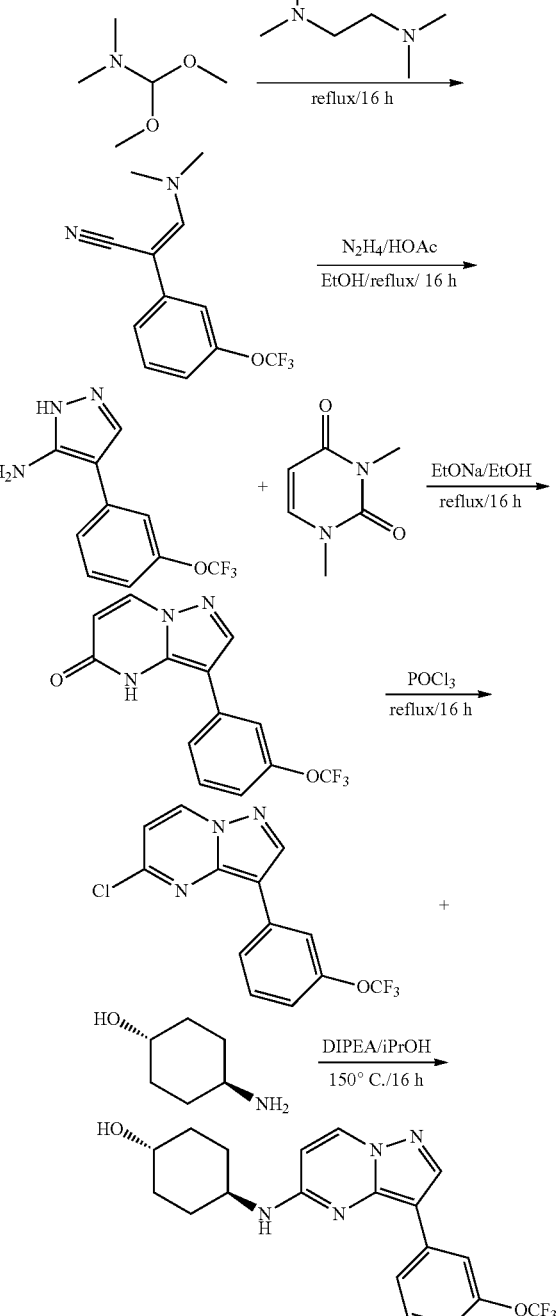

EX. 8-46

Synthesis of 3-(dimethylamino)-2-(3-(trifluoromethoxy)phenyl)acrylonitrile

A mixture of 3-trifluoromethoxyphenylacetonitrile (2.5 grams, 12.43 mmol), DIPEA (0.321 grams, 2.48 mmol), and dimethyl formamide dimethyl acetal (20 mL) were heated at reflux for 4 h. On cooling, the reaction was partitioned between EtOAc and saturated aqueous NH$_4$Cl solution. The aqueous phase was extracted with ethyl acetate and the combined organic phase washed with brine and concenrated in vacuo. The crude product was purified by chromatography (ethyl acetate/hexane, 0-10%) on silica gel (24 grams) to give pure product (2.3 grams, 8.98 mmol, 72% yield.).

Synthesis of 4-(3-(trifluoromethoxy)phenyl)-1H-pyrazol-5-amine 5

A mixture of acrylnitrile (2.0 g, 7.81 mmol), hydrazine hydrate (4.53 grams, 39.0 mmol), and glacial acetaic acid (2.34 grams, 39.0 mmol) and ethanol (20 mL) were heated at reflux for 16 h. On cooling, the reaction was diluted with water, extracted with AcOEt and the combined organic phase washed with brine and concenrated in vacuo (1.90 grams, 7.84 mmol, 100% yield.).
$^1$H-NMR (CDCl$_3$/400 MHz): δ 7.64 (m, 1H), 7.42 (m, 4H), 7.06 (d, J=7.6 Hz, 1H). MS (ES$^+$, m/z): (M+H)$^+$: 244.3.

Synthesis of 3-(3-(trifluoromethoxy)phenyl)pyrazolo[1,5-a]pyrimidin-5(4H)-one A mixture of pyrazole (0.8 grams, 3.29 mmol), 1,3-dimethyluracil (0.51 grams, 3.62 mmol), and dry EtOH 10 mL were treated dropwise with sodium ethoxide (0.29 grams, 4.28 mmol) and on completion of addition the reaction was heated at reflux for 16 h. On cooling the reaction was concentrated in vacuo and the residue added to ice, neutralised with acetic acid and the resulting precipitate filtered, washed with water and dried to give the product (0.4 grams, 1.36 mmol, 41% yield.). No chromatography was needed for this step.
$^1$H-NMR (CDCl$_3$/400 MHz): δ 8.42 (d, J=8.0 Hz, 1H), 8.09 (s, 1H), 7.62 (d, J=7.6 Hz, 1H), 7.52 (m, 2H), 7.20 (d, J=8.8 Hz, 1H), 6.16 (d, J=7.6 Hz, 1H).

Synthesis of 5-chloro-3-(3-(trifluoromethoxy)phenyl)pyrazolo[1,5-a]pyrimidine A mixture of pyrazolepyrimidinone (0.5 grams, 1.69 mmol) was treated with POCl$_3$ 10 mL and the mixture was heated at relux for overnight. On cooling, after remove the solvent under rotovapor, the reaction was poured onto ice, cautiously made basic with saturated aqueous NaHCO$_3$ solution and extracted with EtOAc. The combined organic phases were washed with brine and concentrated in vacuo to give the product (0.3 grams, 0.96 mmol, 56% yield.).
$^1$H-NMR (CDCl$_3$/400 MHz): δ 8.56 (d, J=7.6 Hz, 1H), 8.39 (s, 1H), 7.92 (d, J=7.6 Hz, 1H), 7.85 (m, 2H), 7.45 (t, J=8.0 Hz, 1H), 7.12 (d, J=8.4 Hz, 1H), 6.85 (d, J=7.2 Hz, 1H). MS (ES$^+$, m/z): (M+H)$^+$: 314.3.

Synthesis of 4-((3-(3-(trifluoromethoxy)phenyl)pyrazolo[1,5-a]pyrimidin-5-yl)amino)cyclohexanol A solution of 3-bromo-5-chloropyrazolo[1,5-a]pyrimidine (0.03 grams, 0.096 mmol) and trans-1,4-diamocyclohexane (0.017 grams, 0.143 mmol) in iso-propanol (5 mL) was added DIPEA (0.025 grams, 0.191 mmol) and the mixture was heated at 150° C. for 12 h under microwave irradiation. The resulting dark brown solution was cooled down and was concentrated under reduced pressure. The solid was further purified by using combiflash chromatography (12 g column), eluent: 0-6% CH$_3$OH/DCM and obtained product (0.020 grams, 0.051 mmol, 53% yield.).
$^1$H-NMR (CD$_3$OD/400 MHz): δ 8.22 (s, 1H), 8.18 (m, 2H), 7.80 (d, J=8.0 Hz, 1H), 7.34 (t, J=8.4 Hz, 1H), 6.96 (m, 1H), 6.17 (d, J=7.6 Hz, 1H), 3.90 (m, 1H), 3.58 (m, 1H), 2.18 (m, 2H), 2.00 (m, 2H), 1.38 (m, 4H). MS (ES$^+$, m/z): (M+H)$^+$: 393.5.

EX. 8-47 to EX. 8-53 were prepared using similar procedures as in EX. 8-46.

47. 4-((3-(3-(Trifluoromethoxy)phenyl)pyrazolo[1,5-a]pyrimidin-5-yl)amino)-trans-cyclohexyl)propan-2-ol (EX. 8-47)

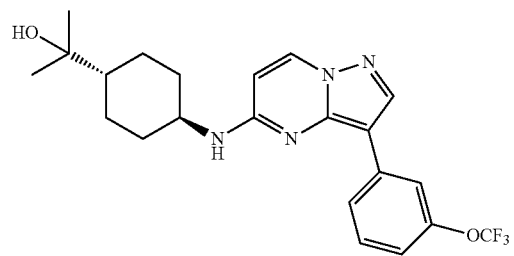

EX. 8-47

$^1$H-NMR (CD$_3$OD/400 MHz): δ 8.38 (s, 1H), 8.22 (m, 2H), 7.78 (d, J=8.0 Hz, 1H), 7.38 (t, J=8.0 Hz, 1H), 6.97 (d, J=7.6 Hz, 1H), 6.22 (d, J=7.6 Hz, 1H), 3.90 (m, 1H), 2.25 (m, 2H), 1.97 (m, 2H), 2.00 (m, 2H), 1.37 (m, 1H), 1.30 (m, 4H), 1.16 (s, 6H). MS (ES$^+$, m/z): (M+H)$^+$: 435.5.

48. 1-Methyl-4-((3-(3-(trifluoromethoxy)phenyl)pyrazolo[1,5-a]pyrimidin-5-yl)amino)-trans-cyclohexanol (EX. 8-48)

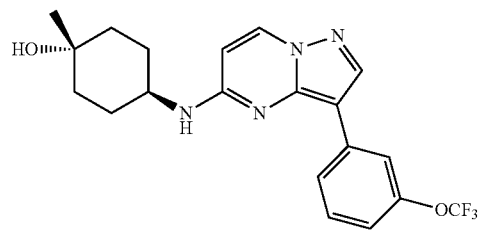

EX. 8-48

$^1$H-NMR (CD$_3$OD/400 MHz): δ 8.25 (m, 3H), 7.95 (d, J=8.0 Hz, 1H), 7.40 (t, J=8.0 Hz, 1H), 6.99 (d, J=7.6 Hz, 1H), 6.29 (d, J=7.6 Hz, 1H), 4.10 (m, 1H), 2.11 (m, 2H), 1.74 (m, 2H), 1.62 (m, 4H), 1.28 (s, 3H). MS (ES$^+$, m/z): (M+H)$^+$: 407.5.

49. 4-(trans-Methoxycyclohexyl)-3-(3-(trifluoromethoxy)phenyl)pyrazolo[1,5-a]pyrimidin-5-amine (EX. 8-49)

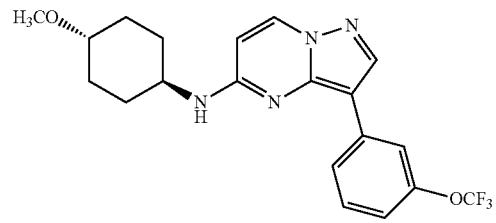

EX. 8-49

¹H-NMR (CD₃OD/400 MHz): δ 8.30 (m, 1H), 8.22 (m, 2H), 7.82 (d, J=8.0 Hz, 1H), 7.38 (t, J=8.0 Hz, 1H), 6.38 (m, 1H), 6.22 (d, J=7.6 Hz, 1H), 3.95 (m, 1H), 3.26 (m, 1H), 2.22 (m, 2H), 2.14 (m, 2H), 1.38 (m, 4H). MS (ES⁺, m/z): (M+H)⁺: 407.5.

50. N-(Tetrahydro-2H-pyran-4-yl)-3-(3-(trifluoromethoxy)phenyl)pyrazolo[1,5-a]pyrimidin-5-amine (EX. 8-50)

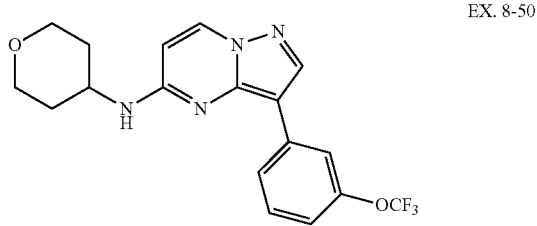 [SMILES: FC(F)(F)Oc1cccc(-c2cnn3ccc(NC4CCOCC4)nc23)c1]

EX. 8-50

¹H-NMR (CDCl₃/400 MHz): δ 8.32 (s, 1H), 8.29 (m, 2H), 7.83 (d, J=8.0 Hz, 1H), 7.41 (t, J=8.0 Hz, 1H), 7.02 (d, J=8.0 Hz, 1H), 6.29 (d, J=8.0 Hz, 1H), 4.24 (m, 1H), 4.02 (m, 2H), 3.60 (t, J=12.0 Hz, 2H), 2.12 (m, 2H), 1.62 (m, 2H). MS (ES⁺, m/z): (M+H)⁺: 379.4.

51. 4-(((3-(3-(Trifluoromethoxy)phenyl)pyrazolo[1,5-a]pyrimidin-5-yl)amino)methyl)tetrahydro-2H-thiopyran 1,1-dioxide (EX. 8-51)

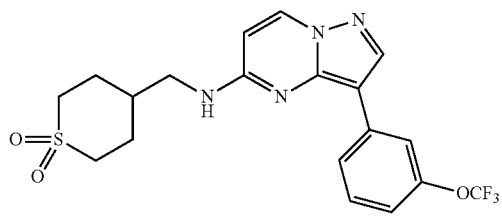

EX. 8-51

¹H-NMR (CD₃OD/400 MHz): δ 8.24 (m, 2H), 8.21 (s, 1H), 7.70 (d, J=8.0 Hz, 1H), 7.38 (d, J=8.0 Hz, 1H), 7.23 (m, 1H), 6.07 (d, J=7.2 Hz, 1H), 3.51 (t, J=6.4 Hz, 2H), 3.06 (m, 2H), 3.00 (m, 2H), 2.22 (m, 3H), 1.96 (m, 2H). MS (ES⁺, m/z): (M+H)⁺: 441.4.

52. N-(3-(3-(Trifluoromethoxy)phenyl)pyrazolo[1,5-a]pyrimidin-5-yl)cyclohexane-1,4-trans-diamine (EX. 8-52)

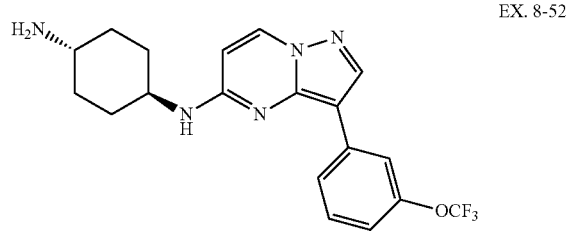 [SMILES: N[C@H]1CC[C@H](Nc2ccn3ncc(-c4cccc(OC(F)(F)F)c4)c3n2)CC1]

EX. 8-52

¹H-NMR (CD₃OD/400 MHz): δ 8.24 (m, 3H), 7.87 (d, J=7.6 Hz, 1H), 7.39 (t, J=8.0 Hz, 1H), 6.99 (d, J=8.0 Hz, 1H), 6.24 (d, J=7.6 Hz, 1H), 3.95 (m, 1H), 2.86 (m, 1H), 2.24 (m, 2H), 1.8 (m, 2H), 1.37 (t, J=9.2 Hz, 4H). MS (ES⁺, m/z): (M+H)⁺: 392.4.

53. (S)-1-(3-(3-(Trifluoromethoxy)phenyl)pyrazolo[1,5-a]pyrimidin-5-yl)piperidin-3-amine (EX. 8-53)

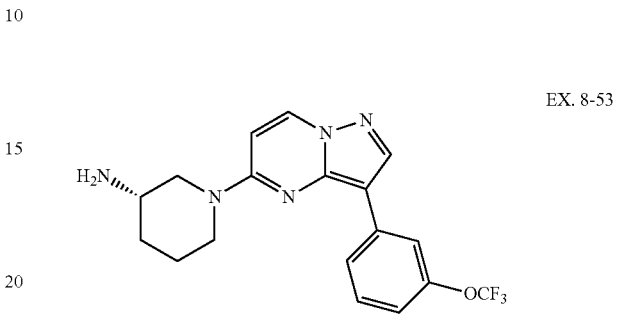

EX. 8-53

¹H-NMR (CD₃OD/400 MHz): δ 8.32 (d, J=8.0 Hz, 1H), 8.24 (m, 1H), 8.07 (m, 1H), 7.85 (d, J=5.6 Hz, 1H), 7.38 (t, J=8.0 Hz, 1H), 6.95 (d, J=7.6 Hz, 1H), 6.61 (d, J=7.6 Hz, 1H), 4.22 (m, 2H), 3.17 (m, 2H), 2.91 (m, 1H), 2.10 (m, 1H), 1.80 (m, 1H), 1.60 (m, 1H), 1.50 (m, 1H). MS (ES⁺, m/z): (M+H)⁺: 378.5.

54. 4-((3-(3-(Trifluoromethyl)phenyl)pyrazolo[1,5a]pyrimidin-5-yl)amino)-trans-cyclohexanol (EX 8-54)

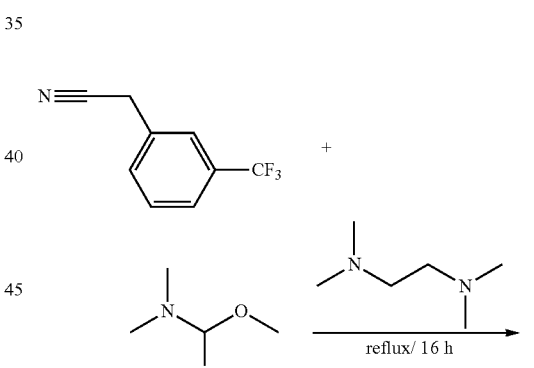

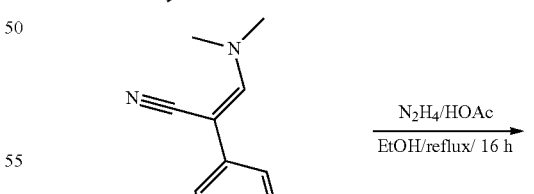

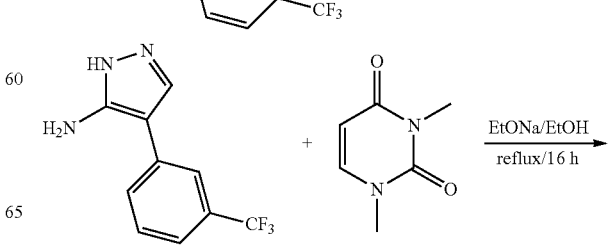

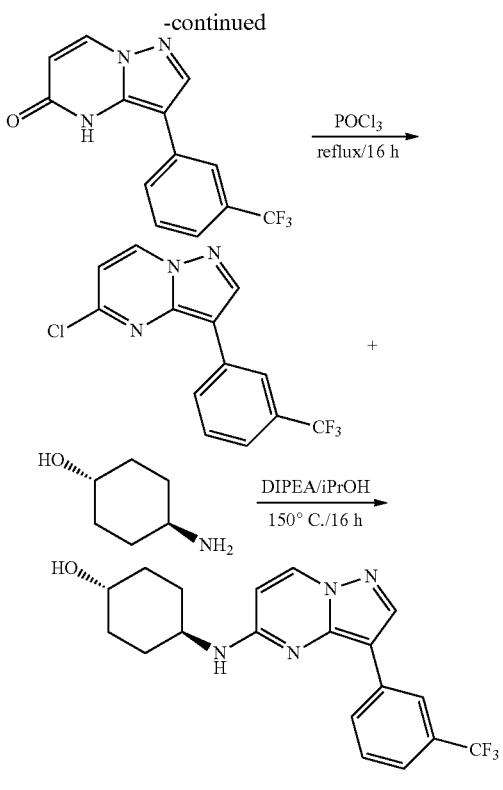

EX. 8-54

A mixture of 2-(3-(trifluoromethyl)phenyl)acetonitrile (4.55 g, 24.58 mmol), 1,1-dimethoxy-N,N-dimethylmethanamine (13.10 ml, 98 mmol), and $N^1,N^1,N^2,N^2$-tetramethylethane-1,2-diamine (0.737 ml, 4.92 mmol) were heated to reflux for 5 h. After cooling to RT, the mixture was partitioned between saturated aqueous NH₄Cl and EtOAc and extracted three times with EtOAc. The combined organics were washed with brine, dried over Na₂SO₄, and concentrated in vacuo. After absorbing on celite, the compound was purified by Isco (40 g silica, 10% to 70% EtOAc/hexanes) to give pure 3-(dimethylamino)-2-(3-(trifluoromethyl)phenyl)acrylonitrile (2.93 g, 50% yield).

¹H NMR (400 MHz, CDCl₃): 7.48 (m, 2H), 7.41-7.34 (m, 2H), 6.94 (s, 1H), 3.25 (s, 6H).

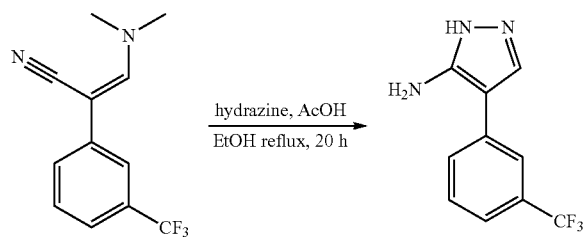 [SMILES: CN(C)/C=C(\C#N)c1cccc(C(F)(F)F)c1 ; Nc1[nH]ncc1-c1cccc(C(F)(F)F)c1]

To a mixture of 3-(dimethylamino)-2-(3-(trifluoromethyl) phenyl)acrylonitrile (2.93 g, 12.20 mmol) in ethanol (35 ml) was added hydrazine hydrate (3.80 ml, 122 mmol) and acetic acid (6.98 ml, 122 mmol). Upon to reflux; a solution formed. After 5 hours, 0.25 mL of hydrazine hydrate was added and the reaction refluxed an additional 15 hours. The volatiles were removed in vacuo, and the residue partitioned between EtOAc and water. After extracting three times with EtOAc, the combined organics were washed twice with saturated aqueous NaHCO₃, dried over Na₂SO₄, and concentrated in vacuo to cleanly give 4-(3-(trifluoromethyl) phenyl)-1H-pyrazol-5-amine (2.7 g, 97% yield) as a light yellow oil.

¹H NMR (400 MHz, CDCl₃): 7.69 (m, 1H), 7.63 (m, 1H), 7.58 (s, 1H), 7.50 (m, 2H), 5.78 (br s, 3H).

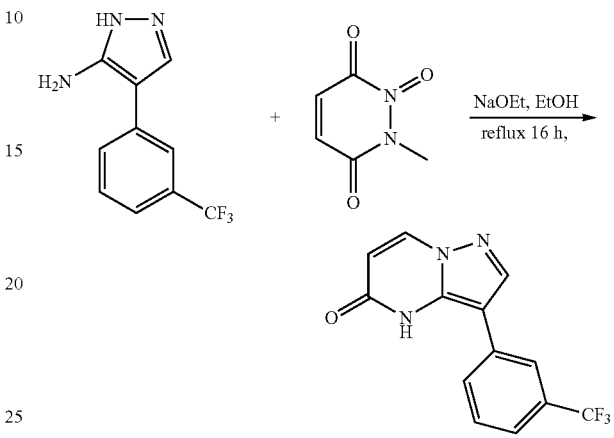

To a mixture of 4-(3-(trifluoromethyl)phenyl)-1H-pyrazol-5-amine (2.7 g, 11.88 mmol) and 1,3-dimethylpyrimidine-2,4(1H,3H)-dione (1.999 g, 14.26 mmol) in ethanol (35 ml) was added sodium ethoxide (1.132 g, 16.64 mmol). After heating to reflux 16 hours under Agonr, the reaction was cooled to RT and the volatiles removed in vacuo. The mixture was diluted with 30 mL H₂O and acidified to pH=4 with AcOH. The resulting solid was collected by vacuum filtration. The solid was taken up in a 4:1 DCM/2-propanol solution, washed with water, dried over Na₂SO₄, and rotovaced to give pure 3-(3-(trifluoromethyl)phenyl)pyrazolo[1,5-a]pyrimidin-5(4H)-one (2.07 g, 7.41 mmol, 62.4% yield).

¹H NMR (400 MHz, DMSO-d6): 12.38 (br s, 1H), 8.62 (d, 1H), 8.38 (s, 1H), 8.05 (m, 2H), 7.60 (m, 2H), 6.20 (m, 1H).

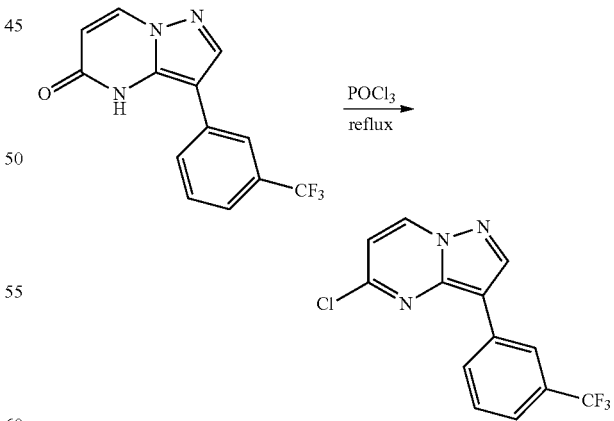

A mixture of 3-(3-(trifluoromethyl)phenyl)pyrazolo[1,5-a]pyrimidin-5(4H)-one (2.07 g, 7.41 mmol) and POCl₃ (6.91 ml, 74.1 mmol) was heated to 107° C. The heating was continued for 16 hours. The reaction mixture was cooled to RT and the POCl₃ removed in vacuo to give a waxy solid. The solid was triturated multiple times with Et₂O and the Et₂O layers were combined and rotovaced. The resulting residue was taken up in DCM and washed with saturated aqueous NaHCO₃, dried over Na₂SO₄ and concentrated in vacuo to give 5-chloro-3-(3-(trifluoromethyl)phenyl)pyrazolo[1,5-a]pyrimidine (1.47 g, 67% yield) as a brown solid.

¹H NMR (400 MHz, CDCl₃): 8.60 (d, 1H), 8.47 (s, 1H), 8.24 (d, 1H), 8.19 (s, 1H), 7.55 (m, 2H), 6.87 (d, 1H).

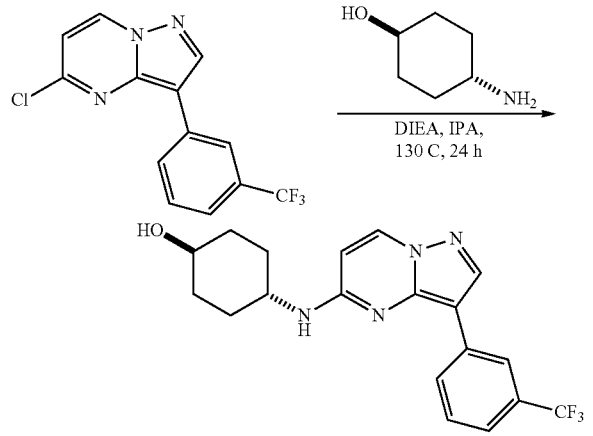

A mixture of 5-chloro-3-(3-(trifluoromethyl)phenyl)pyrazolo[1,5-a]pyrimidine (100 mg, 0.336 mmol), 4-aminocyclohexanol (58.0 mg, 0.504 mmol), and DIEA (0.117 ml, 0.672 mmol) in 2-propanol (3 ml) was irradiated to 135° C. for 14 h in a Biotage microwave. After cooling, the mixture was diluted with saturated aqueous NaHCO₃, and extracted three times with EtOAc. The combined extracts were washed with brine, dried over Na₂SO₄ and concentrated in vacuo. After absorbing on celite, the compound was purified by Isco (12 g silica, 1/5/4 MeOH/EtOAc/hex) to give trans-4-((3-(3-(trifluoromethyl)phenyl)pyrazolo[1,5-a]pyrimidin-5-yl)amino)cyclohexanol (101 mg, 80% yield) as a white solid.

¹H NMR (400 MHz, CD₃OD): 8.72 (s, 1H), 8.29 (s, 1H), 8.50 (d, 1H), 8.09 (d, 1H), 7.50 (t, 1H), 7.39 (d, 1H), 6.25 (d, 1H), 3.98 (m, 1H), 3.62 (m, 1H), 2.23 (m, 2H), 2.03 (m, 2H), 1.55-1.32 (m, 4H). MS (ES⁺, m/z): (M+H)⁺: 377.5.

EX. 8-55 to EX. 8-60 were prepared using similar procedures as in EX. 8-54.

55. 1-Methyl-4-((3-(3-(trifluoromethyl)phenyl)pyrazolo[1,5-a]pyrimidin-5-yl)amino)-trans-cyclohexanol (EX. 8-55)

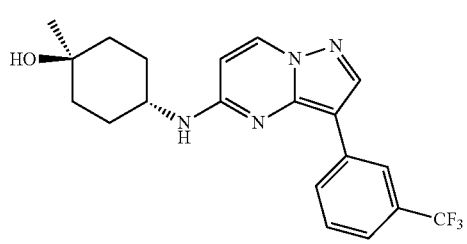

¹H NMR (400 MHz, CD₃OD): 8.69 (s, 1H), 8.29 (s, 1H), 8.25 (d, 1H), 8.11 (d, 1H), 7.30 (t, 1H), 7.39 (d, 1H), 6.31 (d, 1H), 4.09 (m, 1H), 2.15 (m, 2H), 1.79-1.52 (m, 6H), 1.30 (s, 3H). MS (ES⁺, m/z): (M+H)⁺: 391.5.

56. 4-((3-(3-(Trifluoromethyl)phenyl)pyrazolo[1,5-a]pyrimidin-5-yl)amino)-trans-cyclohexyl)propan-2-ol (EX. 8-56)

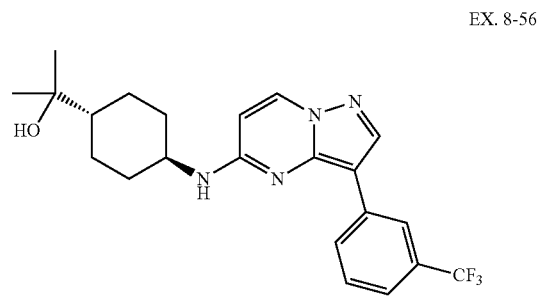 [SMILES: CC(C)(O)[C@H]1CC[C@H](Nc2ccn3ncc(-c4cccc(C(F)(F)F)c4)c3n2)CC1]

¹H NMR (400 MHz, CD₃OD): 8.78 (s, 1H), 8.18 (s, 1H), 8.24 (d, 1H), 8.05 (d, 1H), 7.49 (t, 1H), 7.38 (d, 1H), 6.25 (d, 1H), 3.95 (m, 1H), 2.28 (m, 2H), 1.95 (m, 2H), 1.32 (m, 5H), 1.20 (s, 6H). MS (ES⁺, m/z): (M+H)⁺: 419.5.

57. 4-(trans-Methoxycyclohexyl)-3-(3-(trifluoromethyl)phenyl)pyrazolo[1,5-a]pyrimidin-5-amine (EX. 8-57)

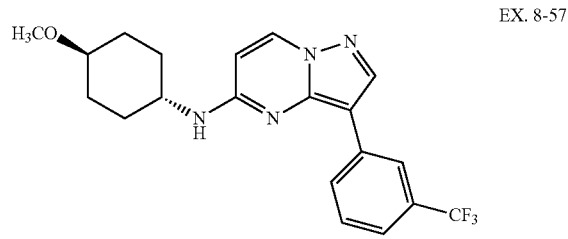 [SMILES: CO[C@H]1CC[C@H](Nc2ccn3ncc(-c4cccc(C(F)(F)F)c4)c3n2)CC1]

¹H NMR (400 MHz, DMSO-d6): 8.76 (s, 1H), 8.49 (d, 1H), 8.45 (s, 1H), 8.13 (d, 1H), 7.66 (d, 1H), 7.56 (t, 1H), 7.42 (d, 1H), 6.30 (d, 1H), 3.75 (m, 1H), 3.27 (s, 3H), 3.19 (m, 1H), 2.10 (m, 4H), 1.30 (m, 4H). MS (ES⁺, m/z): (M+H)⁺: 391.5.

58. N-(Tetrahydro-2H-pyran-4-yl)-3-(3-(trifluoromethyl)phenyl)pyrazolo[1,5-a]pyrimidin-5-amine (EX. 8-58)

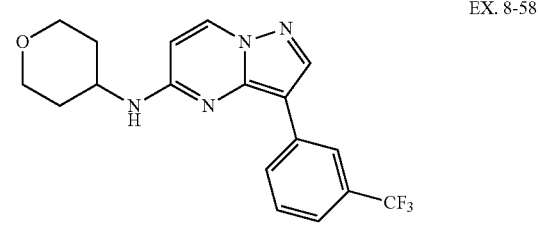 [SMILES: FC(F)(F)c1cccc(-c2cnn3ccc(NC4CCOCC4)nc23)c1]

¹H NMR (400 MHz, DMSO-d6): 8.73 (s, 1H), 8.52 (d, 1H), 8.47 (s, 1H), 8.15 (d, 1H), 7.77 (d, 1H), 7.55 (t, 1H), 7.43 (d, 1H), 6.33 (d, 1H), 4.08 (m, 1H), 3.93 (m, 2H), 3.43 (m, 2H), 2.05 (m, 2H), 1.53 (m, 2H). MS (ES+, m/z): (M+H)+: 363.5.

59. 4-(((3-(3-(Trifluoromethyl)phenyl)pyrazolo[1,5-a]pyrimidin-5-yl)amino)methyl)tetrahydro-2H-thiopyran 1,1-dioxide (EX. 8-59)

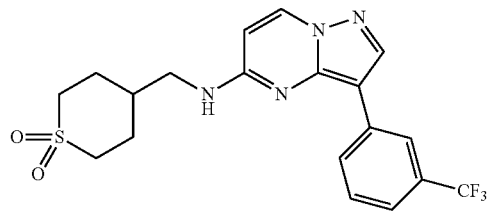

EX. 8-59

1H NMR (400 MHz, CD3OD): 8.66 (s, 1H), 8.31 (s, 1H), 8.29 (s, 1H), 8.12 (d, 1H), 7.52 (t, 1H), 7.40 (d, 1H), 6.31 (d, 1H), 3.50 (d, 2H), 3.18 (m, 4H), 2.21 (m, 3H), 1.88 (m, 2H). MS (ES+, m/z): (M+H)+: 425.5.

60. 4-(3-(3-(Trifluoromethyl)phenyl)pyrazolo[1,5-a]pyrimidin-5-yl)thiomorpholine 1,1-dioxide (EX. 8-60)

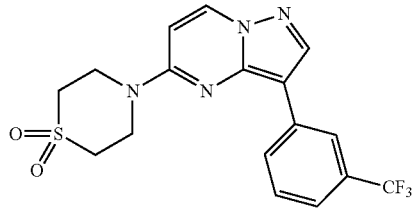

EX. 8-60

1H NMR (400 MHz, DMSO-d6): 8.82 (d, 1H), 8.61 (s, 1H), 8.48 (m, 1H), 8.28 (d, 1H), 7.61 (t, 1H), 7.48 (d, 1H), 6.98 (d, 1H), 4.22 (m, 4H), 3.28 (m, 4H). MS (ES+, m/z): (M+H)+: 397.4.

61. 4-((3-(3-Chlorophenyl)pyrazolo[1,5-a]pyrimidin-5-yl)amino)-trans-cyclohexanol (EX. 8-61)

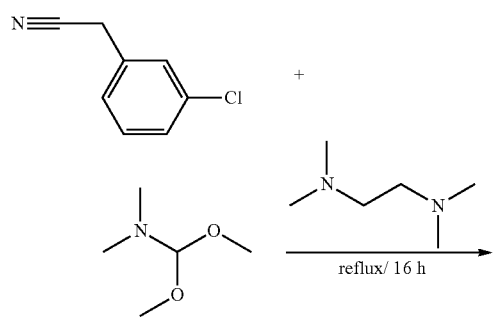

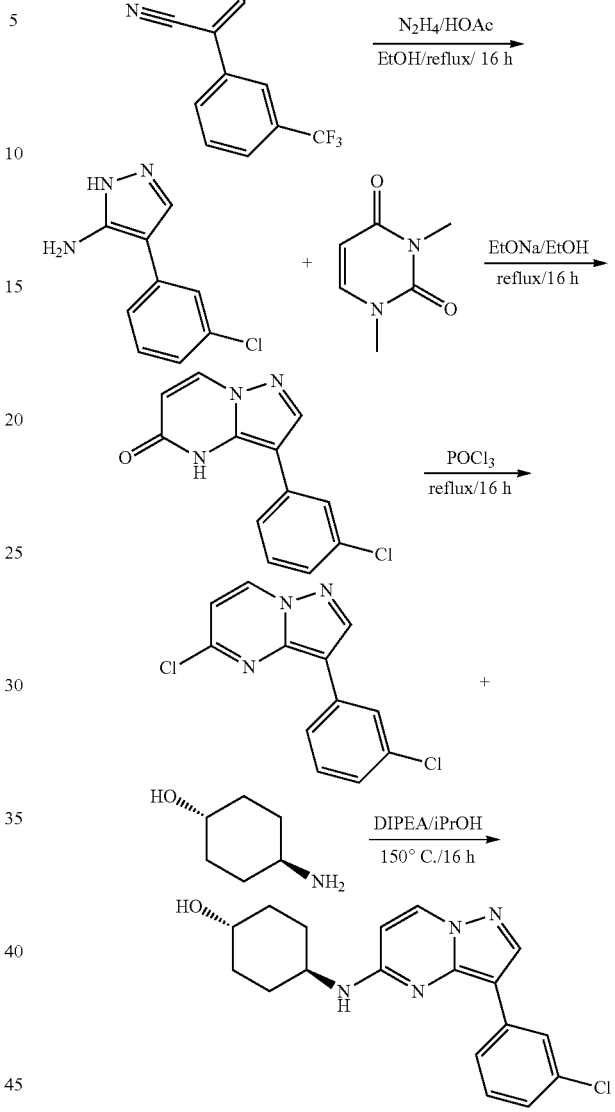

EX. 8-61

Synthesis of 3-(dimethylamino)-2-(3-chlorophenyl)acrylonitile

A mixture of 3-chlorophenylacetonitrile (5 grams, 33.0 mmol), N,N,N',N'-tetramethyl-ethane-1,2-diamine (0.767 grams, 6.60 mmol), and dimethyl formamide dimethyl acetal (20 mL) were heated at reflux for 4 h. On cooling, the reaction was partitioned between EtOAc and saturated aqueous NH4Cl solution. The aqueous phase was extracted with ethyl acetate and the combined organic phase washed with brine and concenrated in vacuo. The crude product was purified by chromatography (ethyl acetate/hexane, 0-10%) on silica gel (24 grams) to give pure product (6.8 grams, 33.0 mmol, 100% yield.).

1H-NMR (CDCl3/400 MHz): δ 7.31 (m, 2H), 7.22 (m, 2H), 7.08 (m, 1H), 3.31 (s, 3H), 3.30 (s, 3H).

Synthesis of 4-(3-chlorophenyl)-1H-pyrazol-5-amine

A mixture of acrylnitrile (5.0 g, 24.19 mmol), hydrazine hydrate (7.75 grams, 242 mmol), and glacial acetaic acid (14.53 grams, 242 mmol) and ethanol (20 mL) were heated at reflux for 16 h. On cooling, the reaction was diluted with water, extracted with AcOEt and the combined organic phase washed with brine and concenrated in vacuo (4.0 grams, 20.66 mmol, 85% yield.).

$^1$H-NMR (CDCl$_3$/400 MHz): δ 7.63 (m, 1H), 7.52 (m, 1H), 7.42 (d, J=8.0 Hz, 1H), 7.33 (t, J=8.0 Hz, 1H), 7.17 (d, J=8.0 Hz, 1H). MS (ES$^+$, m/z): (M+H)$^+$: 194.3.

Synthesis of 3-(3-chlorophenyl)pyrazolo[1,5-a]pyrimidin-5(4H)-one

A mixture of pyrazole (4.0 grams, 20.66 mmol), 1,3-dimethyluracil (3.47 grams, 24.79 mmol), and dry EtOH 10 mL were treated dropwise with sodium ethoxide (1.97 grams, 28.9 mmol) and on completion of addition the reaction was heated at reflux for 16 h. On cooling the reaction was concentrated in vacuo and the residue added to ice, neutralised with acetic acid and the resulting precipitate filtered, washed with water and dried to give the product (4.0 grams, 16.28 mmol, 79% yield.). No chromatography was needed for this step.

$^1$H-NMR (CDCl$_3$/400 MHz): δ 8.38 (d, J=8.4 Hz, 1H), 8.04 (s, 1H), 7.65 (s, 1H), 7.65 (s, 1H), 7.51 (m, 1H), 7.40 (t, J=8.0 Hz, 1H), 7.27 (d, J=8.0 Hz, 1H), 6.12 (d, J=7.6 Hz, 1H). MS (ES$^+$, m/z): (M+H)$^+$: 246.3.

Synthesis of 5-chloro-3-(3-chlorophenyl)pyrazolo[1,5-a]pyrimidine

A mixture of pyrazolepyrimidinone (4.0 grams, 16.28 mmol) was treated with POCl$_3$ 10 mL and the mixture was heated at relux for overnight. On cooling, after remove the solvent under rotovapor, the reaction was poured onto ice, cautiously made basic with saturated aqueous NaHCO$_3$ solution and extracted with EtOAc. The combined organic phases were washed with brine and concentrated in vacuo to give the product (0.65 grams, 2.46 mmol, 15% yield.).

$^1$H-NMR (CDCl$_3$/400 MHz): δ 8.89 (d, J=7.4 Hz, 1H), 8.61 (s, 1H), 8.10 (m, 1H), 7.96 (d, J=7.6 Hz, 1H), 7.40 (t, J=8.0 Hz, 1H), 7.26 (d, J=8.0 Hz, 1H), 7.06 (d, J=7.2 Hz, 1H). MS (ES$^+$, m/z): (M)$^+$: 264.3.

Synthesis of 4-((3-(3-chlorophenyl)pyrazolo[1,5-a]pyrimidin-5-yl)amino)cyclohexanol A solution of 3-chloro-5-chloropyrazolo[1,5-a]pyrimidine (0.150 grams, 0.568 mmol) and trans-1,4-diamocyclohexane (0.131 grams, 1.14 mmol) in iso-propanol (5 mL) was added DIPEA (0.177 grams, 2.272 mmol) and the mixture was heated at 150° C. for 12 h under microwave irradiation. The resulting dark brown solution was cooled down and was concentrated under reduced pressure. The solid was further purified by using combiflash chromatography (12 g column), eluent: 0-6% CH3OH/DCM and obtained product (0.100 grams, 0.292 mmol, 52% yield.).

$^1$H-NMR (CD$_3$OD/400 MHz): δ 8.41 (s, 1H), 8.24 (d, J=8.0 Hz, 2H), 7.80 (d, J=8.0 Hz, 1H), 7.30 (t, J=8.4 Hz, 1H), 7.10 (m, 1H), 6.25 (d, J=7.6 Hz, 1H), 3.95 (m, 1H), 3.63 (m, 1H), 2.26 (m, 2H), 2.04 (m, 2H), 1.55 (m, 2H), 1.39 (m, 2H). MS (ES$^+$, m/z): (M+H)$^+$: 343.5.

EX. 8-62 to EX. 8-67 and EX. 8-69 were prepared using similar procedures as in EX. 8-61.

62. 4-((3-(3-Chlorophenyl)pyrazolo[1,5-a]pyrimidin-5-yl)amino)-1-methyl-trans-cyclohexanol (EX. 8-62)

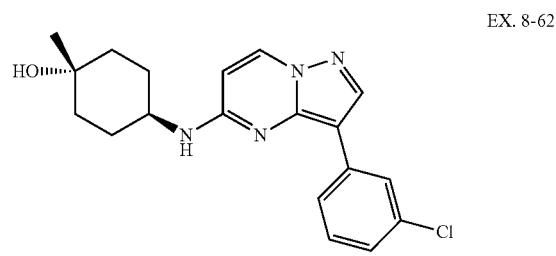 [SMILES: C[C@]1(O)CC[C@H](Nc2ccn3ncc(-c4cccc(Cl)c4)c3n2)CC1]

EX. 8-62

$^1$H-NMR (CD$_3$OD/400 MHz): δ 8.36 (s, 1H), 8.23 (m, 2H), 7.84 (d, J=8.0 Hz, 1H), 7.30 (t, J=8.0 Hz, 1H), 7.11 (d, J=7.6 Hz, 1H), 6.29 (d, J=7.6 Hz, 1H), 4.02 (m, 1H), 2.20 (m, 2H), 1.75 (m, 4H), 1.50 (m, 2H), 1.29 (s, 6H). MS (ES$^+$, m/z): (M+H)$^+$: 357.5.

63. 4-((3-(3-Chlorophenyl)pyrazolo[1,5-a]pyrimidin-5-yl)amino)-trans-cyclohexyl)propan-2-ol (EX 8-63)

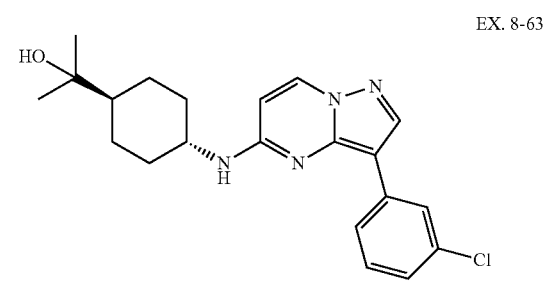 [SMILES: CC(C)(O)[C@H]1CC[C@H](Nc2ccn3ncc(-c4cccc(Cl)c4)c3n2)CC1]

EX. 8-63

$^1$H-NMR (CD$_3$OD/400 MHz): δ 8.35 (s, 1H), 8.12 (m, 2H), 7.72 (d, J=8.0 Hz, 1H), 7.27 (t, J=8.0 Hz, 1H), 7.09 (d, J=7.6 Hz, 1H), 6.20 (d, J=7.6 Hz, 1H), 3.95 (m, 1H), 2.30 (m, 2H), 1.94 (m, 2H), 1.32 (m, 4H), 1.50 (s, 6H). MS (ES$^+$, m/z): (M+H)$^+$: 385.5.

64. 3-((3-Chlorophenyl)-N-4-methoxy-trans-cyclohexyl)pyrazolo[1,5-a]pyrimidin-5-amine (EX. 8-64)

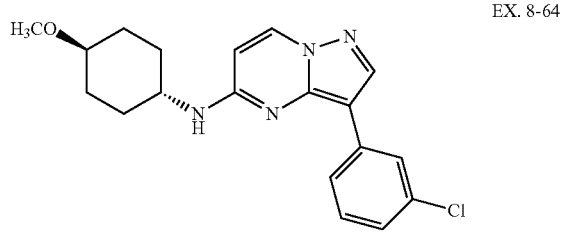 [SMILES: CO[C@H]1CC[C@H](Nc2ccn3ncc(-c4cccc(Cl)c4)c3n2)CC1]

EX. 8-64

$^1$H-NMR (CD$_3$OD/400 MHz): δ 8.40 (s, 1H), 8.23 (m, 2H), 7.80 (d, J=8.0 Hz, 1H), 7.29 (t, J=8.0 Hz, 1H), 7.05 (d,

J=8.0 Hz, 1H), 6.22 (d, J=7.6 Hz, 1H), 3.95 (m, 1H), 3.30 (m, 1H), 2.25 (m, 2H), 2.15 (m, 2H), 1.45 (m, 4H). MS (ES⁺, m/z): (M+H)⁺: 357.5.

65. 3-(3-Chlorophenyl)-N-(tetrahydro-2H-pyran-4-yl)pyrazolo[1,5-a]pyrimidin-5-amine (EX. 8-65)

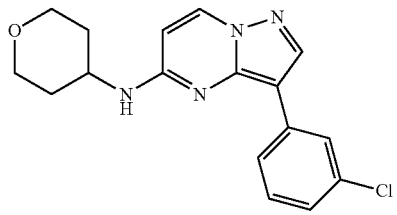

¹H-NMR (CDCl₃/400 MHz): δ 8.32 (s, 1H), 8.15 (m, 2H), 7.72 (d, J=8.0 Hz, 1H), 7.26 (t, J=8.0 Hz, 1H), 7.08 (d, J=8.0 Hz, 1H), 6.23 (d, J=8.0 Hz, 1H), 4.20 (m, 1H), 4.00 (m, 2H), 3.62 (t, J=12.0 Hz, 2H), 2.17 (m, 2H), 1.62 (m, 2H). MS (ES⁺, m/z): (M+H)⁺: 329.5.

66. 4-(((3-(3-Chlorophenyl)pyrazolo[1,5-a]pyrimidin-5-yl)amino)methyl)tetrahydro-2H-thiopyran 1,1-dioxide (EX. 8-66)

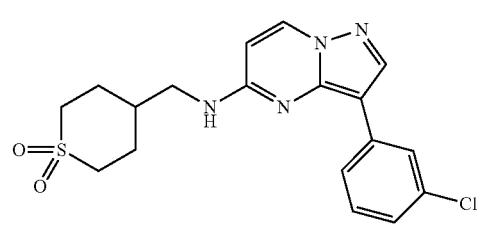

¹H-NMR (CD₃OD/400 MHz): δ 8.35 (s, 1H), 8.28 (d, J=8.0 Hz, 1H), 8.24 (s, 1H), 7.81 (d, J=8.0 Hz, 1H), 7.31 (t, J=7.2 Hz, 1H), 7.11 (d, J=7.2 Hz, 1H), 6.29 (d, J=7.2 Hz, 1H), 3.46 (m, 2H), 3.10 (m, 4H), 2.27 (m, 3H), 1.89 (m, 2H). MS (ES⁺, m/z): (M+H)⁺: 391.4.

67. N-((1-Methylpiperidin-4-yl)methyl)-3-(3-(trifluoromethoxy)phenyl)pyrazolo[1,5-a]pyrimidin-5-amine (EX. 8-67)

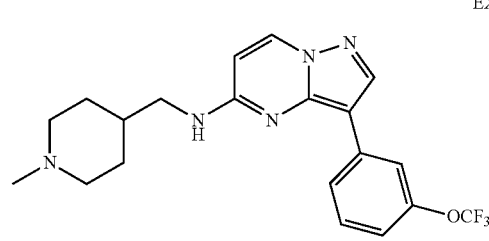

¹H-NMR (CD₃OD/400 MHz): δ 8.26 (m, 3H), 7.86 (d, J=8.0 Hz, 1H), 7.37 (m, 1H), 6.99 (d, J=8.0 Hz, 1H), 6.28 (d, J=7.2 Hz, 1H), 3.41 (d, J=6.0 Hz, 2H), 2.80 (d, J=12.0 Hz, 1H), 2.30 (s, 3H), 2.11 (t, J=12.0 Hz, 1H), 1.89 (m, 3H), 1.44 (m, 2H), 1.29 (m, 2H). MS (ES⁺, m/z): (M+H)⁺: 391.4.

68. N1-(3-(3-Chlorophenyl)imidazo[1,2-b]pyridazin-6-yl)cyclohexane-1,4-trans-diamine (EX. 8-68)

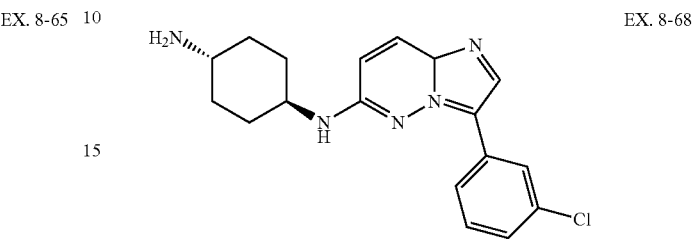

EX.8-68 was prepared using similar procedures as in EX. 8-8.

¹H-NMR (CD₃OD/400 MHz): δ 8.42 (s, 1H), 7.84 (d, J=8.0 Hz, 1H), 7.78 (s, 1H), 7.59 (d, J=8.0 Hz, 1H), 7.37 (t, J=8.0 Hz, 1H), 7.27 (m, 1H), 6.66 (d, J=7.6 Hz, 1H), 3.65 (m, 1H), 3.01 (m, 1H), 2.33 (m, 2H), 2.08 (m, 2H), 1.56 (m, 2H), 1.38 (m, 2H). MS (ES⁺, m/z): (M+H)⁺: 325.5.

69. N-(3-(3-chlorophenyl)pyrazolo[1,5-a]pyrimidin-5-yl)cyclohexane-1,4-trans-diamine (EX. 8-69)

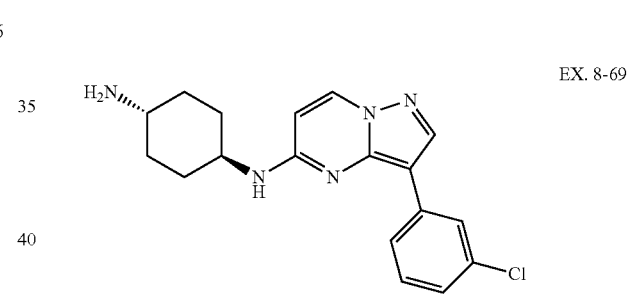

¹H-NMR (CD₃OD/400 MHz): δ 8.37 (s, 1H), 8.23 (m, 2H), 7.80 (d, J=8.0 Hz, 1H), 7.28 (t, J=7.6 Hz, 1H), 7.09 (d, J=7.6 Hz, 1H), 6.23 (d, J=7.2 Hz, 1H), 3.90 (m, 1H), 2.75 (m, 1H), 2.27 (m, 2H), 2.05 (m, 2H), 1.36 (m, 4H). MS (ES⁺, m/z): (M+H)⁺: 325.5.

70. N¹-(3-(3-chlorophenyl)imidazo[1,2-b]pyridazin-6-yl)cyclohexane-1,3-diamine (EX. 8-70)

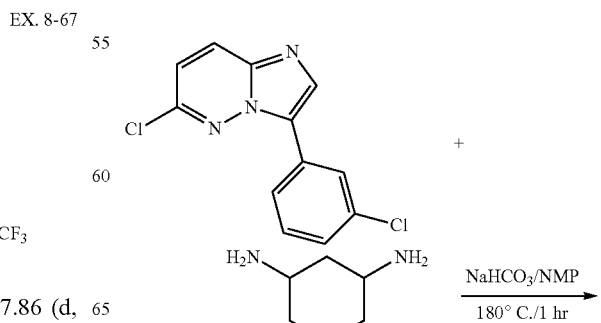

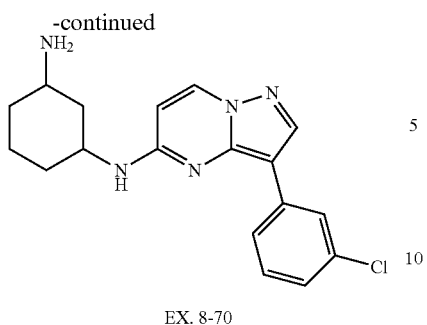

EX. 8-70

To a solution of 6-chloro-3-(3-chlorophenyl)imidazo[1,2-b]pyridazine (100 mg, 0.38 mmol) and cyclohexane-1,3-diamine (43 mg, 0.38 mmol) in NMP (1.0 mL) was added NaHCO$_3$ (32 mg, 0.38 mmol), the mixture was stirred at 180° C. for 60 mins under microwave irradiation. The mixture was purified by flash chromatograph to give N$^1$-(3-(3-chlorophenyl)imidazo[1,2-b]pyridazin-6-yl)cyclohexane-1,3-diamine (30 mg, 0.088 mmol, 23%) as a pale yellow solid.

$^1$H-NMR (CD$_3$OD/400 MHz): δ 8.44 (s, 1H), 7.84 (d, 1H), 7.78 (m, 1H), 7.58 (d, 1H), 7.28 (m, 1H), 7.25 (m, 1H), 6.65 (d, 1H), 3.75 (m, 1H), 2.94 (m, 1H), 2.41 (m, 1H), 2.20 (m, 1H), 1.95 (m, 2H), 1.51 (m, 1H), 1.16 (m, 3H). MS (ES$^+$, m/z): (M+H)$^+$: 342.5.

71. (S)-1-(3-(3-chlorphenyl)imidazo[1,2-b]pyridazin-6-yl)piperidin-3-amine (EX. 8-71)

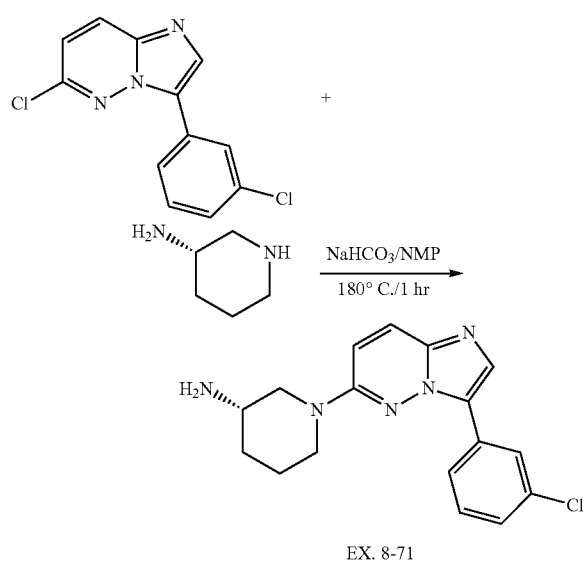

EX. 8-71

To a solution of 6-chloro-3-(3-chlorophenyl)imidazo[1,2-b]pyridazine (200 mg, 0.78 mmol) and (S)-Piperidin-3-amine (290 mg, 2.12 mmol) in NMP (1.0 mL) was added NaHCO$_3$ (118 mg, 1.52 mmol), the mixture was stirred at 180° C. for 60 mins under microwave irradiation. The mixture was purified by flash chromatograph to give (S)-1-(3-(3-chlorophenyl)imidazo[1,2-b]pyridazin-6-yl)piperidin-3-amine (32 mg, 0.098 mmol, 13%) as a pale yellow solid.

$^1$H-NMR (CD$_3$OD/400 MHz): δ 8.19 (s, 1H), 7.87 (d, J=7.6 Hz, 1H), 7.79 (s, 1H), 7.66 (d, J=10.0 Hz, 1H), 7.34 (t, J=8.0 Hz, 1H), 7.23 (d, J=8.0 Hz, 1H), 7.07 (d, J=10.0 Hz, 1H), 3.97 (m, 1H), 3.95 (m, 1H), 2.99 (m, 1H), 2.83 (m, 2H), 1.98 (m, 1H), 1.79 (m, 1H), 1.60 (m, 1H), 1.36 (m, 1H). MS (ES$^+$, m/z): (M+H)$^+$: 328.6.

72. 4-((3-(3-chlorophenyl)imidazo[1,2-b]pyridazin-6-yl)amino)cyclohexanone (EX. 8-72)

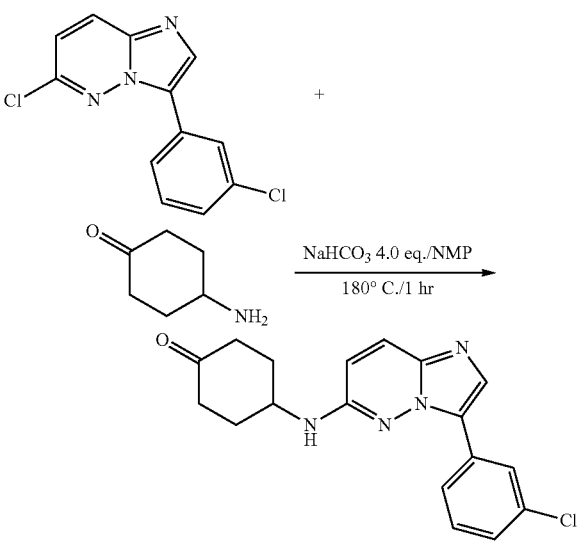

EX. 8-72

To a solution of 6-chloro-3-(3-chlorophenyl)imidazo[1,2-b]pyridazine (200 mg, 0.757 mmol) and 4-aminocyclohexanone (290 mg, 2.56 mmol) in NMP (1.0 mL) was added NaHCO$_3$ (118 mg, 1.52 mmol), the mixture was stirred at 180° C. for 60 mins under microwave irradiation. The mixture was purified by flash chromatograph to give 4-((3-(3-chlorophenyl)imidazo[1,2-b]pyridazin-6-yl)amino)cyclohexanone (40 mg, 0.117 mmol, 16%) as a pale yellow solid.

$^1$H-NMR (CD$_3$Cl/400 MHz): δ 8.38 (s, 1H), 7.83 (s, 1H), 7.76 (d, J=7.6 Hz, 2H), 7.37 (t, J=8.0 Hz, 1H), 7.29 (m, 1H), 6.64 (d, J=9.6 Hz, 1H), 4.90 (m, 1H), 4.25 (m, 1H), 2.53 (m, 6H), 1.80 (m, 2H). MS (ES$^+$, m/z): (M+H)$^+$: 341.4.

73. 4-trans-((3-(3-chlorophenyl)imidazo[1,2-b]pyridazin-6-yl)amino)cyclohexanecarbonitrile (EX. 8-73)

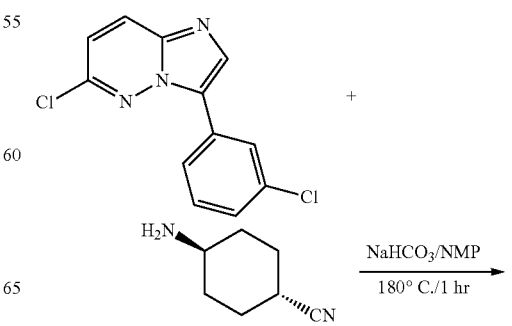

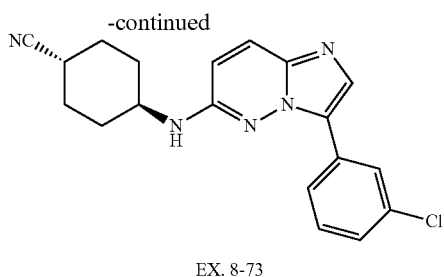

EX. 8-73

To a solution of 6-chloro-3-(3-chlorophenyl)imidazo[1,2-b]pyridazine (80 mg, 0.303 mmol) and trans-4-aminocyclohexanecarbonitrile (38 mg, 0.303 mmol) in NMP (1.0 mL) was added NaHCO$_3$ (102 mg, 1.212 mmol), the mixture was stirred at 180° C. for 60 mins under microwave irradiation. The mixture was purified by flash chromatograph to give 4-trans-((3-(3-chlorophenyl)imidazo[1,2-b]pyridazin-6-yl)amino)cyclohexanecarbonitrile (20 mg, 0.057 mmol, 23%) as white solid.

$^1$H-NMR (CD$_3$OD/400 MHz): δ 8.40 (s, 1H), 7.83 (d, 1H), 7.78 (s, 1H), 7.56 (d, 1H), 7.38 (m, 1H), 7.29 (m, 1H), 6.63 (d, 1H), 3.67 (m, 1H), 2.65 (m, 1H), 2.30 (m, 2H), 2.20 (m, 2H), 1.75 (m, 2H), 1.32 (m, 2H). MS (ES$^+$, m/z): (M+H)$^+$: 352.5.

75. 2-(trans-4-((3-(3-fluorophenyl)imidazo[1,2-b]pyridazin-6-yl)amino)cyclohexyl)propan-2-ol (EX. 8-75)

phenyl)boronic acid (273 mg, 1.96 mmol), K$_2$CO$_3$ (811 mg, 5.88 mmol) and Pd(dppf)$_2$Cl$_2$ (79 mg, 0.098 mmol). The reaction mixture was stirred at 80° C. overnight under N$_2$. TLC (PE: EA=5:1) showed the starting material was consumed. The mixture was cooled and concentrated. The residue was purified by column chromatography on silica gel (petroleum ether/EtOAc=20:1 to 1:1) to give 6-chloro-3-(3-fluorophenyl)imidazo[1,2-b]pyridazine (300 mg, 56%) as a yellow solid.

To a solution of give 6-chloro-3-(3-fluorophenyl)imidazo[1,2-b]pyridazine (100 mg, 0.404 mmol) in NMP (2 mL) was added 2-(trans-4-aminocyclohexyl)propan-2-ol (95 mg, 0.6 mmol) and NaHCO$_3$ (101.8 mg, 1.21 mmol). The mixture was purged with nitrogen and kept at 180° C. for 30 min with M.W. reaction. LCMS showed the reaction was complete. The mixture was partitioned between water (100 mL) and EtOAc (50 mL). The aqueous layer was extracted with EtOAc (50 mL*3). The combined extracts were dried over Na$_2$SO$_4$, filtered and concentrated in vacuo. The residue was purified by prep. HPLC to give EX. 8-75 (10.6 mg, 7.2%) as a yellow solid.

$^1$H NMR (MeOD, 400 MHz): δ 8.26 (dt, J$_1$=11.34 Hz, J$_2$=2.06 Hz, 1H), 7.88 (d, J=7.90 Hz, 1H), 7.86 (s, 1H), 7.63 (d, J=9.96 Hz, 1H), 7.48-7.43 (m, 1H), 7.07 (td, J$_1$=8.42 Hz, J$_2$=2.75 Hz, 1H), 6.71 (d, J=9.62 Hz, 1H), 3.68 (br, 1H), 2.36 (br, 2H), 2.00 (br, 2H), 1.42-1.26 (m, 5H), 1.21 (s, 6H). MS (ES$^+$, m/z): (M+H)$^+$: 369.3

76. 2-(trans-4-(((3-(3-chlorophenyl)imidazo[1,2-b]pyridazin-6-yl)amino)methyl)cyclohexyl)propan-2-ol (EX. 8-76)

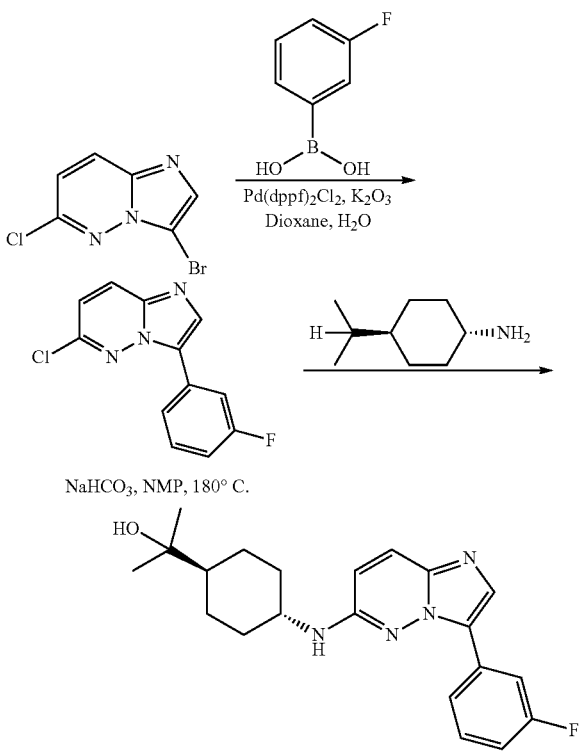

EX. 8-75

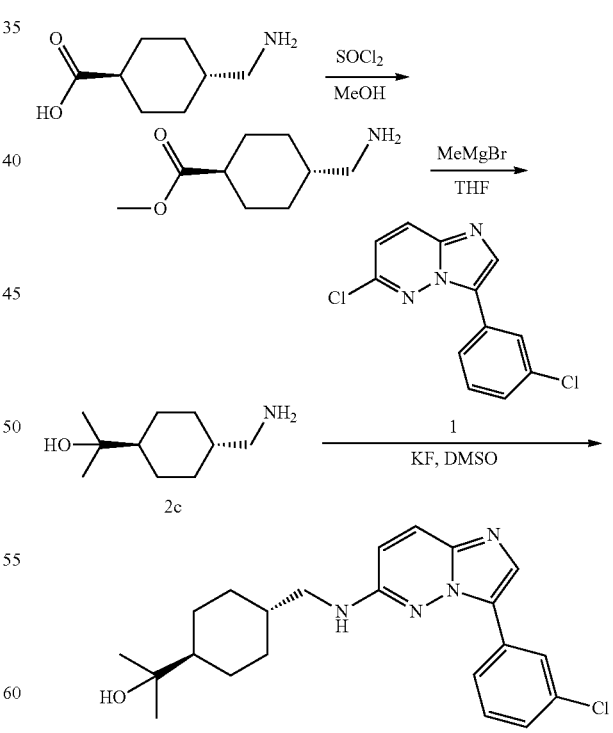

EX. 8-76

To a solution of 3-bromo-6-chloroimidazo[1,2-b]pyridazine (500 mg, 2.15 mmol) in a mixed solvent of dioxane (5 mL) and water (0.5 mL) was added (3-fluoro- To a solution of trans-4-(aminomethyl)cyclohexanecarboxylic acid (2 g, 12.7 mmol) in MeOH (64 mL) was added dropwise thionyl chloride (0.93 mL, 12.7 mmol) at room temperature. The resulting mixture was stirred at room temperature for 4 h. The mixture was concentrated in vacuo to dryness to give trans-methyl 4-(aminomethyl)cyclohexanecarboxylate (2.5 g, 115%) as HCl salts.

To a solution of trans-methyl 4-(aminomethyl)cyclohexanecarboxylate (1 g, 5.8 mmol) in THF (50 mL) was added dropwise methylmagnesium bromide (7.7 mL, 23.2 mmol) at −78° C. The mixture was stirred at room temperature for 2 h. TLC (PE: EA=5:1) showed the reaction was complete. The mixture was quenched by the addition of NH$_4$Cl (100 mL) and extracted with EtOAc (100 mL×3). The combined extracts were dried over Na$_2$SO$_4$, filtered and concentrated in vacuo to give 2-(trans-4-(aminomethyl)cyclohexyl)propan-2-ol (0.42 g, 39.2%) as a yellow solid.

A mixture of 6-chloro-3-(3-chlorophenyl)imidazo[1,2-b]pyridazine (100 mg, 0.38 mmol), 2-(trans-4-(aminomethyl)cyclohexyl)propan-2-ol (140 mg, 0.76 mmol) and KF (51 mg, 0.88 mmol) in DMSO (2 mL) was stirred at 130° C. overnight. LCMS showed the reaction was complete. The mixture was poured into water (100 mL) and extracted with EtOAc (50 mL×3). The combined extracts were dried over Na$_2$SO$_4$, filtered and concentrated in vacuo. The residue was purified by prep-HPLC to give EX. 8-76 (12 mg, 8%) as a yellow solid.

$^1$H NMR (MeOD, 400 MHz): δ 8.44 (s, 1H), 8.05 (s, 1H), 7.98 (d, J=7.56 Hz, 1H), 7.78 (d, J=9.62 Hz, 1H), 7.50 (t, J=7.56 Hz, 1H), 7.43 (d, J=8.25 Hz, 1H), 6.97 (d, J=9.62 Hz, 1H), 3.27 (d, J=6.87 Hz, 2H), 2.03 (d, J=10.65 Hz, 2H), 1.94 (s, J=10.65 Hz, 2H), 1.77 (br, 1H), 1.35-1.31 (m, 1H), 1.15 (s, 6H), 1.15-1.02 (m, 4H). MS (ES$^+$, m/z): (M+H)$^+$: 399.3.

77. 2-(trans-4-((3-(3-chlorophenyl)imidazo[1,2-b]pyridazin-6-yl)oxy)cyclohexyl)propan-2-ol (EX 8-77)

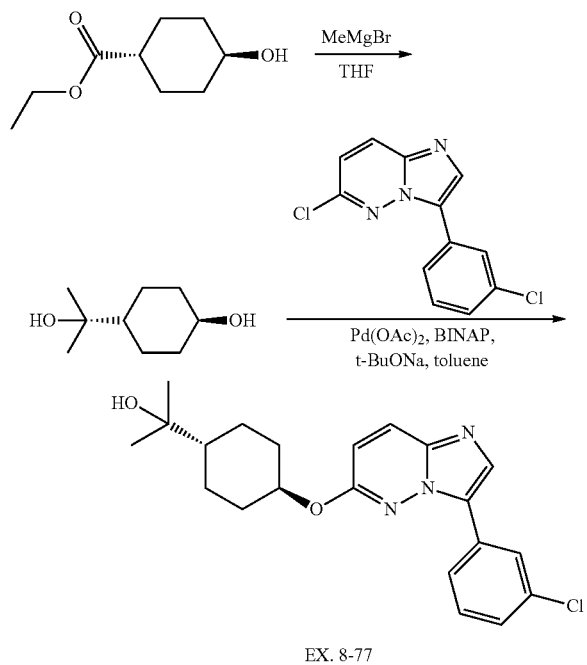

EX. 8-77

To a solution of trans-ethyl 4-hydroxycyclohexanecarboxylate (1 g, 5.8 mmol) in THF (50 mL) was added dropwise methylmagnesium bromide (7.7 mL, 23.2 mmol) at −78° C. The mixture was stirred at room temperature for 2 h. TLC (PE: EA=1:1) showed the reaction was complete. The mixture was quenched by the addition of NH$_4$Cl (100 mL) and extracted with EtOAc (100 mL*3). The combined extracts were dried over Na$_2$SO$_4$, filtered and concentrated in vacuo to give trans-4-(2-hydroxypropan-2-yl)cyclohexanol (0.88 g, 96%) as a yellow solid.

To a solution of 6-chloro-3-(3-chlorophenyl)imidazo[1,2-b]pyridazine (100 mg, 0.378 mmol) in toluene (2 mL) was added trans-4-(2-hydroxypropan-2-yl)cyclohexanol (179.8 mg, 1.14 mmol), BINAP (23.5 mg, 0.038 mmol), Pd(OAc)$_2$ (8.78 mg, 0.038 mmol) and t-BuONa (60.5 mg, 0.76 mmol). The mixture was filled with nitrogen and kept 120° C. for 1 h with M.W. reaction. LCMS showed the reaction was complete. The mixture was poured into brine (100 mL) and extracted with EtOAc (100 mL*3). The combined extracts were dried over Na$_2$SO$_4$, filtered and concentrated in vacuo. The residue was purified by prep. HPLC to give trans-4-(2-hydroxypropan-2-yl)cyclohexanol (13 mg, 8.6%) as a yellow solid.

$^1$H NMR (DMSO, 400 MHz): δ 8.41 (s, 1H), 8.18 (s, 1H), 8.05 (d, J=9.62 Hz, 1H), 7.97 (d, J=7.56 Hz, 1H), 7.48 (t, J=7.56 Hz, 1H), 7.38 (d, J=7.56 Hz, 1H), 6.89 (d, J=9.88 Hz, 1H), 4.84-4.79 (m, 1H), 4.11 (s, 1H), 2.28 (d, J=7.82 Hz, 2H), 1.88 (d, J=9.88 Hz, 2H), 1.44-1.36 (m, 2H), 1.25-1.18 (m, 3H), 1.02 (s, 6H), MS (ES$^+$, m/z): (M+H$^+$): 386.2

78. trans-N1-(tert-Butyl)-N4-(3-(3-chlorophenyl)imidazo[1,2-b]pyridazin-6-yl)cyclohexane-1,4-diamine (EX. 8-78)

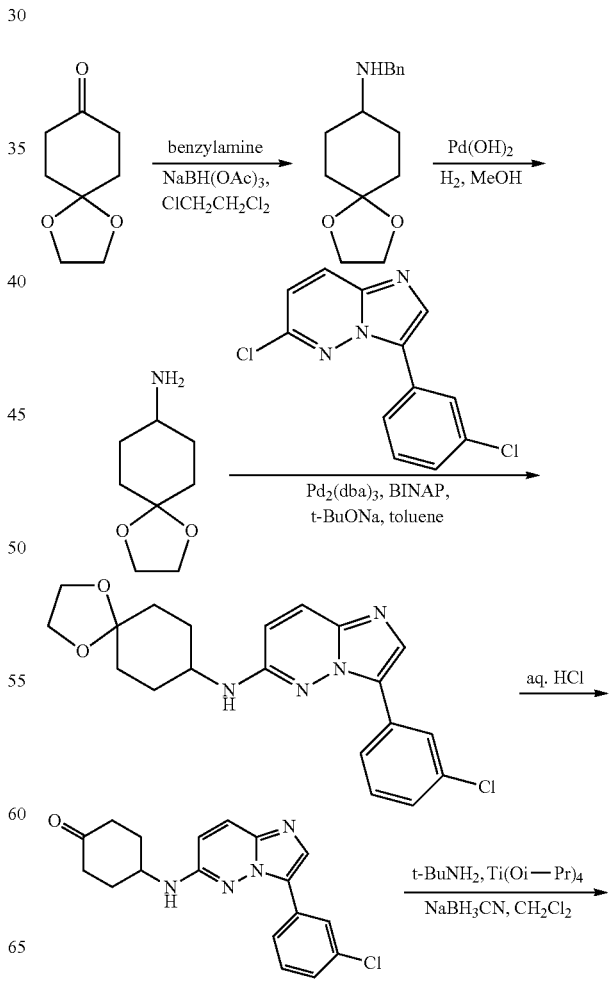

-continued

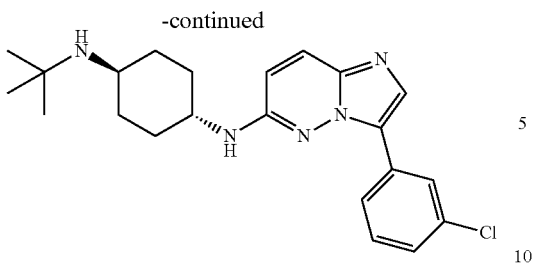

EX. 8-78

To a solution of 1,4-dioxaspiro[4.5]decan-8-one (10 g, 6.4 mmol) and benzylamine (7 mL, 6.4 mmol) in 1,2-dichloroethane (220 mL) was treated with NaBH(OAc)$_3$ (19 g, 89.6 mmol). The mixture was stirred at room temperature for 1 h. TLC (PE: EA=1:1) showed the reaction was complete. The mixture was partitioned between sat. aq. NaHCO$_3$ (500 mL) and EtOAc (200 mL). The organic layer was dried over Na$_2$SO$_4$, filtered and concentrated in vacuo to give N-benzyl-1,4-dioxaspiro[4.5]decan-8-amine (18 g, 115%) as a yellow liquid, which was used in the next step directly.

A mixture of N-benzyl-1,4-dioxaspiro[4.5]decan-8-amine (3 g, 12.2 mmol) and Palladium hydroxide (0.9 g) in MeOH (120 mL) was hydrogenated under 50 psi of H$_2$ at room temperature. The mixture was stirred at room temperature for 24 h. TLC (CH$_2$Cl$_2$: MeOH=10:1) showed the reaction was complete. The mixture was filtered and the filtrated was concentrated in vacuo to give 1,4-dioxaspiro[4.5]decan-8-amine (2.1 g, 110%) as a brown oil.

A mixture of 6-chloro-3-(3-chlorophenyl)imidazo[1,2-b]pyridazine (500 mg, 1.89 mmol), 4-dioxaspiro[4.5]decan-8-amine (297 mg, 1.89 mmol), BINAP (117.7 mg, 0.189 mmol), t-BuONa (302.4 mg, 3.78 mmol) and Pd$_2$(dba)$_3$ in toluene (10 mL) was filled with N$_2$ and stirred at 110° C. overnight. TLC (PE: EA=1:1) showed the starting material was almost consumed. The mixture was partitioned between water (150 mL) and EtOAc (100 mL). The organic layer was dried over Na$_2$SO$_4$, filtered and concentrated in vucuo. The residue was purified by combi flash to give 3-(3-chlorophenyl)-N-(1,4-dioxaspiro[4.5]decan-8-yl)imidazo[1,2-b]pyridazin-6-amine (420 mg, 57.8%) as a yellow solid.

To a solution of 3-(3-chlorophenyl)-N-(1,4-dioxaspiro[4.5]decan-8-yl)imidazo[1,2-b]pyridazin-6-amine (210 mg, 0.55 mmol) in THF (3 mL) was added 3 N HCl (3 mL). The resulting mixture was stirred at room temperature for 2 h. TLC (EtOAc) showed the reaction was complete. The mixture was poured into sat. NaHCO$_3$ (aq) and extracted with EtOAc (100 mL×3). The organic layers were dried over Na$_2$SO$_4$, filtered and concentrated in vacuo to give 4-((3-(3-chlorophenyl)imidazo[1,2-b]pyridazin-6-yl)amino)cyclohexanone (190 mg, 102%) as a yellow solid.

To a 0° C. solution of 4-((3-(3-chlorophenyl)imidazo[1,2-b]pyridazin-6-yl)amino)cyclohexanone (80 mg, 0.23 mmol) and t-Butylamine (17.2 mg, 0.23 mmol) in CH$_2$Cl$_2$ (1.2 mL) was added dropwise Ti(Oi-Pr)$_4$ (0.27 mL, 0.92 mmol). The resulting mixture was stirred at room temperature overnight. LCMS showed the reaction was complete. The mixture was poured into water (150 mL) and extracted with EtOAc (100 mL*3). The organic layers were dried over Na$_2$SO$_4$, filtered and concentrated in vacuo. The residue was purified by prep. HPLC to give EX. 8-78 (15 mg, 16.5%) as a white solid.

$^1$H NMR (MeOD, 400 MHz): δ 8.56 (t, J=1.72 Hz, 1H), 8.45 (br, 0.66H), 7.91 (d, J=7.93 Hz, 1H), 7.88 (s, 1H), 7.67 (d, J=9.66 Hz, 1H), 7.46 (t, J=7.93 Hz, 1H), 7.35 (dd, J$_1$=7.93 Hz, J$_2$=1.03 Hz, 1H), 6.75 (d, J=9.66 Hz, 1H), 3.78 (tt, J$_1$=11.04 Hz, J$_2$=3.45 Hz, 1H), 3.42 (tt, J$_1$=12.07 Hz, J$_2$=3.79 Hz, 1H), 2.42 (d, J=11.04 Hz, 2H), 2.23 (d, J=12.42 Hz, 2H), 1.79 (q, J=12.42 Hz, 2H), 1.54 (q, J=12.07 Hz, 2H), 1.46 (s, 9H), MS (ES$^+$, m/z): (M+H$^+$): 398.3.

79. N-(trans-4-(2-aminopropan-2-yl)cyclohexyl)-3-(3-chlorophenyl)imidazo[1,2-b]pyridazin-6-amine (EX. 8-79)

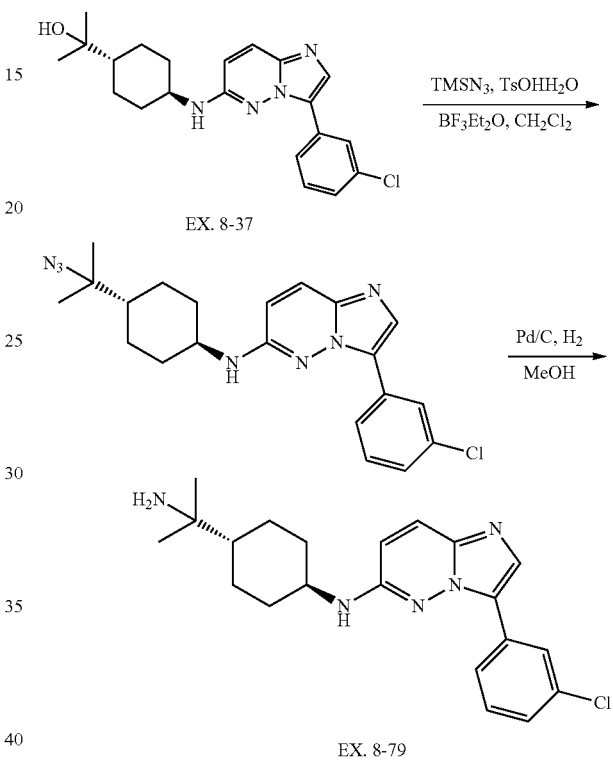

To a solution of TMSN$_3$ (93 mg, 0.78 mmol), TsOH H$_2$O (49 mg, 0.26 mmol) and BF$_3$Et$_2$O (74 mg, 0.52 mmol) in CH$_2$Cl$_2$ (1.3 mL) was slowly added dropwise a solution of EX. 8-37 (100 mg, 0.26 mmol) in CH$_2$Cl$_2$ (1 mL) at 0° C. After the addition, the reaction mixture was stirred at room temperature overnight. TLC (CH$_2$Cl$_2$: MeOH=10:1) showed the reaction was complete. The mixture was poured into water (150 mL) and extracted with EtOAc (100 mL*3). The organic layers were dried over Na$_2$SO$_4$, filtered and concentrated in vacuo to give crude N-(trans-4-(2-azidopropan-2-yl)cyclohexyl)-3-(3-chlorophenyl)imidazo[1,2-b]pyridazin-6-amine (80 mg) as a yellow oil, which was used in the next step directly.

A mixture of N-(trans-4-(2-azidopropan-2-yl)cyclohexyl)-3-(3-chlorophenyl)imidazo[1,2-b]pyridazin-6-amine (90 mg, 0.22 mmol) and Pd/C (30 mg) in MeOH (5 mL) and CH$_2$Cl$_2$ (5 mL) was hydrogenated under 50 psi of H$_2$ at room temperature for 48 h. LCMS showed the reaction was complete. The mixture was filtered and the filtrate was concentrated in vacuo. The residue was purified by prep. HPLC to give EX. 8-79 (4 mg, 5%) as an off-white solid.

$^1$H NMR (MeOD, 400 MHz): δ 8.49 (s, 1H), 8.29 (br, 0.68H), 7.79 (d, J=7.56 Hz, 1H), 7.77 (s, 1H), 7.56 (d, J=9.62 Hz, 1H), 7.34 (t, J=7.56 Hz, 1H), 7.23 (d, J=7.56 Hz, 1H), 6.62 (d, J=9.62 Hz, 1H), 3.65 (tt, J=11.68 Hz, J$_2$=4.12

Hz, 1H), 2.29 (d, J=11.68 Hz, 2H), 1.81 (s, J=12.37 Hz, 2H), 1.52 (t, J=11.68 Hz, 1H), 1.36 (q, J=11.68 Hz, 4H), 1.39-1.29 (m, 4H), 1.25 (s, 6H). MS (ES+, m/z): (M+H+): 384.2.

80. N-(trans-4-((3-(3-chlorophenyl)imidazo[1,2-b]pyridazin-6-yl)amino)cyclohexyl)methanesulfonamide (EX. 8-80)

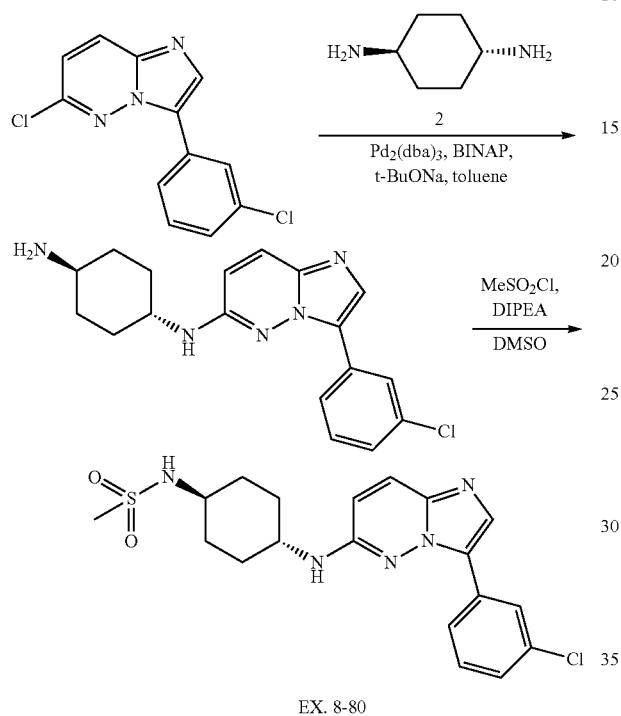

EX. 8-80

To a mixture of 6-chloro-3-(3-chlorophenyl)imidazo[1,2-b]pyridazine (500 mg, 1.89 mmol) in toluene (10 mL) was added trans-cyclohexane-1,4-diamine (215.9 mg, 1.89 mmol), t-BuONa (302.4 mg, 3.78 mmol), BINAP (117.7 mg, 0.189 mmol), Pd$_2$(dba)$_3$ (173 mg, 0.189 mmol). The mixture was filled with N$_2$ and heated at 110° C. for 4 h. TLC (PE: EA=1:1) showed the reaction was complete. The reaction was poured into water (150 mL), extracted with EA (3×50 mL). The organic layer was dried and condensed. The residue was purified by combi flash (CH$_2$Cl$_2$: MeOH=0~10: 1) to give trans-N1-(3-(3-chlorophenyl)imidazo[1,2-b]pyridazin-6-yl)cyclohexane-1,4-diamine (240 mg, yield: 37%) as a yellow solid.

To a 0° C. solution of trans-N1-(3-(3-chlorophenyl)imidazo[1,2-b]pyridazin-6-yl)cyclohexane-1,4-diamine (50 mg, 0.146 mmol) and DIPEA (0.08 mL, 0.44 mmol) in DMSO (0.6 mL) was added dropwise MeSO$_3$Cl (20 mg, 0.176 mmol). The resulting mixture was stirred at room temperature for 6 h. TLC (CH$_2$Cl$_2$: MeOH=10:1) showed most of starting material was converted. The mixture was partitioned between water (50 mL) and EtOAc (50 mL) and separated. The aqueous layer was extracted with EtOAc (50 mL×3). The combined extracts were dried over Na$_2$SO$_4$, filtered and concentrated in vacuo. The residue was purified by prep-HPLC to give EX. 8-80 (10.8 mg, 18%) as a white solid.

$^1$H NMR (DMSO, 400 MHz): δ 8.53 (s, 1H), 8.23 (br, 0.4H), 8.01 (d, J=8.0 Hz, 1H), 7.99 (s, 1H), 7.75 (d, J=9.6 Hz, 1H), 7.45 (t, J=8.0 Hz, 1H), 7.35 (dd, J$_1$=7.6 Hz, J$_2$=1.2 Hz, 1H), 7.10 (d, J=7.6 Hz, 1H), 7.07 (d, J=6.4 Hz, 1H), 6.69 (d, J=9.6 Hz, 1H), 3.54-3.51 (m, 1H), 3.21-3.15 (m, 1H), 2.92 (s, 3H), 2.17 (d, J=10.4 Hz, 2H), 1.98 (d, J=10.4 Hz, 2H), 1.46-1.30 (m, 4H). MS (ES+, m/z): (M+H+): 420.2

81. 4-((3-(3-chlorophenyl)imidazo[1,2-b]pyridazin-6-yl)amino)cyclohexane-1-sulfonamide (EX. 8-81)

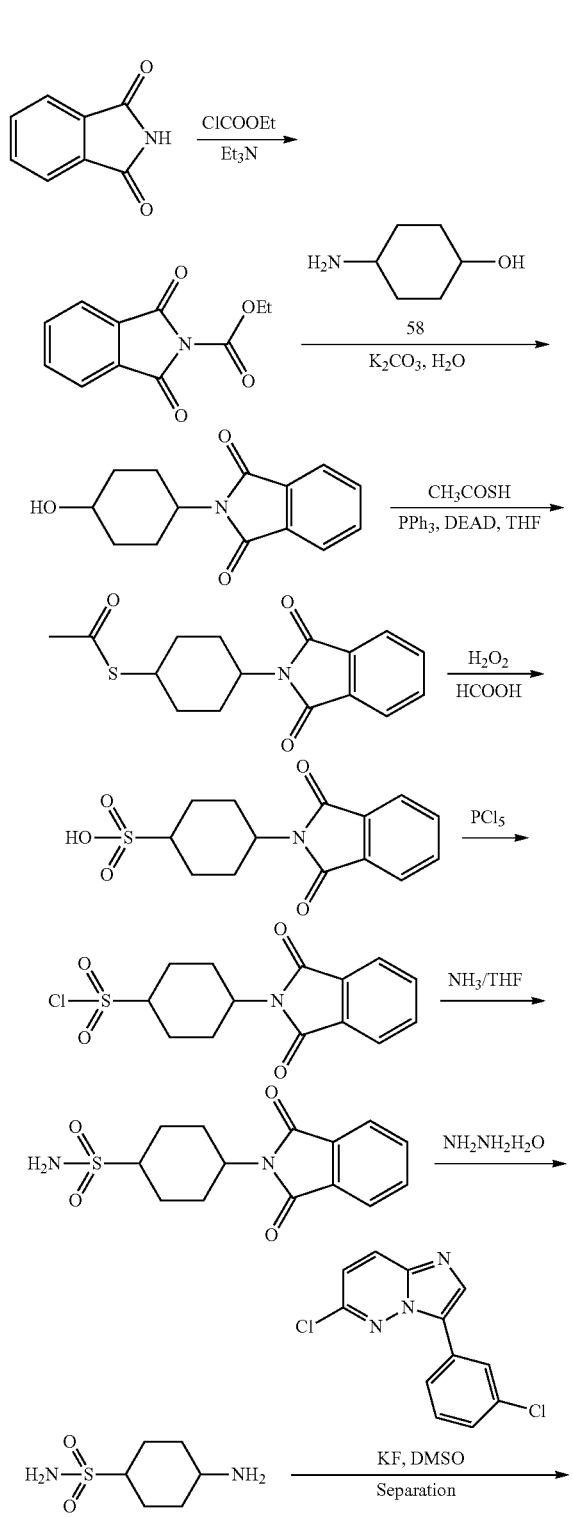

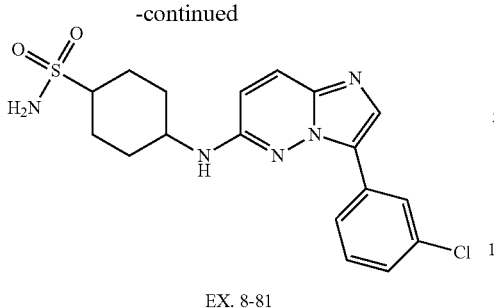

EX. 8-81

To a solution of isoindoline-1,3-dione (2 g, 13.6 mmol) in Et₃N (60 mL) was added ClCOOEt (2.55 g, 16.33 mmol) at 0° C. The mixture was warmed to room temperature and stirred at room temperature for 4 h. The mixture was filtered and the solid was partitioned between water (150 mL) and EtOAc (50 mL) and adjusted pH value to 6 with 1 N HCl. The organic layer was washed with brine and dried over Na₂SO₄, filtered and concentrated in vacuo to give ethyl 1,3-dioxoisoindoline-2-carboxylate (1.67 g, 53.08%) as a white solid.

To a solution of ethyl 1,3-dioxoisoindoline-2-carboxylate (1.67 g, 7.19 mmol) in water (16 mL) was added 4-amino-cyclohexanol (1.31 g, 8.63 mmol), followed by K₂CO₃ (1.59 g, 11.5 mmol). The mixture was stirred at room temperature for 2 h. TLC (PE: EA=1:1) showed the reaction was complete. The mixture was filtered and the solid was dried under vacuum to give 2-(4-hydroxycyclohexyl)isoindoline-1,3-dione (1 g, 56.82%) as a brown solid.

To a solution of PPh₃ (1.28 g, 4.9 mmol) in THF (12 mL) was added dropwise DEAD (852 mg, 4.9 mmol) at −10° C. After the white solid was appeared, compound 2-(4-hydroxycyclohexyl)isoindoline-1,3-dione (600 mg, 2.45 mmol) was added, followed by CH₃COSH (0.35 mL, 4.9 mmol) at −10° C. The mixture was stirred at room temperature overnight. TLC (PE: EA=1:1) showed the reaction was complete. The mixture was poured into water (200 mL) and extracted with EtOAc (100 mL). The aqueous layer was extracted with EtOAc (100 mL×3). The combined extracts were dried over Na₂SO₄, filtered and concentrated in vacuo to give S-(4-(1,3-dioxoisoindolin-2-yl)cyclohexyl) ethanethioate (600 mg, 81%) as a white solid.

A solution of hydrogen peroxide (0.8 mL) in formic acid (8 mL) was stirred at room temperature for 1 h. After cooling in an ice bath, a mixture of compound 60 (400 mg, 1.32 mmol) in formic acid (2 mL) was added while keeping the temperature at 0° C. The mixture was stirred at room temperature overnight. TLC (PE: EA=1:1) showed the reaction was complete. The mixture was cooled in an ice bath and solid Na₂SO₃ was added slowly till the iodine-starch did not go blue. The mixture was mixed with silica gel and concentrated in vacuo. The residue was purified by combi flash (CH₂Cl₂: MeOH=10:1) to give 4-(1,3-dioxoisoindolin-2-yl)cyclohexane-1-sulfonic acid (400 mg, 98%) as a white solid.

A mixture of 4-(1,3-dioxoisoindolin-2-yl)cyclohexane-1-sulfonic acid (6.8 g, 22 mmol) and PCl₅ (5 g, 24 mmol) was stirred at room temperature for 30 min. And then the mixture was heated at 100° C. and stirred for 2 h. After cooling to room temperature, the mixture was washed with EtOAc (150 mL×3). The combined extracts were concentrated in vacuo to give crude 4-(1,3-dioxoisoindolin-2-yl)cyclohexane-1-sulfonyl chloride (5 g, 68%) as a whit solid, which was used in the next step directly.

A mixture of 4-(1,3-dioxoisoindolin-2-yl)cyclohexane-1-sulfonyl chloride (5 g, 15.2 mmol) in NH₃/THF (150 mL) was stirred at room temperature overnight. The mixture was concentrated in vacuo. The residue was dissolved into about 100 mL of hot water and the solid was filtered under hot condition. The filtrate was concentrated in vacuo to give 4-(1,3-dioxoisoindolin-2-yl)cyclohexane-1-sulfonamide (3 g, 64%) as an off-white solid.

A mixture of 4-(1,3-dioxoisoindolin-2-yl)cyclohexane-1-sulfonamide (3 g, 9.7 mmol) and NH₂NH₂H₂O (1 mL) in EtOH (15 mL) was heated at reflux for 30 min. After cooling, the pH was adjusted with diluted HCl to 5. The mixture was concentrated in vacuo. The residue was dissipated with 35% HCl (10 mL) and heating until all solid material was dissolved. Upon cooling, a crystalline material was filtered and the filtrated was concentrated to give crude 4-aminocyclohexane-1-sulfonamide (700 mg, 40%) as a yellow solid, which was used in the next step directly.

A mixture of 4-aminocyclohexane-1-sulfonamide (200 mg, 1.12 mmol), 6-chloro-3-(3-chlorophenyl)imidazo[1,2-b]pyridazine (200 mg, 0.76 mmol) and KF (500 mg, 8.6 mmol) in DMSO (2 mL) was heated at 120° C. overnight. LCMS showed the reaction was complete. The mixture was poured into brine (80 mL) and extracted with EtOAc (30 mL×3). The combined extracts were dried over Na₂SO₄, filtered and concentrated in vacuo. The residue was purified by to prep. HPLC give two isomers: EX. 8-81 isomer 1 (7.0 mg) and EX. 8-81 isomer 2 (8.1 mg) as white solid.

EX. 8-81 isomer 1. ¹H NMR (MeOD, 400 MHz): δ 8.39 (s, 1H), 8.33 (s, 1H), 8.00-7.97 (m, 2H), 7.58-7.55 (m, 2H), 7.25 (d, J=9.93 Hz, 1H), 3.78 (tt, J₁=11.35 Hz, J₂=3.41 Hz, 1H), 3.02 (tt, J=11.64 Hz, J₂=3.41 Hz, 1H), 2.39 (t, J=11.64 Hz, 4H), 1.79 (d, J=12.49 Hz, 2H), 1.47 (d, J=12.49 Hz, 2H). MS (ES⁺, m/z): (M+H⁺): 406.1.

EX. 8-81 isomer 2. ¹H NMR (MeOD, 400 MHz): δ 8.34 (s, 1H), 8.32 (s, 1H), 8.0 (d, J=9.96 Hz, 1H), 7.97 (d, J=6.87 Hz, 1H), 7.56 (d, J=7.56 Hz, 1H), 7.55 (s, 1H), 7.40 (d, J=9.96 Hz, 1H), 4.08 (t, J=3.44 Hz, 1H), 3.09 (tt, J₁=9.96 Hz, J₂=3.78 Hz, 1H), 2.29-2.25 (m, 2H), 2.15-2.10 (m, 2H), 2.06-1.96 (m, 2H), 1.88-1.80 (m, 2H). MS (ES⁺, m/z): (M+H⁺): 406.2.

82. 2-(trans-3-((3-(3-chlorophenyl)imidazo[1,2-b]pyridazin-6-yl)amino)cyclopentyl)propan-2-ol (EX 8-82)

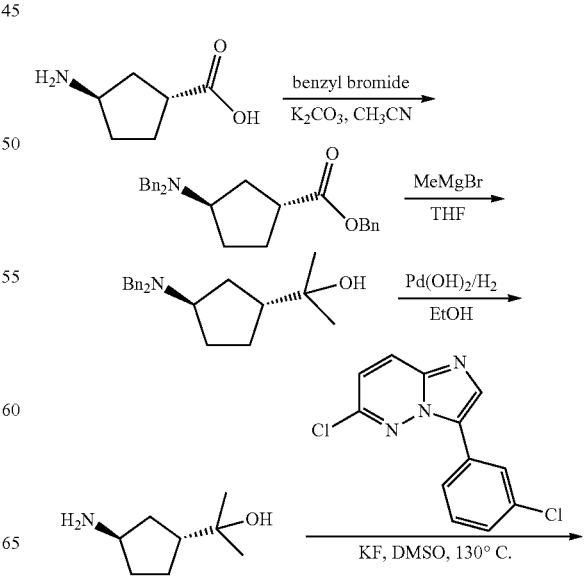

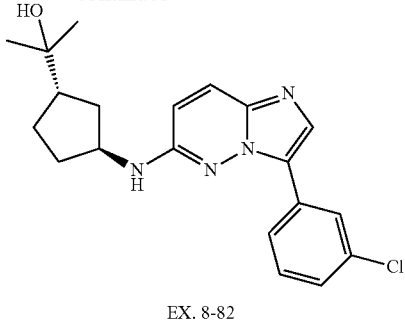

EX. 8-82

To a 80° C. mixture of trans-3-aminocyclopentanecarboxylic acid (1 g, 7.74 mmol) and K$_2$CO$_3$ (3.2 g, 23.22 mmol) in CH$_3$CN (20 mL) was added dropwise a solution of benzyl bromide (3.2 mL, 27.1 mmol) in CH$_3$CN (10 mL). The mixture was heated at 80° C. overnight. The mixture was cooled and poured into water (150 mL) and extracted with EtOAc (100 mL*3). The combined extracts were dried over Na$_2$SO$_4$, filtered and concentrated in vacuo. The residue was purified by combi flash to give trans-benzyl 3-(dibenzylamino)cyclopentanecarboxylate (2.8 g, 90.6%) as a white solid.

To a 0° C. solution of trans-benzyl 3-(dibenzylamino)cyclopentanecarboxylate (2.8 g, 7 mmol) in THF (250 mL) was added dropwise MeMgBr (23 mL, 70 mmol). After the addition, the reaction mixture was stirred at room temperature overnight. TLC (PE) showed the reaction was complete. The mixture was cooled and poured into sat. NH$_4$Cl (300 mL) and extracted with EtOAc (100 mL*3). The combined extracts were dried over Na$_2$SO$_4$, filtered and concentrated in vacuo to give crude 2-(trans-3-(dibenzylamino)cyclopentyl)propan-2-ol (3 g, 133%) as a yellow liquid.

A mixture of 2-(trans-3-(dibenzylamino)cyclopentyl)propan-2-ol (3 g, 9.3 mmol) and Pd(OH)$_2$ (900 mg) in EtOH (30 mL) was hydrogenated under 50 psi of H$_2$ for 48 h at room temperature. TLC (PE: EA=5:1) showed the reaction was complete. The mixture was filtered and concentrated in vacuo to give crude 2-(trans-3-aminocyclopentyl)propan-2-ol (1 g, 77%) as a yellow oil.

A mixture of 2-(trans-3-aminocyclopentyl)propan-2-ol (82 mg, 0.57 mmol), 6-chloro-3-(3-chlorophenyl)imidazo[1,2-b]pyridazine (100 mg, 0.38 mmol) and KF (66.2 mg, 1.14 mmol) in DMSO (1 mL) was stirred at 130° C. overnight. LCMS showed the reaction was complete. The mixture was poured into water (100 mL) and extracted with EtOAc (50 mL*3). The combined extracts were dried over Na$_2$SO$_4$, filtered and concentrated in vacuo. The residue was purified by prep-HPLC to give EX. 8-82 (45 mg, 32%) as an off-white solid.

$^1$H NMR (MeOD, 400 MHz): δ 8.57 (t, J=2.06 Hz, 1H), 7.96 (dt, J$_1$=8.11 Hz, J$_2$=1.32 Hz, 1H), 7.86 (s, 1H), 7.63 (d, J=9.88 Hz, 1H), 7.44 (t, J=8.11 Hz, 1H), 7.33 (d, J=7.76 Hz, 1H), 6.74 (d, J=9.70 Hz, 1H), 4.19-4.12 (m, 1H), 2.41-2.34 (m, 1H), 2.22-2.10 (m, 2H), 1.83-1.62 (m, 3H), 1.51-1.43 (m, 1H), 1.23 (s, 6H). MS (ES$^+$, m/z): (M+H$^+$): 371.1

83. N-(trans-4-((3-(3-chlorophenyl)imidazo[1,2-b]pyridazin-6-yl)amino)cyclohexyl)formamide (EX. 8-83)

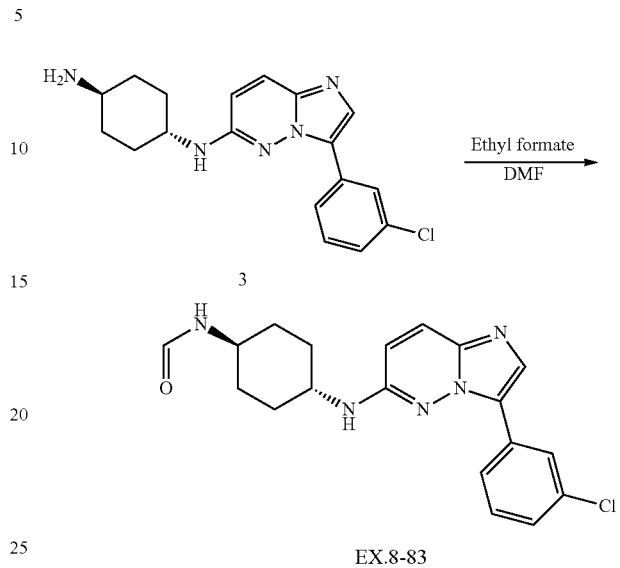

EX.8-83

A mixture of trans-N1-(3-(3-chlorophenyl)imidazo[1,2-b]pyridazin-6-yl)cyclohexane-1,4-diamine (50 mg, 0.146 mmol) and ethyl formate (0.37 mL) in DMF (1.2 mL) was heated at 90° C. for 6 h. LCMS showed the reaction was complete. The mixture was concentrated in vacuo and purified b prep-HPLC to give EX. 8-83 (22 mg, 41%) as an off-white solid.

$^1$H NMR (MeOD, 400 MHz): δ 8.47 (s, 1H), 8.23 (br, 0.36H), 7.98 (s, 1H), 7.88 (d, J=8.0 Hz, 1H), 7.82 (s, 1H), 7.60 (d, J=9.6 Hz, 1H), 7.39 (t, J=8.0 Hz, 1H), 7.29 (d, J=8.0 Hz, 1H), 7.68 (d, J=9.6 Hz, 1H), 3.79 (t, J=11.2 Hz, 1H), 3.70 (t, J=10.8 Hz, 1H), 2.28 (d, J=12 Hz, 2H), 2.02 (d, J=12 Hz, 2H), 1.54-1.36 (m, 4H). MS (ES$^+$, m/z): (M+H$^+$): 370.2

84. N-(trans-4-((3-(3-chlorophenyl)imidazo[1,2-b]pyridazin-6-yl)amino)cyclohexyl)-2-morpholinoacetamide (EX. 8-84)

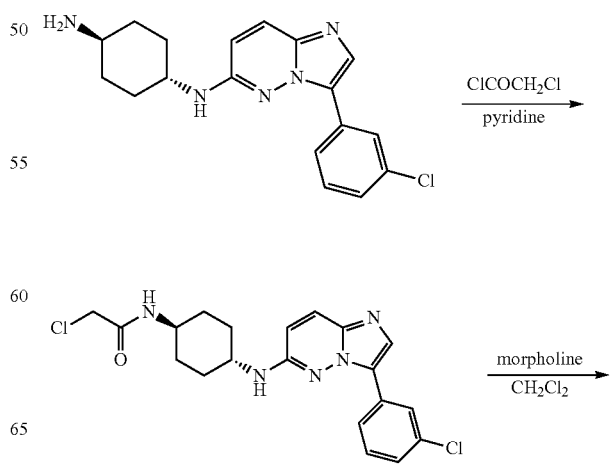

-continued

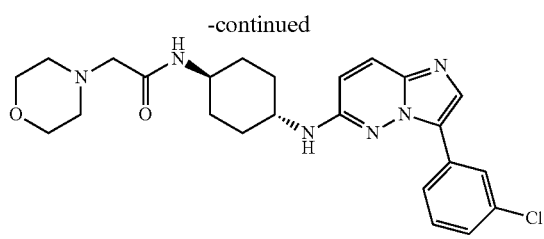

EX. 8-84

To a solution of trans-N1-(3-(3-chlorophenyl)imidazo[1,2-b]pyridazin-6-yl)cyclohexane-1,4-diamine (90 mg, 0.26 mmol) and pyridine (0.08 mL, 1.04 mmol) in CH$_2$Cl$_2$ (2.6 mL) was added dropwise chloroacetyl chloride (0.03 mL, 0.39 mmol). The resulting mixture was stirred at room temperature overnight. TLC (CH$_2$Cl$_2$: MeOH=10:1) showed the reaction was complete. The mixture was poured into sat. aq. NaHCO$_3$ (100 mL) and extracted with EtOAc (50 mL*3). The extracts were dried over Na$_2$SO$_4$, filtered and concentrated in vacuo to give crude 2-chloro-N-(trans-4-((3-(3-chlorophenyl)imidazo[1,2-b]pyridazin-6-yl)amino)cyclohexyl)acetamide (110 mg, 101%) as a yellow solid.

A mixture of 2-chloro-N-(trans-4-((3-(3-chlorophenyl)imidazo[1,2-b]pyridazin-6-yl)amino)cyclohexyl)acetamide (50 mg, 0.12 mmol), morpholine (0.3 mL) and DIPEA (0.2 mL) in CH$_2$Cl$_2$ (0.6 mL) was stirred at 50° C. for 3 h. LCMS showed the reaction was complete. The mixture was concentrated in vacuo. The residue was partitioned between water (100 mL) and EtOAc (50 mL). The organic layer was dried over Na$_2$SO$_4$, filtered and concentrated in vacuo. The residue was purified by prep-HPLC to give EX. 8-84 (9.6 mg, 17%) as a white solid.

$^1$H NMR (MeOD, 400 MHz): δ 8.49 (s, 1H), 7.90 (d, J=7.6 Hz, 1H), 7.88 (s, 1H), 7.66 (d, J=9.6 Hz, 1H), 7.44 (t, J=7.6 Hz, 1H), 7.34 (d, J=8.8 Hz, 1H), 6.75 (d, J=9.6 Hz, 1H), 3.87-3.73 (m, 6H), 3.36-3.30 (m, 1H), 3.36-3.30 (m, 1H), 3.30-3.20 (m, 1H), 2.84 (br, 4H), 2.31 (d, J=12.8 Hz, 2H), 2.02 (d, J=12.8 Hz, 2H), 1.54-1.40 (m, 4H). MS (ES$^+$, m/z): (M+H$^+$): 469.3.

85. trans-4-((3-(3-(trifluoromethyl)phenyl)imidazo[1,2-b]pyridazin-6-yl)amino)cyclohexanecarbonitrile (EX. 8-85)

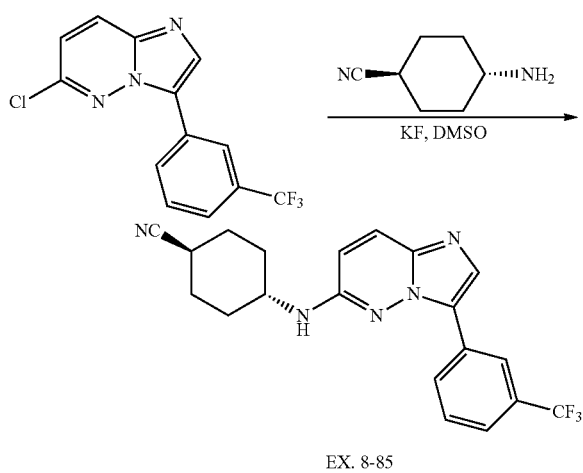

EX. 8-85

A mixture of 6-chloro-3-(3-(trifluoromethyl)phenyl)imidazo[1,2-b]pyridazine (50 mg, 0.168 mmol), Trans-4-aminocyclohexanecarbonitrile (53 mg, 0.22 mmol) and KF (42.2 mg, 0.73 mmol) in DMSO (0.5 mL) was heated at 130° C. overnight. LCMS showed the reaction was almost complete. The mixture was purified by prep. HPLC to give trans-4-((3-(3-(trifluoromethyl)phenyl)imidazo[1,2-b]pyridazin-6-yl)amino)cyclohexanecarbonitrile (20 mg, 30.8%) as an off-white solid.

$^1$H NMR (MeOD, 400 MHz): δ 8.75 (s, 1H), 8.24 (t, J=3.61 Hz, 1H), 7.99 (s, 1H), 7.74-7.69 (m, 3H), 6.84 (d, J=9.79 Hz, 1H), 3.83 (tt, J$_1$=10.82 Hz, J$_2$=3.78 Hz, 1H), 2.71 (tt, J$_1$=11.51 Hz, J$_2$=3.61 Hz, 1H), 2.23 (tt, J$_1$=16.15 Hz, J$_2$=6.18 Hz, 4H), 1.73 (q, J=12.20 Hz, 2H), 1.43 (q, J=12.54 Hz, 2H). MS (ES$^+$, m/z): (M+H$^+$): 386.2.

86. trans-4-((3-(3-(trifluoromethoxy)phenyl)imidazo[1,2-b]pyridazin-6-yl)amino)cyclohexanecarbonitrile (EX. 8-86)

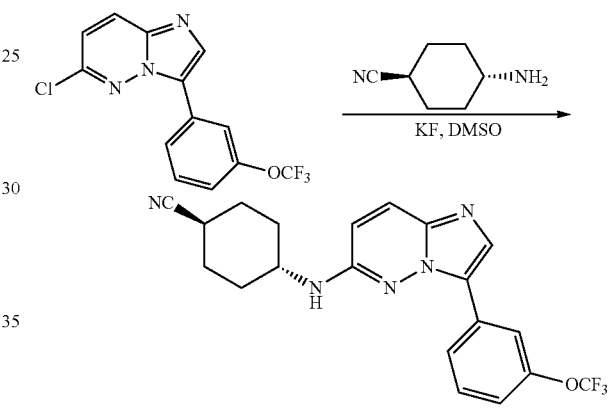

EX. 8-86

EX. 8-86 is prepared from 6-chloro-3-(3-(trifluoromethoxy)phenyl)imidazo[1,2-b]pyridazine using similar procedures as in EX. 8-85.

$^1$H NMR (MeOD, 400 MHz): δ 8.42 (s, 1H), 8.02 (d, J=7.90 Hz, 1H), 7.99 (s, 1H), 7.72 (d, J=9.62 Hz, 1H), 7.60 (t, J=8.25 Hz, 1H), 7.31 (t, J=8.25 Hz, 1H), 6.82 (t, J=9.62 Hz, 1H), 3.82 (tt, J$_1$=10.65 Hz, J$_2$=3.44 Hz, 1H), 2.73 (tt, J$_1$=11.68 Hz, J$_2$=3.44 Hz, 1H), 2.31-2.20 (m, 4H), 1.76 (q, J=12.02 Hz, 2H), 1.43 (q, J=12.02 Hz, 2H). MS (ES$^+$, m/z): (M+H$^+$): 402.2.

87. 2-(trans-4-((3-(3-chlorophenyl)imidazo[1,2-b]pyridazin-6-yl)amino)cyclohexyl)acetonitrile (EX. 8-87)

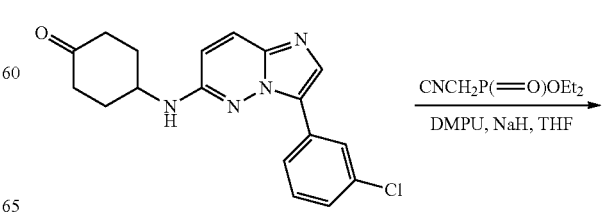

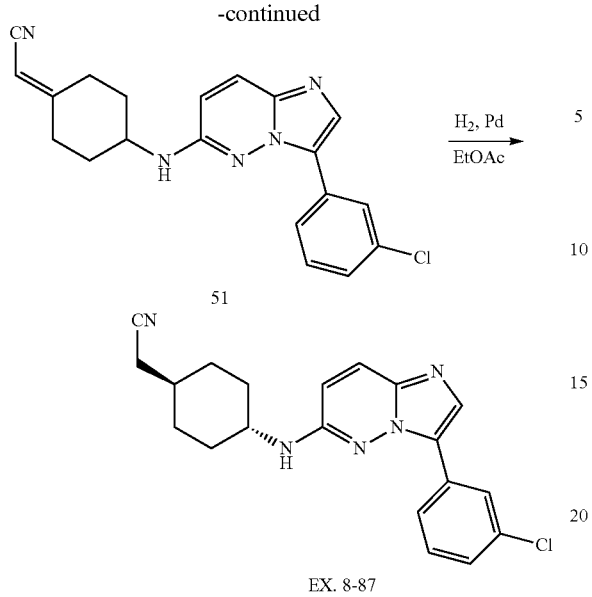

EX. 8-87

To a 0° C. solution of diethyl cyanomethyl phosphonate (0.07 mL, 0.4 mmol) in THF (1.5 mL) was added DMPU (0.27 mL, 1 mmol), followed by NaH (15 mL, 0.37 mmol). After stirring for 10 min, a solution of 4-((3-(3-chlorophenyl)imidazo[1,2-b]pyridazin-6-yl)amino)cyclohexanone (130 mg, 0.38 mmol) in THF (1.5 mL) was added. The resulting mixture was stirred at room temperature for 2 h. TLC (EA) showed most of s.m. was converted into product. The mixture was poured into water (100 mL) and extracted with EtOAc (50 mL*3). The combined extracts were dried over $Na_2SO_4$, filtered and concentrated in vacuo to give crude 2-(4-((3-(3-chlorophenyl)imidazo[1,2-b]pyridazin-6-yl)amino)cyclohexylidene)acetonitrile (100 mg, 69%) as a yellow solid.

A mixture of 2-(4-((3-(3-chlorophenyl)imidazo[1,2-b]pyridazin-6-yl)amino)cyclohexylidene)acetonitrile (100 mg, 0.26 mmol) and 10% Pd/C (100 mg) in EtOAc (2 mL) was stirred under $H_2$ balloon at room temperature for 4 h. LCMS showed the most of s.m was consumed. The mixture was filtered and the filtrate was concentrated in vacuo. The residue was purified by prep. HPLC to give EX. 8-87 (13 mg, 13.7%) as a white solid.

$^1$H NMR (MeOD, 400 MHz): δ 8.51 (s, 1H), 8.17 (br, 0.4H), 7.93 (d, J=7.90 Hz, 1H), 7.87 (s, 1H), 7.64 (d, J=9.96 Hz, 1H), 7.44 (t, J=7.90 Hz, 1H), 7.34 (d, J=7.90 Hz, 1H), 6.73 (d, J=9.96 Hz, 1H), 3.72 (tt, $J_1$=10.31 Hz, $J_2$=3.44 Hz, 1H), 2.46 (d, J=6.18 Hz, 2H), 2.33 (d, J=10.65 Hz, 2H), 1.98 (d, J=10.99 Hz, 2H), 1.77 (br, 1H), 1.48-1.32 (m, 4H). MS ($ES^+$, m/z): $(M+H^+)$: 366.3.

88. trans-4-(((3-(3-chlorophenyl)imidazo[1,2-b]pyridazin-6-yl)amino)methyl)cyclohexanecarbonitrile (EX 8-88)

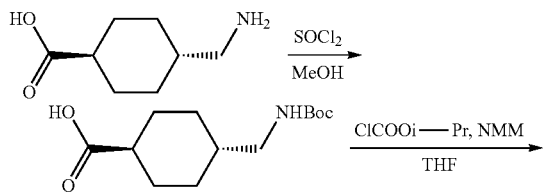

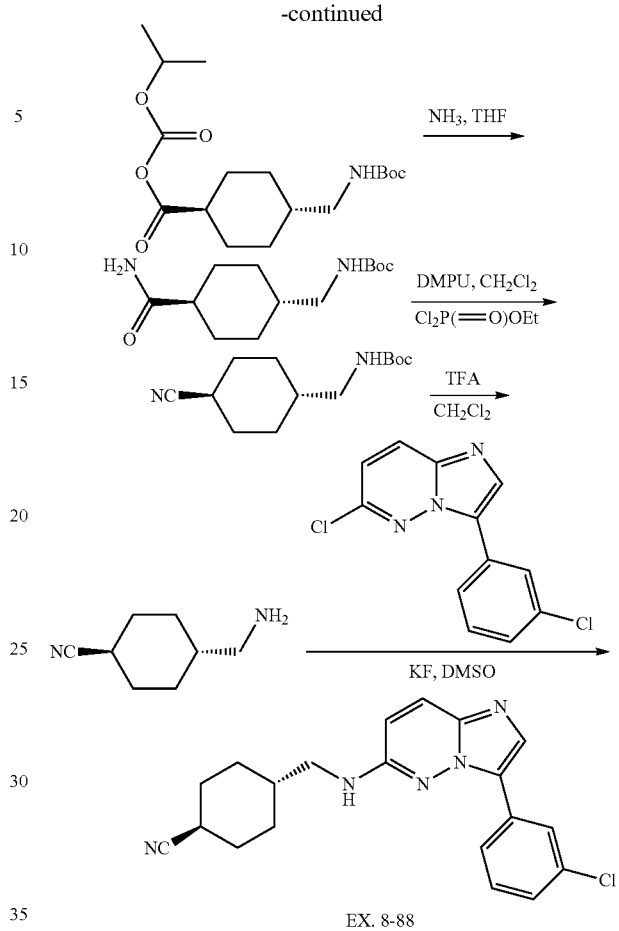

EX. 8-88

To a solution of trans-4-(aminomethyl)cyclohexanecarboxylic acid (2 g, 12.7 mmol) in MeOH (64 mL) was added dropwise thionyl chloride (0.927 mL, 12.7 mmol) at room temperature. The resulting mixture was stirred at room temperature for 4 h. The mixture was concentrated in vacuo to give crude trans-4-(((tert-butoxycarbonyl)amino)methyl)cyclohexanecarboxylic acid (2.5 g, 115%) as HCl salts, which was used in the next step directly.

A suspension of trans-4-(((tert-butoxycarbonyl)amino)methyl)cyclohexanecarboxylic acid (2.27 g, 8.8 mmol) and NMM (1.4 mL, 10.12 mmol) in THF (15 mL) was added dropwise isopropyl chloroformate (1.79 g, 17.6 mmol) below 10° C. The mixture containing trans-4-(((tert-butoxycarbonyl)amino)methyl)cyclohexanecarboxylic (isopropyl carbonic) anhydride was stirred at room temperature for 3 h. TLC (PE: EA=1:1) showed the reaction was complete. The mixture was used in the next step directly.

Above mixture was cooled to 10° C. again and ammonium hydroxide (8.2 mL, 52.8 mmol) was added. The final mixture was stirred at room temperature for 18 h. The mixture was filtered and the filter cake was washed with water three times and dried to give tert-butyl ((trans-4-carbamoylcyclohexyl)methyl)carbamate (1.7 g, 74%) as a white solid.

To a solution of tert-butyl ((trans-4-carbamoylcyclohexyl)methyl)carbamate (1.7 g, 6.6 mmol) in $CH_2Cl_2$ (33 mL) was added DBU (3 g, 19.8 mmol) at room temperature. After stirring for 10 min, ethyl dichlorophosphate (2.2 g, 13.2 mmol) was added. The mixture was stirred at room temperature for 50 min. TLC ($CH_2Cl_2$: MeOH=10:1) showed the reaction was complete. The mixture was poured into sat. NH$_4$Cl (aq., 150 mL) and extracted with CH$_2$Cl$_2$ (100 mL*2). The combined extracts were dried over Na$_2$SO$_4$, filtered and concentrated in vacuo. The residue was purified by combi flash to give tert-butyl ((trans-4-cyanocyclohexyl) methyl)carbamate (1.4 g, 88%) as a white solid.

To a solution of tert-butyl ((trans-4-cyanocyclohexyl) methyl)carbamate (1.4 g, 5.86 mmol) in CH$_2$Cl$_2$ (20 mL) was added TFA (20 mL) at r.t. The resulting mixture was stirred at room temperature for 1 h. TLC (PE: EA=5:1) showed the reaction was complete. The mixture was concentrated in vacuo to give trans-4-(aminomethyl)cyclohexanecarbonitrile (2.6 g, 319%) as TFA salts.

A mixture of 6-chloro-3-(3-chlorophenyl)imidazo[1,2-b] pyridazine (50 mg, 0.189 mmol), -4-(aminomethyl)cyclohexanecarbonitrile (111 mg, 0.25 mmol) and KF (47 mg, 0.82 mmol) in DMSO (0.5 mL) was heated at 130° C. overnight. LCMS showed the reaction was almost complete. The mixture was purified by prep. HPLC to give EX. 8-88 (26 mg, 38%) as an off-white solid.

$^1$H NMR (MeOD, 400 MHz): δ 8.48 (t, J=1.89 Hz, 1H), 8.19 (br, 0.3H), 7.95 (dt, J$_1$=7.90 Hz, J$_2$=1.37 Hz, 1H), 7.86 (s, 1H), 7.66 (d, J=9.62 Hz, 1H), 7.45 (t, J=7.90 Hz, 1H), 7.35 (dq, J$_1$=8.07 Hz, J$_2$=0.86 Hz, 1H), 6.76 (d, J=9.62 Hz, 1H), 3.28 (d, J=6.87 Hz, 2H), 2.60 (tt, J$_1$=12.02 Hz, J$_2$=3.61 Hz, 1H), 2.17-2.13 (m, 2H), 2.05-2.01 (m, 2H), 1.94-1.87 (m, 1H), 1.59 (qd, J$_1$=13.06 Hz, J$_2$=3.26 Hz, 1H), 1.14 (qd, J$_1$=12.71 Hz, J$_2$=3.26 Hz, 1H). MS (ES$^+$, m/z): (M+H$^+$): 366.1.

EX. 8-89, Ex. 8-90 and EX. 8-91 were prepared using similar procedures as in Ex. 8-80.

89. N-(trans-4-((3-(3-fluorophenyl)imidazo[1,2-b] pyridazin-6-yl)amino)cyclohexyl)methanesulfonamide (EX. 8-89)

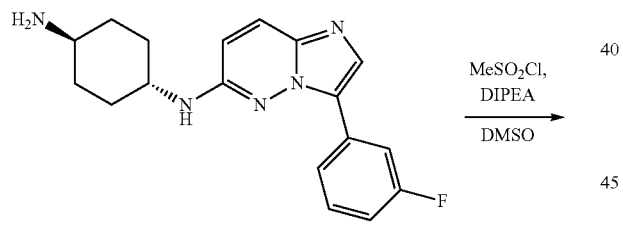

EX. 8-89

To a 0° C. solution of trans-N1-(3-(3-fluorophenyl)imidazo[1,2-b]pyridazin-6-yl)cyclohexane-1,4-diamine (180 mg, 0.55 mmol) and DIPEA (213.2 mg, 1.65 mol) in DMSO (2.8 mL) was added dropwise MeSO$_2$Cl (63.4 mg, 0.55 mmol). The resulting mixture was stirred at room temperature overnight. LCMS showed most of starting material was converted. The mixture was partitioned between brine (100 mL) and EtOAc (50 mL) and separated. The aqueous layer was extracted with EtOAc (50 mL*3). The combined extracts were dried over Na$_2$SO$_4$, filtered and concentrated in vacuo. The residue was purified by prep-HPLC to give EX. 8-89 (13 mg, 6%) as a brown solid.

$^1$H NMR (MeOD, 400 MHz): δ 8.13 (dt, J$_1$=10.65 Hz, J$_2$=2.06 Hz, 1H), 8.07 (s, 1H), 7.89 (d, J=7.90 Hz, 1H), 7.80 (d, J=9.62 Hz, 1H), 7.53 (q, J=7.90 Hz, 1H), 7.17 (td, J$_1$=8.25 Hz, J$_2$=2.40 Hz, 1H), 6.96 (d, J=9.62 Hz, 1H), 3.70 (tt, J$_1$=10.65 Hz, J$_2$=3.78 Hz, 1H), 3.32-3.27 (m, 1H), 2.99 (s, 3H), 2.30 (d, J=12.02 Hz, 2H), 2.15 (d, J=11.68 Hz, 2H), 1.58-1.40 (m, 4H). MS (ES$^+$, m/z): (M+H$^+$): 404.0.

90. N-(trans-4-((3-(3-(trifluoromethyl)phenyl)imidazo[1,2-b]pyridazin-6-yl)amino)cyclohexyl)methanesulfonamide (EX. 8-90)

EX. 8-90

To a 0° C. solution of trans-N1-(3-(3-(trifluoromethyl) phenyl)imidazo[1,2-b]pyridazin-6-yl)cyclohexane-1,4-diamine (130 mg, 0.35 mmol) and DIPEA (135.7 mg, 10.5 mmol) in DMSO (1.75 mL) was added dropwise MeSO$_2$Cl (47.6 mg, 0.42 mmol). The resulting mixture was stirred at room temperature overnight. LCMS showed most of starting material was converted. The mixture was partitioned between brine (100 mL) and EtOAc (50 mL) and separated. The aqueous layer was extracted with EtOAc (50 mL*3). The combined extracts were dried over Na$_2$SO$_4$, filtered and concentrated in vacuo. The residue was purified by prep-HPLC to give EX. 8-90 (30 mg, 18.9%) as a white solid.

$^1$H NMR (MeOD, 400 MHz): δ 8.73 (s, 1H), 8.28 (d, J=6.87 Hz, 1H), 7.93 (s, 1H), 7.69-7.67 (m, 3H), 6.77 (d, J=9.62 Hz, 1H), 3.74 (tt, J$_1$=10.65 Hz, J$_2$=3.78 Hz, 1H), 3.29-3.26 (m, 1H), 2.99 (s, 3H), 2.28 (d, J=11.68 Hz, 2H), 2.12 (d, J=12.35 Hz, 2H), 1.56-1.39 (m, 4H). MS (ES$^+$, m/z): (M+H$^+$): 454.7.

91. N-(trans-4-((3-(3-(trifluoromethoxy)phenyl)imidazo[1,2-b]pyridazin-6-yl)amino)cyclohexyl)methanesulfonamide (EX. 8-91)

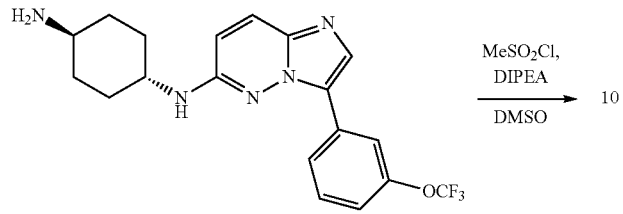

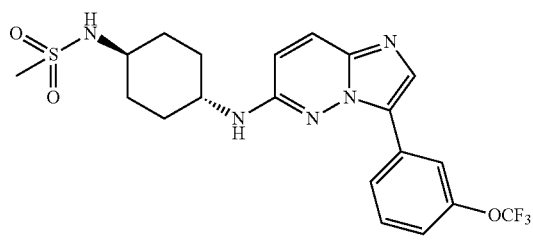

EX. 8-91

To a 0° C. solution of trans-N1-(3-(3-(trifluoromethoxy)phenyl)imidazo[1,2-b]pyridazin-6-yl)cyclohexane-1,4-diamine (180 mg, 0.46 mmol) and DIPEA (178 mg, 1.38 mol) in DMSO (2.0 mL) was added dropwise MeSO$_2$Cl (53 mg, 0.46 mmol). The resulting mixture was stirred at room temperature overnight. LCMS showed most of starting material was converted. The mixture was partitioned between brine (100 mL) and EtOAc (50 mL) and separated. The aqueous layer was extracted with EtOAc (50 mL*3). The combined extracts were dried over Na$_2$SO$_4$, filtered and concentrated in vacuo. The residue was purified by prep-HPLC to give EX. 8-91 (57.1 mg, 26.4%) as a white solid.

$^1$H NMR (MeOD, 400 MHz): δ 8.33 (s, 1H), 8.07 (d, J=8.25 Hz, 1H), 7.88 (s, 1H), 7.65 (d, J=9.62 Hz, 1H), 7.56 (t, J=7.56 Hz, 1H), 7.27 (d, J=8.25 Hz, 1H), 6.73 (d, J=9.62 Hz, 1H), 3.73 (tt, J$_1$=10.99 Hz, J$_2$=3.44 Hz, 1H), 3.32-3.28 (m, 1H), 2.99 (s, 3H), 2.29 (d, J=12.37 Hz, 2H), 2.14 (d, J=11.68 Hz, 2H), 1.57-1.38 (m, 4H). MS (ES$^+$, m/z): (M+H$^+$): 470.2.

92. 4-((3-(3-chlorophenyl)imidazo[1,2-b]pyridazin-6-yl)amino)cyclohexanone oxime (EX. 8-92)

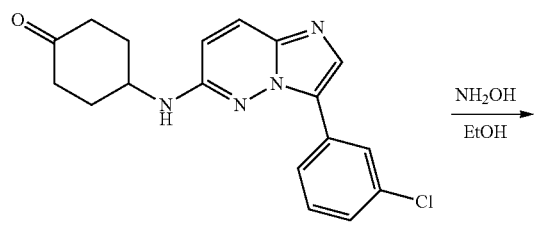

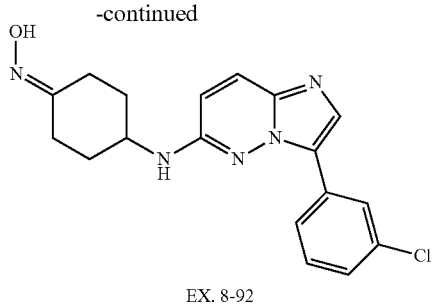

EX. 8-92

To a mixture of hydroxylamine hydrochloride (15.3 mg, 0.22 mmol) and Na$_2$CO$_3$ (28 mg, 0.26 mmol) in water (0.7 mL) was added a solution of 4-((3-(3-chlorophenyl)imidazo[1,2-b]pyridazin-6-yl)amino)cyclohexanone (50 mg, 0.147 mmol) in MeOH (0.5 mL) at 0° C. The resulting mixture was stirred at room temperature for 1 h. LCMS showed the reaction was complete. The mixture was poured into water and extracted with EtOAc (50 mL*3). The combined extracts were dried over Na$_2$SO$_4$, filtered and concentrated in vacuo. The residue was purified by prep-HPLC and then by SFC to give EX. 8-92 (10 mg, 19%) as a white solid.

$^1$H NMR (MeOD, 400 MHz): δ 8.39 (s, 1H), 7.83 (d, J=8.25 Hz, 1H), 7.74 (s, 1H), 7.54 (d, J=9.96 Hz, 1H), 7.34 (t, J=7.90 Hz, 1H), 7.23 (dd, J$_1$=7.99 Hz, J$_2$=1.12 Hz, 1H), 6.64 (d, J=9.71 Hz, 1H), 3.91 (tt, J=10.31 Hz, J$_2$=3.44 Hz, 1H), 3.17-3.15 (m, 1H), 2.40-2.35 (m, 1H), 2.29-2.19 (m, 3H), 2.07-2.00 (m, 2H), 1.51-1.36 (m, 1H). MS (ES$^+$, m/z): (M+H$^+$): 356.1.

93. trans-4-((3-(3-chlorophenyl)imidazo[1,2-b]pyridazin-6-yl)amino)cyclohexanecarboximidamide (EX. 8-93)

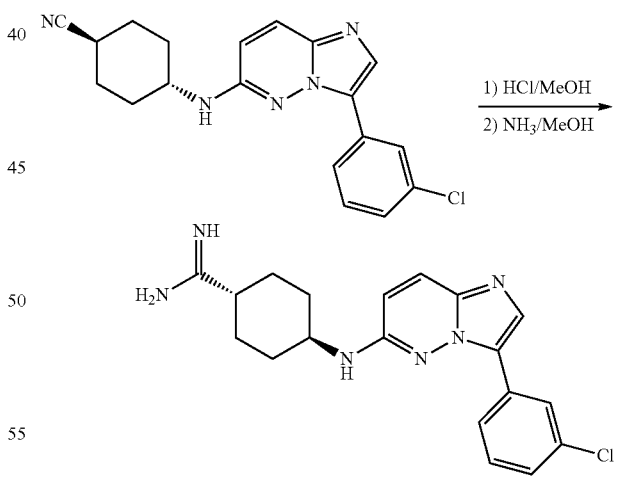

EX. 8-93 trans-4-((3-(3-Chlorophenyl)imidazo[1,2-b]pyridazin-6-yl)amino)cyclohexanecarbonitrile (100 mg, 0.252 mmol) was dissolved into HCl/MeOH (4 mL) and HCl/dioxane (4 mL). The mixture was stirred at room temperature overnight. The mixture was concentrated in vacuo and the residue was dissolved in NH$_3$/MeOH (4 mL). The mixture was stirred at room temperature for 2 h. LCMS showed the reaction was complete. The mixture was concentrated in vacuo. The residue was purified by prep. HPLC to give EX. 8-93 (3.5 mg, 18.4%) as a brown solid.

$^1$H NMR (MeOD, 400 MHz): δ 8.42 (br, 1H), 8.26 (s, 1H), 7.85 (d, J=8.25 Hz, 1H), 7.72 (s, 1H), 7.55 (d, J=9.62 Hz, 1H), 7.35 (t, J=8.25 Hz, 1H), 7.23 (d, J=8.25 Hz, 1H), 6.62 (d, J=9.62 Hz, 1H), 3.66 (tt, $J_1$=11.68 Hz, $J_2$=3.44 Hz, 1H), 2.47 (d, $J_1$=13.06 Hz, $J_2$=3.44 Hz, 1H), 2.36 (d, J=10.31 Hz, 2H), 1.98 (d, J=12.37 Hz, 2H), 1.72 (qd, $J_1$=13.06 Hz, $J_2$=2.40 Hz, 2H), 1.32 (qd, $J_1$=12.71 Hz, $J_2$=2.75 Hz,).

MS (ES$^+$, m/z): (M+H$^+$): 369.1; (M/2+H$^+$): 185.4.

95. trans-N1-(3-(3-chlorophenyl)pyrazolo[1,5-a]pyrimidin-5-yl)cyclohexane-1,4-diamine (EX. 8-95)

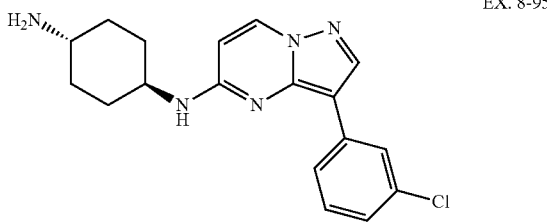

EX. 8-95

EX. 8-95 was prepared using a similar procedures as in EX. 8-96.

96. (S)-1-(3-(3-chlorophenyl)pyrazolo[1,5-a]pyrimidin-5-yl)piperidin-3-amine (EX. 8-96)

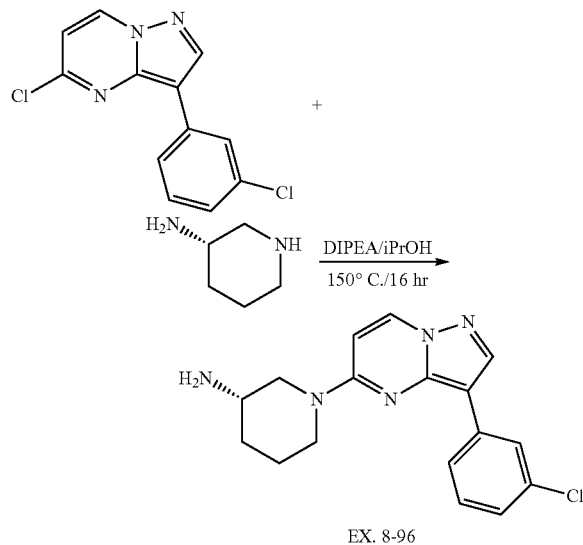

EX. 8-96

A mixture of 5-chloro-3-(3-chlorophenyl)pyrazolo[1,5-a]pyrimidine (100 mg, 0.379 mmol), (S)-piperidin-3-amine (76 mg, 0.757 mmol), and DIEA (0.158 ml, 1.515 mmol) in 2-propanol (3 ml) was irradiated to 150° C. for 14 h in a Biotage microwave. After cooling, the mixture was diluted with saturated aqueous NaHCO$_3$, and extracted three times with EtOAc. The combined extracts were washed with brine, dried over Na$_2$SO$_4$ and concentrated in vacuo. After absorbing on celite, the compound was purified by chromatography (12 g silica, 0-15% methanol/DCM) to give (S)-1-(3-(3-chlorophenyl)pyrazolo[1,5-a]pyrimidin-5-yl)piperidin-3-amine (35 mg, 28% yield) as a white solid.

$^1$H NMR (CD$_3$OD/400 MHz): 8.47 (d, J=8.0 Hz, 1H), 8.29 (s, 1H), 8.03 (s, 1H), 7.92 (m, 1H), 7.33 (t, J=8.0 Hz, 1H), 7.13 (d, J=8.0 Hz, 1H), 6.73 (d, J=8.0 Hz, 1H), 4.27 (m, 1H), 4.02 (m, 1H), 3.50 (m, 1H), 3.40 (m, 1H), 2.20 (m, 1H), 1.90 (m, 1H), 1.80 (m, 2H), 1.36 (m, 1H). MS (ES$^+$, m/z): (M+H)$^+$: 328.5.

97. 4-((3-(3-chlorophenyl)pyrazolo[1,5-a]pyrimidin-5-yl)amino)cyclohexanone (EX. 8-97)

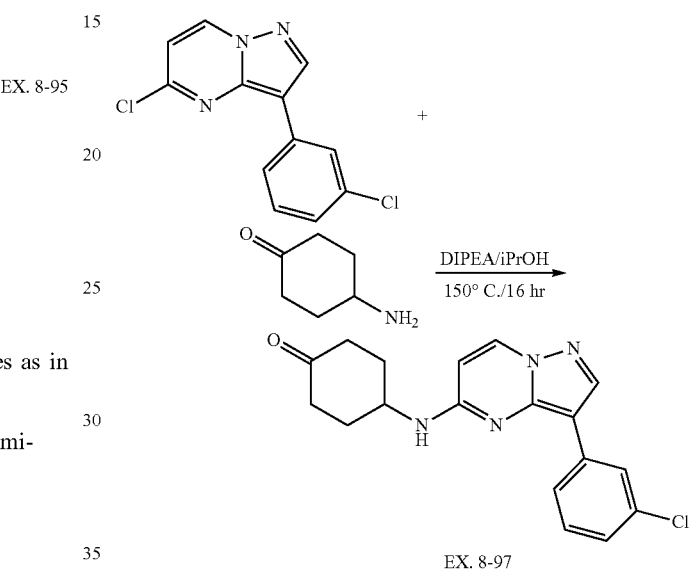

EX. 8-97

A mixture of 5-chloro-3-(3-chlorophenyl)pyrazolo[1,5-a]pyrimidine (100 mg, 0.379 mmol), 4-aminocyclohexanone (43 mg, 0.379 mmol), and DIEA (0.158 ml, 1.515 mmol) in 2-propanol (3 ml) was irradiated to 150° C. for 14 h in a Biotage microwave. After cooling, the mixture was diluted with saturated aqueous NaHCO$_3$, and extracted three times with EtOAc. The combined extracts were washed with brine, dried over Na$_2$SO$_4$ and concentrated in vacuo. After absorbing on celite, the compound was purified by chromatography (12 g silica, 0-15% methanol/DCM) to give 4-((3-(3-chlorophenyl)pyrazolo[1,5-a]pyrimidin-5-yl)amino)cyclohexanone (30 mg, 24% yield) as a white solid.

$^1$H NMR (CD$_3$OD/400 MHz): 8.35 (s, 1H), 8.26 (d, J=7.6 Hz, 1H), 8.21 (d, J=10.4 Hz, 1H), 7.79 (m, 1H), 7.08 (m, 1H), 6.26 (m, 1H), 4.40 (m, 1H), 2.62 (m, 2H), 2.47 (m, 2H), 2.00 (m, 1H), 1.84 (m, 2H), 1.65 (m, 1H). MS (ES$^+$, m/z): (M+H)$^+$: 341.4.

98. 4-trans-((7-amino-3-(3-(trifluoromethoxy)phenyl)pyrazolo[1,5-a]pyrimidin-5-yl)amino)cyclohexyl)propan-2-ol (EX. 8-98)

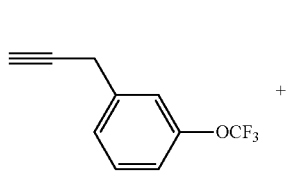

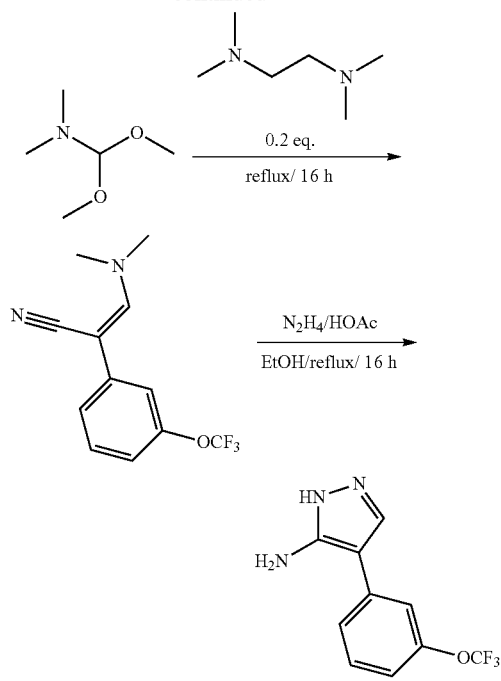

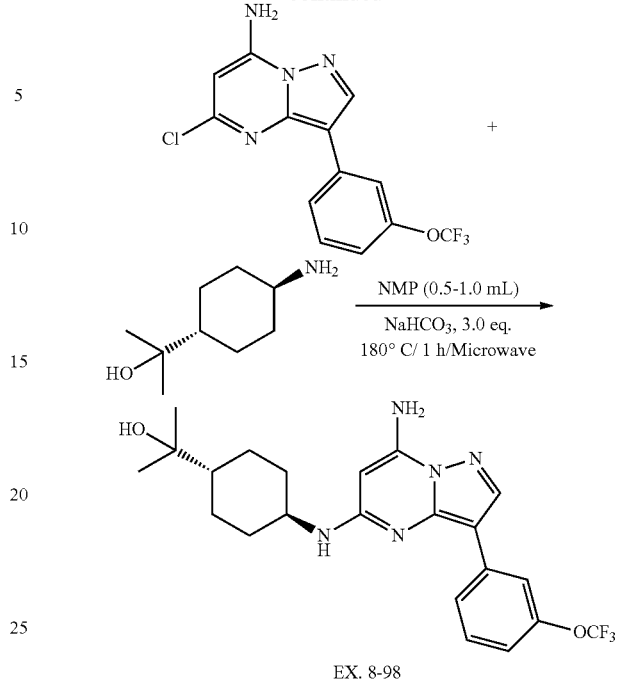

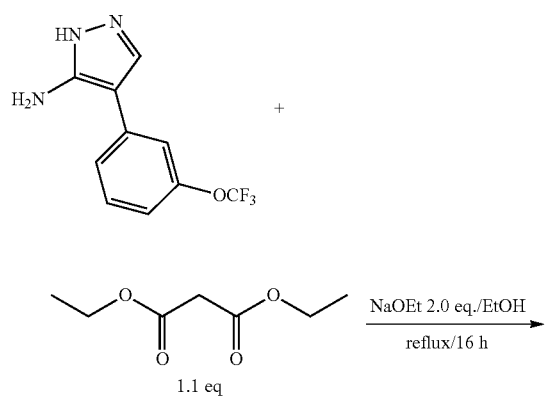

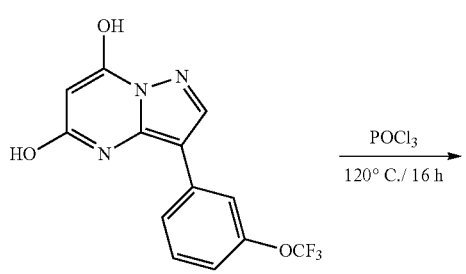

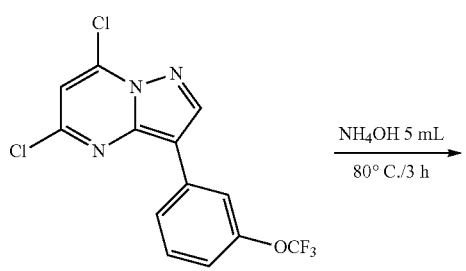

A mixture of 3-trifluoromethoxyphenylacetonitrile (2.5 grams, 12.43 mmol), DIPEA (0.321 grams, 2.48 mmol), and dimethyl formamide dimethyl acetal (20 mL) were heated at reflux for 4 h. On cooling, the reaction mixture was partitioned between EtOAc and saturated aqueous NH$_4$Cl solution. The aqueous phase was extracted with ethyl acetate and the combined organic phase was washed with brine and concentrated in vacuo. The crude product was purified by chromatography (ethyl acetate/hexane, 0-10%) on silica gel (24 grams) to give pure product (2.3 grams, 8.98 mmol, 72% yield.).

Synthesis of
4-(3-(trifluoromethoxy)phenyl)-1H-pyrazol-5-amine

A mixture of acrylnitrile (2.0 g, 7.81 mmol), hydrazine hydrate (4.53 grams, 39.0 mmol), and glacial acetaic acid (2.34 grams, 39.0 mmol) and ethanol (20 mL) were heated at reflux for 16 h. On cooling, the reaction mixture was diluted with water, extracted with AcOEt and the combined organic phase was washed with brine and concentrated in vacuo (1.90 grams, 7.84 mmol, 100% yield.). $^1$H-NMR (CDCl$_3$/400 MHz): δ 7.64 (m, 1H), 7.42 (m, 4H), 7.06 (d, J=7.6 Hz, 1H). MS (ES$^-$, m/z): (M+H)$^+$: 244.3.

A mixture of pyrazole (2.0 g, 8.22 mmol), diethyl malonate (1.32 g, 8.22 mmol), and dry EtOH 20 mL were treated dropwise with sodium ethoxide (1.12 g, 16.45 mmol) and on completion of addition the reaction was heated at reflux for 16 h. On cooling the reaction mixture was concentrated in vacuo and the residue was added to ice, neutralized with actic acid and the resulting precipitate filterated, washed with water and dried to give product 3-(3-trifluoromethoxyphenyl)pyrazolo[1,5-a]pyrimidine-5,7-diol (1.6 g, 5.14 mmol, 63% yield).

A mixture of 3-(3-trifluoromethoxyphenyl)pyrazolo[1,5-a]pyrimidine-5,7-diol (1.0 g, 3.21 mmol) in 20 mL phosphoryl oxychloride was heated at reflux for 16 h. On cooling the reaction mixture was concentrated in vacuo and the residue was extracted with ethyl ether three times. The combined ether solution was washed with NaHCO$_3$ and dried. After removed the solvent, pure product 5,7-dichloro-3-(3-(trifluoromethoxy)phenyl)pyrazolo[1,5-a]pyrimidine was obtained (0.8 g, 2.30 mmol, 72% yield).

To a microwave reactor charged with the 5,7-dichloro product (1.0 g, 2.87 mmoL) and a stirbar was added saturated aqueous NH$_3$ 5 mL. The microwave was sealed and heated to 80° C. for 4 h. After cooled down and extracted with ethyl acetate, the organic phase was dried and concentrated. Chromatography provided pure product 5-chloro-3-(3-(trifluoromethoxy)phenyl)pyrazolo[1,5-a]pyrimidin-7-amine (0.15 g, 0.456 mmol, 16% yield).

$^1$H-NMR (CD$_3$Cl/400 MHz): δ 8.32 (s, 1H), 7.95 (d, J=7.6 Hz, 1H), 7.83 (s, 1H), 7.43 (t, J=8.0 Hz, 1H), 7.07 (d, J=7.6 Hz, 1H), 6.16 (s, 1H), 5.78 (br, 2H). MS (ES$^+$, m/z): (M+H)$^+$: 329.5.

To a solution of 5-chloro-3-(3-(trifluoromethoxy)phenyl)pyrazolo[1,5-a]pyrimidin-7-amine (150 mg, 0.46 mmol) and 4-trans-(aminocyclohexyl)propan-2-ol (144 mg, 0.913 mmol) in NMP (2.0 mL) was added NaHCO$_3$ (43 mg, 0.55 mmol), the mixture was stirred at 180° C. for 60 mins under microwave irradiation. The mixture was purified by flash chromatograph to give 4-trans-((7-amino-3-(3-(trifluoromethoxy)phenyl)pyrazolo[1,5-a]pyrimidin-5-yl)amino)cyclohexyl)propan-2-ol (30 mg, 0.067 mmol, 15%) as a pale yellow solid.

$^1$H-NMR (CD$_3$OD/400 MHz): δ 8.40 (s, 1H), 8.20 (s, 1H), 7.78 (d, J=7.6 Hz, 1H), 7.35 (t, J=8.0 Hz, 1H), 6.94 (d, J=7.6 Hz, 1H), 5.38 (s, 1H), 3.84 (m, 1H), 3.41 (m, 1H), 2.20 (m, 2H), 1.95 (m, 2H), 1.26 (m, 4H), 1.16 (s, 6H). MS (ES$^+$, m/z): (M+H)$^+$: 450.6.

99. 4-(trans-Methoxycyclohexyl)-3-(3-(trifluoromethoxy)phenyl)-[1,2,4]triazolo[4,3-a]pyridin-6-amine (EX. 8-99)

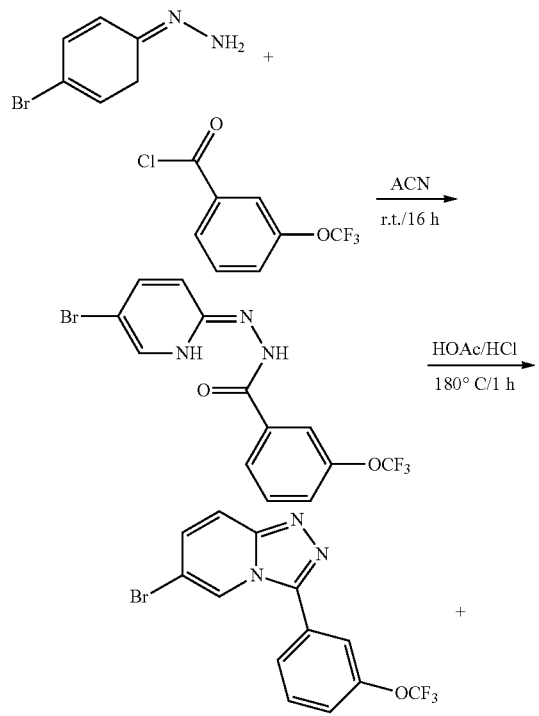

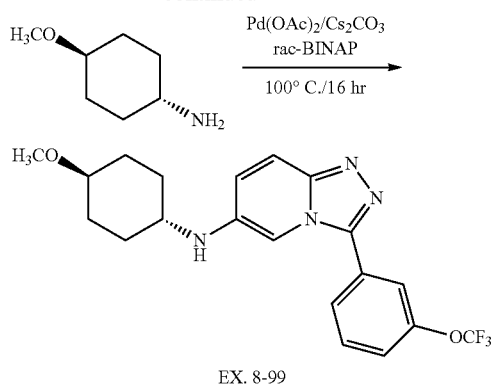

EX. 8-99

Synthesis of N'-(5-bromopyridin-2(1H)-ylidene)-3-(trifluoromethoxy)benzohydrazide To mixture of hydrazinepyridine (1.4 grams, 7.45 mmol) in ACN (15 mL) was added acid chloride (1.672 grams, 7.45 mmol), and the mixture was stirred at r.t. overnight. After stirring overnight, filtration got the pure white solid and dried for the next step directly (2.60 grams, 6.91 mmol, 93% yield).

Synthesis of 6-bromo-3-(3-(trifluoromethoxy)phenyl)-[1,2,4]triazolo[4,3-a]pyridine To a solution of N-(5-bromopyridin-2(1H)-ylidene)-3-(trifluoromethoxy)benzohydrazide (1.0 gram, 2.66 mmol) AcOH 10 mL and 0.5 mL 4M HCl in dioxane were added and the mixture was heated to 180° C. for 1 h. TLC indicated the reaction processed almost completely. After removed the solvent, the residue was dissolved in DCM and washed with saturated NaHCO$_3$. Dried with Na$_2$SO$_4$ and concentrated for chromatography purification (ethyl acetate/hexane, 0-40%). White solid (0.40 grams, 1.117 mmol, 42% yield) was obtained as pure product.

$^1$H-NMR (CD$_3$OD/400 MHz): δ 8.67 (m, 1H), 7.90 (d, J=7.6 Hz, 1H), 7.83 (s, 1H), 7.79 (m, 1H), 7.77 (m, 1H), 7.60 (d, J=8.8 Hz, 1H), 7.56 (d, J=9.6 Hz, 1H). MS (ES$^+$, m/z): (M+H)$^+$: 358.3.

A solution of triazolopyridine (0.15 g, 0.419 mmol) and 4-methoxycyclohexanaime (0.5 mL) in toluene 0.5 mL was added cesium carbonate (0.273 g, 0.838 mmol), rac-BINAP (78 mg, 0.127 mmol) and Pd (OAc)$_2$ (19 mg, 0.084 mmol) and the mixture was heated at 100° C. for 16 h under microwave irradiation. The resulting dark brown solution was cooled down and was concentrated under reduced pressure. The solid was further purified by using combiflash chromatography (12 g column), eluent: 0-10% methanol/DCM and obtained product 4-(Methoxycyclohexyl)-3-(3-(trifluoromethoxy)phenyl)-[1,2,4]triazolo[4,3-a]pyridin-6-amine (40 mg, 0.098 mmol, 24% yield).

$^1$H-NMR (CD$_3$OD/400 MHz): δ 7.85 (d, J=8.0 Hz, 1H), 7.78 (s, 1H), 7.74 (t, J=8.4 Hz, 1H), 7.57 (d, J=10.0 Hz, 1H), 7.50 (d, J=9.2 Hz, 1H), 7.35 (s, 1H), 7.16 (d, J=10.0 Hz, 1H), 3.24 (m, 1H), 3.12 (m, 1H), 2.10 (m, 4H), 1.31 (m, 4H). MS (ES$^+$, m/z): (M+H)$^+$: 407.5.

100. 1-Methyl-4-((3-(3-(trifluoromethoxy)phenyl)-[1,2,4]triazolo[4,3-a]pyridin-6-yl)amino)-trans-cyclohexanol (EX. 8-100)

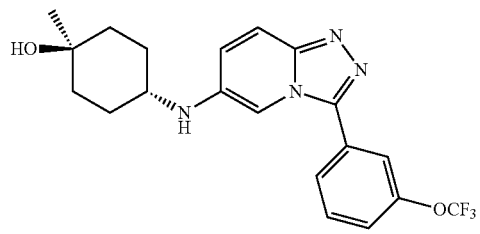

EX. 8-100

A solution of triazolopyridine (0.20 g, 0.558 mmol) and 4-amino-1-methylcyclohexanol (0.216 g, 1.675 mmol) in dioxane 0.5 mL was added cesium carbonate (0.546 g, 1.675 mmol), rac-BINAP (104 mg, 0.168 mmol) and Pd(OAc)$_2$ (25 mg, 0.112 mmol) and the mixture was heated at 100° C. for 16 h under microwave irradiation. The resulting dark brown solution was cooled down and was concentrated under reduced pressure. The solid was further purified by using combiflash chromatography (12 g column), eluent: 0-10% methanol/DCM and obtained product 1-Methyl-4-((3-(3-(trifluoromethoxy)phenyl)-[1,2,4]triazolo[4,3-a]pyridin-6-yl)amino)cyclohexanol (23 mg, 0.057 mmol, 10% yield).

$^1$H-NMR (CD$_3$OD/400 MHz): δ 7.85 (d, J=8.0 Hz, 1H), 7.76 (m, 2H), 7.74 (d, J=9.6 Hz, 1H), 7.50 (d, J=9.2 Hz, 1H), 7.35 (s, 1H), 7.21 (d, J=10.0 Hz, 1H), 3.23 (m, 1H), 1.98 (m, 2H), 1.70 (m, 2H), 1.49 (m, 4H), 1.24 (s, 6H). MS (ES$^+$, m/z): (M+H)$^+$: 407.5.

101. 4-((3-(3-(Trifluoromethoxy)phenyl)-[1,2,4]triazolo[4,3-a]pyridin-6-yl)amino)-trans-cyclohexyl)propan-2-ol (EX. 8-101)

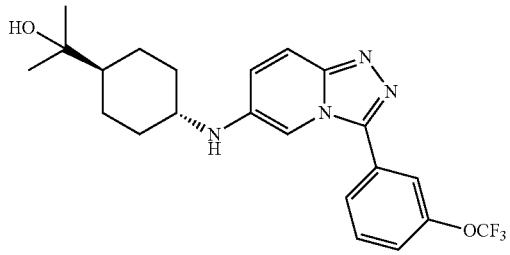

EX. 8-101

A solution of triazolopyridine (0.10 g, 0.279 mmol) and 4-amino-cyclohexylpropanol (0.220 g, 1.396 mmol) in dioxane 0.5 mL was added cesium carbonate (0.182 g, 0.558 mmol), rac-BINAP (52 mg, 0.084 mmol) and Pd(OAc)$_2$ (13 mg, 0.056 mmol) and the mixture was heated at 100° C. for 16 h under microwave irradiation. The resulting dark brown solution was cooled down and was concentrated under reduced pressure. The solid was further purified by using preparative HPLC and obtained product 4-((3-(3-(Trifluoromethoxy)phenyl)-[1,2,4]triazolo[4,3-a]pyridin-6-yl)amino)cyclohexyl)propan-2-ol.

$^1$H-NMR (CD$_3$OD/400 MHz): δ 7.83 (m, 1H), 7.72 (m, 2H), 7.70 (d, J=8.4 Hz, 1H), 7.48 (m, 1H), 7.32 (s, 1H), 7.19 (d, J=8.6 Hz, 1H), 3.26 (m, 1H), 2.25 (m, 2H), 1.93 (m, 2H), 1.29 (m, 4H), 1.17 (s, 6H). MS (ES$^+$, m/z): (M+H)$^+$: 435.6.

102. N-(Tetrahydro-2H-pyran-4-yl)-3-(3-(trifluoromethoxy)phenyl)-[1,2,4]triazolo[4,3-a]pyridin-6-amine (EX. 8-102)

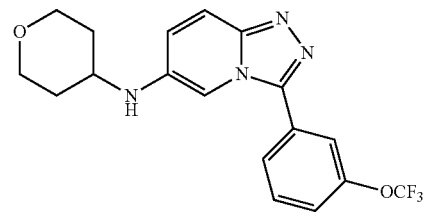

EX. 8-102

A solution of triazolopyridine (0.075 g, 0.209 mmol) and tetrahydro-2H-pyran-4-amine (0.5 mL) in toluene 0.5 mL was added cesium carbonate (0.136 g, 0.419 mmol), rac-BINAP (36 mg, 0.063 mmol) and Pd(OAc)$_2$ (9.4 mg, 0.042 mmol) and the mixture was heated at 100° C. for 16 h under microwave irradiation. The resulting dark brown solution was cooled down and was concentrated under reduced pressure. The solid was further purified by using combiflash chromatography (12 g column), eluent: 0-10% methanol/DCM and obtained product N-(tetrahydro-2H-pyran-4-yl)-3-(3-(trifluoromethoxy)phenyl)-[1,2,4]triazolo[4,3-a]pyridin-6-amine (30 mg, 0.079 mmol, 38% yield).

$^1$H-NMR (CD$_3$OD/400 MHz): δ 7.84 (d, J=8.0 Hz, 1H), 7.77 (s, 1H), 7.73 (t, J=8.0 Hz, 1H), 7.59 (d, J=10.0 Hz, 1H), 7.50 (m, 1H), 7.40 (s, 1H), 7.18 (d, J=9.6 Hz, 1H), 3.94 (m, 2H), 3.47 (m, 2H), 3.38 (m, 1H), 2.00 (m, 2H), 1.52 (m, 2H). MS (ES$^+$, m/z): (M+H)$^+$: 379.5.

103. 4-(((3-(3-(Trifluoromethoxy)phenyl)-[1,2,4]triazolo[4,3-a]pyridin-6-yl)amino)methyl)tetrahydro-2H-thiopyran 1,1-dioxide (EX. 8-103)

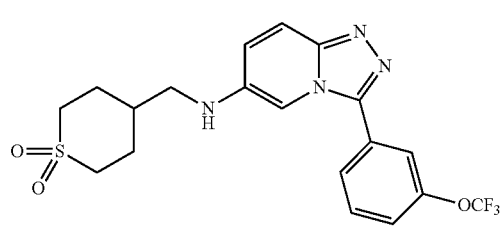

EX. 8-103

A solution of triazolopyridine (0.20 g, 0.558 mmol) and 4-(aminomethyl)tetrahydro-2H-thiopyran-1,1-dioxane (0.220 g, 1.396 mmol) in dioxane 0.5 mL was added cesium carbonate (0.546 g, 1.765 mmol), rac-BINAP (104 mg, 0.168 mmol) and Pd(OAc)$_2$ (25 mg, 0.112 mmol) and the mixture was heated at 100° C. for 16 h under microwave irradiation. The resulting dark brown solution was cooled down and was concentrated under reduced pressure. The solid was further purified by using preparative HPLC and obtained product 4-(((3-(3-(trifluoromethoxy)phenyl)-[1,2,4]triazolo[4,3-a]pyridin-6-yl)amino)methyl)tetrahydro-2H-thiopyran 1,1-dioxide.

104. 4-((3-(3-(Trifluoromethoxy)phenyl)-[1,2,4]triazolo[4,3-a]pyridin-6-yl)amino)-trans-cyclohexanol (EX. 8-104)

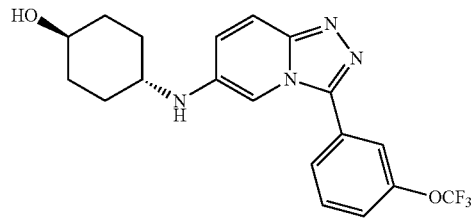

EX. 8-104

To a solution of 4-(methoxycyclohexyl)-3-(3-(trifluoromethoxy)phenyl)-[1,2,4]triazolo[4,3-a]pyridin-6-amine (0.030 gram, 0.074 mmol) in DCM 1.0 mL was added TMSI 0.2 mL. The mixture was stirred at rt. for overnight. TLC indicated pretty clean reaction. After removal the solvent completely, then the residue was quenched with NaHCO$_3$ saturated aqueous solution. Chromatography on silica gel got pure product (0.020 gram, 0.051 mmol, 69% yield).

$^1$H-NMR (CD$_3$OD/400 MHz): δ 7.95 (d, J=8.0 Hz, 1H), 7.87 (m, 3H), 7.73 (d, J=9.2 Hz, 1H), 7.65 (d, J=8.4 Hz, 1H), 7.50 (s, 1H), 3.60 (m, 1H), 3.21 (m, 1H), 2.10 (m, 2H), 1.98 (m, 2H), 1.37 (m, 4H). MS (ES$^+$, m/z): (M+H)$^+$: 393.5.

105. 4-(cis-Bromocyclohexyl)-3-(3-(trifluoromethoxy)phenyl)-[1,2,4]triazolo[4,3-a]pyridin-6-amine (EX. 8-105)

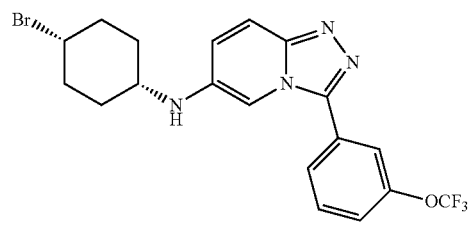

EX. 8-105

To a solution of 4-(trans-methoxycyclohexyl)-3-(3-(trifluoromethoxy)phenyl)-[1,2,4]triazolo[4,3-a]pyridin-6-amine (0.020 gram, 0.049 mmol) in DCM 1.0 mL was added TMSBr 0.25 mL with ice-water cooling. The mixture was stirred at rt. for overnight. TLC indicated pretty clean reaction. After removal the solvent completely, then the residue was quenched with NaHCO$_3$ saturated aqueous solution. Chromatography on silica gel got pure product (0.009 gram, 0.020 mmol, 40% yield).

$^1$H-NMR (CD$_3$OD/400 MHz): δ 7.84 (d, J=8.0 Hz, 1H), 7.77 (s, 1H), 7.73 (t, J=8.0 Hz, 1H), 7.58 (d, J=10.0 Hz, 1H), 7.50 (m, 1H), 7.36 (s, 1H), 7.21 (d, J=10.0 Hz, 1H), 4.55 (m, 1H), 3.22 (m, 1H), 2.12 (m, 2H), 1.99 (m, 2H), 1.86 (m, 4H). MS (ES$^+$, m/z): (M+H)$^+$: 455.4.

$^1$H-NMR (CD$_3$OD/400 MHz): δ 7.92 (d, J=8.0 Hz, 1H), 7.85 (s, 1H), 7.79 (m, 2H), 7.59 (m, 2H), 7.49 (s, 1H), 3.09 (m, 6H), 2.20 (m, 2H), 1.95 (m, 1H), 1.83 (m, 2H). MS (ES$^+$, m/z): (M+H)$^+$: 441.4.

106. 4-(trans-Methoxycyclohexyl)-3-(3-(trifluoromethyl)phenyl)-[1,2,4]triazolo[4,3-a]pyridin-6-amine (EX. 8-106)

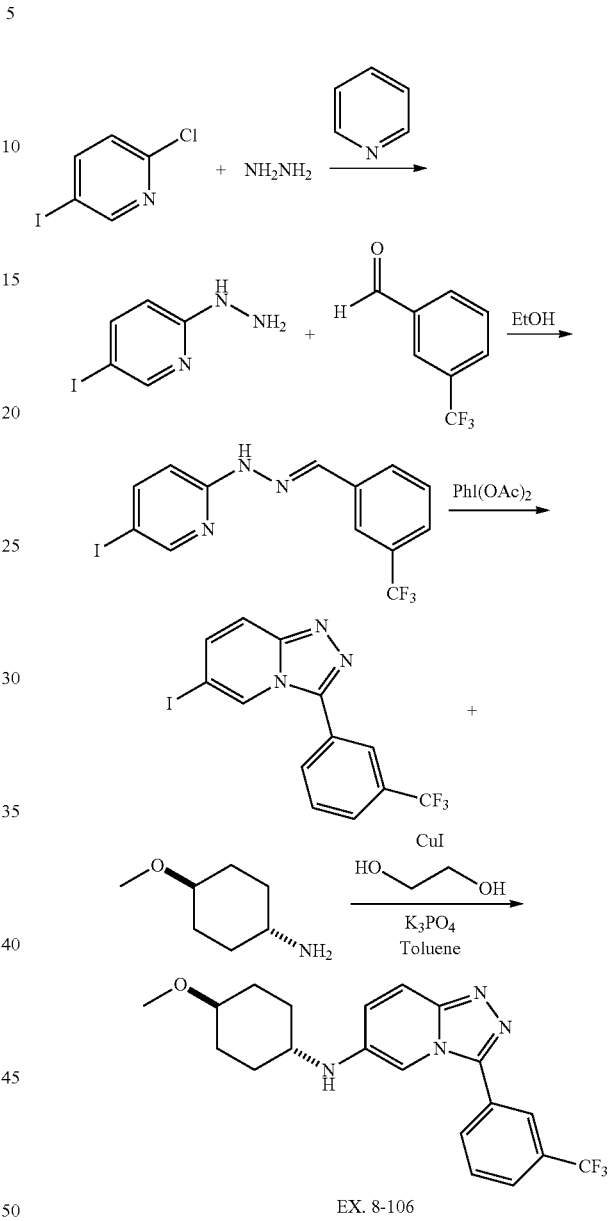

EX. 8-106

Synthesis of 2-hydrazinyl-5-iodopyridine

The solution of 2-chloro-5-iodopyridine (2.0 g, 20.9 mmol), anhydrous hydrazine (3.3 mL, 105 mmol) in pyridine (40 mL) was heated at reflux overnight. After cooling to room temperature, the reaction mixture was concentrated under reduced pressure. To the residue was added 1 N sodium hydroxide solution and it was extracted with EtOAc. The organic layer was separated, dried (sodium sulfate) and concentrated under reduced pressure. To the residue was added hexanes, and the precipitate was collected and dried in vacuo to afford the title compound (1.35 g, 69% yield) as off-white crystals. MS (ES+, m/z): 236.2 (M$^+$+1).

Synthesis of 5-iodo-2-(2-(3-(trifluoromethyl)benzylidene)hydrazinyl)pyridine To a suspension of 5-iodo-2-hydrazinopyridine (1.32 g, 5.62 mmol) in EtOH (90 mL) was added 3-(trifluoromethyl)-benzaldehyde (0.98 g, 5.62 mmol). The mixture was heated at reflux for 5 h under argon. After cooling to RT, the resulting precipitate was collected by filtration and washed with EtOH. The crude product was recrystallized from DCM and hexane to afford the title compound (1.80 g, 82% yield) as a white solid. MS (ES+, m/z): 392.3 (M$^+$+1).

Synthesis of 6-iodo-3-(3-(trifluoromethyl)phenyl)-[1,2,4]triazolo[4,3-a]pyridine To a solution of 5-iodo-2-(2-(3-(trifluoromethyl)benzylidene)hydrazinyl)pyridine (1.60 g, 4.09 mmol) in DCM (10 mL)/EtOH (1 mL), was added PhI(OAc)$_2$ (1.845 g, 5.73 mmol). The mixture was stirred at RT for 5 h, then the solvent was removed in vacuo. The residue was dissolved in DCM and purified on SiO$_2$ column chromatography with 80% 15% MeOH/EA in hexane to afford the title compound (1.21 g, 76% yield) as an off-white solid. MS (ES+, m/z): 390.3 (M$^+$+1).

Synthesis of N-(trans-4-methoxycyclohexyl)-3-(3-(trifluoromethyl)phenyl)-[1,2,4]triazolo[4,3-a]pyridin-6-amine To a suspension of 6-iodo-3-(3-(trifluoromethyl)phenyl)-[1,2,4]triazolo[4,3-a]pyridine (0.078 g, 0.2 mmol) and trans-4-methoxycyclohexanamine (0.078 g, 0.6 mmol) in toluene (0.5 mL) was added CuI (0.023 g, 0.12 mmol), ethane-1,2-diol (0.025 g, 0.4 mmol) and K$_3$PO$_4$ (0.085 g, 0.4 mmol). It was flushed with argon and heated at 90° C. overnight. The mixture was absorbed on SiO$_2$ and the major peak was washed out with 60%-100% 20% MeOH/DCM/0.2% NH$_3$ in hexane. Then the crude product was combined and purified again on C18 column chromatography using 20-40% ACN in water to give the title compounds.

$^1$H NMR (400 MHz, CD$_3$COCD$_3$/CDCl$_3$): 8.00 (m, 2H), 7.66 (m, 3H), 7.38 (m, 1H), 6.96 (m, 1H), 4.58 (br, 1H), 3.22 (s, 3H), 3.08 (m, 1H), 3.07 (m, 1H), 2.00 (m, 2H), 1.18 (m, 4H).

$^{19}$F NMR (376 MHz, CD$_3$COCD$_3$/CDCl$_3$): −57.9. MS (ES+, m/z): 391.5 (M$^+$+1).

107. 4-((3-(3-(Trifluoromethyl)phenyl)-[1,2,4]triazolo[4,3-a]pyridin-6-yl)amino)-trans-cyclohexanol (EX. 8-107)

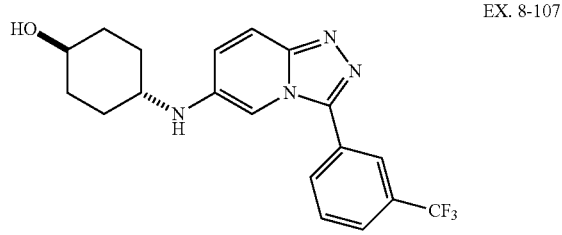 [SMILES: O[C@H]1CC[C@H](Nc2ccc3nnc(-c4cccc(C(F)(F)F)c4)n3c2)CC1]

EX. 8-107

$^1$H NMR (400 MHz, CD$_3$COCD$_3$): 8.23 (m, 2H), 7.87 (m, 2H), 7.59 (m, 1H), 7.58 (m, 1H), 7.12 (dd, J=10.0, 2.0 Hz, 1H), 5.09 (d, J=7.6 Hz, 1H), 3.57 (m, 1H), 3.30 (m, 1H), 2.16 (m, 4H), 1.30 (m, 4H). $^{19}$F NMR (376 MHz, CD$_3$COCD$_3$): −63.4. MS (ES+, m/z): 377.5 (M$^+$+1).

108. 1-Methyl-4-((3-(3-(trifluoromethyl)phenyl)-[1,2,4]triazolo[4,3-a]pyridin-6-yl)amino)-trans-cyclohexanol (EX. 8-108)

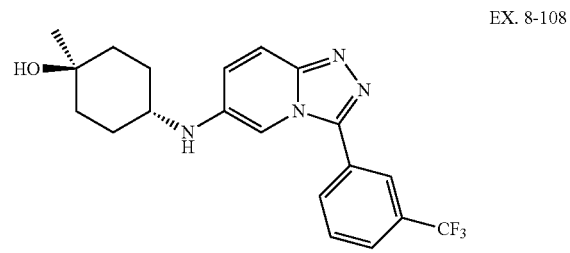 [SMILES: C[C@]1(O)CC[C@H](Nc2ccc3nnc(-c4cccc(C(F)(F)F)c4)n3c2)CC1]

EX. 8-108

To a suspension of 6-bromo-3-(3-(trifluoromethyl)phenyl)-[1,2,4]triazolo[4,3-a]pyridine (0.190 g, 0.56 mmol) and trans-4-amino-1-methylcyclohexanol (0.072 g, 0.56 mmol) in dioxane (1.5 mL) was added rac-Binap (0.104 g, 0.17 mmol), Pd(OAc)$_2$ (0.025 g, 0.11 mmol) and Cs$_2$CO$_3$ (0.362 g, 0.111 mmol). It was flushed with argon then heated at 100° C. overnight. It was absorbed on SiO$_2$ and purified on column chromatography on SiO$_2$ with 40-100% 15% MeOH/EA in hexane. This product was further purified on C18 column chromatography using 20-40% ACN in water.

$^1$H NMR (400 MHz, CD$_3$COCD$_3$): 8.23 (m, 2H), 7.88 (m, 2H), 7.94 (t, J=10.0 Hz, 1H), 7.57 (s, 1H), 7.18 (d, J=10.0 Hz, 1H), 3.39 (m, 1H), 2.07 (m, 2H), 1.70 (m, 2H), 1.55 (m, 4H), 1.21 (s, 3H). MS (ES+, m/z): 391.5 (M$^+$+1).

109. 4-((3-(3-(Trifluoromethyl)phenyl)-[1,2,4]triazolo[4,3-a]pyridin-6-yl)amino)-trans-cyclohexyl) propan-2-ol (EX. 8-109)

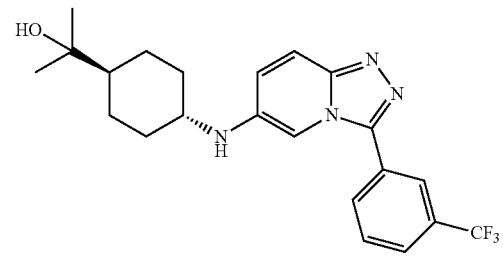

EX. 8-109

1H NMR (400 MHz, CD$_3$COCD$_3$): 8.28 (m, 2H), 7.99 (m, 2H), 7.94 (t, J=8.0 Hz, 1H), 7.73 (s, 1H), 7.53 (d, J=10.0 Hz, 1H), 3.23 (m, 1H), 2.21 (m, 2H), 1.93 (m, 2H), 1.31 (m, 2H), 1.25 (m, 2H), 1.17 (s, 6H). MS (ES+, m/z): 391.5 (M$^+$+1).

110. N-(Tetrahydro-2H-pyran-4-yl)-3-(3-(trifluoromethyl)phenyl)-[1,2,4]triazolo[4,3-a]pyridin-6-amine (EX. 8-110)

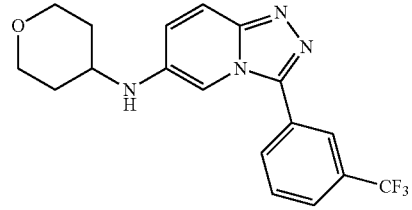

EX. 8-110

To a suspension of 6-iodo-3-(3-(trifluoromethyl)phenyl)-[1,2,4]triazolo[4,3-a]pyridine (0.101 g, 0.26 mmol) and tetrahydro-2H-pyran-4-amine (0.131 g, 1.30 mmol) in toluene (1 mL) was added rac-Binap (0.049 g, 0.078 mmol), Pd(OAc)$_2$ (0.012 g, 0.052 mmol) and Cs$_2$CO$_3$ (0.169 g, 0.52 mmol). It was flushed with argon then heated at 110° C. overnight. It was absorbed on SiO$_2$ and purified on column chromatography on SiO$_2$ with 60% 15% MeOH/EA in hexane. This product was further purified on C18 column chromatography using 20-40% ACN in water.

$^1$H NMR (400 MHz, CD$_3$COCD$_3$): 8.24 (m, 2H), 7.85 (m, 2H), 7.63 (m, 1H), 7.60 (d, J=10.0 Hz, 1H), 7.15 (d, J=10.0 Hz, 1H), 5.21 (br, 1H), 3.88 (m, 2H), 3.50 (m, 1H), 3.43 (m, 2H), 1.95 (m, 2H), 1.49 (m, 2H). $^{19}$F NMR (376 MHz, CD$_3$COCD$_3$): −63.4. MS (ES+, m/z): 363.5 (M$^+$+1).

111. 4-(((3-(3-(Trifluoromethyl)phenyl)-[1,2,4]triazolo[4,3-a]pyridin-6-yl)amino)methyl)tetrahydro-2H-thiopyran 1,1-dioxide (EX. 8-111)

EX. 8-111

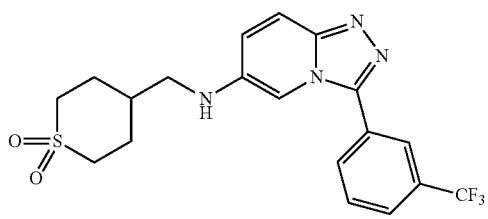

$^1$H NMR (400 MHz, CD$_3$COCD$_3$): 8.27 (m, 2H), 7.94 (m, 1H), 7.90 (m, 1H), 7.84 (d, J=9.6 Hz, 1H), 7.69 (s, 1H), 7.39 (d, J=9.6 Hz, 1H), 3.18 (d, J=6.8 Hz, 2H), 3.09 (m, 2H), 3.01 (m, 2H), 2.25 (m, 2H), 2.15 (m, 1H), 1.85 (m, 2H). MS (ES+, m/z): 425.5 (M$^+$+1).

112. 2-((3-(3-(trifluoromethyl)phenyl)-[1,2,4]triazolo[4,3-a]pyridin-6-yl)oxy)ethanol (EX 8-112)

EX. 8-112

$^1$H NMR (400 MHz, CD$_3$COCD$_3$): 8.20 (m, 2H), 8.00 (m, 1H), 7.83 (m, 2H), 7.74 (m, 1H), 7.25 (m, 1H), 4.15 (m, 2H), 3.97 (m, 2H). $^{19}$F NMR (376 MHz, CD$_3$COCD$_3$): −63.1. MS (ES+, m/z): 324.4 (M$^+$+1).

113. 4-(trans-Methoxycyclohexyl)-3-(3-chlorophenyl)-[1,2,4]triazolo[4,3-a]pyridin-6-amine (EX. 8-113)

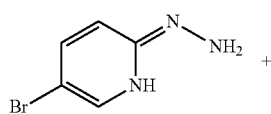

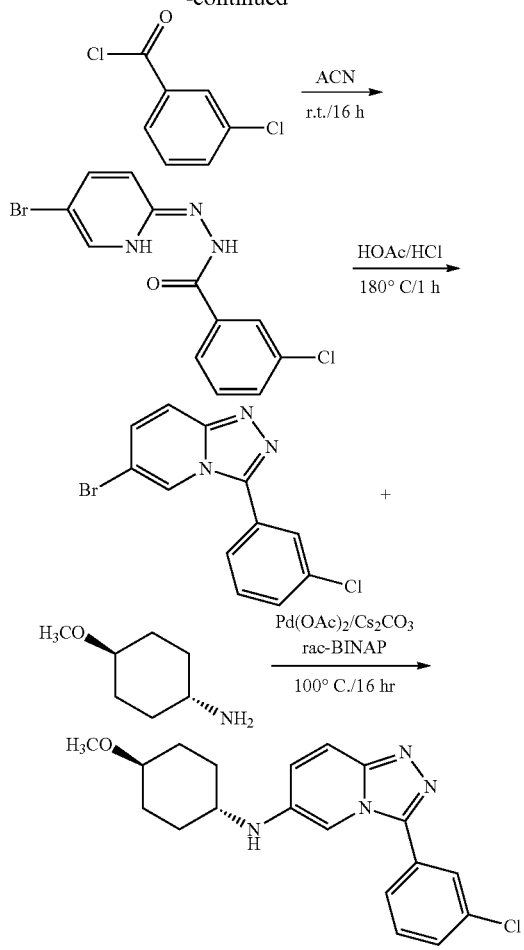

EX. 8-113

Synthesis of N'-(5-bromopyridin-2(1H)-ylidene)-3-chlorobenzohydrazide

To mixture of hydrazinepyridine (2.0 grams, 10.64 mmol) in ACN (15 mL) was added acid chloride (1.86 grams, 10.64 mmol), and the mixture was stirred at r.t. overnight. After stirring overnight, filtration got the pure white solid and dried for the next step directly (3.0 grams, 9.19 mmol, 86% yield). MS (ES$^+$, m/z): (M+H)$^+$: 326.3.

Synthesis of 6-bromo-3-(3-chlorophenyl)-[1,2,4]triazolo[4,3-a]pyridine

To a solution of N-(5-bromopyridin-2(1H)-ylidene)-3-chlorobenzohydrazide (3.0 grams, 9.19 mmol) AcOH 10 mL and 0.5 mL 4M HCl in dioxane were added and the mixture was heated to 180° C. for 1 h. TLC indicated the reaction processed almost completely. After removed the solvent, the residue was dissolved in DCM and washed with saturated NaHCO$_3$. Dried with Na$_2$SO$_4$ and concentrated for chromatography purification (ethyl acetate/hexane, 0-40%). White solid (0.30 grams, 0.972 mmol, 11% yield) was obtained as pure product.

$^1$H-NMR (CD$_3$OD/400 MHz): δ 8.65 (m, 1H), 7.85 (d, J=8.0 Hz, 1H), 7.80 (s, 1H), 7.77 (m, 1H), 7.75 (m, 1H), 7.58 (d, J=8.6 Hz, 1H), 7.56 (d, J=9.2 Hz, 1H). MS (ES$^+$, m/z): (M+H)$^+$: 308.3.

A solution of triazolopyridine (0.13 g, 0.419 mmol) and 4-methoxycyclohexanaime (0.5 mL) in toluene 0.5 mL was added cesium carbonate (0.273 g, 0.838 mmol), rac-BINAP (78 mg, 0.127 mmol) and Pd (OAc)$_2$ (19 mg, 0.084 mmol) and the mixture was heated at 100° C. for 16 h under microwave irradiation. The resulting dark brown solution was cooled down and was concentrated under reduced pressure. The solid was further purified by using combiflash chromatography (12 g column), eluent: 0-10% methanol/DCM and obtained product 4-(Methoxycyclohexyl)-3-(3-(trifluoromethoxy)phenyl)-[1,2,4]triazolo[4,3-a]pyridin-6-amine (50 mg, 0.140 mmol, 33% yield).

$^1$H-NMR (CD$_3$OD/400 MHz): δ 7.83 (s, 1H), 7.75 (d, J=6.8 Hz, 1H), 7.57 (m, 3H), 7.35 (s, 1H), 7.14 (d, J=10.0 Hz, 1H), 3.20 (m, 1H), 3.12 (m, 1H), 2.07 (m, 4H), 1.29 (m, 4H). MS (ES$^+$, m/z): (M+H)$^+$: 357.5.

Example 2

Pim Kinase Activity Assays

1. Pim-1 Kinase Inhibition Assay

One illustrative manner in which Pim-1 kinase activity can be determined is by quantifying the amount of ATP remaining in solution after an in vitro Pim-1 kinase reaction. The Kinase-Glo Assay Kit (Promega, Inc., Madison, Wis.) allows this. The amount of ATP remaining in the solution after the kinase reaction serves as a substrate for the luciferase to catalyze luciferin to oxyluciferin plus one photon of light. Thus, the luminescent signal read by the Luminoskan Ascent Instrument (Thermo Electron Corp., Milford, Mass.) correlates with the amount of ATP present after the kinase reaction and inversely correlates with the amount of kinase activity. This assay is efficient at determining the IC$_{50}$ values of kinase inhibitors against the Pim-1 kinase. These assays are set up in duplicate 50 ul volumes in white, flat bottom 96 well plates. Inhibitors are added to the solution of 1× kinase buffer, 10 uM ATP, 100 uM Pim-1-specific substrate, 50 ng of active Pim-1 enzyme, and water in serial dilutions ranging from micromolar to nanomolar concentrations. This solution is incubated at 30 degrees Celsius at 360 rpm for two hours. Following the incubation, 50 ul of Kinase-Glo reagent is added to each well, including all positive and negative control wells, and incubated at room temperature for 15 minutes. The plate is then read by the Luminoskan Ascent instrument and the results displayed with the Ascent Software version 2.6. The IC$_{50}$ values can then be calculated for each inhibitor tested.

Alternatively, Pim-1 kinase activity can be determined by quantifying the phosphorylation of a known Pim-1 substrate in another in vitro assay. The Z-Lyte Protein Kinase Assay Kit (Invitrogen, Madison Wis.) allows this, using Fluorescent Resonance Energy Transfer (FRET) procedure. Briefly, a known Pim-1 substrate (Serine-Threonine Substrate from Invitrogen), which bears two fluorophores at opposing ends (coumarin and fluorescein) is incubated with Pim-1 enzyme and a potential inhibitor. Following this, the kinase reaction is stopped, and a development reagent is added. This reagent, a protease, will cleave only unphosphorylated substrate, separating the two fluorophores and reducing the amount of FRET which can occur between them. FRET can then be measured using a spectrophotometer, such as the Gemini EM (Molecular Devices). A reduction in FRET is indicative of an active inhibitor.

Alternatively, PIM kinase IC$_{50}$ and K$_i$ determinations were determined at Reaction Biology (Malvern, Pa.). For K$_i$ determination, PIM-1 were incubated with 10-dose, 3-fold serial dilutions of compound starting with 10 μM using 5 different concentrations of ATP (25, 50, 100, 250 and 500 μM ATP for PIM-1; 5, 10, 20, 50 and 100 μM ATP for PIM-2 and PIM-3), and the activity was measured at 0, 5, 10, 15, 20, 30, 45, 60, 75, 90, 105 and 120 minutes. The data was analyzed in a Michaelis-Menton plot to determine apparent K$_m$ and K$_i$ values using GraFit software using a mixed inhibition equation for global fit.

2. Cell-Based Pim-1 Kinase Inhibitor Assays:

Cell culture-based assays can be used to evaluate the ability of compounds of the invention to inhibit one or more cellular activities, such as cancer cell growth and/or survival. Numerous cancer cell lines can be obtained from the American Type Culture Collection (ATCC) and other sources. Briefly, cells are seeded into 96-well, tissue-culture treated, opaque white plates (Thermo Electron, Vantaa, Finland), at between 5000 and 10000 cells per well, depending on the speed of cell proliferation, in 100 μl of appropriate growth medium (determined by the ATCC). Cells are then exposed to the appropriate concentration of drug or an equal amount of DMSO (drug diluent) and allowed to grow in its presence for 96 hours. Following this, 100 μl of Cell-Titer-Glo reagent (Promega, Inc., Madison, Wis.) is added to each well. Plates are then shaken for 2 minutes at room temperature to allow for cell lysis and incubated for 10 minutes at room temperature to stabilize the luminescent signal. Similar to the Kinase-Glo assay reagent from Promega, this reagent contains both luciferase enzyme and its substrate luciferin. Luciferase, activated by ATP in the cell lysate, catalyzes the conversion of luciferin to oxyluciferin, a reaction which produces light. The amount of light produced is proportionate to the amount of ATP in the cell lysate, which is itself proportional to cell number and gives an index of cellular proliferation.

In order to detect specific inhibition of Pim-1 enzyme in cell culture, a Western blot assay will also be performed. For this, cells which have been treated with a potential Pim-1 inhibitor are lysed with a buffer specific for the isolation and preservation of proteins (1% Nonidet P-40, 150 mM NaCl, 50 mM Tris pH 8.0, 5 mM EDTA, 1:500 Protease Inhibitor Cocktail III [Calbiochem], 100 mM NaF, 100 mM Sodium Orthovanadate). The protein concentration in these lysates is then quantified using the BCA Protein Assay Kit (Pierce). Known amounts of protein, e.g. 10 μg, are loaded onto 12% SDS-polyacrylamide gels and are subjected to reducing, denaturing SDS-PAGE. Electrophoresed proteins are transferred to a nitrocellulose membrane, which is then probed with antibodies to p-21 and phospho (Thr 145) p-21. As Threonine-145 of the p-21 protein is a substrate for Pim-1, measuring the amount of phosphorylation at this site in treated cells should provide a means by which to evaluate the efficacy of our Pim-1 inhibitors.

3. Pim-1 Kinase Specific Activity Data:

Using procedures essentially as described above, illustrative compounds were tested for inhibition of Pim-1 kinase activity. IC$_{50}$ values were determined for illustrative compounds against Pim-1 kinase, using the Promega Kinase-Glo assay, the results for which are summarized in Tables IV and V below.

TABLE IV

Compound IC$_{50}$ on Pim1.

| EX. | IC$_{50}$ (nM) | EX. | IC$_{50}$ (nM) |
|---|---|---|---|
| 8-1 | 13 | 8-2 | 18 |
| 8-3 | 30 | 8-4 | 7 |
| 8-5 | 36 | 8-6 | 30 |

TABLE IV-continued

Compound IC$_{50}$ on Pim1.

| EX. | IC$_{50}$ (nM) | EX. | IC$_{50}$ (nM) |
|---|---|---|---|
| 8-7 | 10 | 8-8 | 4 |
| 8-9 | 13 | 8-10 | 9 |
| 8-11 | 8 | 8-12 | 81 |
| 8-13 | 58 | 8-14 | 1190 |
| 8-15 | 2830 | 8-16 | 503 |
| 8-17 | 173 | 8-18 | 53 |
| 8-19 | 13 | 8-20 | 16 |
| 8-21 | 46 | 8-22 | 41 |
| 8-23 | 1630 | 8-24 | 34 |
| 8-25 | 30 | 8-26 | 28 |
| 8-27 | 23 | 8-28 | 553 |
| 8-29 | 5 | 8-30 | 103 |
| 8-31 | 1 | 8-32 | 115 |
| 8-33 | 33 | 8-34 | 241 |
| 8-35 | 7 | 8-36 | 145 |
| 8-37 | 4 | 8-38 | 18 |
| 8-39 | 48 | 8-40 | 200 |
| 8-41 | 226 | 8-42 | 1970 |
| 8-43 | 523 | 8-44 | 153 |
| 8-45 | 16 | 8-46 | 27 |
| 8-47 | 204 | 8-48 | 197 |
| 8-49 | 378 | 8-50 | 633 |
| 8-51 | 148 | 8-52 | 5 |
| 8-53 | 132 | 8-54 | 25 |
| 8-55 | 54 | 8-56 | 17 |
| 8-57 | 66 | 8-58 | 149 |
| 8-59 | 111 | 8-60 | NA |
| 8-61 | 237 | 8-62 | 378 |
| 8-63 | 23 | 8-64 | 68 |
| 8-65 | 186 | 8-66 | 164 |
| 8-67 | 45 | 8-68 | 4 |
| 8-69 | 24 | 8-70 | 8 |
| 8-71 | 12 | 8-72 | 58 |
| 8-73 | 17 | 8-75 | 56 |
| 8-76 | 687 | 8-77 | 14 |
| 8-78 | 206 | 8-79 | 2 |
| 8-80 | 52 | 8-82 | 34 |
| 8-83 | 89 | 8-84 | 239 |
| 8-85 | 19 | 8-86 | 14 |
| 8-88 | 69 | 8-92 | 38 |
| 8-95 | 24 | 8-96 | 94 |
| 8-97 | 168 | 8-98 | 470 |

TABLE V

Compound IC$_{50}$ on Pim1.

| EX. | IC$_{50}$(nM) | EX. | IC$_{50}$(nM) |
|---|---|---|---|
| 8-99 | 83 | 8-100 | 1644 |
| 8-101 | 488 | 8-102 | 3250 |
| 8-103 | 3805 | 8-104 | 684 |
| 8-105 | 2490 | 8-106 | 518 |
| 8-107 | 3948 | 8-108 | 70 |
| 8-109 | 3870 | 8-110 | 3165 |
| 8-111 | >30 μM | 8-112 | >30 μM |
| 8-113 | 722 | | |

Example 3 hERG Activity Assays

Representative compounds were tested for hERG activity using the Fast Patch assay available from WuXiApptec (Shanghai China). The hERG activity for representative compounds is provided in Table VI below.

TABLE VI hERG Activity of Representative Compounds

| Compound | hERG IC50 (μM) |
|---|---|
| 8-37 | >30 |
| 8-35 | 30 |
| 8-64 | >30 |
| 8-39 | >30 |
| 8-31 | >30 |
| 8-30 | 12 |
| 8-29 | 10 |
| 8-10 | >30 |
| 8-9 | 26 |
| 8-11 | >30 |
| 8-63 | >30 |
| 8-54 | >30 |
| 8-56 | >30 |
| 8-46 | >30 |
| 8-1 | 16 |
| 8-13 | 10 |

Example 4

Cell Based Assays

The cellular potency of a representative compound (8-31) was determined by measuring its effect on baseline phosphorylation of BAD (BCL-2 antagonist of cell death), a known substrate of PIM, on serine 112 by over-expression of PIM-1 and BAD in HEK-293 cells. Over-expression of the catalytically inactive mutant PIM-1 (K67M) did not increase phosphorylation of BAD compared to BAD transfection alone (data not shown), and was used as a negative control to subtract BAD phosphorylation by cellular kinases other than PIM-1.

Compound 8-31 demonstrated potent PIM-1 specific cellular activity in the PIM-1/BAD over-expression system with an average EC$_{50}$=67 nM (FIG. 1).

Example 5

Tumor Xenografts

Figures 2A, 2B:
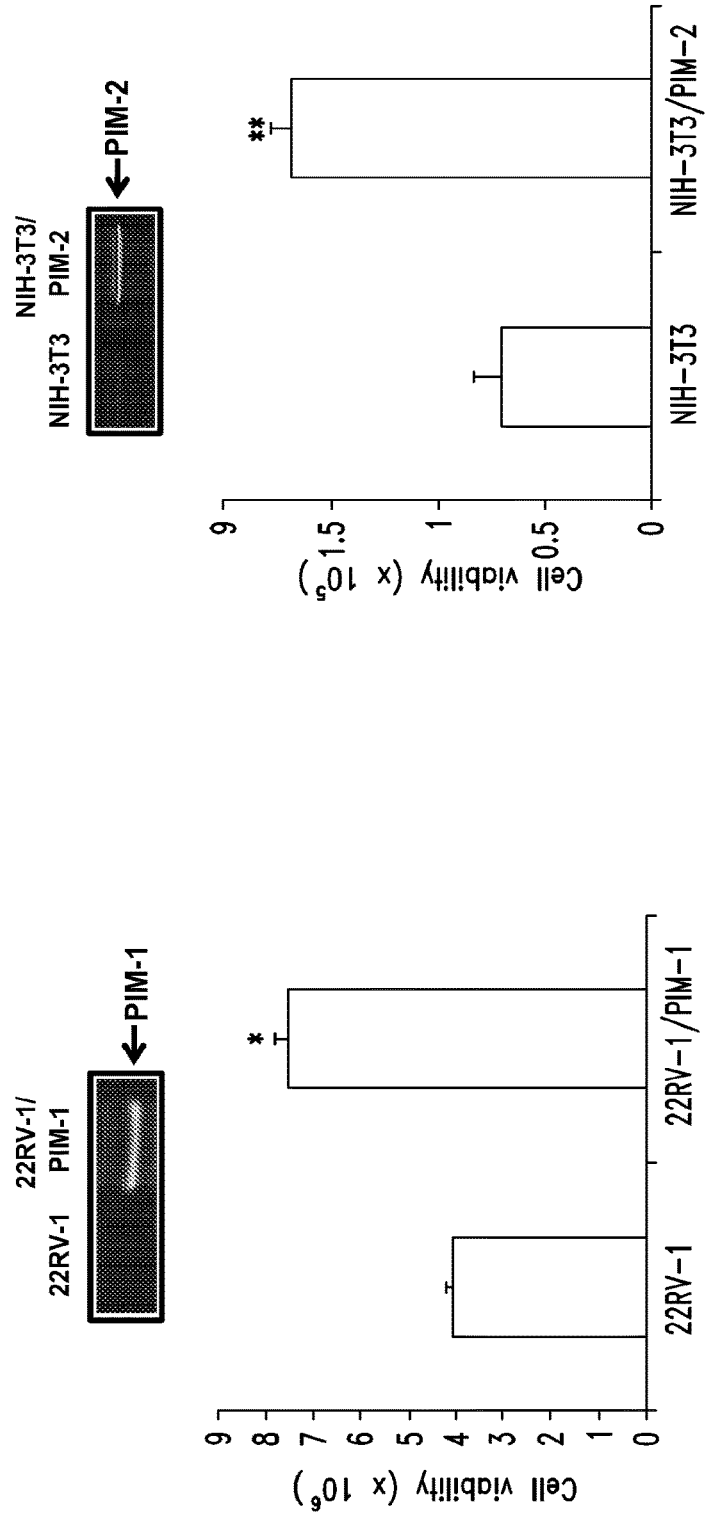
FIGS. 2A and 2B illustrates cell growth rate in cell culture.
Figure 3A:
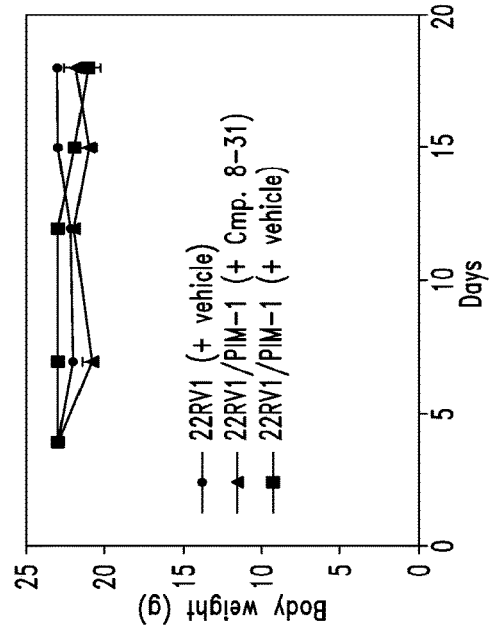
FIGS. 3A and 3B present tumor regression and body weight data.
Figure 3A:
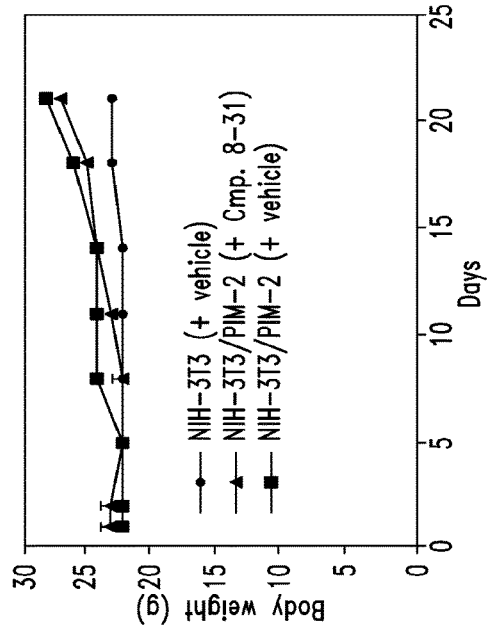
Figure 3B:
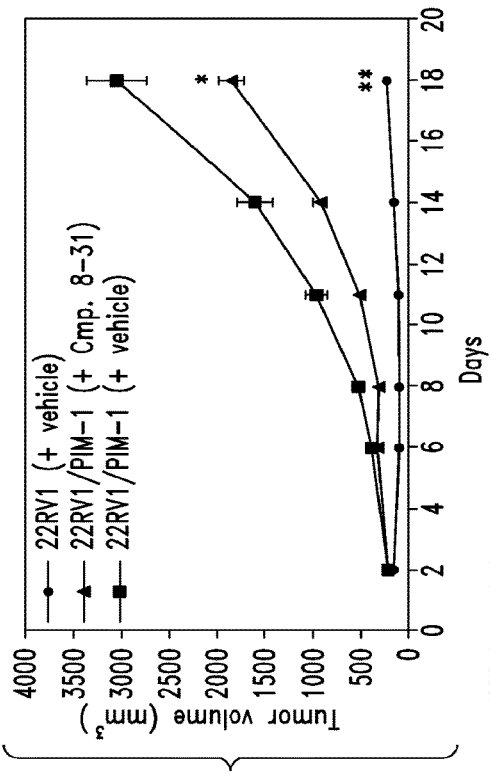
Figure 3B:
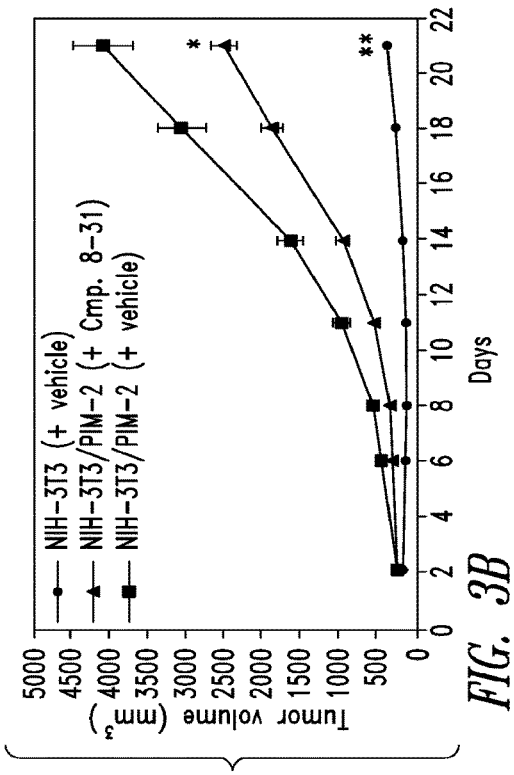

In an effort to demonstrate tumorigenicity of the PIM kinases and to evaluate representative compounds (e.g., EX. 8-31) in PIM-driven tumor xenografts, PIM-1 and PIM-2 over-expression cell lines were developed. The prostate cancer cell line 22RV1 engineered to over-express PIM-1 as previously described (Mumenthaler, et al, Mol. Cancer Ther., 2009, 8(10)2882-93) was evaluated in vivo. A second model engineered to over-express PIM-2 was established using the NIH-3T3 mouse fibroblast cell line. Both cell backgrounds displayed increased expression of PIM-1 or PIM-2 kinase by Western blot, and significantly enhanced the observed growth rate in cell culture (FIG. 2). PIM-1 overexpression in 22RV1 cells significantly enhanced subcutaneous tumor growth compared to the parental cell line when grown as mouse xenografts (22RV1/PIM-1+vehicle vs. 22RV1+vehicle), and the growth was significantly reduced by administration of compound 8-31 (22RV1/PIM-1+vehicle vs. 22RV1/PIM-1+compound 8-31) (FIG. 3A). PIM-1 over-expression demonstrated a similar effect on xenograft growth in the presence or absence of vehicle treatment (data not shown). No significant changes in body weight were observed in mice from any group. Similarly, PIM-2 over-expression in NIH-3T3 cells significantly induced subcutaneous tumor growth compared to the parental cell line when grown as mouse xenografts (NIH-3T3/PIM-2+vehicle vs. NIH-3T3+vehicle), and the growth was significantly inhibited by compound 8-31 (NIH-3T3/PIM-2+vehicle vs. NIH-3T3/PIM-2+compound 8-31) (FIG. 3B). Likewise, PIM-2 over-expression demonstrated a similar effect on xenograft growth with or without vehicle administration (data not shown). No significant changes in body weight were observed in any group.

Example 6

Translational Models

Figure 4A:
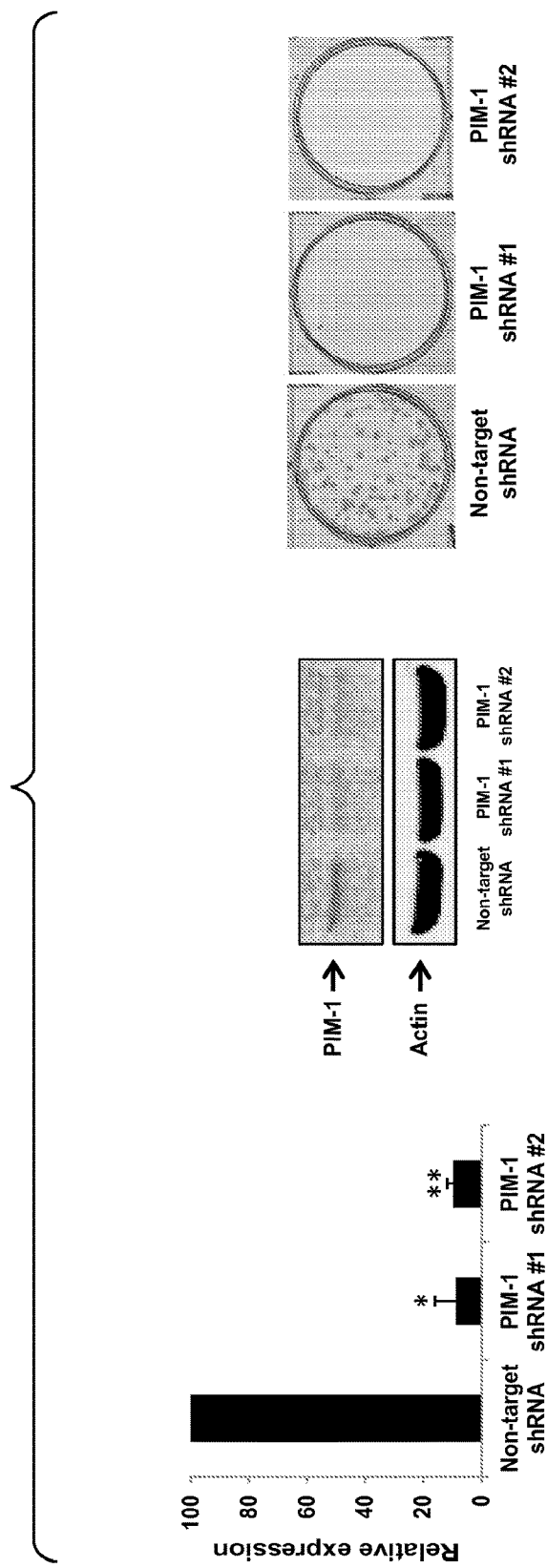
FIGS. 4A, 4B and 4C show colony growth data.
Figures 4B, 4C:
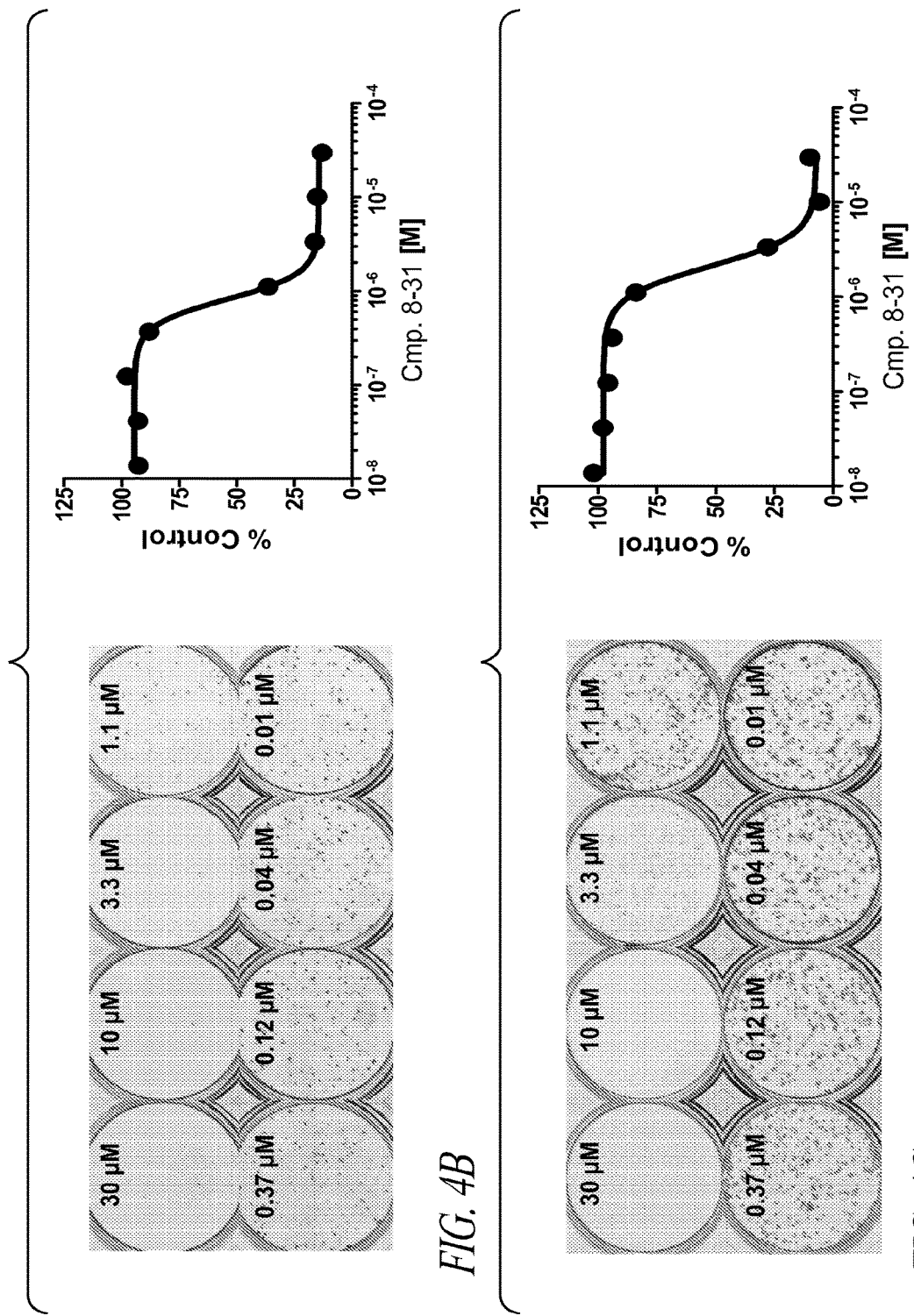

Translational models were also explored for PIM dependency using shRNA knockdown. The UM-UC-3 urinary epithelial bladder carcinoma cell line was used to verify and validate dependency on PIM-1 for growth. PIM-1 mRNA was significantly reduced using two independent shRNAs targeting PIM-1 compared to the non-target shRNA control (FIG. 4A). Further, PIM-1 protein was reduced using PIM-1 shRNA compared to non-target shRNA, and 2D-colony growth was markedly reduced with PIM-1 knockdown (FIG. 4A), comparable to a previous report in the literature (Guo, S (2010) J Exp Clin Cancer Res 29:161). Reduction of PIM-1 mRNA and growth also were observed using both PIM-1 and PIM-2 shRNA in the androgen-independent prostate carcinoma cell line PC-3 (data not shown). Finally, compound 8-31 reduced colony growth of UM-UC-3 and PC-3 cells (FIGS. 4B and 4C), confirming the PIM-1 dependent growth for both cell lines.

Example 7

Growth Inhibition of Mouse Xenograft Tumors

Figure 5A:
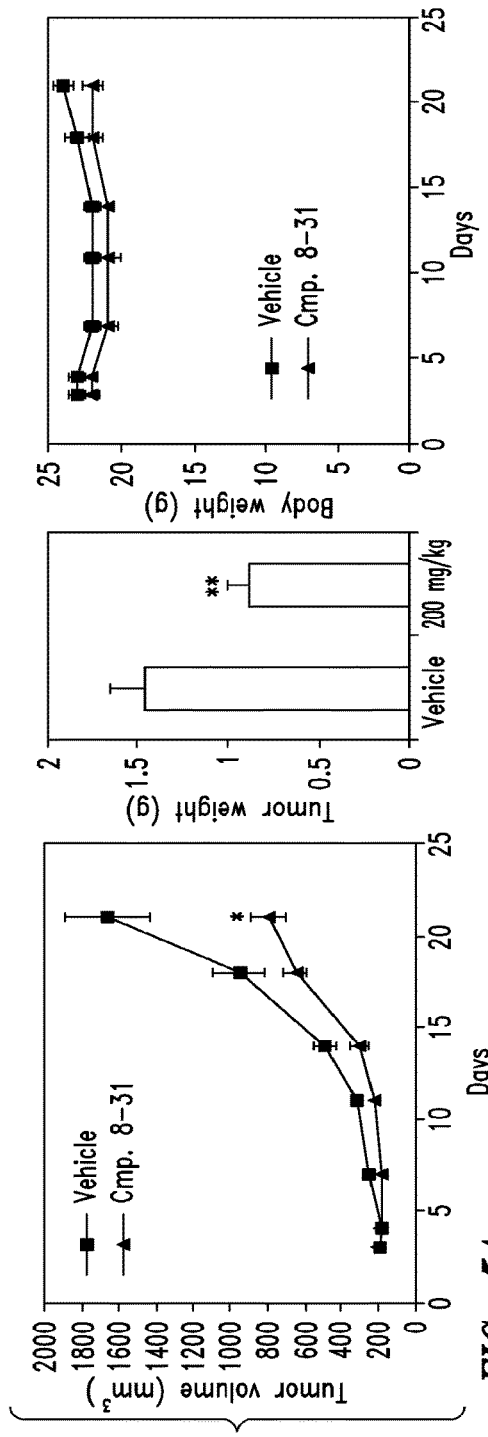
FIGS. 5A and 5B are graphs showing tumor regression and body weight data.
Figure 5B:
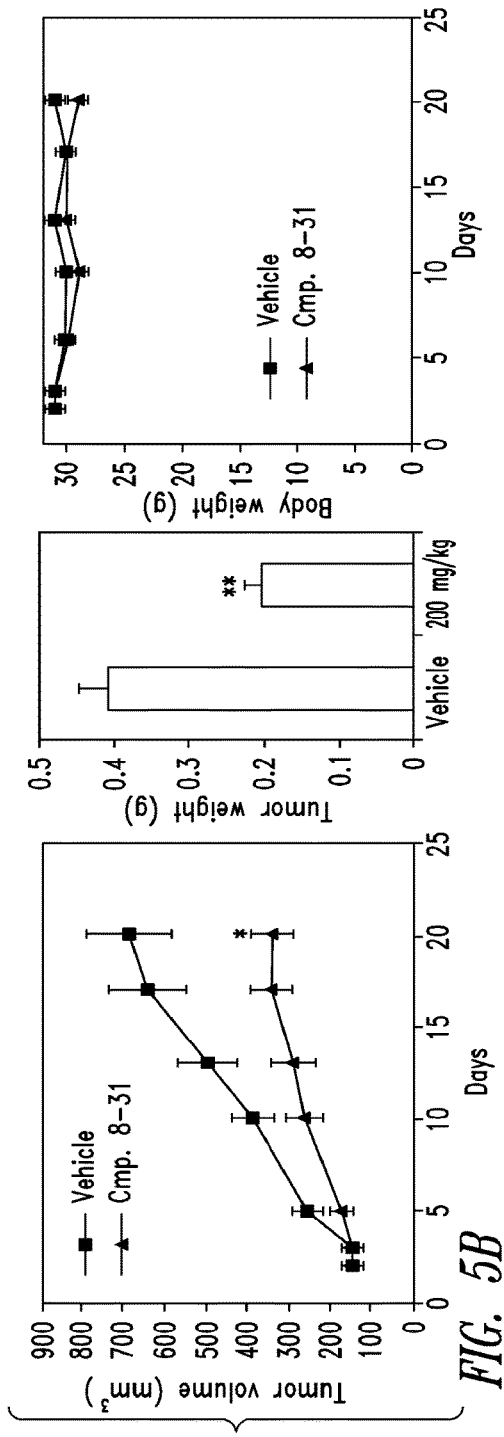

Compound 8-31 was tested for inhibiting the growth of established mouse xenograft tumors using the UM-UC-3 and PC-3 solid tumor cell lines that were tested in vitro. Oral dosing of 200 mg/kg of compound 8-31 significantly reduced both UM-UC-3 and PC-3 tumor growth measured by volume (caliper) and by final tumor weight, with no significant changes in body weight or gross adverse toxicity (FIG. 5). In addition, dosing of compound 8-31 at 125 mg/kg in each model led to significant tumor growth inhibition, albeit less than that observed with 200 mg/kg, indicating a dose-response effect and a therapeutic window (data not shown). Pharmacokinetic studies of the PC-3 tumor-burdened mice revealed that 200 mg/kg compound 8-31 dosing led to plasma and tumor tissue levels above the in vitro proliferation $EC_{50}$ (data not shown).

Example 8

Hematological Cancer Cell Screening

Figure 6:
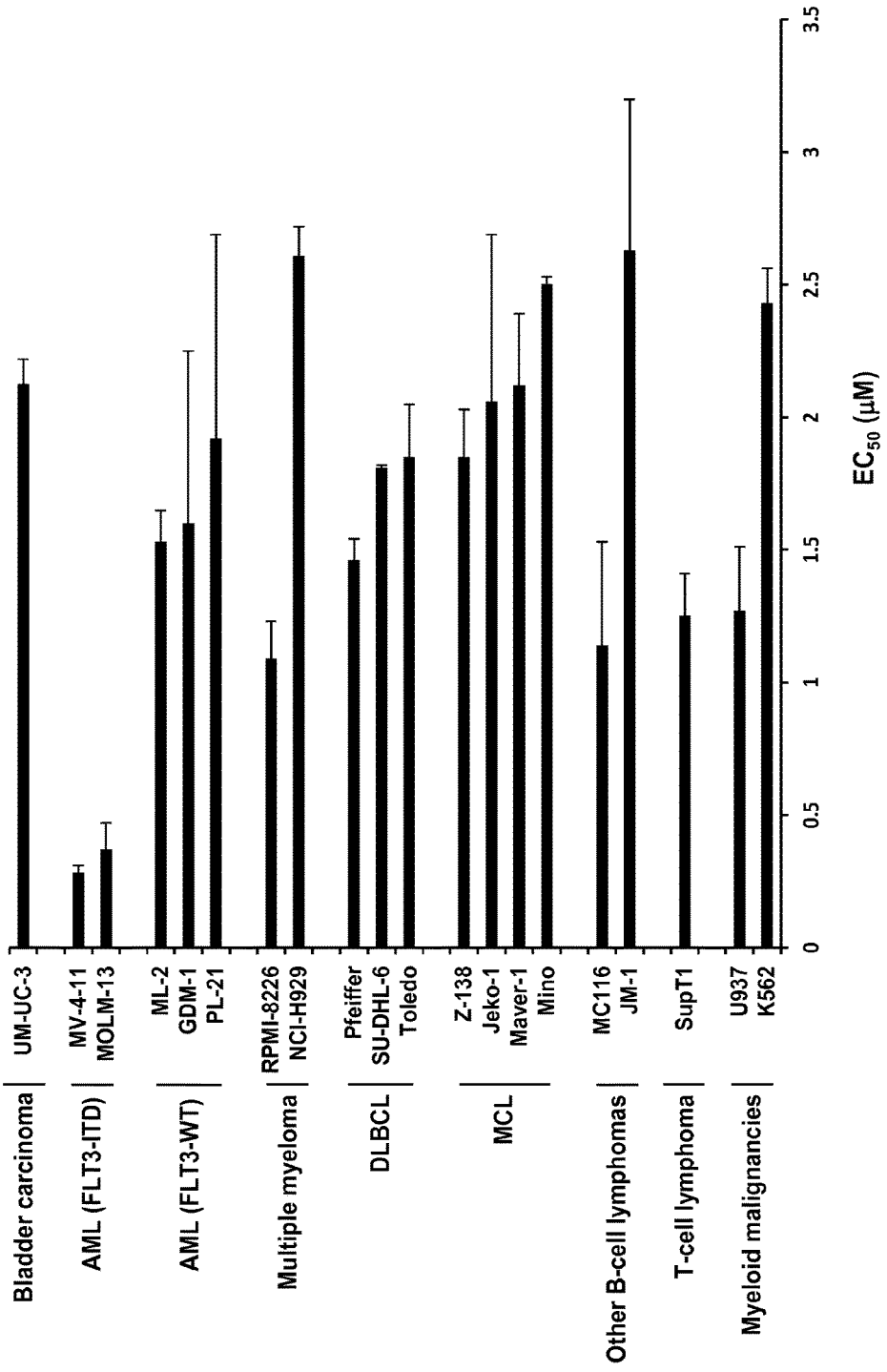
FIG. 6 presents data from hematological cancer screening.

PIM kinases are implicated in the survival of hematological cancers, therefore compound 8-31 was screened against a panel of hematological cell lines using an in vitro viability assay. Over 35 cell lines were tested, and the most sensitive cell lines from various indications were selected and verified by multiple $EC_{50}$ determinations (FIG. 6). Compound 8-31 displayed nearly equivalent $EC_{50}$ values for the most sensitive hematological cell lines compared to the bladder line, UM-UC-3, in the range of 1-2 µM. Anti-proliferative activity using PIM-2 shRNA against FLT3-ITD driven leukemia lines has been observed (Adam (2006) Cancer Res 66:3828-35 data not shown). Notably, MV-4-11 and MOLM-13 were particularly sensitive to SGI-9481, while not wishing to be bound by theory, it is believed that this is potentially due to the combination of PIM kinase and FLT3 inhibition, although the activity could be possibly attributed to the FLT3 activity of the compound alone. While not wishing to be bound by theory, the inhibitory activity of compound 8-31 (and other compounds of the invention) against multiple members of the phosphatidyl inositol-3-kinase (PI3K) family observed in the selectivity study may impart additional advantage when targeting different tumor types Example 9

Mouse Xenograft Studies

Compound 8-31 demonstrated significant tumor growth inhibition in mouse xenograft studies with ML-2 cells (wild-type FLT3) (FIG. 7A), similar to the level of reduction observed in the solid tumor models. Treatment of established xenografts of MV-4-11 (FLT3-ITD) with compound 8-31 also induced regressions (FIG. 7B). While not wishing to be bound by theory, these data indicate that AML models are sensitive to compound 8-31, where FLT3-ITD status enhanced the antitumor effects observed.

We claim:

1. A method for modulating a proviral insertion in murine kinase in a subject in need thereof, the method comprising administering to the subject a therapeutically effective amount of a compound having one of the following structures:

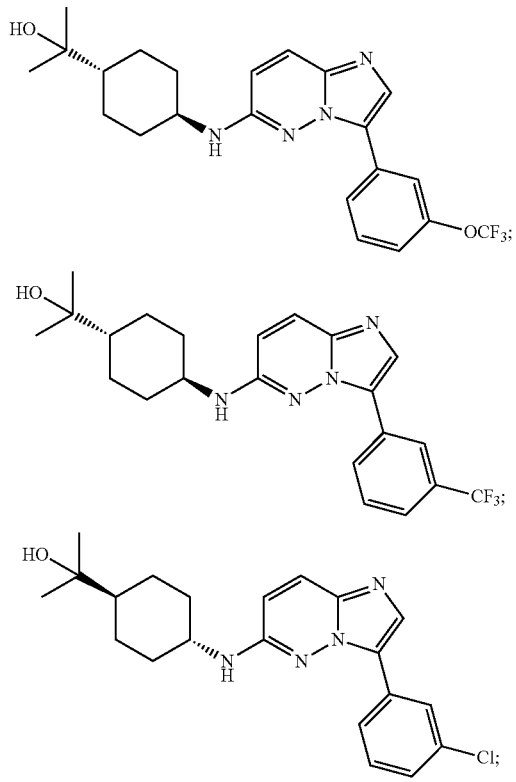

-continued

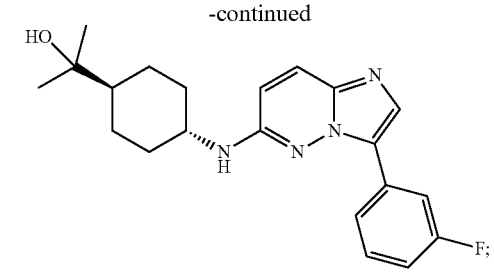

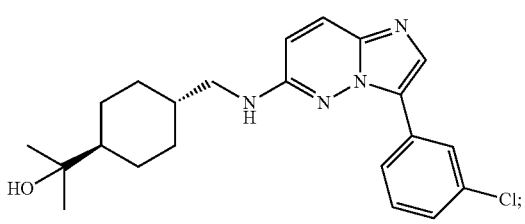

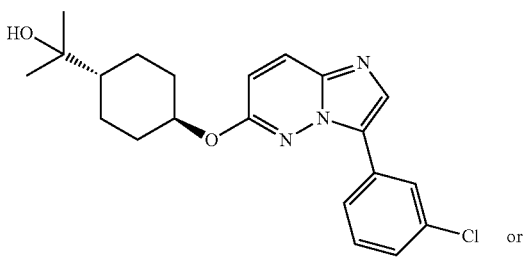

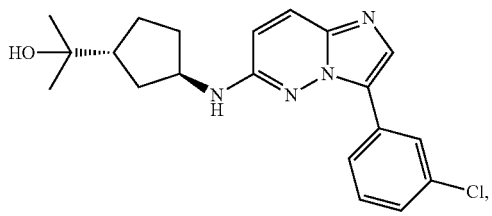 [SMILES: CC(C)(O)[C@@H]1CC[C@@H](Nc2ccc3ncc(-c4cccc(Cl)c4)n3n2)C1]

or a pharmaceutically acceptable salt thereof.

2. The method of claim 1, wherein the subject has an autoimmune disease or an inflammatory disease.

3. The method of claim 1, wherein the subject has psoriasis or Crohn's disease.

4. The method of claim 1, wherein the subject has fibrosis.

5. The method of claim 1, wherein the subject has a hyperproliferative disorder.

6. The method of claim 1, wherein the subject has a chronic leukemia.

7. The method of claim 1, wherein the subject has an acute leukemia.

8. The method of claim 1, wherein the subject has a proviral insertion in murine kinase-expressing cancer.

9. The method of claim 8, wherein the cancer is a hematological malignancy.

10. The method of claim 9, wherein the hematological malignancy is acute myeloid leukemia.

11. The method of claim 8, wherein the cancer is bladder cancer.

12. The method of claim 8, wherein the cancer is prostate cancer.

13. The method of claim 8, wherein the cancer is a solid tumor.

14. The method of claim 1, wherein the subject has lung cancer, non-small-cell lung cancer, oat-cell cancer, bone cancer, pancreatic cancer, skin cancer, dermatofibrosarcoma protuberans, head or neck cancer, cutaneous melanoma, intraocular melanoma, uterine cancer, ovarian cancer, colorectal cancer, anal region cancer, stomach cancer, colon cancer, breast cancer, a gynecologic tumor, Hodgkin's disease, hepatocellular cancer, esophagus cancer, small intestine cancer, endocrine system cancer, sarcoma of soft tissues, urethra cancer, penis cancer, prostate cancer, chronic leukemia, acute leukemia, a pediatric solid tumor, hypereosinophilia, lymphocytic lymphoma, bladder cancer, kidney cancer, ureter cancer, a pediatric malignancy, a neoplasm of the central nervous system, Barrett's esophagus, neoplastic cutaneous disease, mycosis fungoides or benign prostatic hypertrophy.

15. The method of claim 1, wherein the subject has a uterine sarcoma, carcinoma of the fallopian tubes, carcinoma of the endometrium, carcinoma of the cervix, carcinoma of the vagina, carcinoma of the vulva, thyroid cancer, pancreatic cancer, parathyroid cancer, adrenal gland cancer, renal cell carcinoma, carcinoma of the renal pelvis, primary central nervous system lymphoma, a spinal axis tumor, medulloblastoma, a brain stem glioma or a pituitary adenoma.

16. The method of claim 1, wherein the subject has diabetic retinopathy, retinal ischemia, retinal neovascularization, hepatic cirrhosis, angiogenesis or atherosclerosis.

17. The method of claim 1, wherein the compound has the following structure:

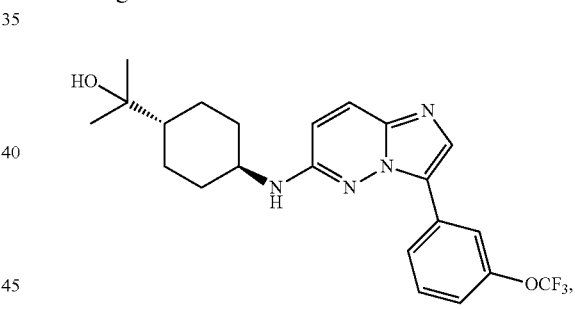

or a pharmaceutically acceptable salt thereof.

18. The method of claim 1, wherein the compound has the following structure:

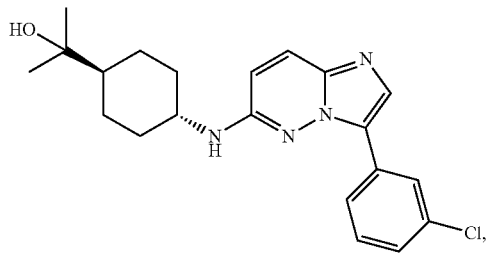

or a pharmaceutically acceptable salt thereof.

19. The method of claim 1, wherein the compound has the following structure:

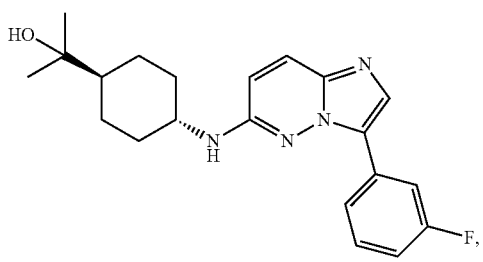

or a pharmaceutically acceptable salt thereof.

20. The method of claim 1, wherein the compound has the following structure:

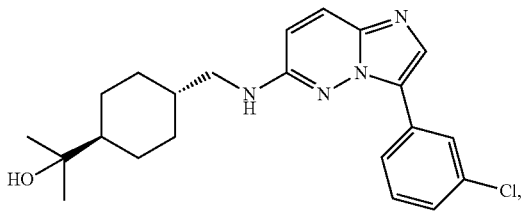 [SMILES: CC(C)(O)[C@H]1CC[C@H](CNc2ccc3ncc(-c4cccc(Cl)c4)n3n2)CC1]

or a pharmaceutically acceptable salt thereof.

21. The method of claim 1, wherein the compound has the following structure:

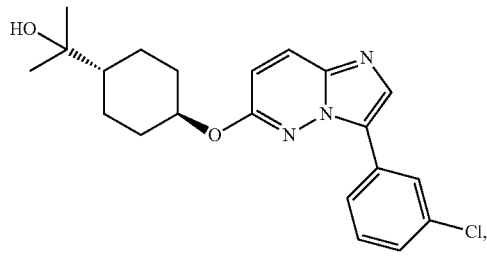 [SMILES: CC(C)(O)[C@H]1CC[C@H](Oc2ccc3ncc(-c4cccc(Cl)c4)n3n2)CC1]

or a pharmaceutically acceptable salt thereof.

22. The method of claim 1, wherein the compound has the following structure:

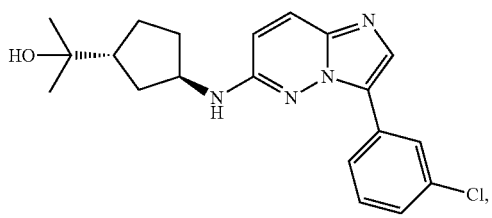 [SMILES: CC(C)(O)[C@@H]1CC[C@@H](Nc2ccc3ncc(-c4cccc(Cl)c4)n3n2)C1]

or a pharmaceutically acceptable salt thereof.

23. The method of claim 1, wherein the compound has the following structure:

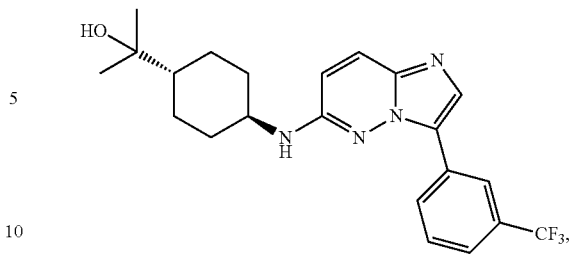

or a pharmaceutically acceptable salt thereof.

24. The method of claim 23, wherein the subject has a proviral insertion in murine kinase-expressing cancer.

25. The method of claim 24, wherein the cancer is a solid tumor.

26. The method of claim 23, wherein the subject has lung cancer, non-small-cell lung cancer, oat-cell cancer, bone cancer, pancreatic cancer, skin cancer, dermatofibrosarcoma protuberans, head or neck cancer, cutaneous melanoma, intraocular melanoma, uterine cancer, ovarian cancer, colorectal cancer, anal region cancer, stomach cancer, colon cancer, breast cancer, a gynecologic tumor, Hodgkin's disease, hepatocellular cancer, esophagus cancer, small intestine cancer, endocrine system cancer, sarcoma of soft tissues, urethra cancer, penis cancer, prostate cancer, chronic leukemia, acute leukemia, a pediatric solid tumor, hypereosinophilia, lymphocytic lymphoma, bladder cancer, kidney cancer, ureter cancer, a pediatric malignancy, a neoplasm of the central nervous system, Barrett's esophagus, neoplastic cutaneous disease, mycosis fungoides or benign prostatic hypertrophy.

27. The method of claim 23, wherein the subject has a uterine sarcoma, carcinoma of the fallopian tubes, carcinoma of the endometrium, carcinoma of the cervix, carcinoma of the vagina, carcinoma of the vulva, thyroid cancer, pancreatic cancer, parathyroid cancer, adrenal gland cancer, renal cell carcinoma, carcinoma of the renal pelvis, primary central nervous system lymphoma, a spinal axis tumor, medulloblastoma, a brain stem glioma or a pituitary adenoma.

28. The method of claim 23, wherein the subject has diabetic retinopathy, retinal ischemia, retinal neovascularization, hepatic cirrhosis, angiogenesis or atherosclerosis.

29. The method of claim 23, wherein the subject has an autoimmune disease or an inflammatory disease.

30. The method of claim 23, wherein the subject has psoriasis or Crohn's disease.

31. The method of claim 23, wherein the subject has fibrosis.

32. The method of claim 23, wherein the subject has a hyperproliferative disorder.

33. The method of claim 23, wherein the subject has a chronic leukemia.

34. The method of claim 23, wherein the subject has an acute leukemia.

35. The method of claim 24, wherein the cancer is bladder cancer.

36. The method of claim 24, wherein the cancer is prostate cancer.

37. The method of claim 24, wherein the cancer is a hematological malignancy.

38. The method of claim 37, wherein the hematological malignancy is acute myeloid leukemia.

39. The method of claim 23, wherein the modulating is in hematopoietic cells.

40. The method of claim 23, wherein the modulating is in bone marrow.

41. The method of claim 1, wherein the modulating is in hematopoietic cells.

42. The method of claim 1, wherein the modulating is in bone marrow.

* * * * *